(12) United States Patent
Saadat et al.

(10) Patent No.: US 12,409,300 B2
(45) Date of Patent: *Sep. 9, 2025

(54) METHODS FOR REMOVING A BLOOD CLOT MATERIAL

(71) Applicant: Inquis Medical, Inc., Menlo Park, CA (US)

(72) Inventors: Vahid Saadat, Atherton, CA (US); William Jason Fox, San Mateo, CA (US); Neekon Saadat, Atherton, CA (US); Mojgan Saadat, Atherton, CA (US); Mahyar Z. Kermani, San Ramon, CA (US); Michael Pare, Menlo Park, CA (US)

(73) Assignee: Inquis Medical, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/329,535

(22) Filed: Jun. 5, 2023

(65) Prior Publication Data

US 2023/0310804 A1     Oct. 5, 2023

Related U.S. Application Data

(63) Continuation of application No. 17/866,462, filed on Jul. 15, 2022, now Pat. No. 11,730,925, which is a
(Continued)

(51) Int. Cl.
*A61M 25/01* (2006.01)
*A61B 17/22* (2006.01)
(Continued)

(52) U.S. Cl.
CPC ............. *A61M 25/01* (2013.01); *A61B 17/22* (2013.01); *A61B 17/3207* (2013.01);
(Continued)

(58) Field of Classification Search
CPC ........ A61B 17/3207; A61B 17/320783; A61B 17/22; A61B 2017/00026;
(Continued)

(56) References Cited

U.S. PATENT DOCUMENTS

| 4,368,730 A | 1/1983 | Sharrock |
| 4,733,669 A | 3/1988 | Segal |

(Continued)

FOREIGN PATENT DOCUMENTS

| DE | 212015000300 U1 | 9/2017 |
| EP | 1292244 B1 | 1/2007 |

(Continued)

OTHER PUBLICATIONS

Saadat et al.; U.S. Appl. No. 18/555,859 entitled "Devices, systems and methods for removing obstructive material from body lumens," filed Oct. 17, 2023.

(Continued)

*Primary Examiner* — Michael J Tsai
*Assistant Examiner* — Justin L Zamory
(74) *Attorney, Agent, or Firm* — Shay Glenn LLP

(57) ABSTRACT

Described here are methods and apparatuses for removing a clot material from a patient. For example, an apparatus as described herein may include a flexible elongate body having a suction lumen, a first pair of sensors (e.g., electrodes), and a controller configured to identify a clot material based on signals from the first pair of sensors.

20 Claims, 67 Drawing Sheets

Related U.S. Application Data continuation of application No. PCT/US2022/035392, filed on Jun. 28, 2022.

(60) Provisional application No. 63/345,028, filed on May 23, 2022, provisional application No. 63/310,989, filed on Feb. 16, 2022, provisional application No. 63/287,049, filed on Dec. 7, 2021, provisional application No. 63/203,672, filed on Jul. 27, 2021, provisional application No. 63/202,880, filed on Jun. 28, 2021.

(51) Int. Cl.
*A61B 17/3207* (2006.01)
*A61B 17/00* (2006.01)

(52) U.S. Cl.
CPC .............. *A61B 17/320783* (2013.01); *A61B 2017/00026* (2013.01); *A61B 2017/00039* (2013.01); *A61B 2017/00119* (2013.01); *A61B 2017/22079* (2013.01); *A61B 2217/005* (2013.01)

(58) Field of Classification Search
CPC .......... A61B 2017/00039; A61B 2017/00119; A61B 2017/22079; A61B 2217/005; A61B 5/283; A61B 5/053; A61M 25/01; A61M 25/0012; A61M 2025/0002; A61N 1/0476; A61N 1/3614; A61N 1/36521
See application file for complete search history.

(56) References Cited

U.S. PATENT DOCUMENTS

| | | |
|---|---|---|
| 4,967,753 A | 11/1990 | Haase et al. |
| 5,248,297 A | 9/1993 | Takase et al. |
| 5,417,703 A | 5/1995 | Brown et al. |
| 5,569,275 A | 10/1996 | Kotula et al. |
| 5,603,703 A | 2/1997 | Elsberry et al. |
| 5,662,671 A | 9/1997 | Barbut et al. |
| 5,730,752 A | 3/1998 | Alden et al. |
| 5,749,914 A | 5/1998 | Janssen |
| 5,772,402 A | 6/1998 | Goodman |
| 5,827,229 A | 10/1998 | Auth et al. |
| 5,954,737 A | 9/1999 | Lee |
| 6,027,450 A | 2/2000 | Brown et al. |
| 6,089,235 A | 7/2000 | Hastings et al. |
| 6,152,882 A * | 11/2000 | Prutchi .................. A61N 1/056 607/9 |
| 6,428,551 B1 | 8/2002 | Hall et al. |
| 6,589,227 B2 | 7/2003 | Klint |
| 6,638,293 B1 * | 10/2003 | Makower ............... A61B 17/11 606/200 |
| 6,719,717 B1 | 4/2004 | Johnson et al. |
| 6,719,718 B2 | 4/2004 | Bonnette et al. |
| 6,849,068 B1 | 2/2005 | Bagaoisan et al. |
| 6,979,318 B1 | 12/2005 | McDonald et al. |
| 7,294,117 B2 | 11/2007 | Tine et al. |
| 7,608,063 B2 | 10/2009 | Le et al. |
| 7,655,016 B2 | 2/2010 | Demarais et al. |
| 7,699,790 B2 | 4/2010 | Simpson |
| 7,713,235 B2 | 5/2010 | Torrance et al. |
| 7,734,332 B2 | 6/2010 | Sher |
| 7,771,445 B2 | 8/2010 | Heitzmann et al. |
| 7,854,740 B2 | 12/2010 | Carey |
| 7,927,346 B2 | 4/2011 | VanCamp et al. |
| 7,938,820 B2 | 5/2011 | Webster et al. |
| 7,942,852 B2 | 5/2011 | Mas et al. |
| 7,947,012 B2 | 5/2011 | Spurchise et al. |
| 8,048,032 B2 | 11/2011 | Root et al. |
| 8,133,214 B2 | 3/2012 | Hayase et al. |
| 8,150,499 B2 | 4/2012 | Gelbart et al. |
| 8,208,990 B2 | 6/2012 | Maschke |
| 8,246,640 B2 | 8/2012 | Rosenthal et al. |
| 8,252,020 B2 | 8/2012 | Hauser et al. |
| 8,265,745 B2 | 9/2012 | Hauck et al. |
| 8,273,023 B2 | 9/2012 | Razavi |
| 8,298,252 B2 | 10/2012 | Krolik et al. |
| 8,343,084 B2 | 1/2013 | Nowakowski et al. |
| 8,366,615 B2 | 2/2013 | Razavi |
| 8,409,237 B2 | 4/2013 | Galdonik et al. |
| 8,430,837 B2 | 4/2013 | Jenson et al. |
| 8,465,452 B2 | 6/2013 | Kassab |
| 8,496,653 B2 | 7/2013 | Steinke |
| 8,613,717 B2 | 12/2013 | Aklog et al. |
| 8,771,289 B2 | 7/2014 | Mohiuddin et al. |
| 8,814,890 B2 | 8/2014 | Miyata et al. |
| 8,920,402 B2 | 12/2014 | Nash et al. |
| 8,920,448 B2 | 12/2014 | To et al. |
| 9,050,126 B2 | 6/2015 | Rivers et al. |
| 9,055,964 B2 | 6/2015 | Cartier et al. |
| 9,060,895 B2 | 6/2015 | Hartley et al. |
| 9,084,857 B2 | 7/2015 | Cully et al. |
| 9,248,221 B2 | 2/2016 | Look et al. |
| 9,254,140 B2 | 2/2016 | Song et al. |
| 9,259,290 B2 | 2/2016 | Jenkins et al. |
| 9,282,992 B2 | 3/2016 | Levine et al. |
| 9,402,938 B2 | 8/2016 | Aklog et al. |
| 9,415,188 B2 | 8/2016 | He et al. |
| 9,433,427 B2 | 9/2016 | Look et al. |
| 9,492,226 B2 | 11/2016 | Fish et al. |
| 9,510,854 B2 | 12/2016 | Mallaby |
| 9,655,633 B2 | 5/2017 | Leynov et al. |
| 9,668,767 B2 | 6/2017 | To et al. |
| 9,700,216 B2 | 7/2017 | Razavi et al. |
| 9,801,527 B2 | 10/2017 | Ferren et al. |
| 9,801,642 B2 | 10/2017 | Thor et al. |
| 9,808,266 B2 | 11/2017 | Ray et al. |
| 9,883,877 B2 | 2/2018 | Look et al. |
| 10,130,386 B2 | 11/2018 | Simpson et al. |
| 10,226,263 B2 | 3/2019 | Look et al. |
| 10,226,268 B2 | 3/2019 | Ulm |
| 10,238,456 B2 | 3/2019 | Murphy et al. |
| 10,271,873 B2 | 4/2019 | Steingisser et al. |
| 10,285,720 B2 | 5/2019 | Gilvarry et al. |
| 10,383,983 B2 | 8/2019 | Aklog et al. |
| 10,413,317 B2 | 9/2019 | Whiseant |
| 10,517,617 B2 | 12/2019 | Aklog et al. |
| 10,661,053 B2 | 5/2020 | Yang et al. |
| 10,716,586 B2 | 7/2020 | Krolik et al. |
| 10,722,238 B2 | 7/2020 | Sutton et al. |
| 10,743,907 B2 | 8/2020 | Bruzzi et al. |
| 10,751,159 B2 | 8/2020 | Janardhan et al. |
| 10,835,257 B2 | 11/2020 | Ferrera et al. |
| 10,888,337 B2 | 1/2021 | Shen et al. |
| 10,912,482 B2 | 2/2021 | Bozsak et al. |
| 10,945,758 B1 | 3/2021 | Davis et al. |
| 11,013,523 B2 | 5/2021 | Arad Hadar |
| 11,089,947 B2 | 8/2021 | Govari |
| 11,197,683 B1 | 12/2021 | Teigen et al. |
| 11,253,277 B2 | 2/2022 | Buck et al. |
| 11,259,821 B2 | 3/2022 | Buck et al. |
| 11,376,028 B1 | 7/2022 | Saadat et al. |
| 11,383,064 B2 | 7/2022 | Garrison et al. |
| 11,395,665 B2 | 7/2022 | Yang et al. |
| 11,510,577 B2 | 11/2022 | Bozsak et al. |
| 11,568,990 B2 | 1/2023 | Lebedev et al. |
| 11,730,924 B2 | 8/2023 | Saadat et al. |
| 11,730,925 B2 | 8/2023 | Saadat et al. |
| 11,779,238 B2 | 10/2023 | Sweeney et al. |
| 11,849,963 B2 | 12/2023 | Quick |
| 2001/0049486 A1 | 12/2001 | Evans et al. |
| 2002/0165575 A1 * | 11/2002 | Saleh ....................... A61F 2/01 606/200 |
| 2002/0177800 A1 | 11/2002 | Bagaoisan et al. |
| 2003/0191493 A1 | 10/2003 | Epstein et al. |
| 2004/0049225 A1 | 3/2004 | Denison |
| 2006/0004325 A1 | 1/2006 | Hamatake et al. |
| 2006/0122575 A1 | 6/2006 | Wakabayashi |
| 2007/0060944 A1 | 3/2007 | Boldenow et al. |
| 2007/0083195 A1 | 4/2007 | Werneth et al. |
| 2007/0106211 A1 | 5/2007 | Tine et al. |
| 2007/0191812 A1 | 8/2007 | Nishide et al. |

(56) References Cited

U.S. PATENT DOCUMENTS

| | | |
|---|---|---|
| 2008/0161840 A1 | 7/2008 | Osiroff et al. |
| 2008/0228231 A1 | 9/2008 | Raphael et al. |
| 2008/0243153 A1 | 10/2008 | Nguyen et al. |
| 2009/0069828 A1 | 3/2009 | Martin et al. |
| 2009/0177069 A1* | 7/2009 | Razavi ............. A61B 5/283 600/371 |
| 2009/0221957 A1 | 9/2009 | Bowman et al. |
| 2010/0023033 A1 | 1/2010 | Mauch et al. |
| 2010/0041984 A1 | 2/2010 | Shapland et al. |
| 2010/0204712 A1 | 8/2010 | Mallaby |
| 2010/0286708 A1 | 11/2010 | Rittman |
| 2011/0137399 A1 | 6/2011 | Chomas et al. |
| 2011/0160740 A1 | 6/2011 | Makower et al. |
| 2011/0230799 A1 | 9/2011 | Christian et al. |
| 2012/0041474 A1 | 2/2012 | Eckhouse et al. |
| 2012/0071838 A1 | 3/2012 | Fojtik |
| 2013/0158578 A1 | 6/2013 | Ghodke et al. |
| 2013/0178790 A1 | 7/2013 | Tekulve |
| 2013/0268048 A1 | 10/2013 | Watson et al. |
| 2013/0317589 A1 | 11/2013 | Martin et al. |
| 2014/0046244 A1 | 2/2014 | Ray et al. |
| 2014/0051968 A1 | 2/2014 | Isham et al. |
| 2014/0058294 A1 | 2/2014 | Gross et al. |
| 2014/0094741 A1* | 4/2014 | Bellisario ......... A61M 25/0069 604/39 |
| 2014/0222049 A1 | 8/2014 | Fruland et al. |
| 2015/0005781 A1 | 1/2015 | Lund-Clausen et al. |
| 2015/0011856 A1 | 1/2015 | Arevalos |
| 2015/0250982 A1 | 9/2015 | Osypka |
| 2015/0305765 A1 | 10/2015 | Fojtik et al. |
| 2015/0374405 A1 | 12/2015 | Takuma |
| 2016/0000499 A1 | 1/2016 | Lennox et al. |
| 2016/0067464 A1 | 3/2016 | Kim et al. |
| 2016/0089227 A1 | 3/2016 | Loh |
| 2016/0113676 A1 | 4/2016 | Tada et al. |
| 2016/0166265 A1 | 6/2016 | Nita |
| 2016/0166266 A1 | 6/2016 | Nita |
| 2016/0184562 A1 | 6/2016 | Ludin et al. |
| 2016/0278856 A1* | 9/2016 | Panescu ............. A61B 5/068 |
| 2016/0310020 A1 | 10/2016 | Warnking et al. |
| 2016/0346037 A1 | 12/2016 | Truckal et al. |
| 2016/0354100 A1 | 12/2016 | Darian |
| 2017/0043137 A1 | 2/2017 | Felkins et al. |
| 2017/0065396 A1 | 3/2017 | Look et al. |
| 2017/0224283 A1 | 8/2017 | Kassab et al. |
| 2017/0258512 A1 | 9/2017 | Germain et al. |
| 2018/0042623 A1 | 2/2018 | Batiste |
| 2018/0206865 A1 | 7/2018 | Martin et al. |
| 2018/0235644 A1 | 8/2018 | Jaffe et al. |
| 2018/0344248 A1 | 12/2018 | Zeng et al. |
| 2019/0142453 A1 | 5/2019 | Efremkin |
| 2019/0167287 A1 | 6/2019 | Vale et al. |
| 2019/0175210 A1 | 6/2019 | Wittens |
| 2019/0262031 A1 | 8/2019 | Efremkin |
| 2019/0298396 A1 | 10/2019 | Gamba et al. |
| 2019/0313941 A1 | 10/2019 | Radjabi |
| 2019/0358387 A1 | 11/2019 | Elbrady et al. |
| 2019/0365469 A1 | 12/2019 | Efremkin |
| 2019/0380651 A1 | 12/2019 | Carreel et al. |
| 2019/0388002 A1 | 12/2019 | Bozsak et al. |
| 2020/0054432 A1 | 2/2020 | Martin |
| 2020/0100839 A1 | 4/2020 | Efremkin |
| 2020/0129202 A1 | 4/2020 | Schoenle et al. |
| 2020/0129741 A1 | 4/2020 | Kawwas et al. |
| 2020/0164117 A1 | 5/2020 | Culhane et al. |
| 2020/0170666 A1 | 6/2020 | Trosper et al. |
| 2020/0188016 A1 | 6/2020 | Miller et al. |
| 2020/0205738 A1 | 7/2020 | Adawi et al. |
| 2020/0246029 A1 | 8/2020 | Singleton et al. |
| 2020/0253670 A1 | 8/2020 | Doisneau et al. |
| 2020/0261112 A1 | 8/2020 | Jamous et al. |
| 2020/0281612 A1 | 9/2020 | Kelly et al. |
| 2020/0281648 A1 | 9/2020 | Schultheis et al. |
| 2020/0297362 A1 | 9/2020 | Deville et al. |
| 2020/0305900 A1 | 10/2020 | Vale et al. |
| 2021/0007760 A1 | 1/2021 | Reisin |
| 2021/0068852 A1* | 3/2021 | Spence ............. A61B 17/32037 |
| 2021/0161544 A1 | 6/2021 | Casey |
| 2021/0161545 A1 | 6/2021 | Bhogal et al. |
| 2021/0220528 A1 | 7/2021 | Jalgaonkar et al. |
| 2021/0236257 A1 | 8/2021 | Walzman |
| 2021/0267613 A1 | 9/2021 | Follmer et al. |
| 2021/0361305 A1 | 11/2021 | Mogi et al. |
| 2022/0001141 A1 | 1/2022 | Yourgenlow et al. |
| 2022/0361901 A1 | 11/2022 | De Leon et al. |
| 2022/0409223 A1 | 12/2022 | Saadat et al. |
| 2023/0310751 A1 | 10/2023 | Merritt et al. |
| 2024/0299048 A1 | 9/2024 | Saadat et al. |
| 2024/0307659 A1 | 9/2024 | Saadat et al. |
| 2025/0058084 A1 | 2/2025 | Saadat et al. |

FOREIGN PATENT DOCUMENTS

| | | |
|---|---|---|
| EP | 2138200 A1 | 12/2009 |
| EP | 2782514 B1 | 12/2016 |
| EP | 2787893 B1 | 2/2017 |
| EP | 3244813 A1 | 11/2017 |
| EP | 3311875 A1 | 4/2018 |
| EP | 2231256 B1 | 5/2018 |
| EP | 1617893 B1 | 6/2018 |
| EP | 2299916 B1 | 8/2018 |
| EP | 2309934 B1 | 11/2018 |
| EP | 3705067 A2 | 9/2020 |
| EP | 3787523 A1 | 3/2021 |
| EP | 2908901 B1 | 5/2021 |
| EP | 4119069 A1 | 1/2023 |
| FR | 2903292 A1 | 1/2008 |
| JP | 2019187457 A | 10/2019 |
| JP | 2022062169 A | 4/2022 |
| JP | 2023022170 A | 2/2023 |
| WO | WO98/38929 A1 | 9/1998 |
| WO | WO2014/147815 A1 | 9/2014 |
| WO | WO2015/003134 A1 | 1/2015 |
| WO | WO2017/072663 A1 | 5/2017 |
| WO | WO2017/154748 A1 | 9/2017 |
| WO | WO2017/161204 A1 | 9/2017 |
| WO | WO2019/070782 A1 | 4/2019 |
| WO | WO2020/160179 A1 | 8/2020 |
| WO | WO2021/016213 A1 | 1/2021 |
| WO | WO2021/180826 A1 | 9/2021 |
| WO | WO2021/263033 A1 | 12/2021 |
| WO | WO2022/157270 A1 | 7/2022 |
| WO | WO2022/221643 A1 | 10/2022 |
| WO | WO2022/261448 A1 | 12/2022 |
| WO | WO2023/278495 A2 | 1/2023 |
| WO | WO2023/020961 A1 | 2/2023 |

OTHER PUBLICATIONS

Saadat et al.; U.S. Appl. No. 18/329,532 entitled "Apparatuses and methods for tracking obstructive material within a suction catheter," filed Jun. 5, 2023.

Saadat et al.; U.S. Appl. No. 18/720,594 entitled "Clot sending methods and apparatuses," filed Jun. 14, 2024.

PCR Online; First-in-human data for sensome ciot-sensing guidewire used in ischemic stroke treatment demonstrate ability to automate clot characterization with no safety issues; 4 pages; retrieved from the internet (https://www.pcronline.com/News/Press-releases/2024/First-in-human-data-for-Sensome-clot-sensing-guidewire-used-in-ischemio-stroke-tr eatment-demonstrate-ability-to-automate-clot-characterization-with-no-safety-issues?utm_source=chatgpt.com) on Feb. 18, 2025.

PCR Online; Sensome announces data from two new studies showing clot-sensing guidewire successfully identifies fresh clot to support decision-making in peripheral artery disease treatment; 4 pages; retrieved from the internet (https://www.pcronline.com/News/Press-releases/2024/Sensome-announces-data-from-two-new-studies-showing-clot-sensing-guidewire-successfully-identifies-fresh-clot-to-support-decision-making-in-peripheral-artery-disease-treatment?utm_source=chatgpt.com) on Feb. 18, 2025.

Rice et al.; CLOTILD a smart guidewire sensing clot characteristics during the mechanical thrombectomy procedure—results from the

(56) References Cited

OTHER PUBLICATIONS

Clot Out study; 1 page; retrieved from the internet (https://www.sensome.com/_files/ugd/9575e7_0370965f17994ee193753e4b4df10e1a.pdf) on Feb. 18, 2025.

Childs et al.; U.S. Appl. No. 18/859,162 entitled "Aspiration apparatuses for clot removal," filed Oct. 22, 2024.

* cited by examiner

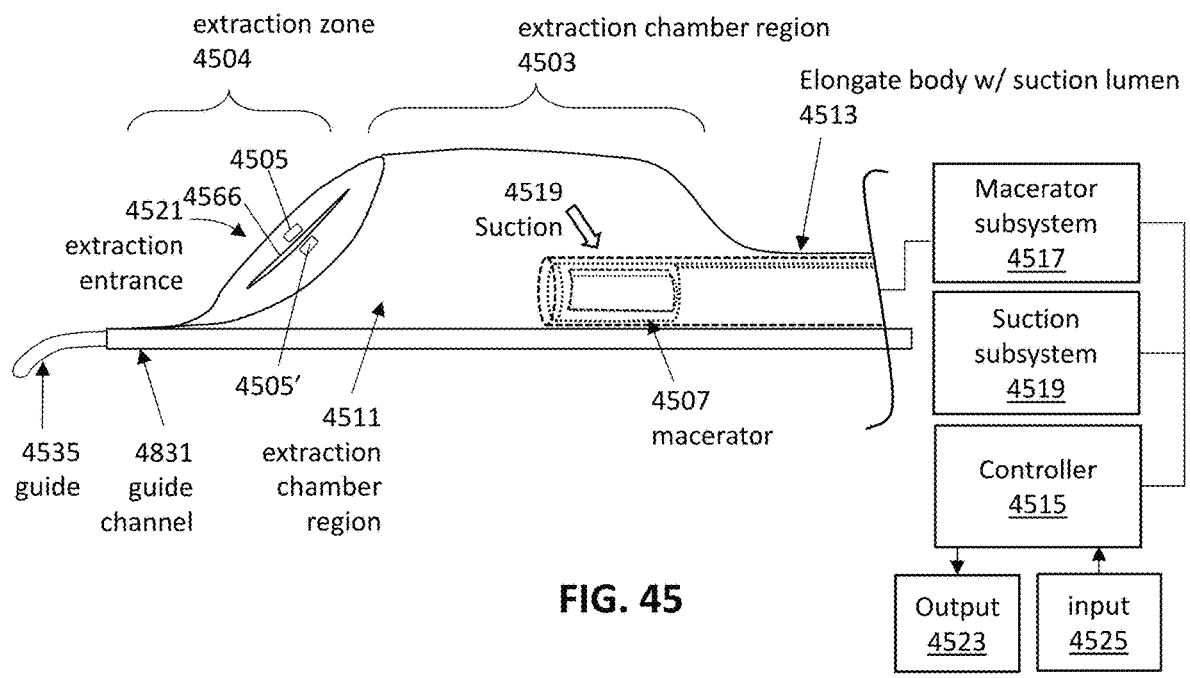
FIG. 45
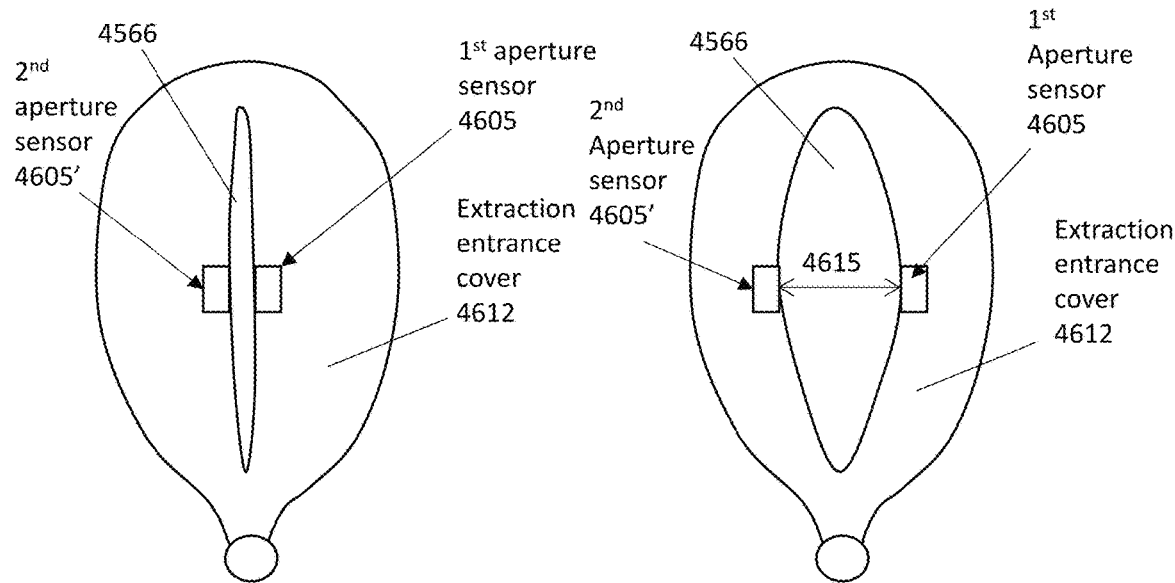
FIG. 46A      FIG. 46B

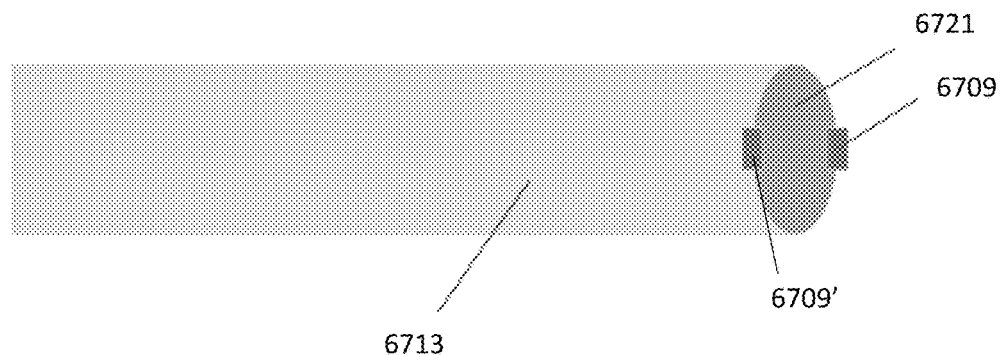
FIG. 67
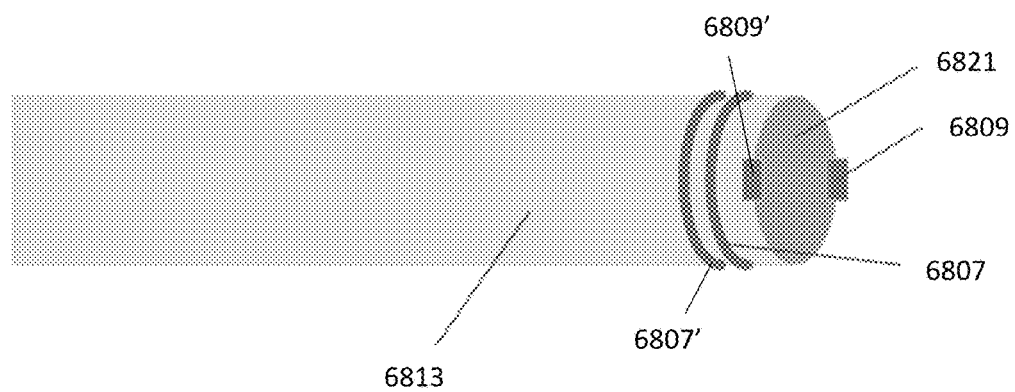
FIG. 68
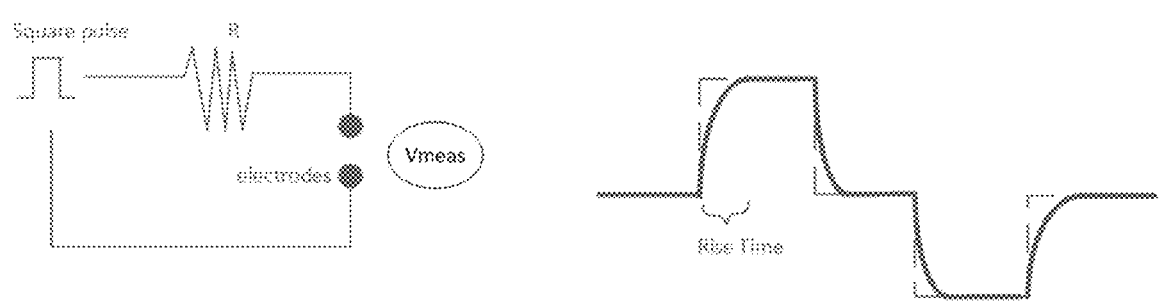
FIG. 69A  FIG. 69B

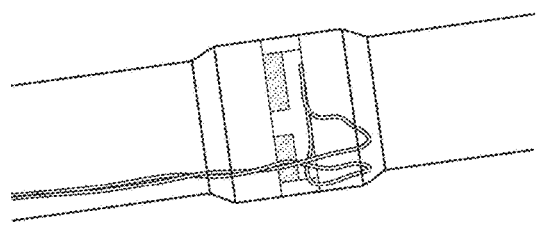
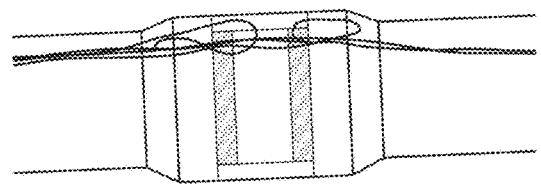
FIG. 79A  FIG. 79B
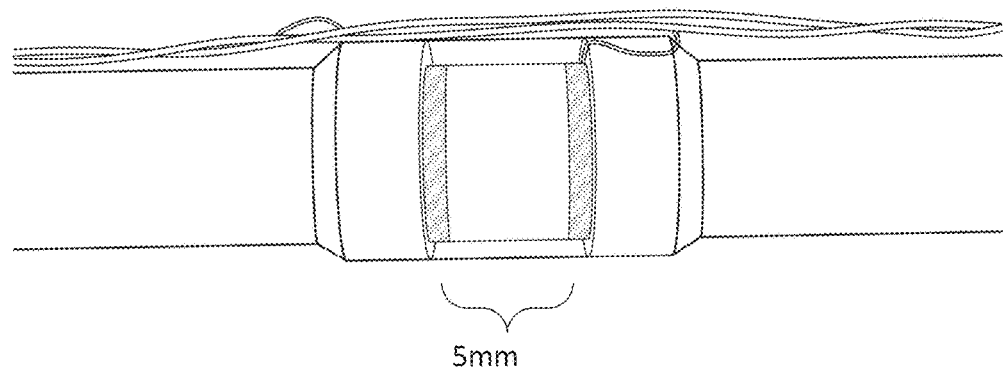
FIG. 80
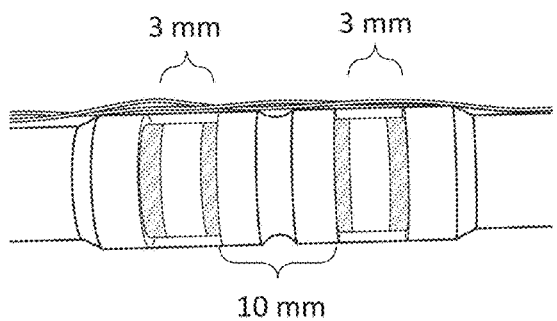
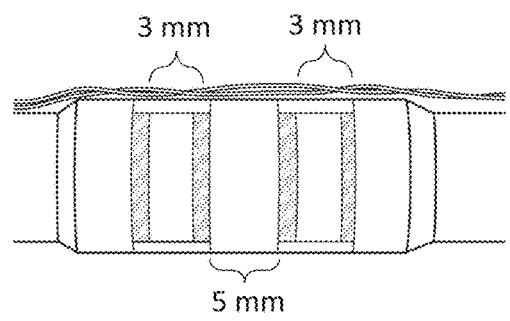
FIG. 81A  FIG. 81B

METHODS FOR REMOVING A BLOOD CLOT MATERIAL

CLAIM OF PRIORITY

This patent application is a continuation of U.S. patent application Ser. No. 17/866,462, titled "APPARATUSES AND METHODS FOR TRACKING OBSTRUCTIVE MATERIAL WITHIN A SUCTION CATHETER," filed Jul. 15, 2022, now U.S. Patent Application Publication No. 2022/0409857, which is a continuation of PCT International Patent Application No. PCT/US2022/035392, titled "APPARATUSES AND METHODS FOR CONTROLLING REMOVAL OF OBSTRUCTIVE MATERIAL," filed Jun. 28, 2022, which claims priority to U.S. Provisional Patent Applications No. 63/202,880, titled, "DEVICES, SYSTEMS, AND METHODS FOR SENSING CLOT MATERIAL," filed on Jun. 28, 2021, U.S. Provisional Patent Applications No. 63/203,672, titled "APPARATUSES AND METHODS FOR CONTROLLING REMOVAL OF OBSTRUCTIVE MATERIAL," filed on Jul. 27, 2021; U.S. Provisional Patent Applications No. 63/287,049, titled "APPARATUSES AND METHODS FOR CONTROLLING REMOVAL OF OBSTRUCTIVE MATERIAL," filed on Dec. 7, 2021; U.S. Provisional Patent Applications No. 63/310,989, titled "APPARATUSES AND METHODS FOR CONTROLLING REMOVAL OF OBSTRUCTIVE MATERIAL," filed on Feb. 16, 2022; and Provisional Patent Applications No. 63/345,028, titled "APPARATUSES AND METHODS FOR CONTROLLING REMOVAL OF OBSTRUCTIVE MATERIAL," filed on May 23, 2022. Each of these is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Blockage of blood vessels, including both veins and arteries may result in serious medical and health issues. For example, a thromboembolism is characteristic of numerous common, life-threatening conditions. Examples of potentially fatal diseases resulting from thrombotic occlusion include pulmonary embolism, deep vein thrombosis, and acute limb ischemia. Acute pulmonary embolism is a significant cause of death in the United States. Pulmonary embolism can be a complication from deep vein thrombosis, which has an annual incidence of 1% in patients 60 years and older. All of the aforementioned diseases are examples of conditions in which treatment may include aspiration or evacuation of clot and/or blood.

However, vacuum-assisted thrombectomy systems must sometimes be terminated due to the risk of excessive blood loss by the patient, especially when using large aspiration catheters. During aspiration thrombectomy, prior to contacting the clot material and/or when the catheter tip falls out of contact with the clot material (e.g., thrombus or other occlusive material), the tip is exposed to healthy blood and may remove blood at full flow. Under such conditions, the blood loss rate may be excessive, and in some cases, may result in premature termination of the procedure. The blood loss rate may be in the range of 20-25 cc per second with an 8 French size catheter. With a maximum tolerable blood loss of 300-1000 mL, the catheter cannot run in unrestricted mode for more than approximately 20 to 50 seconds. When a physician operates the system manually, the aggregate blood loss may reach an unacceptable level before sufficient clot is removed. In addition, reliably identifying whether the tip of the catheter is in contact with clot or is undesirably aspirating healthy, clot-free blood is a significant problem, and such manual control is not optimum.

This problem may be exacerbated where clot is hard and difficult to remove, which may delay the time that the suction is applied and lengthen the procedure overall. Although a macerator may be used with clot removal, control of maceration may make guidance and control of the catheter (e.g., suction catheter) difficult.

It may also be difficult to determine when clot has been taken into the lumen of the aspiration apparatus, including when the aspiration apparatus is clogged. In addition, it would be very helpful to accurately and/or quantitatively determine how much clot has been removed.

It would therefore be desirable to provide methods and apparatuses (e.g., systems, devices, etc.) for controlling the aspiration of thrombus and clot using aspiration catheters that limits or minimizes blood loss. It would be particularly useful to provide apparatus and methods including maceration control in which limit or minimize blood loss during the aspiration procedures. The methods and apparatuses described herein may address these issues.

SUMMARY OF THE DISCLOSURE

Described herein are methods and apparatuses (e.g., devices and/or systems, including suction/thrombectomy devices, suction/thrombectomy catheters and systems for controlling them) for removing obstructive material in a body lumen, such as clot material. Although the following discussion refers mainly to clot material, the present technology is configured to remove other types of obstructive material, such as clot (e.g., thrombus) material, e.g., plaque, and/or other obstructive material, including vegetation (e.g., bacterial material surrounded by a platelet/fibrin layer). In general, the methods and apparatuses described herein are configured to control the operation of a suction catheter and/or a macerator in conjunction with a suction catheter. In some embodiments, the present technology comprises one or more sensors that are coupled to and/or integrated with one or more components of the treatment system, such as a suction catheter, which may also be referred to herein as an aspiration catheter. The one or more sensors may provide sensor data that the system, including a controller with one or more processors, may analyze to verify the presence of clot material, so that the controller may coordinate operation of the suction catheter and/or macerator. These apparatuses (e.g., devices, systems, etc.) may provide accurate and rapid confirmation that clot material is near, adjacent to (including in contact with) and/or within the lumen of the aspiration apparatus. In some examples these apparatuses may provide rapid and accurate estimation of the amount of clot removed. These apparatuses may also provide an indication of the rate of removal of the clot (e.g., travel of the clot material within the lumen of the aspiration apparatus).

The one or more sensors described herein may be positioned at specific locations on or in the suction catheter and/or (in some optional examples) macerator assembly. The location(s) of the sensor may be important in providing control information for controlling and/or coordinating the activity of the suction catheter and/or macerator assembly. As will be described herein, any appropriate type of sensor may be used, including combinations of different types of sensors. Sensor types may include sensors for detecting an electrical property, such as impedance (e.g., bioimpedance, including bioimpedance spectroscopy), sensors for detecting pressure, and/or sensors for detecting optical characteristics (e.g., optical spectroscopy). Sensor types may include ultrasound sensors. Sensor types may include optical sensors (including sensors for detecting color). Any combination of these sensors may be used.

Sensor may be present on a distal and/or lateral external region of the catheter, and/or within the catheter lumen (e.g., at a distal end region, proximal end region, and one or more medial end regions). For example, pairs of sensing electrodes may be used external and/or within the suction catheter.

The methods and apparatuses described herein may generally use these sensors to provide output (visual, audio, data, etc.) to a user and/or stored for later analysis. For example, these methods and apparatuses may be used to provide output to a user (e.g., doctor, nurse, surgeon, technician, etc.) that clot material is near, adjacent to and/or within the suction catheter. In some examples, these apparatuses may provide an indication that clot material has entered and passed through (or is jammed within) the lumen of the suction catheter. These methods and apparatuses may optionally be used to automatically and/or semi-automatically control the operation of one or more aspects of the apparatus, such as the application of suction, maceration, etc. For example, the apparatus may automatically or semi-automatically control turning on/off aspiration and/or adjusting the level of aspiration (increasing, decreasing, etc.).

For example, described herein are methods, including methods of controlling a suction catheter. These methods may include: detecting a clot material with a distal end of a suction catheter using a first sensor or set of sensors on the distal end of the suction catheter; starting or increasing suction through the suction catheter once the clot material has been detected; confirming that the clot material has been drawn into the suction catheter using a second sensor or set of sensors within the distal end of the suction catheter to detect the clot material within the distal end of the suction catheter; and stopping or reducing the application of suction through the suction catheter after the clot material is no longer detected by the first sensor or set of sensors and the second sensor or set of sensors.

A method may include: inserting a suction catheter into a lumen of a blood vessel; detecting clot material with a distal end of the suction catheter using a first sensor and/or set of sensors on the distal end of the suction catheter, wherein detecting the clot material comprises processing a signal from the first sensor or set of sensors to confirm the presence of clot material; starting or increasing suction through the suction catheter once the clot material has been detected; monitoring that the clot material has been drawn into the suction catheter using a second sensor or set of sensors within the distal end of the suction catheter; and stopping or reducing the application of suction through the suction catheter after the clot material is no longer detected by the first sensor or set of sensors and the second sensor or set of sensors.

In general, the methods described herein may be used to confirm the presence and/or proximity of clot material relative to the sensor. As mentioned, detecting clot material using the first sensor or set of sensors may comprise detecting the clot material by one or more of: electrical property (e.g., impedance), ultrasound and/or optical detection. In particular, detecting the clot material by the first sensor or set of sensors may comprise detecting clot material by impedance.

Any of these methods and apparatuses may be configured to start or increase suction when the controller determines that clot material is near or on the distal end of the catheter and/or within the catheter, and in particular within the distal end of the catheter. The controller may process signals from the sensors or sets of sensors to confirm the identity of clot material, rather than blood, vessel wall, or other non-clot material. In some examples, multiple sensor types or modalities may be used to confirm the identity of clot material, such as bioimpedance (or bioimpedance spectroscopy) and/or ultrasound and/or one or more optical properties (e.g., color). The controller may start suction when the controller determines that clot is nearby one or more of the sensors. In some examples the suction catheter may include a low level of suction (e.g., between 0.5-50 mmHg); thus, the controller may increase the suction to a higher (or high) level of suction when clot is identified or confirmed (e.g., to greater than about 300 mmHg, greater than 350 mmHg, greater than 400 mmHg, etc.).

Similarly, a second sensor and/or set of sensors may be configured to sense the same modality or a different modality from the first sensor or set of sensors. Any of the sensors within the first or second set of sensors may be configured to sense different modalities (e.g., impedance, ultrasound, optics, etc.). Thus, any of these methods may confirm (using the controller) that the clot material has been drawn into the suction catheter by detecting clot material within the lumen of the suction catheter using the second sensor or set of sensors by one or more of: impedance, ultrasound and/or optical detection.

In general, the methods and apparatuses described herein may process a signal from the first sensor or set of sensors to confirm the presence of clot material and/or the second sensor or set of sensors to confirm the presence of clot material. Processing of the sensor signals may include averaging (time averaging), windowing, or the like. Signal processing of sensed signals may be analog or digital signal processing, as signals from the sensor(s) may be continuous and/or analog or may be sampled with a sample frequency and digitized. Signals may be transmitted in real time to the controller for processing. The controller may process the signals in real time, or with a slight delay to allow for processing. Signals may be processed and/or stored, and/or transmitted for display and/or storage during a medical procedure.

For example, signals from one or more sensors, including in particular adjacent sensors of the same type or different types may be processed using one or more analog signal processing techniques, such as by convolving the signals. Analog signals may be transformed from the time domain to the frequency domain (e.g., by Fourier transform, Laplacian transform, etc.) or by expression as a Bode Plot, including with frequency spectral impedance measurements. Digital signal processing may also be performed, e.g., including functional analysis and/or numerical analysis techniques, such as decomposition into intrinsic mode functions and/or wavelets. Any of these methods and apparatuses may determine noise in the sensor to help distinguish and validate contact or proximity to clot material.

The controller may confirm clot material based on characteristics of sensed values. For example, signals from the first and/or second sensors or sets of sensors may be processed to reduce noise and/or to amplify signal and may then be compared to known or expected values corresponding to clot material within a predetermined or calculated confidence range, to allow the controller to distinguish between clot material, blood and vessel wall. For example, in any of these examples, processing may include processing to distinguish from contacting a lumen wall of a vessel in which the suction catheter is positioned.

The methods and apparatuses described herein may offer numerous advantages to systems that measure pressure or flow in order to control the operation of the suction, but which are unable to confirm the identity and/or characteristics of clot material. In some cases, the methods and apparatuses described herein may also include sensors for detecting pressure and/or flow within the lumen of the suction catheter.

In general, these methods and apparatuses may be configured to start or increase suction after a starting delay. In some examples, the starting delay may allow further sensing and processing to determine and/or confirm clot material is present, and/or to allow the user or apparatus to be configured for suction and/or macerating of clot material. The starting delay may be, for example, a predetermined delay (e.g., between 0.1 second and 10 seconds, between 0.1 second and 8 seconds, between 0.1 second and 7.5 seconds, between 0.1 second and 6 seconds, between 0.1 second and 5 seconds, between 0.1 second and 4 seconds, between 0.1 second and 3 seconds, between 0.1 seconds and 2 seconds, between 0.1 second and 1 second, etc.); in some examples the starting delay may be defined based on user input. For example, in some (semi-automatic) configurations, the apparatus may alert the user that the suction can or should begin once clot material has been confirmed at or near the distal end of the apparatus and may enable the user to thereafter manually initiate suction. This may be useful for many reasons, including allowing the user to position the macerator within the lumen of the suction catheter.

As described above these methods and apparatuses may be configured to allow automatic stopping or reducing of the suction (and/or in some examples, a macerator, if one is included), including stopping automatically after clot material is not detected within the suction catheter and distal to the end of the suction catheter. In general, these methods and apparatuses may be configured to stop or reduce the application of suction by stopping or reducing the application of suction through the suction catheter after a predetermined delay period once the clot material is no longer detected by the first sensor or set of sensors and the second sensor or set of sensors. The stop delay may be, e.g., between 0.1 second and 10 seconds, between 0.1 second and 8 seconds, between 0.1 second and 7.5 seconds, between 0.1 second and 6 seconds, between 0.1 second and 5 seconds, between 0.1 second and 4 seconds, between 0.1 second and 3 seconds, between 0.1 seconds and 2 seconds, between 0.1 second and 1 second, etc. In some examples the system may emit a stop alert that may indicate stopping of the suction catheter (and/or macerator) or may alert the user to manually stop suction and/or macerator operation. As used herein, an alert may be an audible alert (tone, chime, etc.) and/or a visible alert (light, indicator, etc.), a tactile alert (e.g., buzzer, vibration, etc.).

Any of the methods described herein may be used for removing clot material from a lumen of the body, such as a blood vessel (e.g., artery, vein, etc.). In some examples, these methods may include methods of performing a thrombectomy using suction. The medical method may be performed with suction alone or in combination with another device or sub-system, such as a mechanical device (e.g., stent-retriever device). The methods and apparatuses described herein may be used in any appropriate region of the body, including, but not limited to the lungs (e.g., within a pulmonary artery), the peripheral vasculature, the neurovasculature, etc.

Also described herein are apparatuses for performing any of these methods, including apparatuses for controlling suction within a suction catheter. For example, an apparatus may include: a suction catheter; a first sensor or set of sensors on a distal end face of suction catheter; a second sensor or set of sensors within the lumen of the suction catheter; and a controller comprising one or more processors, wherein the controller is configured to activate or increase suction through the suction catheter when a signal from the first sensor and/or set of sensors indicates that a clot material is in front of the distal end of the suction catheter and/or aligned with a certain portion of the suction catheter (such as an opening(s) in the catheter wall).

Any of these apparatuses may include a macerator within (and/or configured to fit within) the lumen of the suction catheter. Additional examples of macerators are described below. The macerator may be a separate element that is slidably disposed within the lumen of the suction catheter, e.g., can be inserted or removed, within the lumen, or it can be integrated into the suction catheter. As will be described in greater detail below, the macerator may also be controlled by the same controller (or a separate controller) as the suction through the suction catheter. The sensors (e.g., first sensor or set of sensors and the second sensor or set of sensors) may provide input to the controller (or controllers) for processing to identify the presence and/or proximity of clot material at or near the distal end of the suction catheter as well as within the lumen of the suction catheter.

The sensor or set of sensors within the lumen of the catheter may be positioned along all or a portion of the length of the lumen of the catheter. In some examples the apparatus may include one or more sensors within a distal end region of the lumen of the suction catheter. The distal end region may include the length of the suction catheter lumen extending proximally from the distal end of the suction catheter towards a macerator, which may be located more proximally within the lumen of the catheter. Any of the examples described herein may include a macerator; however, these methods and apparatuses may also be used or adapted for use without a macerator, as described herein. In some examples this distal end region may be referred to as the monitored distal end region. In some examples the distal end region may have a larger inner diameter than the inner diameter of the more proximal region of the suction catheter; sensors may be included within this larger region. Alternatively the distal end region may have the same outer diameter (or optionally a smaller outer diameter) than the more proximal region of the catheter, including the region immediately proximal. One or more sensors (e.g., in some examples a second sensor or set of sensors) may be contained within the larger diameter distal end region or they may extend proximally past this larger diameter region. The larger diameter region may be expandable (e.g., may be biased to expand) as will be described for some examples.

In any of these apparatuses the one or more sensors within the lumen may be coupled (via a wire or wirelessly) to the controller. Similarly, the one or more sensors on the distal end of the suction catheter (the first sensor or sets of sensors) may be wired or wireless connected to the controller. For example, in any of these apparatuses one or more electrical connections (wires, lines, traces, etc.) may be made between the sensor(s) and the controller either directly or indirectly.

In some examples each sensor is coupled via a wire or wires extending proximally down (along the outside or within a sidewall of) the suction catheter to ultimately connect to the controller. Separate power and data lines may be used, or the same (power and data) may be used on the same apparatus.

In some examples the apparatus may include a pump that is coupled to the controller. Any appropriate pump providing suction may be used. For example, the pump may be a positive displacement pump (e.g., diaphragm, gear, peristaltic, piston pump, etc.) or a dynamic pump (centrifugal, etc.). The pump may be controlled by the controller. For example, the controller may output a control signal to turn the pump on, turn the pump off, or adjust the rate or suction applied by the pump. Thus, the apparatus may include a pump coupled to the controller. Optionally, the suction may be provided by a manually actuated pump (vacuum source).

In some examples the pump is not included directly with the apparatus but instead (or in addition) the apparatus may include one or more valves and/or manifolds to modulate a source of suction, e.g., received from "wall" suction or by a separate pump. Thus, the system may include a suction interface that may control the suction into the suction catheter to allow suction (turn on), disallow suction (turn off), or adjust the level of suction (higher/lower, including within predetermined ranges of negative pressure). The suction interface may be part of the controller or may be coupled to the controller. For example, the controller may include one or more valves for adjusting the suction through the suction catheter. In some examples the apparatus may include a pump, and the controller may regulate the applied suction by controlling a suction interface, rather than the pump directly.

As mentioned above, the first sensor or set of sensors and/or the second sensor or set of sensors may one or more of: an acoustic sensor, an electrical (e.g., bioimpedance sensor), and an optical sensor. The sensors in the first set of sensors may be the same or different. Similarly, the sensors in the second set of sensors may be the same or different. The first sensor may be the same as the second sensor. The first set of sensors may be the same or different from the second set of sensors. In some examples, groups of sensors (pairs or sensor, three or more sensors, etc.) may be combined at a similar location to provide multiple sensing modalities at approximately the same (or the same) location(s). In general, the sensor(s) may be one or more of: an acoustic sensor, an electrical (e.g., bioimpedance) sensor, and an optical sensor.

In any of these apparatuses the first sensor or set of sensors may be arranged on a deformable cover extending at least partially over the distal end of the suction catheter. The deformable cover may deform to open or close to allow clot material into the lumen of the suction catheter, while limiting the flow of blood into the suction catheter. The deformable cover may be a sheet of material, e.g., a polymeric material, such as but not limited to silicone, that may expand/contract. The deformable cover may include one or more openings, and/or slits, cuts, etc. for allowing the cover to yield to allow clot material into the cover. In some examples the first sensor or set of sensors may be arranged on the periphery of the distal face opening of the suction catheter. The first sensor or set of sensors may generally be forward-looking, e.g., looking distally within the lumen.

As used herein, the term distally or proximally may refer to the direction away from or towards the body of the user operating the device. For example, the distal end of the suction catheter is usually the end that is inserted into the subject (e.g., patient) by the user and is moved away from the user into the subject.

As mentioned above, in general these apparatuses may include a set of sensors (e.g., optionally a second sensor or set of sensors) that are within the lumen of the suction catheter, which may be referred to as internal sensor(s). The internal sensor or set of sensors may be arranged on a sidewall of the lumen of the suction catheter. In some examples, the internal sensor or set of sensors may be on the macerator component that is within the lumen of the suction catheter. In some examples the internal set of sensors may be on both the wall (sidewall) of the lumen and the outside of the macerator ("macerator component"). Thus, in some examples the position of the internal sensor or set of sensors may be adjustable within the lumen of the suction catheter. The internal sensors may optionally be referred to as a second sensor or set of sensors when used with an external sensor or set of sensors. Internal sensors or sensors may be used without an external sensor or set of sensors ("first sensor or set of sensors).

The one or more processors within the controller may control the application of suction through the suction catheter, by controlling the pump directly and/or indirectly (e.g., using one or more valves, etc.)

In some examples the processor may be configured to deactivate or decrease suction through the suction catheter a predetermined delay time (stop delay) after the signal from the first sensor or set of sensors indicates that the clot material is not in front of the distal end of the suction catheter and the second sensor or set of sensors indicates that the clot material is not within the lumen of the suction catheter. The stop delay may be based on a predefined time period (e.g., between 0.1 second and 10 seconds, between 0.1 second and 8 seconds, between 0.1 second and 7.5 seconds, between 0.1 second and 6 seconds, between 0.1 second and 5 seconds, between 0.1 second and 4 seconds, between 0.1 second and 3 seconds, between 0.1 seconds and 2 seconds, between 0.1 second and 1 second, etc.). In any of these methods and apparatuses, the stop delay may be based on one or more of: a length of the suction catheter, a flow rate of material within the suction catheter, and a strength of the suction applied.

For example, described herein are apparatuses including: a suction catheter; a first sensor or set of sensors on a distal end face of suction catheter; a second sensor or set of sensors within the lumen of the suction catheter; and a controller receiving input from the first sensor or set of sensors and the second sensor or set of sensors and comprising one or more processors, wherein the one or more processors is configured to analyze a signal from the first sensor or set of sensor to confirm that the a clot material is in contact with or adjacent to the first sensor or set of sensors, and to confirm that the clot material is within the lumen of the suction catheter based on data from the second sensor or set of sensors; further wherein the controller is configured to activate or increase suction through the suction catheter when the one or more processors indicates that the clot material is in front of the distal end of the suction catheter, and wherein the controller is configured to deactivate or decrease suction through the suction catheter a predetermined time period from when the processor indicates that the clot material is not in front of the distal end of the suction catheter and that the processor confirms that the clot material is not within the lumen of the suction catheter.

Also described herein are methods and apparatuses for controlling a macerator within a suction catheter. In any of these apparatuses the macerator may be controlled separately from (or without) control of the suction through the suction catheter as described above. For example, the methods and apparatuses (systems and devices) described herein may include just methods and apparatuses for controlling a macerator within a suction catheter.

For example, described herein are methods including: applying suction to draw a clot into a suction catheter; detecting a clot material within the suction catheter using a sensor or set of sensors within distal end of the suction catheter; driving a macerator within the suction catheter once the clot material has been detected within the suction catheter; and stopping driving the macerator after the clot material is no longer detected by the sensor or set of sensors within the suction catheter.

A method may include, for example: applying suction to draw a clot into a suction catheter; detecting a clot material within the suction catheter using a sensor or set of sensors that are positioned on a macerator within a distal end of the suction catheter; driving the macerator once the clot material has been detected; and stopping driving the macerator after the clot material is no longer detected by the sensor or set of sensors.

The sensor or set of sensors may be on the macerator. For example, the sensor or set of sensors may be on the outside of the macerator. In some examples the one or more sensors may be on the distal end region of the macerator near the cutting member (e.g., cutting element) of the macerator. In some examples the one or more sensors may be on the distal end region of the elongated body of the macerator. In general, a macerator may be used to unclog the suction catheter.

The macerator is generally configured to disrupt obstructive material. The macerator may include a wire, blade, or the like, or multiple wires, blades, plates, threads, etc. The cutting member (e.g., wire, blades, threads, etc.) may move, and in some examples may rotate to cut clot material. For example, in some examples a macerator may include a plurality of maceration wires having a linear configuration. Alternatively, or in combination, the maceration wires may be partially or fully straight, round, bent, helical about an axis, or have a profile that is random, or any combination thereof. The macerator may have at its distal end a distal hub coupled to an inner macerator shaft (e.g., rotating shaft) and at a proximal end may include a proximal hub. The plurality of maceration wires may be attached to a macerator drive shaft, to the distal hub, or a proximal hub, or any combination thereof. The inner shaft may be concentrically surrounded by an outer shaft. The macerator inner shaft and outer shaft may be flexible. The inner (rotatable shaft) may be a drive shaft.

In some examples the macerator includes a threaded distal blade within a macerator distal housing having one or more opening for receiving and disrupting clot material so that it may more easily be removed down the suction catheter.

Thus, any of the methods described herein may include driving the macerator by driving rotation of the macerator (e.g., the drive shaft) to rotate or otherwise actuate the cutting member of the macerator. In some examples the macerator may be driven or actuated by extending the cutting member out of a protective housing (e.g., distal housing). The macerator may be positioned within the lumen of the suction catheter, e.g., by advancing distally within the lumen of the suction catheter. Any of these methods may include extending the macerator within the lumen of the suction catheter prior to applying suction to draw the clot into the suction catheter.

Any of these methods may also include applying suction by applying intermittent suction. Suction may be applied in a pattern (e.g., a repeating pattern of high/low negative pressure), or in an oscillating pattern. Suction may be applied at a constant level.

In any of the methods and apparatuses described herein the clot material may be detected by the sensor or set of sensors by sensing one or more of: impedance (including impedance spectroscopy), ultrasound and/or optical detection. For example, detecting the clot by the sensor or set of sensors may include detecting clot material by impedance.

Detecting a clot material within the suction catheter using the sensor or set of sensors within distal end of the suction catheter may include detecting clot material on or adjacent to a window exposing a cutter of the macerator.

Also described herein are apparatuses configured to control the action of the macerator based on the presence and/or proximity of the clot material. For example, described herein are apparatus including: a suction catheter having a suction lumen; a macerator comprising an elongate body, wherein the macerator is configured extend distally though the suction catheter to a distal end region of the suction catheter; a sensor or set of sensors within the lumen of suction catheter; and a controller comprising one or more processors, wherein the controller is configured to activate the macerator when a signal from the sensor or set of sensors indicates that a clot material is within the lumen of the suction catheter.

As described above, the sensor or set of sensors (in some examples the second sensor or set of sensors) may be positioned on the macerator. This sensor or set of sensors may be on the lumen of the suction catheter. As discussed above, the sensor or set of sensors may include one or more of: an acoustic sensor, an electrical (e.g., bioimpedance) sensor, and an optical sensor. In any of these examples, sensors within the lumen of the suction catheter may be positioned on a sidewall of the lumen and/or on the macerator.

In any of these methods and apparatuses, the controller may be configured to deactivate the macerator when the signal from the sensor or set of sensors indicates that the clot material is longer in the lumen of the suction catheter. For example, the controller may be connected to a motor driving rotation of a drive shaft for the macerator. The controller may be wired directly or indirectly to the macerator motor (macerator driver). The controller may send digital and/or analog signals to the macerator to turn on (activate) when clot material is within the lumen of the suction catheter, including when clot material is near (proximate) to the cutting member of the macerator (and in some cases only when clot material is near the cutting member). The controller may also send digital and/or analog signals to the macerator to turn off (deactivate) when clot material is not within the lumen of the suction catheter and/or when clot material is not near the macerator cutting member. The controller may generally be configured to activate the macerator by driving rotation of a drive shaft extending through the elongated body.

In some examples the macerator includes one or more side-facing windows configured to expose the cutting member (e.g., a rotating cutting member).

For example, described herein are apparatuses including: a suction catheter having a suction lumen; a macerator comprising an elongate body enclosing a drive shaft, wherein the macerator is configured extend distally through the suction catheter to a distal end region of the suction catheter; a sensor or set of sensors on a distal end region of the macerator; and a controller comprising one or more processors, wherein the controller is configured to activate the macerator when a signal from the sensor or set of sensors detects a clot material and to deactivate the macerator when the signal from the sensor or set of sensors does not detect the clot material.

Any of the methods described herein may include controlling both the suction and the macerator of a suction catheter apparatus by sensing clot and may include any of the component steps of the methods for either discussed above. For example, described herein are methods including: detecting a clot material with a distal end of a suction catheter using a first sensor or set of sensors on the distal end of the suction catheter; starting or increasing suction through the suction catheter once the clot material has been detected; confirming that the clot material has been drawn into the suction catheter using a second sensor or set of sensors within the distal end of the suction catheter to detect the clot material within the distal end of the suction catheter; driving a macerator within the suction catheter once the clot material has been detected within the suction catheter; stopping driving the macerator after the clot material is no longer detected by the second sensor or set of sensors within the suction catheter; and stopping or reducing the application of suction through the suction catheter after the clot material is no longer detected by the first sensor or set of sensors and the second sensor or set of sensors.

For example, a method may include: inserting a suction catheter into a lumen a blood vessel; detecting a clot material with a distal end of the suction catheter using a first sensor or set of sensors on the distal end of the suction catheter, wherein detecting the clot material comprises processing a signal from the first sensor or set of sensors to confirm the presence of clot material; starting or increasing suction through the suction catheter once the clot material has been detected; monitoring that the clot material has been drawn into the suction catheter using a second sensor or set of sensors within the distal end of the suction catheter; driving a macerator within the suction catheter once the clot material is detected within the suction catheter from the second sensor or set of sensors; stopping driving the macerator after the clot material is no longer detected by the second sensor or set of sensors; and stopping or reducing the application of suction through the suction catheter after the clot material is no longer detected by the first sensor or set of sensors and the second sensor or set of sensors.

Any of the apparatuses described herein may also or additional be apparatuses for controlling both suction and maceration of clot material, e.g., controlling both the suction through the suction catheter and the operation of the macerator within the suction catheter. For example, an apparatus may include: a suction catheter having a suction lumen; a macerator comprising an elongate body, wherein the macerator is configured extend distally though the suction catheter to a distal end region of the suction catheter; a first sensor or set of sensors on a distal end face of suction catheter; a second sensor or set of sensors within the lumen of the suction catheter; and a controller comprising one or more processors, wherein the controller is configured to activate or increase suction through the suction catheter when a signal from the first sensor or set of sensors indicates that a clot material is in front of the distal end of the suction catheter, further wherein the controller is configured to activate the macerator when a signal from the second sensor or set of sensors indicates that a clot material is within the lumen of the suction catheter.

In some examples, the apparatus includes: a suction catheter having a suction lumen a macerator comprising an elongate body enclosing a drive shaft, wherein the macerator is configured extend distally through the lumen of the suction catheter to a distal end region of the suction catheter; a first sensor or set of sensors on a distal end face of suction catheter; a second sensor or set of sensors within the lumen of the suction catheter; and a controller receiving input from the first sensor or set of sensors and the second sensor or set of sensors and comprising one or more processors, wherein the one or more processors is configured to analyze a signal from the first sensor or set of sensor to validate that the a clot material is in contact with or adjacent to the first sensor or set of sensors, and to validate that the clot material is within the lumen of the suction catheter based on data from the second sensor or set of sensors; further wherein the controller is configured to activate or increase suction through the suction catheter when the one or more processors indicates that the clot material is in front of the distal end of the suction catheter, further wherein the controller is configured to activate the macerator when a signal from the second sensor or set of sensors detects the clot material and to deactivate the macerator when the signal from the second sensor or set of sensors does not detect the clot material, and wherein the controller is configured to deactivate or decrease suction through the suction catheter a predetermined time period from when the processor indicates that the clot material is not in front of the distal end of the suction catheter and that the processor confirms that the clot material is not within the lumen of the suction catheter.

In general, described herein are methods of detecting an obstruction (e.g., clot) to control suction for removing and/or sensing the obstruction using a thrombectomy device (including but not limited to a suction catheter) and/or for controlling a macerator within the thrombectomy device.

For example, any of the methods described herein may include a method comprising: moving a thrombectomy device within a blood vessel; detecting an obstruction within an extraction zone distal to an extraction entrance of the thrombectomy device using a sensor configured to sense the obstruction within the extraction zone of the thrombectomy device; determining if the obstruction is a vessel wall or a clot material; triggering a clot extraction response if the obstruction is clot material, wherein the clot extraction response comprises one or more of: signaling to a user that the thrombectomy device is in contact with clot material, activating an extractor to remove the clot material from the extraction entrance, and/or activating a macerator within an extraction chamber region of the thrombectomy device; and stopping the extractor when clot material is no longer within the extraction chamber region based at least in part on one or more of: a sensor configured to sense clot material within the extraction chamber region, and a change in macerator response.

Any appropriate thrombectomy device may be used in the methods described herein, including, but not limited to, thrombectomy devices that apply suction. The thrombectomy device may be mechanical thrombectomy devices that remove clot by grabbing and/or otherwise pulling the clot. For example, the thrombectomy devices may include stent-based thrombectomy devices or thrombectomy device that pull a mesh or other material to engage and capture clot, either with or without suction.

In general these methods and apparatuses may be configured to determine the distance between a clot material and a wall of the vessel. The clot material may be a thrombus, atheroma, emboli, plaque, etc. In some examples the clot material may be within a blood vessel and/or a pulmonary vessel. For example, the clot material may be a pulmonary embolism.

In general, the apparatuses described herein may include an extraction zone that is distal to an extraction entrance of the thrombectomy device. For example, the extraction zone may be a region within a few mm (e.g., within 10 mm, within 9 mm, within 8 mm, within 7 mm, within 6 mm, within 5 mm, within 4 mm, within 3 mm, within 1 mm, etc.) of the entrance into the portion of the thrombectomy device that removes the clot material. The extraction entrance may be the entrance into a chamber of the device, such as the entrance into a suction catheter in variations that remove clot by applying suction. In some examples, the extraction entrance may be at least partially covered; for example, the extraction entrance may be covered by a material, such as a membrane, having an aperture ("extraction aperture" or simply "aperture") formed therethrough. The extraction entrance may be covered by a fluid-impermeable material; the covering material may be a membrane that is elastomeric.

Detecting the obstruction within the extraction zone may comprises sensing the obstruction by one or more techniques, such as by bioimpedance. For example, detecting the obstruction within the extraction zone may comprise detecting a change in pressure. Detecting the obstruction within the extraction zone may comprise optically detecting a clot material. Detecting the obstruction within the extraction zone may comprise detecting contact with the obstruction using a contact sensor.

In some examples, the sensor may comprise a contact sensor and wherein detecting the obstruction within the extraction zone comprises detecting contact with the contact sensor.

Determining if the obstruction is a vessel wall or a clot material may comprise applying suction and determining if the obstruction is drawn into the extraction chamber region of the thrombectomy device through the extraction entrance. In some examples, determining if the obstruction is a vessel wall or a clot material comprises applying suction and determining if the obstruction is drawn into the extraction chamber region of the thrombectomy device a predetermined distance beyond the extraction entrance. For example, determining if the obstruction is a vessel wall or a clot material may comprise applying suction, waiting for 100-1000 milliseconds and determining a change in macerator response for the macerator within the extraction chamber. Determining if the obstruction is a vessel wall or a clot material may comprise applying suction and monitoring the pressure within the extraction chamber.

In any of these methods, triggering the clot extraction response may comprise emitting a signal that the thrombectomy device is in contact with clot material. The signal may be audible (e.g., a tone, buzz, beep, recorded message, etc.), and/or visual (e.g., a light/LED, display, etc.), tactile (e.g., vibration, resistance, etc.), or the like. In any of these methods, triggering the clot extraction response may comprise automatically activating the extractor to remove the clot material from the extraction entrance by applying or increasing suction through the thrombectomy device, wherein the extractor comprises a source of suction. For example, triggering the clot extraction response may comprise automatically activating the extractor to remove the clot material from the extraction entrance, wherein the extractor comprises a mechanical extractor. In some examples triggering the clot extraction response comprises automatically activating or increasing a macerator within the extraction chamber region of the thrombectomy device. Alternatively or additionally, these methods and apparatuses may comprise emitting a signal that a clot material is (or was) in the suction catheter, including providing an alert that the suction catheter is clogged and/or where in the lumen of the catheter the clog is present (e.g., distal end region, proximal end region or one or more intermediate regions).

In any of these methods and apparatuses, detecting the obstruction within the extraction zone may comprise detecting the obstruction on an external side of a cover covering the extraction entrance of the thrombectomy device, wherein the cover comprises an expandable aperture through which clot material may be drawn.

Also described herein are thrombectomy devices that may perform any of these methods. For example, an apparatus may comprise: an elongate body having a suction lumen extending therethrough; an extraction chamber region at a distal end region of the elongate body in fluid communication with the suction lumen; an extraction entrance into the extraction chamber region at a distal end of the extraction chamber region; an obstruction sensor configured to sense an obstruction in an extraction zone distal to the extraction entrance; and a controller configured to detect an obstruction within the extraction zone using the obstruction sensor, to determine if the obstruction is a vessel wall or a clot material, and to trigger an alert indicating a nature of the obstruction, wherein the controller is further configured for manual or automatic activation of suction within the extraction chamber region when the controller determines that the obstruction is clot material.

Any of the apparatuses described herein may include a macerator within the extraction chamber region configured to macerate clot material within the extraction chamber region.

As mentioned, an of these apparatuses may include a cover over the extraction entrance. The cover may comprise an expandable aperture therethrough. The aperture may be a slit, cut, flap, or the like. The extraction chamber region may be expandable.

In any of these apparatuses, the obstruction sensor may comprise a contact sensor. The obstruction sensor comprises a pressure sensor. The obstruction sensor may comprise an optical sensor. The obstruction sensor may comprise a bioimpedance sensor having two or more electrodes.

Any of these apparatuses may including a suction regulator coupled to the controller, wherein the controller may be configured to apply suction using the suction regulator to determine if the obstruction is a vessel wall or clot material.

In general, any of these apparatuses may include an extraction chamber. The extraction chamber may refer to the distal end region of the suction catheter lumen, which may otherwise be similar or identical to the proximal or more intermediate regions of the catheter lumen; alternatively, in some examples the extraction chamber may be a structurally distinct region of the catheter. The extraction chamber may be partially or fully covered by a cover, as mentioned above. The extraction chamber may be an expandable region. The extraction chamber may be partially or completely closed off to prevent blood loss into the apparatus (e.g., when drawing suction) or may minimize blood loss through the apparatus, as described herein. Thus, in general, the extraction chamber may refer to the distal end region of a catheter (such as a suction catheter) as described herein.

Any of these apparatuses may include an extraction chamber sensor configured to detect the obstruction within the extraction chamber; in some examples the controller is configured to determine if the obstruction is a vessel wall or clot material based on an output of the extraction chamber sensor when applying suction. The extraction chamber sensor may be one or more of: a contact sensor, a pressure sensor, an optical sensor, or an electrical (e.g., bioimpedance) sensor. In some examples, the controller is configured to determine if the obstruction is a vessel wall or clot material based on a change in macerator response.

In general, any of these apparatuses may include a macerator and a macerator driver to drive operation of the macerator. The macerator may be operated to reciprocate one or more members and/or to rotate one or more members, driven by the macerator driver. The controller may be configured to detect a change in the energy applied to drive the macerator to determine if the obstruction is a vessel wall or clot material. In some examples the controller may be configured to detect a change in vibration of the macerator to determine if the obstruction is a vessel wall or clot material. In any of these apparatuses the controller may be configured to determine a load on the macerator or a chance in load of the macerator based on the sounds emitted by the macerator and/or driver (e.g., drive shaft, etc.). Thus, any of these apparatuses may include a microphone input for detecting sounds from the apparatus (e.g., from the macerator).

For example, an apparatus as described herein may include: an elongate body having a suction lumen extending therethrough; an extraction chamber region at a distal end region of the elongate body in fluid communication with the suction lumen; a macerator within the extraction chamber region configured to macerate clot material within the extraction chamber region; an extraction entrance into the extraction chamber region at a distal end of the extraction chamber region; an obstruction sensor configured to sense an obstruction within an extraction zone distal to the extraction entrance; and a controller configured to detect the obstruction within the extraction zone using the obstruction sensor, to determine if the obstruction is a vessel wall or a clot material, and to trigger an alert indicating a nature of the obstruction, wherein the controller is further configured for manual or automatic activation of suction within the extraction chamber region when the controller determines that the obstruction is clot material; wherein the controller is further configured to stop suction through the extraction chamber region when the controller determines that there is no more clot material in the extraction chamber region.

Also described herein are methods of optically detecting clot and distinguishing wall from clot by spectrometry. For example, a method may include: moving a thrombectomy device within a blood vessel; detecting an obstruction within an extraction zone distal to an extraction entrance of the thrombectomy device using an optical sensor on the thrombectomy device; determining if the obstruction is a vessel wall or a clot material based on reflectance spectral values of the obstruction; triggering a clot extraction response if the obstruction is clot material, wherein the clot extraction response comprises one or more of: signaling to a user that the thrombectomy device is adjacent to clot material, applying suction from the extraction entrance, and/or activating a macerator within an extraction chamber region of the thrombectomy device; and stopping suction when clot material is no longer detected within the extraction chamber region.

Any of these methods may include detecting clot material within the extraction chamber region based at least in part on one or more of: a sensor configured to sense clot material within the extraction chamber region, and a change in macerator response. As mentioned, the method may include detecting the obstruction within the extraction zone by detecting the obstruction on an external side of a cover covering the extraction entrance of the thrombectomy device, wherein the cover comprises an expandable aperture through which clot material may be drawn. Detecting the obstruction within the extraction zone using the optical sensor may comprise detecting contact between the optical sensor and the obstruction. In some examples detecting the obstruction with the extraction zone using the optic sensor may comprise detecting an oxygenation level of the obstruction.

In general, triggering the clot extraction response may comprise emitting a signal that the thrombectomy device is in contact with clot material. In some examples triggering the clot extraction response comprises automatically activating or increasing suction to remove the clot material from the extraction entrance by applying or increasing suction through the thrombectomy device. Triggering the clot extraction response may comprise automatically activating or increasing macerator activity within the extraction chamber region of the thrombectomy device.

In any of these methods and apparatuses, stopping suction may comprise stopping suction after a predetermined period after clot material is no longer detected within the extraction chamber region.

Also described herein are methods of mechanically removing clot (without or in addition to suction). For example, a method may include: detecting an obstruction within an extraction zone adjacent to an extraction entrance of a thrombectomy device within a blood vessel using an optical sensor on the thrombectomy device; determining if the obstruction is a vessel wall or a clot material based on reflectance spectral values of the obstruction; triggering a clot extraction response if the obstruction is clot material, wherein the clot extraction response comprises one or more of: signaling to a user that the thrombectomy device is in contact with clot material, activating an extractor to capture the clot material, and/or activating a macerator within an extraction chamber region of the thrombectomy device; and stopping the extractor when the clot material is no longer detected within the extraction chamber region.

In some examples, activating the extractor to capture the clot material comprises applying suction from the extraction entrance.

Also described herein are thrombectomy device that include one or more optical sensor. For example, an apparatus may include: an elongate body having a suction lumen extending therethrough; an extraction chamber region at a distal end region of the elongate body in fluid communication with the suction lumen; an extraction entrance into the extraction chamber region at a distal end of the extraction chamber region; an optical sensor configured to sense an obstruction within an extraction zone distal to the extraction entrance; a light source coupled to the optical sensor; an optical detector coupled to the optical sensor; and a controller coupled to the optical detector and configured to detect the obstruction within the extraction zone and to determine if the obstruction is a vessel wall or a clot material based on reflectance spectral values of the obstruction, wherein the controller is further configured to trigger an alert indicating a nature of the obstruction and to provide for manual or automatic activation of suction within the extraction chamber region when the controller determines that the obstruction is clot material.

The optical sensor may comprise a sensing fiber and an emitting fiber. The distal ends of the sensing fiber and emitting fiber may be, in some examples, embedded within a spherical material having a first index of refraction, further wherein the sphere is at least partially coated or covered with a material having a second index of refraction. For example, any of these apparatuses may include a macerator within the extraction chamber region configured to macerate clot material within the extraction chamber region; The apparatus may include a cover over the extraction entrance, the cover comprising an expandable aperture therethrough. The extraction chamber region may be expandable.

Any of these apparatuses may include a suction regulator coupled to the controller, wherein the controller is configured to apply suction using the suction regulator to determine if the obstruction is a vessel wall or clot material.

As mentioned, the controller may be further configured to determine if the obstruction is a vessel wall or clot material based on a change in macerator response. Any of these apparatuses may include a macerator driver, wherein the controller is configured to detect a change in the energy applied to drive the macerator to determine if the obstruction is a vessel wall or clot material. The controller may be configured to detect a change in vibration of the macerator to determine if the obstruction is a vessel wall or clot material.

For example, an apparatus may include an elongate body having a suction lumen extending therethrough; an extraction chamber region at a distal end region of the elongate body in fluid communication with the suction lumen; a macerator within the extraction chamber region configured to macerate clot material within the extraction chamber region; an extraction entrance into the extraction chamber region at a distal end of the extraction chamber region; an optical sensor configured to sense an obstruction within an extraction zone distal to the extraction entrance; a light source coupled to the optical sensor; an optical detector coupled to the optical sensor; and a controller coupled to the optical detector and configured to detect the obstruction within the extraction zone and to determine if the obstruction is a vessel wall or a clot material based on reflectance spectral values of the obstruction, wherein the controller is further configured to trigger an alert indicating a nature of the obstruction and to provide for manual or automatic activation of suction within the extraction chamber region when the controller determines that the obstruction is clot material; wherein the controller is further configured to stop suction when clot material is no longer detected within the extraction chamber region based at least in part on one or more of: a sensor configured to sense clot material within the extraction chamber region, and a change in the macerator response.

Also described herein are methods of detecting a clot (and/or distinguishing between a clot material a vessel wall or other material) based on contact pressure. For example, a method may include: moving a thrombectomy device within a blood vessel; detecting contact between an obstruction within an extraction zone adjacent to an extraction entrance of the thrombectomy device using a sensor on a distal end of the thrombectomy device in or adjacent to the extraction zone; determining if the obstruction is a vessel wall or a clot material by applying suction from the extraction entrance and detecting the obstruction within an extraction chamber region of the thrombectomy device; triggering a clot extraction response if the obstruction is clot material, wherein the clot extraction response comprises one or more of: signaling to a user that the thrombectomy device is in contact with clot material, applying or increasing suction, and/or activating a macerator within an extraction chamber region of the thrombectomy device; and stopping suction when clot material is no longer detected within the extraction chamber region.

Detecting the obstruction within the extraction chamber region may be based at least in part on one or more of: a sensor configured to sense clot material within the extraction chamber region, and a change in macerator response. For example, detecting contact may comprise optically detecting contact. Detecting contact may comprise detecting contact using a pressure sensor. In some examples, detecting contact comprises detecting contact using a contact sensing balloon.

In any of these methods, determining if the obstruction is a vessel wall or a clot material by applying suction may comprise applying a pulse of suction (e.g., a pulse that is between 5 second and 1 msec, e.g., between 2 seconds and 1 msec, between 1 second and 1 msec, less than 5 seconds, less than 4 seconds, less than 3 seconds, less than 2 seconds, less than 1 second, 900 msec or less, 800 msec or less, 700 msec or less, 600 msec or less, 500 msec or less, 400 msec or less, 300 msec or less, 200 msec or less, 100 msec or less, 75 msec or less, 50 msec or less, etc. In any of these methods and apparatuses the method or apparatus may apply a low-level of constant or variable suction and the pulse may be a pulse of higher suction (e.g., that is 2× higher, 3× higher, 4× higher, 5× higher, 10× higher, 15× higher, 20× higher, 50× higher, 100× higher, etc.).

Any of these methods may include determining if the obstruction is a vessel wall or a clot material by detecting clot material using a sensor configured to detect the obstruction within the extraction chamber. For example, the sensor may include one of: a bioimpedance sensor, an optical sensor, a pressure sensor, a contact sensor. Determining if the obstruction is a vessel wall or a clot material may include detecting clot material based on a change in response of the macerator, as mentioned above. For example, the change in response of the macerator may comprise a change in the electrical load of the macerator. The change in response of the macerator may comprise a vibrational change of the macerator. The change in response of the macerator may comprise an acoustic change of the macerator.

In any of these methods and apparatuses, triggering the clot extraction response may comprise emitting a signal that the thrombectomy device is in contact with clot material. Triggering the clot extraction response may comprise automatically activating the extractor to remove the clot material from the extraction entrance by applying or increasing suction through the thrombectomy device, wherein the extractor comprises a source of suction. Triggering the clot extraction response may comprise automatically activating the extractor to remove the clot material from the extraction entrance, wherein the extractor comprises a mechanical extractor. In some examples, triggering the clot extraction response comprises automatically activating or increasing a macerator within the extraction chamber region of the thrombectomy device.

Detecting the obstruction within the extraction zone may comprise detecting the obstruction on an external side of a cover covering the extraction entrance of the thrombectomy device, wherein the cover comprises an expandable aperture through which clot material may be drawn.

Also described herein are methods of mechanically removing clot (without or in addition to suction. In some of these examples suction may be used to distinguish wall from clot. For example, a method may include: moving a thrombectomy device within a blood vessel; detecting contact between an obstruction within an extraction zone distal to an extraction entrance of the thrombectomy device using a sensor on a distal end of the thrombectomy device in or adjacent to the extraction zone; determining if the obstruction is a vessel wall or a clot material by applying suction from the extraction entrance and detecting the obstruction within an extraction chamber region of the thrombectomy device; triggering a clot extraction response if the obstruction is clot material, wherein the clot extraction response comprises one or more of: signaling to a user that the thrombectomy device is in contact with clot material, activating an extractor to capture the clot material, and/or activating a macerator within an extraction chamber region of the thrombectomy device; and stopping extraction when clot material is no longer detected within the extraction chamber region. In any of these methods activating an extractor to capture the clot material may include applying suction from the extraction entrance.

Also described herein are thrombectomy devices including one or more pressure sensor that are configured to detect clot near or within an extraction chamber. For example, an apparatus comprising: an elongate body having a suction lumen extending therethrough; an extraction chamber region at a distal end region of the elongate body in fluid communication with the suction lumen; an extraction entrance into a distal end of the extraction chamber region; a contact sensor within an extraction zone adjacent to the extraction entrance, wherein the contact sensor is configured to detect a contact pressure; a sensing subsystem configured to detect clot material within extraction chamber region; and a controller coupled to the contact detector and the sensing subsystem, and configured to detect contact with an obstruction within the extraction zone based on the contact sensor, and to determine if the obstruction is a vessel wall or a clot material based on the sensing subsystem, wherein the controller is further configured to trigger an alert indicating a nature of the obstruction and to provide for manual or automatic activation of suction within the extraction chamber region when the controller determines that the obstruction is clot material; wherein the controller is further configured to stop suction when clot material is no longer detected within the extraction chamber region.

The sensing subsystem may comprise one or more of: a bioimpedance sensor, a pressure sensor, and an optical sensor. The apparatus may include a macerator within the extraction chamber region configured to macerate clot material within the extraction chamber region. In any of these apparatuses the sensing subsystem may be configured to detect a change in macerator response. As mentioned, any of these apparatuses may include a cover over the extraction entrance, the cover comprising an expandable aperture therethrough. The extraction chamber region may be expandable.

Also described herein are methods of detecting clot, e.g., by applying a pulse of suction (e.g., on demand or periodically) to see if clot is pulled partially or completely into the extraction chamber and/or into the cover, and apparatuses configured to perform this method. The presence of clot material may be confirmed by detecting a change in the macerator activity and/or by an internal sensor sensing within the chamber. For example, a method may include: detecting clot material within an extraction zone distal to an extraction entrance of a thrombectomy device within a blood vessel by applying a pulse of suction through the extraction entrance; confirming the clot material is within the extraction zone by detecting clot material within an extraction chamber region of the thrombectomy device during or immediately after the pulse of suction; triggering a clot extraction response if clot material is confirmed within the extraction zone, wherein the clot extraction response comprises one or more of: signaling to a user that the thrombectomy device is in contact with clot material, activating an extractor to capture the clot material, and/or activating a macerator within an extraction chamber region of the thrombectomy device; and stopping extraction when clot material is no longer detected within the extraction chamber region.

Detecting the clot material within the extraction chamber region may be based at least in part on one or more of: a sensor configured to sense clot material within the extraction chamber region, and a change in macerator response. Applying the pulse of suction may comprise applying a pulse of suction having a predetermined duration of between about 0.1 second and 10 seconds. Detecting clot material within the extraction chamber region of the thrombectomy device during or immediately after the pulse of suction may comprise detecting clot material using a sensor configured to detect the obstruction within the extraction chamber.

The sensor may include one or more of: a bioimpedance sensor, an optical sensor, a pressure sensor, a contact sensor. Alternatively or additionally, detecting clot material within the extraction chamber region of the thrombectomy device during or immediately after the pulse of suction may comprise detecting clot material based on a change in response of the macerator. The change in response of the macerator may comprises a change in the electrical load of the macerator and/or a vibrational change of the macerator and/or a change in the sound of the macerator, e.g., an acoustic change of the macerator.

In any of these examples, triggering the clot extraction response comprises emitting a signal that the thrombectomy device is in contact with clot material. Triggering the clot extraction response may comprise automatically activating the extractor to remove the clot material from the extraction entrance by applying or increasing suction through the thrombectomy device, wherein the extractor comprises a source of suction. Triggering the clot extraction response may comprise automatically activating the extractor to remove the clot material from the extraction entrance, wherein the extractor comprises a mechanical extractor. Triggering the clot extraction response may comprise automatically activating or increasing a macerator within the extraction chamber region of the thrombectomy device.

Detecting the clot material within the extraction zone may comprise applying the pulse of suction through an expandable aperture within a cover covering the extraction entrance of the thrombectomy device For example, a method may include: moving a thrombectomy device within a blood vessel; detecting a clot material within an extraction zone adjacent to an extraction entrance of the thrombectomy device by applying a pulse of suction through the extraction entrance while operating a macerator within an extraction chamber region of the thrombectomy device during or immediately after the pulse of suction, and confirming clot material within the extraction zone based on a change in macerator response; triggering a clot extraction response if clot material is confirmed within the extraction zone, wherein the clot extraction response comprises one or more of: signaling to a user that the thrombectomy device is in contact with clot material, activating a mechanical extractor to capture the clot material, and/or activating a macerator within an extraction chamber region of the thrombectomy device; and stopping extraction after clot material is no longer detected within the extraction chamber region based on a change in macerator response.

Also described herein are apparatus comprising: an elongate body having a suction lumen extending therethrough; an extraction chamber region at a distal end region of the elongate body in fluid communication with the suction lumen; an extraction entrance into a distal end of the extraction chamber region; a macerator within the extraction chamber region; and a controller configured to couple to a suction regulator and to control the application of a pulse of suction from the suction regulator through the extraction entrance when the macerator is running and to confirm the presence of clot material within the extraction chamber region by detecting a change in a macerator response during the pulse of suction, further wherein the controller is configured to perform one or more of: signal the presence of a clot material, activate a suction to capture the clot material, activate the macerator and/or stop suction after clot material is no longer detected within the extraction chamber region based on the macerator response during capture of the clot material.

Also described herein are methods of detecting clot using sensors that detect opening of the aperture into the extraction chamber (e.g., separation of the side of the aperture that are partially of fully closed). For example, a method may include: moving a thrombectomy device within a blood vessel; detecting clot material within an extraction zone adjacent to an extraction entrance of the thrombectomy device by applying a pulse of suction through the extraction entrance and detecting a separation between two or more sides of an aperture through a cover over the extraction entrance of the thrombectomy device; triggering a clot extraction response if the separation between the two or more sides exceeds a threshold, wherein the clot extraction response comprises one or more of: signaling to a user that the thrombectomy device is in contact with clot material, activating suction to capture the clot material, and/or activating a macerator within the extraction chamber region.

Any of these methods may include stopping the clot extraction response when clot is no longer detected outside of the extraction region and/or within the extraction chamber, either immediately or after a delay (permitting clot material already within the apparatus to be cleared). For example, any of these methods and apparatuses may be configured to stop the clot extraction process after the separation between the two or more sides no longer exceeds the threshold while applying suction.

Detecting the separation between two or more leaflets may comprise detecting separation between two or more electrodes on the leaflets based on an impedance measurement. Detecting the separation between two or more leaflets may comprise optically detecting separation between the two or more leaflets.

Also described herein are apparatus comprising: an extraction chamber region at a distal end region of an elongate body in fluid communication with a suction lumen; an extraction entrance into the extraction chamber region; a cover covering the extraction entrance; an aperture through the cover, the aperture having two or more sides; a sensor configured to detect a separation between the two or more sides of the aperture; and a controller configured to couple to a suction regulator and to control the application of a pulse of suction from the suction regulator through the extraction entrance and to trigger a clot extraction response if the separation between the two or more sides exceeds a threshold, wherein the clot extraction response comprises one or more of: signaling contact with a clot material, activating suction to capture the clot material, and/or activating a macerator within the extraction chamber region. The apparatus may include a macerator within the extraction chamber region. The controller may be further configured to stop suction after the separation between the two or more sides is less than the threshold.

In general, described herein are apparatuses for detecting a clot material within an aspiration catheter (having a suction lumen) using a sensor that is within (or at least partially within) the suction lumen. In some examples the sensor is a deflection sensor, that includes a deflectable member. The apparatus (e.g., a controller and/or sensing circuitry) may detect deflection of the deflectable member in order to confirm that clot material is present within the suction lumen, and/or to distinguish between clot material at the distal end or distal end region of the device and vessel wall.

For example, described herein are apparatuses including: an elongate body having a suction lumen extending therethrough; a deflection sensor extending at least partially into the suction lumen, the deflection sensor comprising a deflectable member having a first region that is coupled to a wall location within the suction lumen and a second region separated from the first region by a length of the deflectable member, wherein the deflectable member has an undeflected configuration and a deflected configuration, wherein in the deflected configuration the second region has an axially offset relative to the wall location that is different from the axial offset between the second region and the wall location in the undeflected configuration; and a controller configured to detect an obstruction within the suction lumen based on a signal from the deflection sensor indicating a deflection of the deflectable member.

The deflectable member may be configured as an elongate member that projects into and/or across the suction lumen (e.g., across the distal end region, also referred to herein as the clot extraction chamber region, of the suction lumen). The deflectable member may be arranged, in the first configuration, transverse to the long axis of the suction lumen. In some examples the deflectable member may be arranged along the longitudinal axis and/or helically wound around the longitudinal axis (as a spring, etc.). In some examples the deflectable member may be referred to as whisker; for example, the deflectable member may comprise a deflectable whisker.

The deflectable sensor may comprise a first electrode at the first region and a second electrode on a wall of the suction lumen opposite from the deflectable member, wherein when the deflectable member is in the undeflected configuration the deflectable member extends across the suction lumen so that the first electrode is proximate to the second electrode, and when the deflectable member is in the deflected configuration the first electrode and the second electrode are axially spaced further apart as compared to the undeflected configuration. In some examples the apparatus may include a third electrode that is axially spaced within the suction lumen relative to the wall location so that in the deflected configuration the first electrode is closer to the third electrode than as compared to the undeflected configuration.

In some examples the deflectable member comprises a shape sensing optical fiber. Alternatively or additionally, in some examples the deflectable member comprises a piezoelectric material. For example, the controller may be configured to detect transitioning of the deflectable member between the undeflected and deflected configurations based on a piezoelectric signal. In some examples the deflectable member comprises a variable resistive material that changes resistivity when bending; the controller may be configured to detect a change in resistance as the deflectable member bends.

In any of these examples, the controller may be configured to determine if the obstruction is a vessel wall or a clot material. For example, the controller may be configured to use a signal from the deflection sensor that represent deflection of the deflectable member, and/or or more of pressure with the suction lumen and/or flow within the suction lumen to determine if a clot material is stuck within the suction lumen, including in particular at a distal end of the suction lumen (often referred to as "lollypopping" in which a portion of a large clot is stuck in the distal end region of the In some examples the deflectable member is in a distal end region of the suction lumen that is configured as an extraction chamber region. The deflectable member may extend proud from the wall of the suction lumen in the first configuration and may be configured to deflect so that the second region of the deflectable member is axially and radially displaced relative to the undeflected configuration. In some examples the extraction chamber region is expandable; alternatively, in some examples the extraction chamber region is not differentiated from the rest of the suction lumen but refers to a distal region of the suction lumen at the distal end of the apparatus. In any of these apparatuses, the wall location within the suction lumen is within about 5 mm from a distal end of the suction lumen of the elongate body.

The deflectable member may generally be configured to couple to the wall of the suction lumen at a first region (e.g., first end) an to deflect or deform so that a second region (e.g., second end region) of the deflectable member moves relative to the first region when a force is applied by a material within the suction lumen, such as blood or clot material. In general, the deflectable member is configured to elastically deflect so that it returns to the first (undeflected) configuration when the force from interacting with material in the suction lumen is removed. In some cases the deflectable member is formed of a superelastic material such as a nickel-titanium material (e.g., Nitinol) and/or a polymeric material. The deflectable member may comprise a polymeric inner liner, a reinforced layer, and a polymeric outer jacket. In some examples, in the first configuration the first electrode is separated from the second electrode by between about 0.01 mm and about 2 mm.

In any of these apparatuses the suction lumen may be covered or partially covered. F or example, the apparatus may include a cover over a distal end of the suction lumen, the cover having an expandable aperture therethrough. In any of these apparatuses the suction lumen may be surrounded by a deformable lip.

Any of these apparatuses may include a macerator within the suction lumen and configured to macerate clot material within the suction lumen. Any of these apparatuses may include a macerator drive. The controller may control the application of energy to drive the macerator (e.g., to rotate a drive shaft/drive wire of the macerator) either manually or automatically. In some examples the controller is configured to apply pulsed suction.

As mentioned, the apparatus may include a pressure sensor configured to determine pressure within the suction lumen. Any of these apparatuses may include a flow sensor configured to determine flow through the suction lumen.

The controller may be configured to trigger an alert indicating a nature of the obstruction. The controller may be configured for manual or automatic activation of suction when the controller determines that the obstruction is clot material.

Any of these apparatuses may include one or more stops within the suction lumen to prevent advancing of a macerator distally over the deflectable member.

The apparatuses described herein may include multiple deflection sensors within the suction lumen. For example, the apparatus may include a second deflectable member extending from a wall of the suction lumen, wherein the second deflectable member is located at a more proximal region of suction lumen.

For example, described herein are apparatuses (e.g., thrombectomy apparatuses) configured for removing material from within a vessel using one or more deflectable whiskers to confirm and/or detect the presence of clot material and/or to distinguish between clot material and vessel wall. Any of these apparatuses may include: an elongate body having a suction lumen extending therethrough; a deflectable whisker extending from a wall of the suction lumen; a first electrode at a distal end region of the deflectable whisker; a second electrode on the wall of the suction lumen opposite from the deflectable whisker, wherein the deflectable whisker has a first configuration in which the deflectable whisker extends across the suction lumen so that the first electrode is proximate to the second electrode, and a second configuration in which the deflectable whisker is deflected so that the first electrode is spaced further apart from the second electrode as compared to the first configuration; and a controller configured to detect an obstruction within the suction lumen based on an electrical signal between the first electrode and the second electrode, indicating deflection of the deflectable whisker.

In some examples the apparatus may include: an elongate body having a suction lumen extending therethrough, wherein a distal end region of the suction lumen is configured as an extraction chamber region; a deflectable whisker extending from a wall of the extraction chamber region; a first electrode at a distal end region of the deflectable whisker; a second electrode on the wall of the suction lumen opposite from the deflectable whisker, wherein the deflectable whisker has a first configuration in which the deflectable whisker extends proud across the extraction chamber region so that the first electrode is proximate to the second electrode and a second configuration in which the deflectable whisker is deflected so that the first electrode is spaced apart from the second electrode as compared to the first configuration; and a controller configured to detect an obstruction within the extraction chamber region based on an electrical signal between the first electrode and the second electrode and to determine if the obstruction is a vessel wall or a clot material.

In any of these apparatuses the controller may be configured to determine if the obstruction is a vessel wall or a clot material. For example, the controller may include one or more processors that may analyze the electrical signal (e.g., impedance, conductance, etc.) between the first and second electrode and, based on the electrical properties over time (e.g., a comparison between the impedance before, during and/or after the application of suction, such as a pulse of suction) to determine if the whisker is deflected because of clot material within the suction lumen, e.g., within the extraction chamber region.

In any of these apparatuses and methods, the deflectable whisker may be in a distal end region of the suction lumen configured as an extraction chamber region. The deflectable whisker may extend proud from the wall of the suction lumen in the first configuration and may be deflected so that the distal end region of the deflectable whisker is axially and radially displaced relative to the second electrode in the second configuration. The extraction chamber region may be expandable, as described above.

In some examples, the deflectable whisker may be within about 5 mm from a distal end of the suction lumen of the elongate body. The deflectable whisker may include a superelastic material. In some examples the deflectable whisker comprises a polymeric inner liner, a reinforced layer, and a polymeric outer jacket.

In any of these examples the apparatus may include a cover over a distal end of the suction lumen, and the cover may have an expandable aperture therethrough.

Any of these apparatuses may include a macerator within the suction lumen and configured to macerate clot material within the suction lumen, as described above. The macerator may be prevented from damaging the deflectable whiskers, either by limiting the travel of the macerator within the suction lumen (e.g., preventing it from traveling over the whisker) and/or including one or more features on the macerator, such as a distally-extending sleeve or cuff that deflects the deflectable whisker distally and away from the macerator opening(s).

Any of these apparatuses may include a pressure sensor configured to determine pressure within the suction lumen, and/or a flow sensor (e.g., a thermal anemometer, such as a hot-wire anemometer). To determine flow within the suction lumen.

Any of these apparatuses may include a macerator driver. The controller may control the drive (e.g., drive wire) of a rotating cutting element within the macerator.

In any of these apparatuses, the controller may be configured to apply pulsed suction. The use of pulsed suction may allow the apparatus to determine that clot material is present.

In any of these apparatuses, the controller may be configured to trigger an alert indicating a nature of the obstruction. The controller may be further configured for manual or automatic activation of suction when the controller determines that the obstruction is clot material.

The apparatuses described herein may include a plurality of deflectable whiskers. For example, the apparatus may include a second deflectable whisker extending from a wall of the suction lumen, wherein the second deflectable whisker is located at a more proximal region of suction lumen.

In some examples the first firs electrode may be kept separate (e.g., non-contracting) the second electrode. This may enhance sensitivity of the apparatus. For example the first electrode may be separated from the second electrode by between about 0.01 mm and about 2 mm.

Also described herein are methods of controlling an apparatus as described herein, and/or methods of removing a clot material, and/or methods of distinguishing a clot material from a vessel wall. These methods may be particularly well suited for removing clot material without removing an excess of blood.

For example, a method may include: applying suction through a suction lumen of a device within a blood vessel; detecting deflection of a deflectable member extending at least partially within an extraction chamber region at a distal end region of the suction lumen; determining if the deflection was caused by a clot material caught in the extraction chamber region; triggering a clot extraction response if clot material is caught in the extraction chamber region, wherein the clot extraction response comprises one or more of: signaling to a user that the device is adjacent to clot material, applying continuous suction through the suction lumen, and/or activating a macerator within an extraction chamber region of the device.

Applying suction may include applying a pulse of suction. Pulsing suction may allow the apparatus to detect clot material and/or remove clot material without removing an excessive amount of blood from the subject. The pulse of suction may be, e.g., 2 seconds or faster (e.g., 1.5 sec or faster, 1 sec or faster, 0.9 seconds or faster, 0.7 sec or faster, 0.6 sec or faster, 0.5 sec or faster, 0.4 sec or faster, 0.3 sec or faster, 0.2 sec or faster, 0.1 sec or faster, 50 msec or faster, 10 msec or faster, 5 msec or faster, 1 msec or faster, etc.).

Any of these methods may include stopping suction when the deflectable member indicates that clot material is no longer within the extraction chamber region and/or no longer within the suction lumen (e.g., using one or more deflectable members). Stopping suction may include stopping suction after a predetermined period after clot material is no longer detected within the suction lumen (e.g., after 1 second, after 2 seconds, after 3 seconds, after 4 seconds, after 5 seconds, after 6 seconds, after 7 seconds, after, 8 seconds, after 9 seconds, after 10 seconds, after, 12 seconds, after 15 seconds, etc.). Suction may be manually or automatically stopped.

Any of these methods may include sensing one or more of: a pressure within the suction lumen and/or a flow rate through the suction lumen. The method may further include using one or more of pressure within the suction lumen and/or flow rate through the suction lumen to determine that a clot material is within (e.g., trapped within) the suction lumen. Any of these methods may also include using one or more of pressure within the suction lumen and/or flow rate through the suction lumen to distinguish between vessel wall and clot material.

Triggering the clot extraction response may include emitting a signal that the device is in contact with clot material. In some examples triggering the clot extraction response comprises automatically activating or increasing suction to remove the clot material from the extraction chamber region by applying or increasing suction through the suction lumen. Alternatively or additionally triggering the clot extraction response may comprise automatically activating or increasing macerator activity within the extraction chamber region.

The deflectable member may be part of a deflection sensor that identifies deflection of the deflectable member by sensing one or more parameters, such as electrical or mechanical parameters. The deflectable member may be part of a sensing circuit configured to detect the change in shape or deflection of the deflection member within the suction lumen (or a region of the suction lumen, such as the extraction chamber region. Note that in any of the apparatuses described herein a distinct extraction chamber region may be included as part of or in fluid communication with the suction lumen. Alternatively in some examples the extraction chamber region may be an unpartitioned (undivided) section of the suction lumen (e.g., at or near the distal end).

For example, detecting deflection of the deflectable member comprises detecting a change in a resistance, conductance or inductance of the deflectable member. In some examples detecting deflection of the deflectable member comprises detecting a change in shape of the deflectable member using an optical fiber bend sensor. In some examples detecting deflection of the deflectable member comprises detecting a change in voltage or current in a sensing circuit to which the deflectable member is electrically coupled.

For example, a method may include; moving a device within a blood vessel; applying suction through a suction lumen of the device; detecting an obstruction within an extraction chamber region at a distal end region of the suction lumen through the device using a deflectable whisker extending at least partially across the extraction chamber region; determining if the obstruction is a vessel wall or a clot material based on an electrical signal between a first electrode at a distal end of the deflectable whisker and a second electrode in communication with a wall of the extraction chamber region; triggering a clot extraction response if the obstruction is clot material, wherein the clot extraction response comprises one or more of: signaling to a user that the device is adjacent to clot material, applying continuous suction through the suction lumen, and/or activating a macerator within an extraction chamber region of the device.

In any of these methods, applying suction may include applying a pulse (or pulses) of suction.

Any of these methods may include stopping suction when clot material is no longer detected within the extraction chamber region. For example, stopping suction may include stopping suction after a predetermined period after clot material is no longer detected within the suction lumen.

These methods may also include sensing one or more of: a pressure within the suction lumen and/or a flow rate through the suction lumen.

As described above, triggering the clot extraction response may comprise emitting a signal that the device is in contact with clot material. For example, triggering the clot extraction response may comprise automatically activating or increasing suction to remove the clot material from the extraction chamber region by applying or increasing suction through the suction lumen. In some examples triggering the clot extraction response comprises automatically activating or increasing macerator activity within the extraction chamber region.

Also described herein are methods of performing a pulmonary embolectomy. For example, a method of performing a pulmonary embolectomy may include: advancing an aspiration catheter into a pulmonary artery (e.g., in some examples, the left pulmonary artery); applying aspiration through the aspiration catheter; determining, when flow through the aspiration catheter is occluded, an identity of the occlusion as clot material or as vessel anatomy; and outputting an indicator of the identity of the clot material. Advancing the aspiration catheter may comprise advancing the aspiration catheter through a pulmonic valve and around a bend into the pulmonary artery.

In general, determining the identity of the occlusion as clot material or as vessel anatomy may include detecting clot material using an intraluminal sensor. For example, determining the identity of the occlusion as clot material or as vessel anatomy may comprise deflecting a deflectable member within a lumen of the aspiration catheter. Determining the identity of the occlusion as clot material or as vessel anatomy may comprise optically confirming that the occlusion is clot material.

In any of these examples, outputting the indicator may comprise triggering an alert to a user. Outputting the indicator may comprise stopping the application of aspiration when the identity of the occlusion is vessel anatomy.

Also described herein are methods and apparatuses for determining characteristics of the clot material within the suction lumen. For example, described herein are apparatuses comprising: an elongate body having a suction lumen extending therethrough; a first internal impedance sensor at a distal end region of the suction lumen; a second internal impedance sensor at a proximal region of the suction lumen; and a controller configured to track a clot material within the suction lumen based on a signal from the first internal impedance sensor and the second internal impedance sensor.

For example, an apparatus may include: an elongate body having a suction lumen extending therethrough; a first internal impedance sensor at a distal end region of the suction lumen comprising a first pair of annular electrodes extending adjacently at least partially around the suction lumen; a second internal impedance sensor at a proximal region of the suction lumen comprising a second pair of annular electrodes extending adjacently at least partially around the suction lumen; and a controller configured to track a clot material within the suction lumen based on an impedance signal over time from the first internal impedance sensor and an impedance signal over time from the second internal impedance sensor and to determine a size estimate of the clot material.

The first internal impedance sensor may comprise a pair of annular electrodes extending radially around the suction lumen. In some examples the annular electrodes comprise ring electrodes extending radially around the suction lumen (completely or partially). In some examples the annular electrodes comprise helical electrodes. The pair of annular electrodes may be separated from each other by between 1 and 20 mm (e.g., between 5 mm and 20 mm, between 5 mm and 10 mm, etc.). The pair of annular electrodes may each extend greater than 40 degrees radially around the suction lumen. Either or both the first impedance sensor or the second impedance sensor (or both) may include an alternating electrical power source configured to establish and control a variable voltage between the annular electrodes of the first internal impedance sensor. The controller may be further configured to determine a size of the clot material based on the signal from the first internal impedance sensor and the second internal impedance sensor. In some examples the controller is configured to determine a rate of flow of the clot material within the suction lumen. The controller may be configured to distinguish between clot material and vessel wall based on the signal from the first internal impedance sensor and the second internal impedance sensor. In some examples the controller is further configured to modulate suction through the suction catheter based on at least the signal from the first internal impedance sensor.

Also described herein are methods of tracking clot material within the suction catheter by detecting an impedance signal over time from a first impedance sensor (e.g., a first pair of annular electrodes) in the distal end region of the suction lumen and by detecting an impedance signal over time from a second impedance sensor at a proximal region of the suction lumen. The method may include identifying matching patterns representing the clot material from both the first impedance sensor and the second impedance sensor and determining the time delay between the matching patterns to estimate the rate of travel of the clot material within the suction lumen. The method may also include estimating the time that the clot material took to pass the second impedance sensor at the proximal end of the suction lumen to estimate a length of the clot material and/or using a known cross-sectional area of the suction lumen to estimate an amount (e.g., volume, size, etc.) of the clot material removed.

Any of these methods may include applying an alternating electrical power (e.g., AC Voltage) to establish and control a variable voltage between the sensing electrodes forming the first impedance sensor and/or the second impedance sensor. Separate AC voltages may be applied from different or the same AC voltage source. Any of the these methods may include distinguishing between the vessel wall and clot material using signals form the first impedance sensor and the second impedance sensor.

Any of these methods may include outputting the tacking data, e.g., outputting the rate of removal of the clot material and/or outputting the size (e.g., length, volume, etc.) of clot material removed through the suction lumen, and/or outputting the presence and/or location of a clot within the suction lumen.

For example, in general, described herein are methods of detecting and/or tracking clot material within the lumen of the suction catheter using impedance sensing. These methods and apparatuses may be particularly useful for determining if clot material is still in the lumen of the catheter. In general, it may be very helpful to know if clot material is within the lumen, as if clot material is stuck in the lumen, the suction/pressure alone may not be sufficient to detect the material. When clot material is stuck within the lumen, the physician may need to know this including when it is desired to apply contrast through the lumen. If clot material is still present in the catheter, clot material may be driven back out and into the patient, which could lead to more problems for the patient. For example, described herein are apparatuses comprising: a flexible elongate catheter having a suction lumen extending therethrough; an internal electrical impedance sensor comprising two or more electrodes within the suction lumen; and a controller coupled to the internal electrical impedance sensor and configured to apply an alternating current between the two or more electrodes and to detect an obstructive material within the suction lumen based on electrical impedance signals from the internal electrical impedance sensor.

In any of these apparatuses, the internal electrical impedance sensor may be configured to operate at 50 kHz or greater (e.g., 100 kHz or higher, etc.). The internal electrical impedance sensor may be within about 20 mm of an aspiration opening into the suction lumen at a distal end region of the flexible elongate catheter. The controller may be further configured to output a signal indicating obstructive material is within the suction lumen.

The controller may be configured to apply the alternating current after beginning suction through the suction lumen.

Any of these apparatuses may include a second internal electrical impedance sensor comprising two or more electrodes at a proximal region of the suction lumen.

The apparatus may include a current generator configured to apply the alternating current.

In general, the two or more electrodes may be any appropriate electrode. In some example, the two or more electrodes comprise annular electrodes extending at least partially radially around the suction lumen. For example, the annular electrodes may comprise helical electrodes. The annular electrodes may be separated from each other by between 0.1 and 20 mm. The annular electrodes may each extend 30 degrees or more radially around the suction lumen For example, described herein are apparatus comprising: a flexible elongate catheter having a suction lumen extending therethrough; an internal electrical impedance sensor comprising two or more electrodes within the suction lumen between a proximal and a distal end of the flexible elongate catheter; and a controller coupled to the internal electrical impedance sensor and configured to apply an alternating current between the two or more electrodes, to detect an obstructive material within the suction lumen based on electrical impedance signals from the internal electrical impedance sensor, and to output a signal indicating obstructive material is within the suction lumen.

In general, these apparatuses may include just the catheter (for use with a controller and other system components) or may include just the controller and other system components for use with a catheter as described herein. For example, the apparatus may include comprising: a flexible elongate catheter having a suction lumen extending therethrough; an aspiration opening at a distal end region of the flexible elongate catheter; a first internal electrical impedance sensor comprising two or more electrodes extending at least partially around the suction lumen at a distal end region of the suction lumen; a second internal electrical impedance sensor comprising two or more electrodes extending at least partially around the suction lumen at a proximal region of the suction lumen; and one or more connectors at a proximal end region of the flexible elongate catheter, wherein the one or more connectors are in electrical communication with the first internal electrical impedance sensor and the second internal electrical impedance sensor, further wherein the one or more connectors are configured to couple to a controller to provide electrical impedance input to detect an obstructive material within the suction lumen based on electrical impedance signals from the first internal electrical impedance sensor and the second internal electrical impedance sensor.

The first internal electrical impedance sensor may be within about 20 mm of an aspiration opening into the suction lumen. Any of these apparatuses may include a proximal suction port in communication with the suction lumen. The aspiration opening may be on a tapered side of the distal end region of the flexible elongate catheter. The two or more electrodes of the first internal electrical impedance sensor may comprise annular electrodes. The annular electrodes of the first internal electrical impedance sensor may comprise helical electrodes. The annular electrodes of the first internal electrical impedance sensor may be separated from each other by between 0.1 and 20 mm. The annular electrodes of the first internal electrical impedance sensor may each extend 30 degrees or more radially around the suction lumen.

Also described herein are methods of detecting an obstructive material within a lumen of an aspiration catheter, the method comprising: applying suction through a lumen of the aspiration catheter; applying a variable current between two or more electrodes of a first internal electrical impedance sensor within the lumen of the aspiration catheter between a proximal and distal ends of the aspiration catheter to generate an impedance signal; and detecting the obstructive material within the lumen of the aspiration catheter based on the impedance signal. Detecting the obstructive material may comprise distinguishing obstructive material from blood within the lumen of the aspiration catheter based on the impedance signal. Any of these methods may include outputting a signal indicating obstructive material is within the lumen of the aspiration catheter.

Any of these methods may include analyzing the impedance signal to detect a change in impedance indicating obstructive material is within a proximity of the first internal electrical impedance sensor. Applying the variable current may comprise applying variable current having a frequency of 50 kHz or more. Any of these methods may include determining if the obstructive material is clogged within the lumen based on the impedance signal.

In any of these methods applying the variable current between two or more electrodes may comprise applying a plurality of frequencies to obtain an impedance spectrum, wherein detecting the obstructive material within the lumen comprises using the impedance spectrum to detect the obstructive material. Any of these methods may include determining a rate of movement of the obstructive material within the lumen. The methods may include applying the same or a different variable current between two or more electrodes of a second internal electrical impedance sensor within the lumen of the aspiration catheter and detecting the obstructive material within the lumen of the aspiration catheter near the second internal electrical impedance sensor.

Also described herein are apparatuses that are configured to determine the identify of a material at the aspiration opening using electrical impedance. For example, the methods and apparatuses described herein may include one or more sensors at the aspiration opening (aspiration opening sensors) to distinguish between clot and vessel wall. In these apparatuses and methods a force (e.g., suction) may be applied between the material and aspiration opening at the distal end (tip) region. In general, it may be difficult to distinguish between clot and vessel wall, particularly when initially applying suction, during which time the material may block the aspiration opening in to the suction lumen, and it may be unclear if it is blocked because the apparatus is against the vessel wall or is against a large clot. Generally this may lead to long delays while the physician waits to see if the material will be cleared by the suction (or by an increase in suction). Thus, it would be beneficial to more quickly distinguish between clot material and wall material more accurate and quickly. Further, it may be particularly beneficial to provide an analysis technique that isolates the material (clot or wall) from blood and/or from situations in which both wall and vessel contact the aspiration opening, which may give an ambiguous result. As described herein, the use of impedance sensing electrodes at the distal aspiration opening (or just recessed relative to the distal aspiration opening) may permit the rapid identification of either wall or clot material.

For example, described herein are apparatuses comprising: a flexible elongate body having a suction lumen extending therethrough; an aspiration opening into the suction lumen at a distal end region of the flexible elongate body; an aspiration opening sensor comprising two or more electrodes positioned at a rim of the aspiration opening; and a controller coupled to the aspiration opening sensor and configured to distinguish between clot and vessel wall based on an impedance signal between the two or more electrodes when a force is applied to the flexible elongate body or through the suction lumen. The controller may be configured to distinguish between clot and vessel wall when a negative pressure within the suction lumen exceeds a threshold. The controller may be configured to distinguish between clot and vessel wall when a mechanical force is applied against the aspiration opening above a threshold.

In some examples the aspiration opening is on a tapered side of the distal end region of the flexible elongate body. The two or more electrodes of the aspiration opening sensor may be recessed from the rim. The two or more electrodes of the aspiration opening sensor may be recessed into the suction lumen at the rim. The two or more electrodes of the aspiration opening sensor may be spaced equally apparat from each other on the rim of the aspiration opening. The two or more electrodes of the aspiration opening sensor may be positioned opposite each other across the aspiration opening. In some examples the two or more electrodes of the aspiration opening sensor are positioned opposite each other across the aspiration opening at a region of minimum diameter.

Any of these apparatuses may include a plurality of smaller flow-modifying openings into the suction lumen positioned adjacent to the aspiration opening, and a second impedance sensor comprising two or more electrodes positioned adjacent to the plurality of smaller flow-modifying openings.

An apparatus may include: a flexible elongate body having a suction lumen extending therethrough; an aspiration opening into the suction lumen at a distal end region of the flexible elongate body; an aspiration opening sensor comprising two or more electrodes positioned at a rim of the aspiration opening; and a controller coupled to the aspiration opening sensor and configured to distinguish between clot and vessel wall based on an impedance signal between the two or more electrodes when a negative pressure applied through the suction lumen exceeds a threshold.

Also described herein are apparatuses comprising: a flexible elongate body having a suction lumen extending therethrough; an aspiration opening into the suction lumen at a distal end region of the flexible elongate body; an aspiration opening sensor comprising two or more electrodes positioned at a rim of the aspiration opening; a proximal suction port in communication with the suction lumen; and one or more connectors at a proximal end region of the flexible elongate body, wherein the one or more connectors are in electrical communication with the two or more electrodes of the aspiration opening sensor, further wherein the one or more connectors are configured to couple to a controller to provide electrical impedance input to distinguish between clot and vessel wall when a force is applied to the flexible elongate body or through the suction lumen.

The apparatus may include a second set of two or more electrodes within the suction lumen proximal to the aspiration opening sensor, further the one or more connectors may be in electrical communication with the second set of two or more electrodes to provide differential electrical impedance input from the two or more electrodes of the aspiration opening sensor to distinguish between clot and vessel wall when a force is applied to the flexible elongate body or through the suction lumen.

The aspiration opening is angled. The two or more electrodes of the aspiration opening sensor may be recessed from the rim. The two or more electrodes of the aspiration opening sensor may be recessed into the suction lumen at the rim. The two or more electrodes of the aspiration opening sensor may be spaced equally apart from each other on the rim of the aspiration opening. The two or more electrodes of the aspiration opening sensor may be positioned opposite each other across the aspiration opening. The two or more electrodes of the aspiration opening sensor may be positioned opposite each other across the aspiration opening at a region of minimum diameter.

Any of these apparatuses may include a plurality of smaller flow-modifying openings into the suction lumen positioned adjacent to the aspiration opening, and/or a second impedance sensor comprising two or more electrodes positioned adjacent to the plurality of smaller flow-modifying openings.

Also described herein are methods of distinguishing a blood clot from a vessel wall, the method comprising: applying suction through a lumen of a flexible elongate catheter, wherein the flexible elongate catheter comprises an aspiration opening at a distal end region and two or more electrodes at or adjacent to the aspiration opening; and determining, when a force at the aspiration opening exceeds a threshold value, if the aspiration opening is engaged with a blood clot or with the vessel wall based on an impedance measured from the two or more electrodes at or adjacent to the aspiration opening.

The force at the aspiration opening may include a negative pressure within the lumen. Any of these methods may include emitting an alert indicating if the aspiration opening is engaged with one or both of blood clot and vessel wall.

The methods described herein may include applying alternating current having a frequency of between about 1 kHz and 1 MHz. For example, the alternating current may have a frequency of between about 10 kHz and 100 kHz.

The methods described herein may include delaying the step of determining if the aspiration opening is engaged with a blood clot or with the vessel wall for a delay period after the force exceeds the threshold value. In any of these methods, determining if the aspiration opening is engaged with blood clot or with vessel wall may be based on a difference in impedance measurements from the two or more electrodes at or adjacent to the aspiration opening and a second set of two or more electrodes positioned proximally from the two or more electrodes at or adjacent to the aspiration opening. Any of these methods may include adjusting suction through the lumen based on the impedance measured from the two or more electrodes at or adjacent to the aspiration opening.

Also described herein are methods of removing an obstructive material from a vessel, the method comprising: applying negative pressure to a suction lumen of a flexible elongate catheter having an aspiration opening and two or more electrodes at or adjacent to the aspiration opening; taking an impedance measurement from the two or more electrodes at or adjacent to the aspiration opening while applying the negative pressure; and adjusting the negative pressure based on the impedance measurement taken.

In general, the methods and apparatuses described herein may track clot material within the lumen of the catheter using impedance sensing. Tracking material may include confirming that the clot material is within (or has left) the suction lumen, determining the rate of flow of the material through the suction lumen, estimating a volume or amount of clot material removed through the suction lumen, or the like.

For example, an apparatus may include: a flexible elongate body having a suction lumen extending therethrough; a first pair of electrodes within the suction lumen; a second pair of electrodes proximal to the first pair of electrodes; and a controller coupled to the first pair of electrodes and the second pair of electrodes and configured to track a clot material within the suction lumen based on electrical impedance signals from the first pair of electrodes and the second pair of electrodes.

The first pair of electrodes may comprise a pair of annular electrodes extending at least partially radially around the suction lumen. The pair of annular electrodes may comprise ring electrodes extending radially around the suction lumen. The pair of annular electrodes may comprise helical electrodes. The pair of annular electrodes may be separated from each other by between 0.1 and 20 mm. The pair of annular electrodes may each extend 30 degrees or more radially around the suction lumen. The first pair of electrodes and the second pair of electrodes may comprise a quad detector. For example, the first pair of electrodes may be spaced from the second pair of electrodes by between 0.1 and 20 mm along a distal-to-proximal length of the suction lumen.

Any of these apparatuses may include an alternating electrical power source coupled to the first pair of electrodes and configured to apply a variable voltage. The controller may be further configured to determine a size of the clot material based on electrical impedance signals from the first pair of electrodes and the second pair of electrodes. The controller may be configured to determine a rate of flow of the clot material within the suction lumen based on electrical impedance signals from the first pair of electrodes and the second pair of electrodes.

The controller may be configured to distinguish between clot material and vessel wall based on electrical impedance signals from the first pair of electrodes and the second pair of electrodes. For example, the controller may be further configured to modulate suction through the suction lumen based at least in part on an electrical impedance signal from the first pair of electrodes.

An apparatus may include: a flexible elongate body having a suction lumen extending therethrough; an aspiration opening into the suction lumen at a distal end region of the flexible elongate body; a first pair of electrodes within the suction lumen and extending at least partially around the suction lumen; a second pair of electrodes proximal to the first pair of electrodes with the suction lumen and extending at least partially around the suction lumen; a proximal suction port in communication with the suction lumen; and one or more connectors at a proximal end region of the flexible elongate body, wherein the one or more connectors are in electrical communication with the first pair of electrodes and the second pair of electrodes, further wherein the one or more connectors are configured to couple to a controller to provide electrical impedance input to track a clot material within the suction lumen based on electrical impedance signals from the first pair of electrodes and the second pair of electrodes. The first pair of electrodes and the second pair of electrodes may comprise a quad detector comprising two pairs of electrodes. The first pair of electrodes and the second pair of electrodes may be spaced apart from each other by between 0.1 and 20 mm along a distal-to-proximal length of the suction lumen.

A method of tracking a clot material within a suction lumen of a catheter may include: receiving a first impedance signal from a first pair of electrodes within the suction lumen; receiving a second impedance signal from a second pair of electrodes within the suction lumen; and estimating one or more of a rate of flow of a clot material and a volume of clot material from the first impedance signal and the second impedance signal. Any of these methods may include outputting the one or more of the rate of flow of the clot material and the volume of the clot material. The method may include detecting a blockage of the catheter based on the first impedance signal and the second impedance signal. Any of these methods may include adjusting a suction through the suction lumen based on the first impedance signal and the second impedance signal.

Estimating the one or more of the rate of flow of a clot material and the volume of clot material may comprise correlating the first impedance signal and the second impedance signal. Estimating the one or more of the rate of flow of a clot material and the volume of clot material may comprise determining a time difference between the correlation of the first impedance signal and the second impedance signal.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 29A shows a section through a distal end region of the apparatus. FIG. 29B shows a longitudinal section through the apparatus.

FIG. 31A shows an apparatus including an optical sensor. FIG. 31B shows an apparatus including a contact sensor based on optical detection of contact.

FIG. 35A shows an apparatus including a contact senor. FIG. 35A shows the distal end region of the apparatus; FIG. 35B shows an example of a proximal end region of the apparatus.

FIG. 45 schematically illustrates one example of a thrombectomy apparatus configured to detect clot material and distinguish between clot material and wall material including sensors for sensing opening of an aperture into a clot extraction region of the apparatus.

FIGS. 46A-46B illustrate the operation of a thrombectomy apparatus configured to detect opening of an aperture into an extraction chamber.

FIGS. 48B-48C shows the apparatus with clot within the extraction chamber of the apparatus.

FIG. 54A shows the deflectable member in a first (undeflected) configuration, while FIG. 54B shows the deflectable member in a second (deflected) configuration, such as when clot material is trapped within the distal end region of the suction lumen. FIG. 54C shows an example of a graph showing the change in electrical properties of the deflectable member in the deflected configuration(s).

FIG. 59B shows a cross-section through a distal end region of the catheter.

FIG. 67 is schematic example of an apparatus including an aspiration opening sensor having two electrodes positioned at a rim of the aspiration opening of an aspiration catheter.

FIG. 68 schematically illustrates an example of an apparatus including an aspiration opening sensor (with two electrodes positioned at a rim of the aspiration opening) and a set of internal impedance sensors slightly proximal to the aspiration opening sensor within the suction lumen.

FIG. 69A is an example of a schematic circuit of an impedance sensor.

FIG. 69B illustrates a trace of an example of an alternating current that may be applied for sensing impedance.

In FIG. 77A the percentage of change in the impedance compared to the impedance of blood is shown relative to vena cava/wall (on left of each pair per frequencies) and clot (on right of each pair per frequency).

FIGS. 77B-77C show the impedance of the aspiration opening sensor for blood (left), vena cava/wall (middle) or clot material (right) at different frequencies (120 Hz, 1 kHz, 10 kHz, 100 kHz, and 1 MHz) in different conditions.

FIGS. 79A and 79B illustrate examples of internal impedance sensors.

FIG. 80 is an example of an internal impedance sensor having an internal ring.

FIGS. 81A and 81B are examples of internal impedance sensors configured as a quad detectors.

DETAILED DESCRIPTION

Figure 1A:
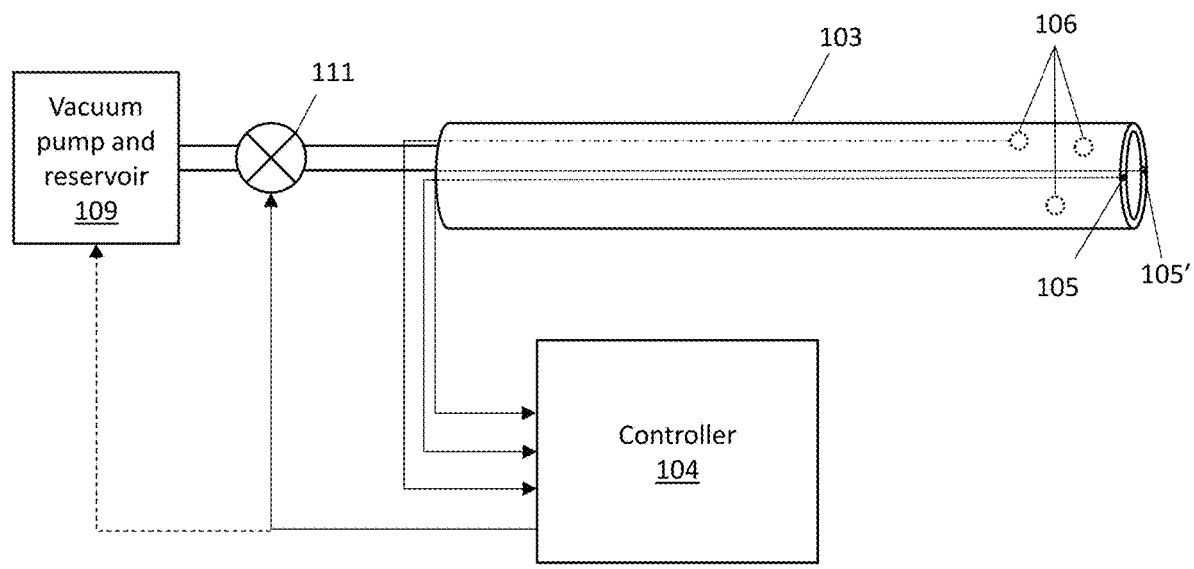
FIG. 1A schematically illustrates one example of an apparatus for controlling a suction catheter.

In general, described herein are methods and apparatuses for removing clot material from a blood vessel. These methods and apparatuses may be particularly well suited for removing clot material while minimizing blood loss. These methods and apparatuses may be used to track clot within and/or removed by the suction catheter, including (but not limited to) confirming clot has been removed, quantifying the amount of clot removed, estimating and/or quantifying the rate of clot removal and/or determining and identifying clogging of the suction catheter. Further, these methods and apparatuses may allow more precise control of suction and/or maceration of clot and may help automate (or semi-automate) clot removal.

Any of the methods and apparatuses described herein may use one or more sensing modalities for detecting the presence and/or for detecting the proximity of, clot material, and in particular detecting the presence and/or proximity of clot material relative to the distal end opening of a suction catheter and within the suction catheter. These methods and apparatuses may use any appropriate type (e.g., mode) of sensor, including, e.g., electrical property (e.g., impedance, such as bioimpedance, bioimpedance spectroscopy, etc.), light (e.g., color), and/or ultrasound. Other types of sensors may also be used. The one or more sensors may be positioned at the distal end (e.g., distal end face) of the catheter, and/or may be present within the lumen of the suction catheter, and/or on the macerator. In some examples the sensors may be configured as deflection sensors that mechanically sense deflection of a deflectable member due to clot material contacting the deflectable member. In some examples the sensors may extend radially around the lumen of the suction catheter at least partially around the circumference (e.g., between 30-360 degrees, between 40-350 degrees, between 60-350 degrees, between 90-360 degrees, between 45-360 degrees, etc.).

Thus, the apparatuses and methods described herein may assist a user (e.g., doctor, surgeon, nurse, technician, etc.) in locating and engaging with thrombus to prevent unnecessary aspiration of whole blood or surrounding structures such as a vessel wall or a valve. These apparatuses may provide improved spatial awareness of the distal end of the suction catheter and/or other regions of the suction catheter or suction catheter lumen. Better spatial awareness at the treatment site at the distal end of the suction catheter can be advantageous during a thrombectomy procedure, for example, as it allows the user to establish proper engagement with clot material before beginning aspiration, while performing aspiration and at the end of aspiration, and thus reduces blood loss during the procedure.

The apparatuses described herein may generally include a suction catheter, which may include one or more sensors on the distal end of the suction catheter and may include or may be used with a source of suction (negative pressure). The apparatus may also include, either as a part of the controller or separate from the controller, a suction regulator that may include valves for modulating the source of suction. In some examples the apparatus may also include a source of positive pressure and the controller may also regulate the operation of the source of positive pressure.

For example, FIG. 1A schematically illustrates one example of an apparatus including suction catheter 103 as described herein. FIG. 1A includes an elongate, and flexible suction catheter (not shown to scale) 103. The suction catheter may be formed of any appropriate material and may include a central (suction) lumen and a distal end opening. The suction catheter may be formed of any appropriate material. One or more (e.g., two are shown in FIG. 1A) sensors 105, 105' are included at the distal end face of the suction catheter. The sensors are connected to a controller 104 that may receive and process data from the sensors. One or more sensors (internal sensor or set of sensors) 106 may also be present within the lumen of the distal end region of the suction catheter and/or within more proximal regions. All of the sensors may provide data input to the controller 104. The connection may be wired through the suction catheter and may connect via one or more connectors to the controller.

The controller may control the suction applied through the suction catheter by either controlling a pump and/or suction reservoir 109 directly or by regulating the pressure from the vacuum pump and reservoir indirectly via a pressure modulator 111 that may include one or more valves, manifolds, etc. to control the pressure within the suction catheter.

Figure 1B:
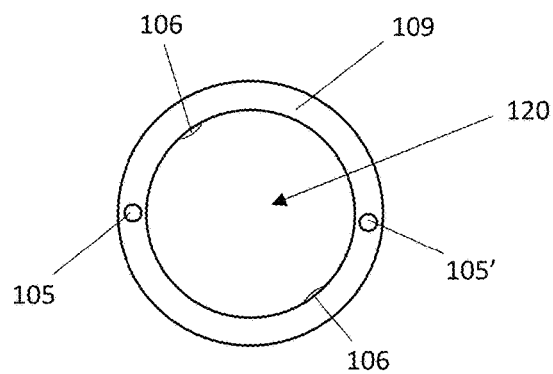
FIG. 1B is an end view of one example of a suction catheter forming part of the apparatus of FIG. 1A.

FIG. 1B shows an end view of the suction catheter of FIG. 1A, showing the distal-facing sensors 105, 105' on the outer edge of the suction catheter, as well as the suction lumen 120 of the catheter. In FIG. 1B, a pair of internal sensors 106 from within the lumen are shown; in practice the sensors may be flush with the inside wall of the catheter, and/or may be recessed into the catheter wall.

The controller may include control circuitry for receiving and/or processing data from the sensors, and for transmitting control signals to the pump modulator 111 or pump 109. For example, the controller may include one or more processors, timing circuitry, a memory, and the like. In some examples the controller may also include one or more outputs, such as a display, a speaker, etc. The controller may connect wireless or via a cable or wire to a remote processor, or computer (e.g., laptop, desktop, etc.). The controller may indicate via output when clot material is present in front of or in the lumen of the suction catheter, and/or when suction is being applied.

Figure 1C:
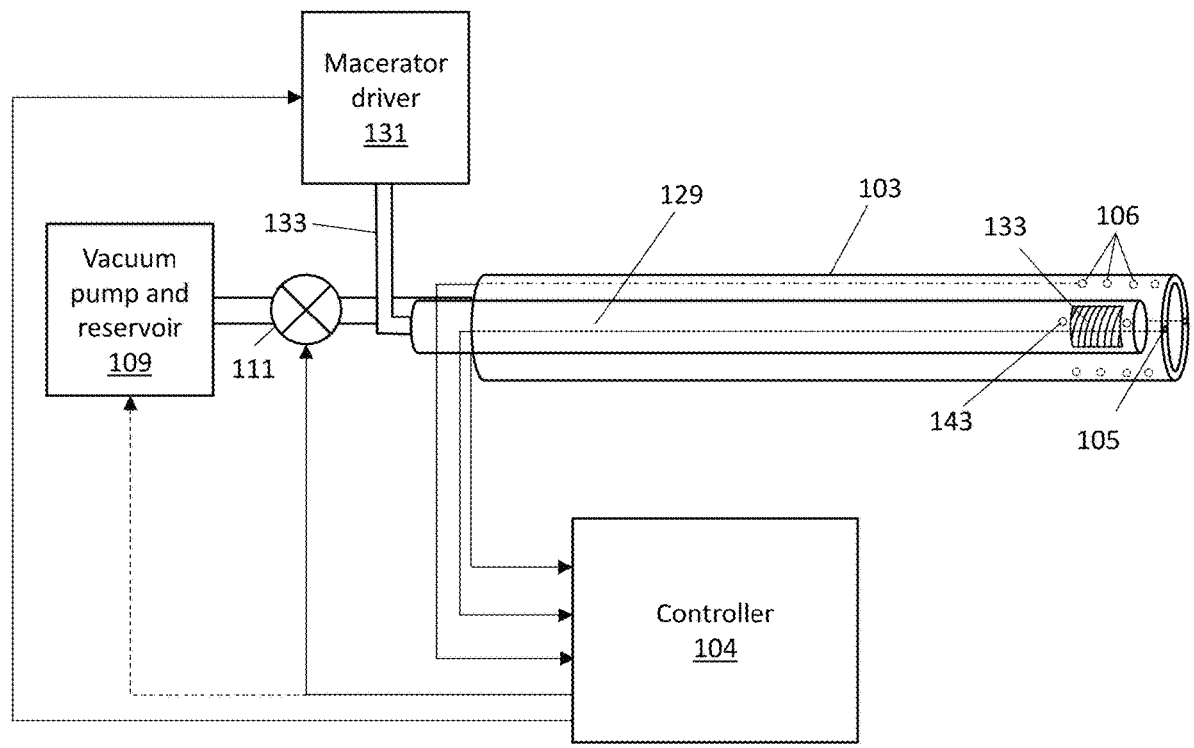
FIG. 1C schematically illustrates another example of an apparatus for controlling a suction catheter.
Figure 1D:
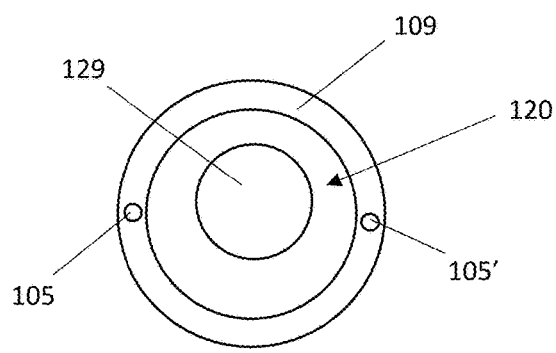
FIG. 1D shows an ed view of the suction catheter portion of the apparatus of FIG. 1C.

Any of these apparatuses may include a macerator to help break up clot material for easier removal from the vessel (and through the lumen of the suction catheter). For example, FIGS. 1C and 1D schematically illustrate an example of an apparatus including a macerator 129 that may be positioned (including removably and/or adjustably positioned) within the lumen of the suction catheter 103, as shown. The apparatus shown in FIG. 1C is configured as a system that also includes the controller 104 receiving input from sensor(s) 105, 105' at the distal end face of the suction catheter as well as sensors 106 within the catheter. As shown in FIG. 1C, the second set of sensors shown may also include one or more sensors 143 on the macerator 129. In FIG. 1C, the macerator includes one or more windows through an elongate and flexible macerator body that expose a cutting member 133 (shown as a rotating thread in FIG. 1C). Any appropriate cutting member may be used, including wires, blades, etc. The macerator may be actuated by a drive 131 (macerator driver) that rotates a flexible drive shaft 133 (macerator drive shaft). As will be described in greater detail below, the controller 104 may control actuation of the macerator in addition to or instead of controlling suction through the suction catheter.

FIG. 1D shows a distal end view of the suction catheter of FIG. 1C. As in FIG. 1B, the catheter may include one or more distal-facing sensors (e.g., impedance electrodes in some examples). In FIG. 1D the macerator 129 is shown in the suction lumen. In this example the sensors within the lumen at or near the distal end portion. FIGS. 1A-1D illustrate examples of suction catheters including sensors. Different types, sizes and sensitivity of sensors may be used.

Figure 2:
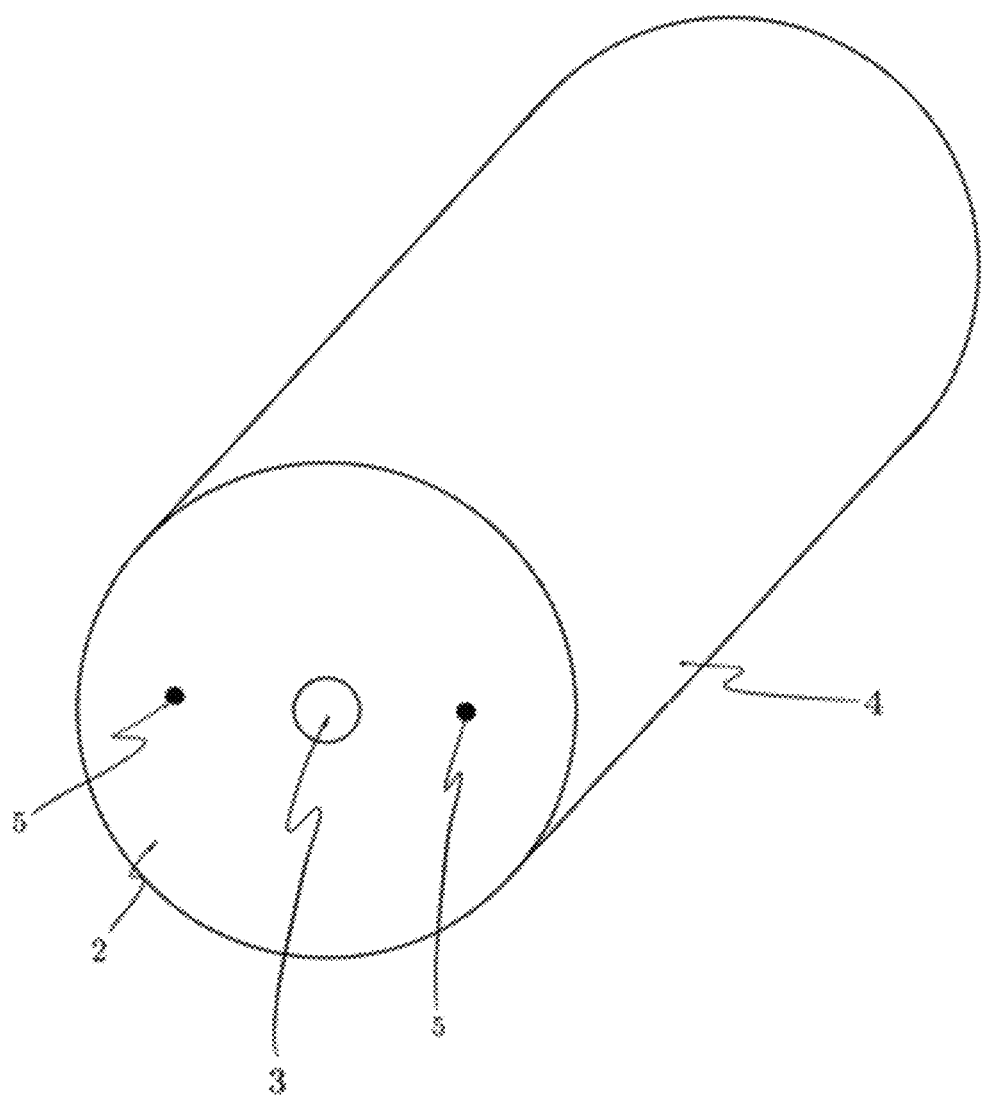
FIG. 2 is an end view of one example of an elongated shaft of a suction catheter as described herein.

FIG. 2 shows a schematic of a distal end region of a suction catheter. In FIG. 2 the distal end face of the catheter is covered by a membrane (e.g., a flexible and deformable polymeric (e.g., silicone) cover 2. The sensors 5, which in this example and in FIGS. 3-12, show the locations and orientation of these sensors on the suction catheter. The suction catheter includes an inner wall (not visible) and an outer wall 4. The flexible cover may include a small opening 3 that may enlarge to allow clot material to pass. In FIG. 2, a pair of sensors 5 are included and may provide input, either continuously or discretely.

Figure 3:
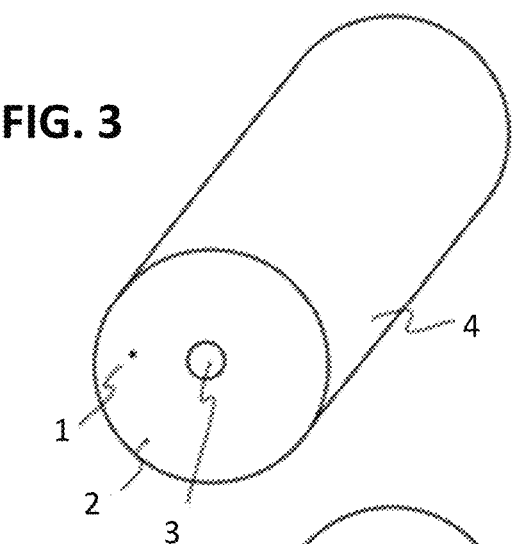
FIG. 3 is an end view of an example of an elongated shaft of a suction catheter including a monopolar impedance sensor on the distal end of the catheter (showing a single electrode on the distal face of the suction catheter).
Figure 4:
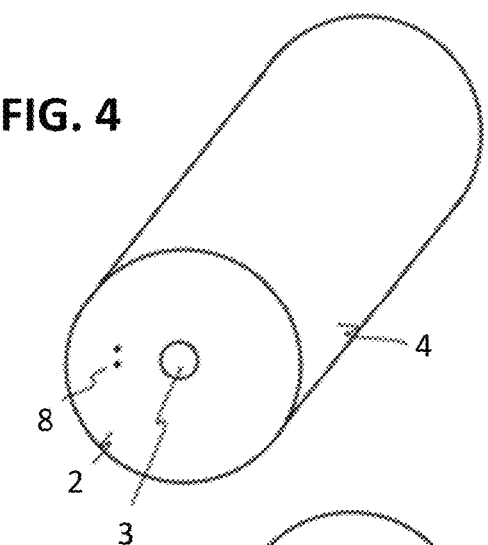
FIG. 4 is an end view of an example of an elongated shaft of a suction catheter including a bipolar impedance sensor on the distal end of the suction catheter (including two proximal electrodes on the distal portion of the catheter).
Figure 5:
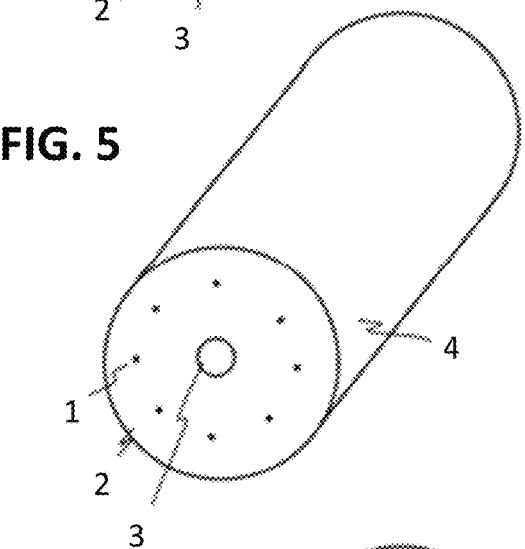
FIG. 5 is an end view an example of an elongated shaft of a suction catheter including a several electrodes situated circumferentially about the opening of the distal portion of the suction catheter (radially distant from the center and outer limit of the distal portion of the catheter)
Figure 6:
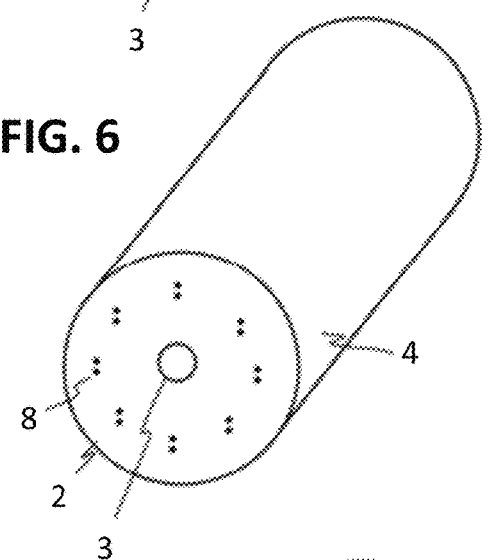
FIG. 6 is an end view of an example of an elongated shaft of a suction catheter including a bipolar impedance sensor on the suction catheter (showing the same circumferential distribution as in FIG. 4. with each monopolar electrode being replaced with proximal pairs of bipolar electrodes).
Figure 7:
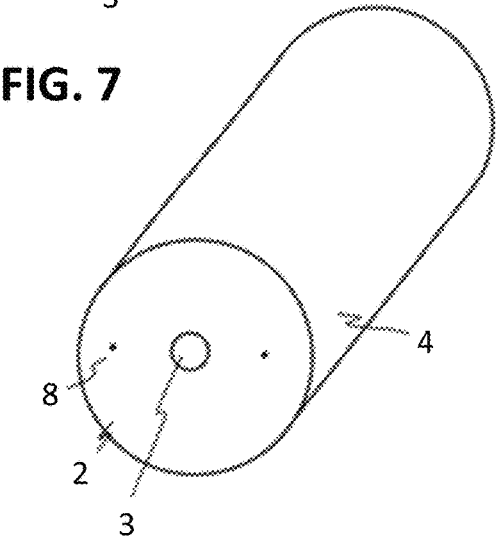
FIG. 7 is an end view an example of an elongated shaft of a suction catheter including a bipolar impedance sensor on the distal portion of the suction catheter (including a single electrode pair with each electrode situated on opposite semicircles of the distal portion of the catheter and radially distal to both the center and outer edge of the distal portion).
Figure 8:
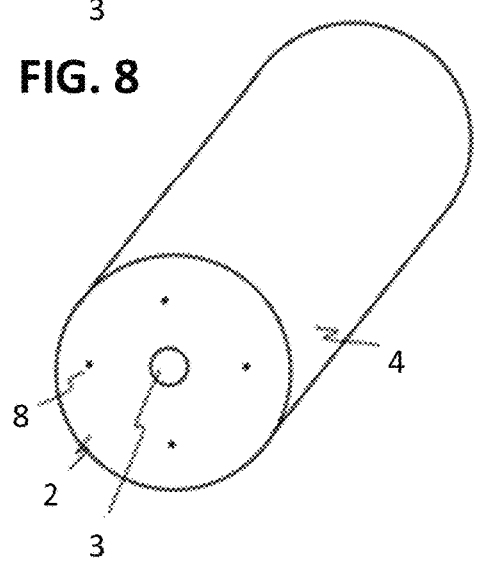
FIG. 8 is an end view an example of an elongated shaft of a suction catheter including a bipolar impedance sensor on the distal portion of the suction catheter (including two electrode pairs with each electrode in each pair situated on opposite semicircles of the distal portion of the suction catheter and with each pair rotated at an angle of 90° relative to one another about the center of the distal portion).

FIGS. 3-13 illustrate alternative examples of the distal end of a suction catheter including sensors arranged on the outer surface (including the distal-facing end) and the inner lumen. In all of FIG. 3-13, the distal end of the suction catheter 4 includes a cover 2 that may be impermeable to blood, but which may include an opening 3 (e.g., a hole, slit(s), etc.), that may expand when clot is drawn into the lumen by suction. This may limit blood loss into the suction catheter both before and during the application of suction upon detection of clot material, as will be described in greater detail below. In FIG. 3, a single sensor 1 is shown. This example may be, e.g., a monopolar bioimpedance sensor. FIG. 4 shows an example in which a bipolar bioimpedance sensor 8 is included on a distal face of the cover. In FIG. 5 a plurality of sensors (e.g., shown in this example as eight sensors) are arranged around the cover, spaced equidistantly. In FIG. 5 the sensors 1 are shown as monopolar bioimpedance sensors (though other sensor types may be used), while in FIG. 6 the sensors 8 are bipolar bioimpedance sensors. In FIG. 7 a pair of radially spaced-apart electrodes 8 (forming a larger bipolar bioimpedance sensor) are shown. FIG. 8 shows two pairs of radially spaced-apart bipolar bioimpedance sensors 8 (either opposite electrodes or adjacent electrodes may be used as a bipolar pair, or partner electrodes may be switched between these pairs).

Figure 9:
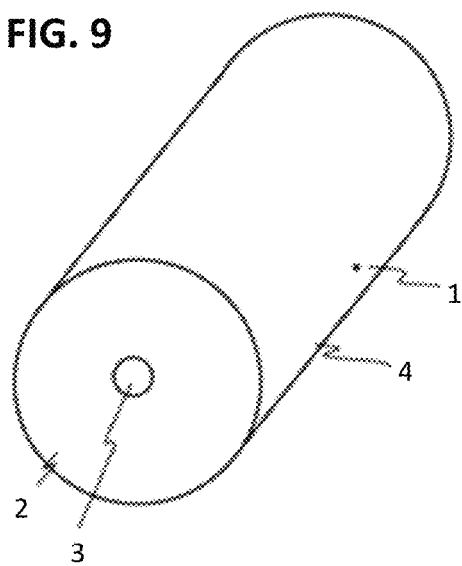
FIG. 9 is an end view an example of an elongated shaft of a suction catheter including a monopolar impedance sensor on an impermeable wall portion of the suction catheter (including a single monopolar electrode externally fitted to the impermeable wall enclosing an inner region).
Figure 10:
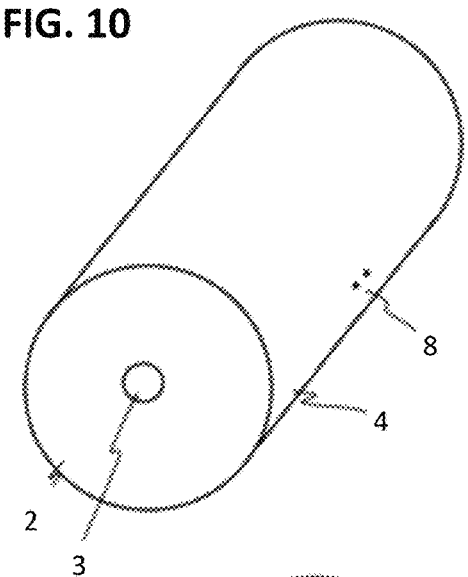
FIG. 10 is an end view an example of an elongated shaft of a suction catheter including bipolar impedance sensor on a wall portion of the suction catheter (showing a single pair of proximal electrodes externally fitted to the wall enclosing an inner region.
Figure 11:
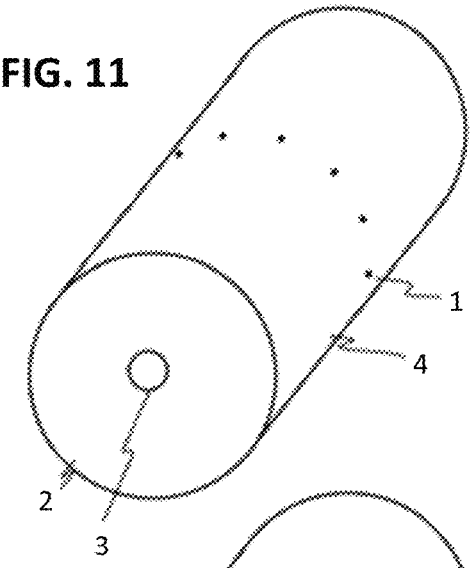
FIG. 11 is an end view of an example of an elongated shaft of a suction catheter including a monopolar impedance sensor on the wall portion of the suction catheter (including several monopolar electrodes fitted circumferentially and externally on the wall enclosing an inner region).
Figure 12:
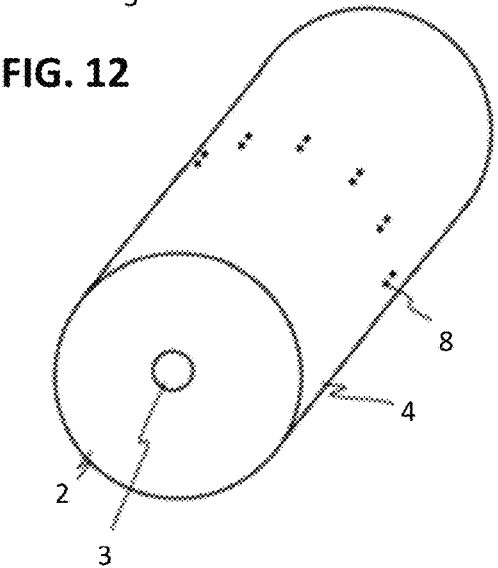
FIG. 12 is an end view an example of an elongated shaft of a suction catheter including a bipolar impedance sensor on the wall portion of the suction catheter (showing several proximal pairs of bipolar electrodes fitted circumferentially and externally on the wall enclosing an inner region).
Figure 13:
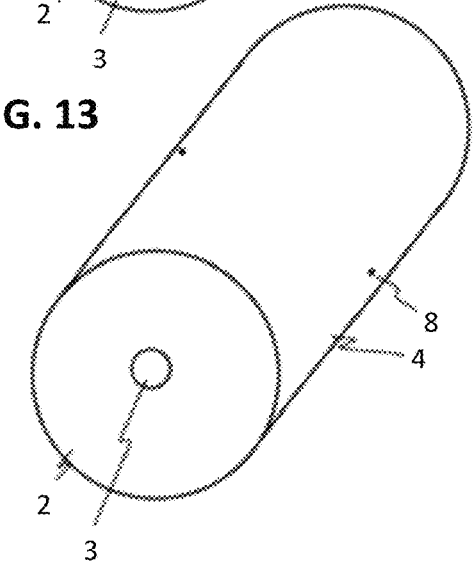
FIG. 13 is an end view an example of an elongated shaft of a suction catheter including a bipolar impedance sensor on the wall portion of the suction catheter (showing a single distal pair of bipolar electrodes situated opposite one another, circumferentially, and externally on the wall enclosing an inner region).

FIGS. 9-13 illustrate examples in which the distal end region of the suction catheter includes one or more sensors within the lumen of the distal end region of the suction catheter. In FIG. 9, a single sensor 1 is shown within the lumen of the catheter. The sensor may be an electrical (e.g., bioimpedance sensor, which may be monopolar or bipolar). For example, FIG. 10 illustrates an example of a bipolar pair of electrodes forming a bioimpedance sensor 8 within the lumen of the distal end of the suction catheter. FIG. 11 shows an example of a suction catheter in which an annual ring of sensors is arranged within the lumen of the distal end of the suction catheter, on a sidewall of the lumen. The annular ring or rings (longitudinally arranged) of sensors may be continuous or discrete; for example, an annual ring of electrodes may be electrically connected to each other to form a single electrical sensor having multiple contact points, as shown in FIGS. 11 and 12. These sensors may be monopolar or bipolar bioimpedance sensors 8, for example, as shown in FIG. 12. FIG. 13 shows an example in which a bipolar bioimpedance sensor is arranged with either electrode on opposite sides of the lumen of the suction catheter.

For simplicity, FIGS. 9-13 illustrate examples in which only a few sensors are show, arranged within the distal end region of the suction catheter. In some examples, a plurality of sensors may be arranged along the length of the lumen extending proximally, allowing tracking of clot material as it passes through the lumen.

Although FIGS. 9-13 show only the sensors within the lumen of the distal end of the suction catheter, in any of these examples one or more sensor(s), including bioimpedance sensors may be positioned on the distal-facing end of the suction catheter (as shown in FIGS. 3-8). In some of these examples one or more sensors for detecting clot material may be positioned proximally along the side length of the outside of the distal end of the suction catheter, which may be useful to indicate when clot material is to the side of the suction catheter.

As mentioned, any appropriate sensor may be used, including but not limited to impedance (e.g., bioimpedance) sensors. One example of a bioimpedance sensor (e.g., electrode) that may be used with the methods and apparatuses described herein is described in Lei et. al., 2013. For example, a bioimpedance sensor may have an electrode spacing of approximately 1.8 mm for bipolar configurations and a titanium aluminum alloy construction with a 1 mm PDMS coating is associated with all impedance values and thresholds mentioned herein. Other bioimpedance sensors may be used in any of the methods and apparatuses described herein.

As mentioned, the apparatus can include a suction catheter having an elongated shaft including a lumen, a negative pressure source configured to be fluidly coupled to the lumen of the suction catheter, and a controller. The elongated shaft may be flexible and may include a proximal portion configured to be extracorporeally positioned during treatment and a distal portion configured to be intravascularly positioned proximate clot material at a treatment site within a blood vessel lumen, such as the lumen of a pulmonary blood vessel or other blood vessel. The suction catheter may include one or more sensors ("sensing devices") configured to sense and/or detect clot material. The sensor(s) can be electrically coupled to the controller such that measurements obtained by the sensor(s) can be processed by the controller. In some examples, the controller can be coupled to the negative pressure source and/or a connection between the negative pressure source (e.g., pressure modulator) and the shaft of the suction catheter so that the controller can control the timing (and in some cases level) of the aspiration applied through the shaft.

Returning to FIG. 1A, the sensor may include a plurality of sensing elements (in some examples electrodes, ultrasound transducers, optical transducers, fiber optics, etc.) at a distal end region of the elongated shaft. The sensing elements can be, for example, one or more electrodes. Any number of sensing elements can be used (e.g., one, two, three, four, etc.) or compound sensing elements (e.g., pairs of electrodes, etc.). The sensing elements can be positioned at the distal end portion of the elongated shaft such that the sensing elements have unobstructed access to the space distal of the elongated shaft and thus can contact and/or accurately sense clot material disposed in the vessel lumen distal to the shaft, including in contact with the distal end of the shaft or nearby the distal end of the shaft (e.g., within 1 mm, 2 mm, 3 mm, 4 mm, 5 mm, 6 mm, 7 mm, 8 mm, 9 mm, 1 cm, etc.). For example, as shown in the end view of FIG. 1B, the sensing elements can be positioned at the distal-facing portion of the tubular sidewall that forms the elongated shaft of the suction catheter. This may be true both in suction catheters including a distal cover (e.g., an elastically deformable cover) and suction catheters that do not have a distal cover. In those examples where the system includes a distal cover (for example as shown in FIG. 2), the sensing elements can be positioned anywhere along the surface of the cover. The sensing elements can be configured to sense proximity of the tip of the elongate shaft of the suction catheter to clot material (e.g., thrombus, embolus, etc.) in blood vessels, which may be used to in combination with existing positioning systems and methods such as fluoroscopy and in controlling aspiration (suction) through the suction catheter, either manually or automatically. This may aid in reducing the volume of blood aspirated during clot removal. The sensing mechanisms may provide signals and indications which enable the user to discriminate between clot material, whole blood, vessel walls, and other surrounding structures in the treatment zone. In some examples, the apparatus may initially attain partial engagement with a clot material. A sensor may be a sensor array that may include several electrodes (e.g., impedance sensors) or optical sensors circumferentially arranged about the distal face of a funnel or tubular opening into the suction catheter, to provide point-measurements of proximity to clot material (and in some cases lumen wall) and enable the practitioner to make directional corrections of the device within the blood vessel to more completely engage with clot material. In some examples the distal end of the suction catheter (e.g., a cylindrical or funnel-shaped opening) may include one or more ultrasound transducers; the ultrasound transducer(s) may be positioned to achieve spatial awareness to the end of the suction catheter.

The schematic shown in FIGS. 1A and 1C illustrate just one general configuration for several examples of the apparatuses described herein. The sensors shown in these examples as well as the examples shown in FIGS. 2-13 are illustrated as electrical (e.g., impedance) sensors, however similar configurations and/or positions may be used for other sensor types (or combinations of sensor types), including ultrasound and/or optical sensors. In some examples the sensors may be an impedance sensing elements that include two electrodes in a dipole configuration which are connected electrically to the controller and/or other signal processing or power components, including sensing, signal processing, and control units.

Optionally, the controller may be connected to one or more valves which regulate the pathway between the elongated shaft and a source of suction (e.g., a vacuum chamber) and/or in some examples a source of positive pressure (e.g., a pressure chamber). Alternatively, the controller may be connected directly to the source of suction and/or positive pressure. For example, the controller may control the action (on/off, rate of pumping, etc.) of the source of suction without an additional valve needed between the pump (suction and/or positive pressure source(s)) and the suction catheter.

In operation, the suction catheter may therefore detect, via the one or more distal-facing sensors (e.g., on the distal end of the suction catheter) when the distal tip is in blood or is near or in contact with clot material. For example, while these sensor(s) are in contact with blood, when using a bioimpedance sensor an alternating current passing through the blood between pairs of sensing electrodes may see a relatively low impedance, generally across an entire frequency spectrum. This relatively low impedance may be processed and categorized in the sensing and signal processing units within the controller. If the impedance is low enough to statistically infer the absence of thrombus proximal to the distal opening into the suction catheter, and the control unit may maintain the suction "off" or at a low level, either by directly controlling the source of negative pressure or by regulating a valve (to be or remain in a closed state) so that the negative pressure does not communicate (or increase) to the suction catheter opening, preventing or limiting blood aspiration therein. As clot material approaches the electrodes of the bioimpedance sensor(s), the impedance may increase and converge to a range of values that indicate characteristic impedance (or impedance spectra) of clot material. The value(s) indicative of clot may be distinguished by the controller from those that indicate vessel wall or other structures that are not clot material. Once the clot material is in full engagement with the sensors (and therefore the distal end of the suction catheter), the controller, upon verifying that the sensor data indicates clot material, may turn on (or otherwise increase) suction. For example, in some cases (depending on the construction of the bioimpedance sensors) an impedance value of approximately 1,000,000 Ohms and above may indicate to the controller that the clot material is near and/or in contact with the distal end of the suction catheter. The controller may increase or turn on suction through the suction catheter. In some examples, the system may begin or increase vacuum pressure once the thrombus makes adequate contact with the sensors and distal end of the suction catheter to aspirate the clot material. As the clot material is aspirated, the impedance may remain above the threshold until the clot material all aspirated from the front of the suction catheter. Importantly, suction of the clot material may be configured and tracked using the sensors within the lumen of the suction catheter.

The use of one or more sensors for detecting clot within the lumen of the suction catheter is surprisingly effective at regulating suction and action of the suction catheter, rather than relying on or requiring pressure or flow sensing. Although pressure and/or flow sensing may be used within the suction catheter, the use of one or more sensors that directly detect clot material is more robust and reliable for controlling negative pressure and, as will be described in greater detail below, for controlling disruption of clot material within the lumen of the suction catheter by controlling maceration within the lumen of the suction catheter.

In some examples the controller may continue to maintain the suction (e.g., at the on state or at a higher state) until both the clot material has been fully aspirated into the suction catheter and until the sensor(s) within the lumen of the suction catheter indicate that the clot material has been removed from the distal end region of the suction catheter. Once clot material has been removed, for example when using bioimpedance sensors, the sensed impedance (or impedance spectrum) will drop back down to the range of impedance values consistent with just blood (e.g., in some examples less than 10,000 Ohms, depending on the frequency) and the controller will turn off or reduce the suction through the suction catheter (e.g., set one or more valves of a suction modulator to a closed state, turn off the suction pump, etc.).

In some examples the suction modulator and/or the source of suction (e.g., pump) may be configured so that the standby/unpowered state is an off state, to prevent unsafe adverse aspiration in the event of damaged or contaminated sensors. For example, a valve in the suction modulator or source of suction may be a normally closed solenoid. Anomaly detection (as known in the art) may be implemented in the controller to prevent unintended and/or undesirable application of suction without the presence of clot material. In general, the controller may include sensing and signal processing for robustly confirming the presence of clot material from sensor data.

When the apparatus includes bioimpedance sensors, these sensors may be configured to include bipolar or monopolar electrodes. Monopolar electrodes and bipolar electrodes may be used nearly equivalently, however monopolar configurations each electrode may represent an individual signal and the controller may incorporate these additional signals. The respective ranges of sensing may be different for these electrodes. In any of these apparatuses, the sensors may be distributed in position, e.g., along the distal portion of the suction catheter, and may provide data (e.g., impedance values for bioimpedance sensors) from separate locations in order to provide spatial information about the clot material relative to the opening into the suction catheter. This information may be processed by the controller to further threshold the timing and/or level of suction applied. In some examples, the controller may establish an impedance threshold for a plurality of (e.g., n) dimensions, based on the number of impedance sensors available (monopolar or bipolar). This multiple-signal configuration could be processed in the controller and exported to an external display for providing the practitioner with additional spatial information about the media proximal to the distal end of the suction catheter.

In general, as mentioned above, the apparatus may provide output to the user from the suction, including a visual display (e.g., video), a numeric value (e.g., some indication of impedance at the distal end and/or within the suction catheter), etc.

For example, the apparatus may include bioimpedance sensors that operate as dipole pairs that are located on the surface (such as the distal-facing surface and/or distal membrane) of a suction catheter. In FIG. 2, for example, the diploe pairs of the sensor may include two separate dipole electrodes 5 situated on opposite halves of the distal membrane 2 which operate as one dipole pair. In the dipole configuration, AC current passes through local tissue surrounding the distal membrane and between both electrodes. The effective resistance of the tissue in immediate contact with the electrodes is the tissue's impedance. Different tissue types exhibit different impedance characteristics. The real-time indicated impedance can be used to determine the tissue-type surrounding the distal-face of the thrombectomy device and can be used for guiding the user to the clot material once general proximity is established through non-invasive navigation such as x-ray fluoroscopy. In this example, when the distal end of the suction catheter (e.g., the distal membrane cover in some example) is only in contact with blood (e.g., whole blood, without significant amounts of clot material), and clot material is not nearby, the impedance detected by the bipolar impedance sensor may be the effective resistance of the blood as current passes through it. The volume sensitivity of an impedance measurement will be a function of the square of the current density in a given tissue volume, the current arc in a two-electrode sensor may span a larger volume of whole-blood than it will of clot material. Therefore, as the user guides the suction catheter to the clot material (e.g., using fluoroscopy or other guidance techniques), the impedance measurements may show a measurable increase in effective resistance despite the lack of contact with clot material. Thus, the bioimpedance sensor may establish proximity in addition to contact with clot material. In blood, at frequencies above 1 kHz, the impedance sensor may consistently indicate an impedance value below 10,000 Ohms, while clot material will return values above 1,000,000 Ohms. Note that the actual values of the impedance for blood and/or clot and/or lumen wall may be different depending on the composition of the sensor (e.g., the electrode materials, etc.), however the relative differences and the ability to discriminate between these materials (blood, clot material, lumen wall, etc.) may remain. The difference between whole blood and clot material impedances may differ on average by about two orders of magnitude, which is more than sufficient to determine when full contact with both electrodes has been established. Similarly, the difference between lumen wall and blood and lumen wall and clot material may be different, particularly at different frequencies within the impedance spectrum.

In any of these methods and apparatuses the apparatus may include a suction catheter that includes a funnel carried by the distal end portion of the suction catheter. Thus, the distal end region of the suction catheter may be funnel-shaped or may be expanded (having an enlarged diameter) relative to the more proximal portion of the suction catheter. The distal face extending across the distal end of the suction catheter (including funnel-shaped suction catheters) may be covered by an elastically deformable material, as mentioned above. In some examples, the distal face comprises a fluid-impermeable material (e.g., a sheet of elastically deformable material) having a single opening and/or slit(s). With aspiration engaged on the external proximal end of the suction catheter, the suction catheter may aspirate clot material within a blood vessel and may remove them (via suction) through the suction catheter to collect them in an externally housed chamber (e.g., vacuum chamber). Real-time fluorography may be used to guide the suction catheter to the location of the clot material within the vessel(s) in order to start the aspiration. However, fluorography is not sufficiently accurate to control the application of suction, as it may not accurately reflect proximity and may not help distinguish between non-clot material and clot material, as it suffers from information loss due to dimensionality reduction. For example, a user may appear to position the distal face of the suction catheter proximal to a target thrombus, however the distal face may be improperly engaged with the thrombus in the orthogonal plane. To accurately begin aspiration the user should be certain of proper engagement with the thrombus. In order to establish proper engagement, a measure of proximity must indicate that a majority area of the distal face of the funnel is in contact with the thrombus, such that minimal amount of blood is aspirated before the thrombus enters the catheter.

In some examples, the apparatus may include an impedance sensor configured to measure impedance to discriminate between the media immediately beyond the distal end of the thrombectomy device. Each cell and tissue type in the body exhibits unique impedance and conductivity characteristics. When a clot forms in the blood, the normally conductive plasma becomes entrapped in the fibrin mesh that provides the clot coherence, and the plasma therefore transitions from conductive liquid to insulated mass. Experimental results show significant increase in impedance between whole and clotted blood, and this difference in impedance may be used to distinguish between thrombus and whole blood at the treatment site. Using an impedance sensor placed at the distal end of the suction catheter and/or within the lumen of the suction catheter may allow the user to distinguish between engagement with blood and thrombus and to accurately track removal of thrombus material, e.g., by relying on impedance alone, which removes the need to aspirate blood before recognizing the state of catheter-clot material engagement.

In some examples, the apparatus may include an ultrasound sensor configured to obtain ultrasound measurements to differentiate between the blood and clot material at the distal end of the suction catheter. Clot material, blood and vessel wall tissue densities vary measurably, in part due to the varying quantities of cells stored in a unit volume for each tissue type, which may be governed by the structure of the cells and the means by which they are held together. Blood, as a heterogeneous mixture of cells and liquid, behaves like a lower-density fluid. Clot material and vessel-wall, however, have higher modulus cell structures that are more compact, and which allow more cells to exist in a unit space therein. Ultrasound may use cell-density to discriminate between the tissue types. Thus, any of these apparatuses may include one or more ultrasound sensors, e.g., at the distal end of the thrombectomy device, to discern between clot material, blood, and vessel wall. In some examples the sensor(s) on the distal end of the catheter include one or more ultrasound sensors, while the sensors within the lumen are bioimpedance sensors (and in some examples, just bioimpedance sensors). Ultrasound sensors may be used to detect engagement with clot material prior to activating aspiration.

Alternatively or additionally, one or more optical sensors may be used, e.g., to obtain one or more optical measurements. For example, optical measurements may be obtained from the distal end of the suction catheter to distinguish between clot material, blood, and vessel wall, e.g., by processing the light reflection and absorption characteristics (and comparing to known characteristics of each tissue). Blood, clot material, and vessel wall tissue typically have measurably separate optical qualities. This may be due to the varying cell structure, cell organization, and tissue cohesion within each type of material. A light emitter and light detector, e.g., a photosensor, may be coupled to a detection/emission sensor on the distal end of the suction catheter. In some examples, the optical components may include a fiber optic material that extends to the distal end of the suction catheter for emitting and/or detecting light signals. Such signals may be processed by the controller and may use the sensed signals to distinguish between thrombus and the surrounding media without engaging aspiration first. Optical sensing may also enable the user to establish proper engagement with clot material prior to activating suction.

In any of these methods and apparatuses, the apparatus may include a controller (which may be configured to detect proximity to clot material), a suction catheter, a mounting surface (e.g., on the suction catheter), one or more electrodes, an oscillating voltage source, and a data processing unit. The voltage source and/or data processing unit may be part of or coupled with the controller.

Figure 14:
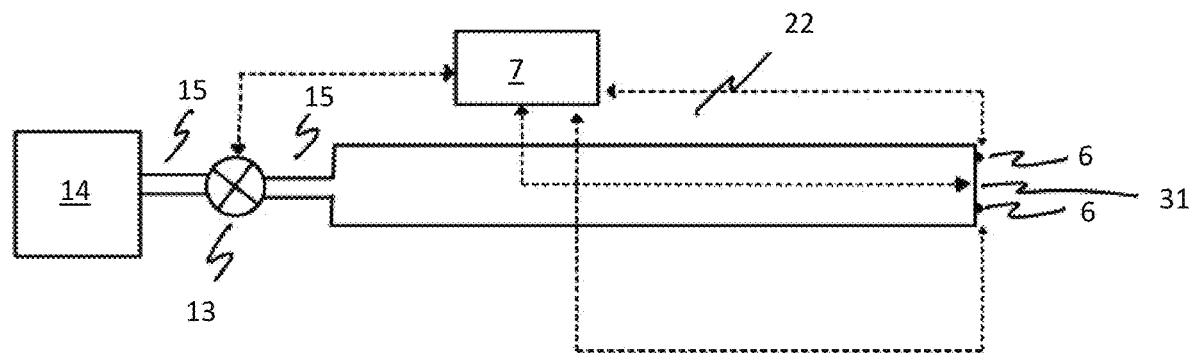
FIG. 14 schematically illustrate an example of an apparatus including a suction catheter in which suction is controlled, at least in part, by a controller receiving input from one or more sensors on a distal-facing portion of the catheter and one or more sensors within the lumen of the suction catheter for sensing clot material at or near these regions.
Figure 15:
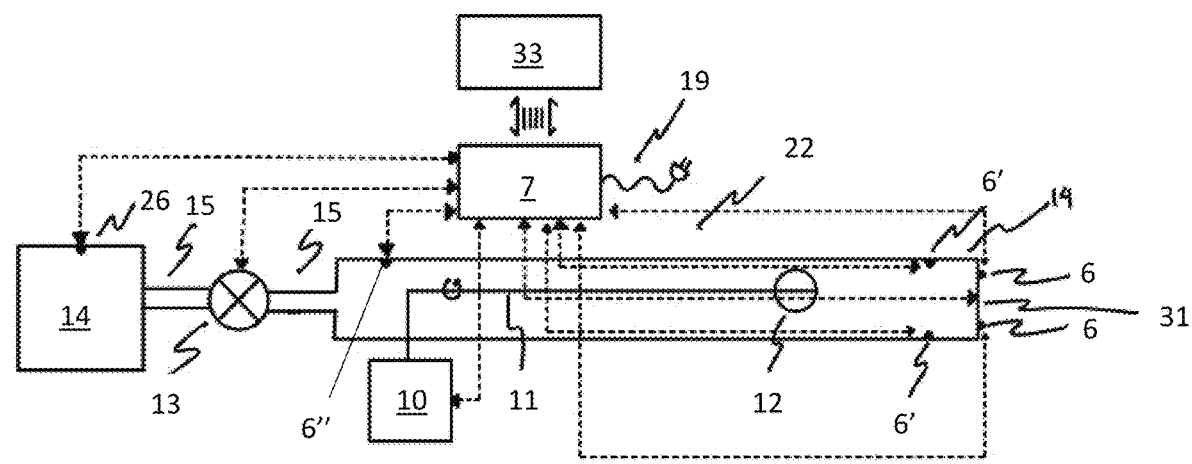
FIG. 15 schematically illustrate an example of an apparatus including a suction catheter and a macerator that are each controlled by a controller receiving input from multiple sensors.
Figure 16:
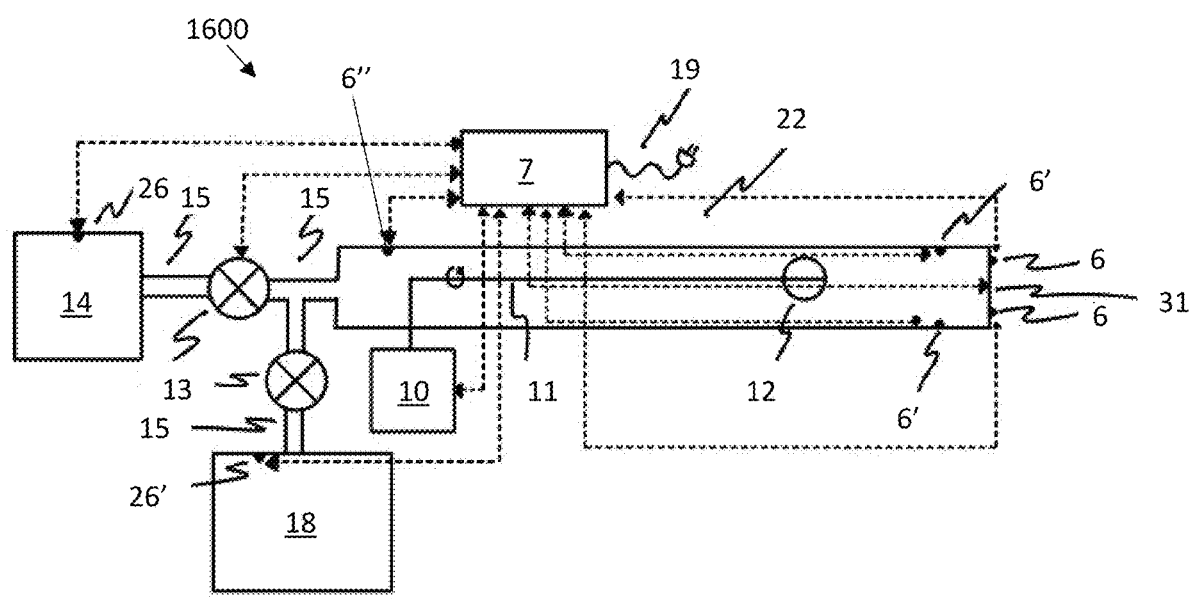
FIG. 16 schematically illustrates an example of an apparatus including a suction catheter and a macerator that are each controlled by a controller receiving input from multiple sensors; the example shown in FIG. 16 also includes positive pressure as well as negative pressure.

FIGS. 14-16 schematically illustrate examples of apparatuses for controlling operation of a suction catheter as described herein, similar to the examples shown in FIGS. 1A and 1C. In all of these examples, the apparatus includes an elongated suction catheter 22, including one or more sensors 6 for sensing clot on a distal-facing end 31 of the suction catheter. The sensors provide data to the controller 7. The controller may include one or more processors and processing hardware, software and/or firmware for processing and analyzing the sensor data received from the sensors. The controller may also control a suction modulator 13 that modulates suction from the suction source 14 (or in some examples may directly control the suction source 14). The suction catheter may connect to the source of suction and/or a suction modulator via one or more tubes 15.

For example, in FIG. 14, the apparatus includes a suction catheter 2 having one or more clot sensors 6 disposed externally at the distal end 31. Any of these apparatuses may also or alternatively include one or more clot sensors disposed internally within the lumen of the catheter, e.g., at known distance d from the distal end of the catheter (not shown in FIG. 14).

These apparatuses may be used to remove large or small clots, including clots that are smaller than the length d while inside of the suction catheter lumen. When engaging a small clot at the distal end, one or multiple clot sensors 6 may activate to indicate the presence of clot. Because a small clot may have a diameter less than or equal to the diameter of the catheter 2, not all clot sensors 6 used for establishing proper engagement prior to aspiration may activate despite adequate conditions for aspiring a small clot being met. In such cases the controller may determine that aspiration should begin or increase in strength based on a determination from the sensor data that the signal is persistent over time (not artifact) and consistent with clot material. Alternatively, a user may decide to manually initiate aspiration by sending an override command signal to the controller.

Thus any of these apparatuses may include a user interface including one or more inputs (buttons, touchscreens, knobs, dials, petals, foot petals, etc.) allowing user control and interaction with the apparatus, including the system. The user interface may be part of the controller 7 or may be separate from the controller and coupled to it. For example, FIG. 15 illustrates an example including an external unit 33. This external unit (or external interface unit) may include user controls, such as (but not limited to) a suction start (e.g., valve open) override input, e.g., button, and a suction stop (e.g., valve closed) override input, e.g., button, that may enable the user to manually override control of the application of signal to either begin aspiration despite inadequate indicated engagement or stop aspiration despite adequate indicated engagement with clot. Other user inputs may be included as part of the controller and/or the external unit. For example, user inputs may allow control of the operation of the apparatus, including the level of suction, turning on/off the macerator, or the like.

Any of the apparatuses described herein may also include a power control circuitry 19 integrated into the control unit 7. The power control circuitry may receive power from a wall power line (e.g., plug) and/or may include a battery. The power control circuitry may power the controller, and in some cases the source(s) of pressure, e.g., pumps, and/or the suction modulator, and the drive unit (e.g., motor) for driving maceration. The power source may be part of the controller and/or may be controlled by the controller.

The example apparatus shown in FIG. 15 also includes a macerator assembly including a cutting member 12 and a macerator drive shaft 11 and a macerator driver 10. The macerator assembly may also be controlled by (and coupled to) the controller 7. Any of the apparatuses described herein may include a macerator assembly and may be configured to control by the controller, using sensor data from sensors 6, including from sensors 6", 6'" within the lumen of the suction catheter 22.

In operation, in some examples a small clot may be proximal to, but not engaged with, the distal end 31 of the catheter 22. The (optional) external clot sensor or sensors 6 may indicate a proximity signal that is slightly elevated in a manner that is characteristic of an approaching clot (e.g., the bioimpedance may be elevated above the level of wall and/or blood when examining the impedance or impedance spectrum, including the change in impedances over time) because of the presence of clot material. In an engaged state, the distal end of the catheter may be in contact with clot material such that the clot material (even small clots) is within, e.g., half of its diameter of the distal end of the suction catheter and aligned with the opening of the suction catheter. In some instances, a small clot may drift such that it remains proximal to the distal end of the suction catheter in the engaged state yet makes substantially closer contact with one portion of the distal end and not equal contact with the entire distal end as mentioned above. In some examples, the system may wait until the clot material is in alignment with the distal opening of the catheter before the controller triggers the application of suction, which may help prevent chipping, slicing, or ejection of clot in the treatment area. Alternatively, in some examples the controller may be configured to apply an initially higher level of suction in order to center and position the clot. During improper or partial engagement of clot material (e.g., when contacting a small clot), one or more sensors closest to the location of the small clot relative to the distal end of the catheter may indicate a measurably higher proximity signal to the controller as compared to the proximity signals of more distal or other peripheral (forward-looking) sensors remaining sensors that are not in contact or close proximity to the off-center ("misaligned") small clot. In some cases, multiple sensors and/or additional sensing such as x-ray fluoroscopy may supplement proximity sensor signals in order to guide the repositioning of the distal end of the catheter relative to a clot material.

The example shown in FIG. 16 illustrates an apparatus similar to that shown in FIG. 15 which also includes a source of positive pressure 18, such as a pump. The controller 7 may directly control the source of positive 18 pressure or the controller may indirectly control the source of positive pressure by controlling a pressure modulator 13 for the positive pressure. In FIG. 16 two different pressure modulators (e.g., including valves, vents, manifolds, etc.) are shown; in some examples the same pressure modulator may be used for controlling both negative and positive pressure. The negative pressure (e.g., suction) source 14 and the positive pressure source 18 may both, individually, include one or more sensors (e.g., pressure sensors 26, 26') for monitoring pressure from the apparatus or within the apparatus. This controller may receive data from these sensors and may adjust the pressures (including turning on/off adjusting up/down) accordingly. In some examples the controller may adjust the final pressure or rates of change of pressure by adjusting the sources of negative and/or positive pressure directly and/or by controlling the one or more pressure modulators 13.

For example, when suction is being applied through the suction catheter, the controller may regulate the amount of the suction (and in some cases the positive pressure). When a suction modulator 13 is used rather than adjusting the suction source directly, the controller may maintain a valve in an open state, so that the source of suction is in fluid communication with the suction catheter. When applying suction through the suction catheter (during aspiration), the clot material may be located inside of the catheter. In some examples, the controller may continually monitor the reported vacuum source state and pressure source state in order to verify successful execution of open and close commands. If the sensed state or states does/do not agree with the internally registered state of the controller, an error may be generated, and the apparatus may temporarily stop applying vacuum (and/or trigger an alert) as a safety measure. In some examples, the vacuum and pressure sources ("reservoirs" or pumps) may contain purge valves which may be controlled by the controller so that during a device error, the controller may automatically (or a user may manually) execute a purge command (e.g., the user may trigger a button disposed on the external unit) to actuate the purge valves disposed for the vacuum and/or pressure reservoirs.

The suction catheter may include clot proximity sensors disposed externally at the distal end of the suction catheter and clot detecting sensors within the lumen of the suction catheter, as described above. In operation, these apparatuses may detect that the clot is ingested (including fully ingested) when the distal-facing clot sensors no longer detect clot. If the internal clot sensors within the lumen of the suction catheter still detect clot material, the clot has not been fully ingested and removed and suction may remain on. The macerator may also remain on. Once clot is no longer detected either outside of the suction catheter or within the lumen of the suction catheter, the controller may turn off the suction until additional clot material is detected. In any of these cases, the apparatus may enable suction to turn on (and in some cases off), but may require manual input (e.g., via an input such as a switch, toggle, foot pedal, etc.) to turn on (or off) suction. In some cases, the apparatus may allow the user to select an automatic mode to have the suction turned on (and/or off) automatically as determined by the controller. For example, the apparatus may include one or more external distal-facing clot sensors and one or more internal clot sensors within the lumen of the suction catheter. The internal sensor(s) may be, for example, at a distance d from the distal opening of the suction catheter. The external sensor or sensors may send a baseline signal (indicating no clot material is present) to the controller while the internal sensor or sensors will send a high proximity signal (indicating the presence of clot material) to the controller once the clot material is fully ingested and is within distance d from the catheter opening. In some examples, proximity signals will communicate between the lumen of the catheter and the externally disposed sensors, so that both external and internal sensors send high proximity signals to the controller, and the controller may jointly analyze the signals to determine the position of the clot material relative to the distal opening of the suction catheter. In some examples, if the controller determines the position of the clot material inside of the catheter lumen to be past a known, predetermined, distance (or absent), and when no further clot material is detected in engagement with the distal opening of the suction catheter, the controller may send a close or off signal to the source of negative pressure (e.g., pump) and/or to a suction modulator. The controller may also verify successful disengagement of aspiration. When additional clot material comes into engagement with the distal end of the suction catheter after the aspiration of clot material, the sequence may be repeated again until no further clot material comes into engagement with the distal end of the suction catheter.

The same general operation may be performed for large and small clot materials. For example, a suction catheter with one or more external, distal-facing clot sensors at the distal end and one or more clot sensors disposed internally within the lumen (e.g., at distance d from the distal end) may also control suction (and maceration) based on both internal signals sensing clot material (e.g., bioimpedance, ultrasound, optics, etc., even without sensing pressure or flow within the lumen) and one or more external signals sensing clot in contact with the distal opening. Any of these apparatuses may determine the relative sizes of the clots. For example, a large clot may be defined as a clot of length greater than or equal to d while inside of the suction catheter. Since large clots may present with a narrow, elongated shape, some large clots may resemble small clots in engagement with the distal end of the catheter and in interaction with clot proximity sensors. The controller may detect that the large clot is fully ingested when the external clot proximity sensor or sensors indicate a baseline proximity signal. In examples including sensors within the lumen, the controller may continue to operate the suction (or a reduced level of suction, but not off) when the internal sensors indicate that the clot is still within the lumen of the suction catheter. For example, the external sensor or sensors may send a baseline signal interpreted by the controller to indicate no clot in close proximity the distal end of the apparatus, while the internal sensor or sensors send a high proximity signal to the controller, indicating the large clot is fully ingested and within distance d from the catheter 2 opening. In some examples, both external and internal sensors may indicate high proximity signals to the controller, and the controller may (using both sets of signals) determine the position of the large clot relative to the distal opening of the catheter 2 during ingestion and transport clot material to a collection vessel.

Although the apparatuses described herein may be operated without pressure sensing within the lumen of the catheter, in some examples a pressure sensor may be included. For example, one or more pressure sensors may be disposed internally within the suction catheter either distal or proximal to the distal end of the suction catheter. In such cases, one or more pressure sensor signals may be sent to the controller to supplement the clot proximity sensor or sensors disposed either internally or externally on the suction catheter. The pressure indicated at the proximal end of the suction catheter may be approximately equal to the pressure applied by the pressure modulator or source of suction. The pressure detected near the distal end of the suction catheter, e.g., within a known distance, d, from the distal opening, may exhibit a slightly higher level when no clot is within the catheter, but may exhibit a higher pressure approximately equal to that of the media beyond the distal end of the suction catheter while a clot material is either passing over or between the distal and proximal pressure sensors. The pressure signals from the ends of the catheter may enable the controller to calculate more accurate representations of the position of the clot material within the suction catheter, and this position may inform commands to the pressure modulator or source or suction, e.g., to stay open in the case of inadequate displacement of clot along the suction catheter.

As mentioned above, in some examples, the controller may implement a method of delayed signal processing or delayed signal response in order to prevent feedback interference with an instantaneous or continuous control system. In such examples, the controller may include a known delay (represented by $t_1$) when stopping suction and/or when starting suction and/or starting maceration and/or stopping maceration. Separate start delays and stop delays may be used. The controller may also introduce intentional delays before changing the speed of the macerator (e.g., turning on the macerator, turning off the macerator, increasing the macerator speed, decreasing the macerator speed, etc.). An intentional delay may also be applied by the controller when updating a graphical user interface or external unit with state information. The addition of internal delay (e.g., of 0.5 second, 1 second, 2 seconds, 3 seconds, etc. or more) may be beneficial. For example, when the controller is using pressure-based internal sensors, changes in the environment within the lumen may initially invoke pressure signal features such as random noise or anomalous spikes. In such cases, implementing an intentional delay may prevent the controller from reacting to illusory or anomalous states by only allowing the controller to perform an action after data artifacts are expected to have subsided. The duration of the intentional delay may be modified by the controller. For example, the controller may modify the delay over time. In such examples, the controller may use a continuous analysis of data patterns and data buffering or recording to enable the controller to autonomously configure the delay duration. The controller may autonomously configure the delay duration, or any other variable mentioned herein through known statistical methods, including but not limited to data signal processing, statistical analysis, thresholding, and artificial neural networks. For example, the value $t_1$ may be adjusted in order to minimize the delay $t_1$ while maximizing the reduction in noise and data artifacts. In some examples, the controller may control a rotating macerator drive shaft that is internally disposed at the distal end of the suction catheter as well as a drive motor 10 coupled to the drive-shaft via an attachment to drive rotation (actuation) of the macerator. The controller may be responsible for modulating macerator speed by supplying or withholding current to the motor and/or by applying control instructions (e.g., digital commands). In some examples, the controller may monitor fluctuations in current drawn by the motor 10 in order to measure clot attributes including but not limited to volume, mass, density, or length. Based on such measurements, the controller may increase or decrease macerator speed and torque in order to optimize the maceration for a specific clot.

Similarly, the controller may modify the rate of the macerator based on the one or more sensors within the lumen of the suction catheter indicating the presence of clot material. The sensor output may be related to the integrity of the clot material, including how hard or compact the clot material is. Thus, the controller may be configured to set the macerator speed and/or toque based on the intensity of the signals (e.g., bioimpedance, ultrasound, optical, etc.) from the one or more sensors within the lumen of the suction catheter. In some examples, the controller may define time-dependent states including but not limited to clot not moving, rapid clot extraction, stagnant sensor input, and biased or contaminated sensor input which are determined by the controller continuously analyzing sensor inputs over a known interval t2 after any state change and using any selection of known analytical methods including but not limited to statistical inference, thresholding, signal enrichment analysis, noise detection, and data signal processing. For example, the controller may partially or fully base control input to any component in electronic communication with the controller based on said time-dependent states. Modulating the activity of components such as valves, motors and user interfaces may enable the treatment of clot according to continuously variable system attributes at the distal end of the catheter. In some examples, the controller may be in bi-directional communication with all of the components with which the controller may interface, including but not limited to sensors, valves, motors, and external user interfaces. The controller may monitor signals produced by the interfacing components and may include signals acquired by monitoring of the analysis and state-change action activations. In some examples, the controller may monitor a component, peripheral device, signal, or other electronic interface (including those not mentioned herein) such that the controller may continually register incoming signals from said interfaces and all devices interfacing with the controller which may be capable of continuously self-reporting state and data signals and may update the controller with measurement data or states at a regular, known frequency. By monitoring components including (but not limited) to clot proximity sensors, pressure sensors, valves, external unit controls, and/or additional user-interface controls, the controller may include and incorporate additional information into control inputs for analysis, thresholding, state coordination, state validation, state-change validation, emergency state-override, and updating external indications of any states or measurements mentioned herein. In some examples the vacuum and positive pressure reservoirs (e.g., pumps) may include pressure sensors disposed internally for continuously measuring and reporting the pressure within each reservoir. The controller may use pressure signals from the vacuum and pressure reservoirs, for example, for regulating pressure applied (negative and/or positive pressure) to the suction catheter, for changing valve states, for modulating the amount of time valves stay open during aspiration, and/or for inferring pressure inside of the distal portion of the suction catheter lumen. The controller may apply suction (e.g., by opening one or more valves) for a known time, $t_2$, before automatically stopping suction (e.g., closing any open valves) and reevaluating, using any selection of available signals and states, whether to reapply suction (e.g., to reopen a valve). This interval method may prevent contaminated sensors, dysfunctional sensors, old commands, or other errors that may occur during operation to prevent the valves from operating. In some instances, the controller's potential failure to register a change of state in the system including the vascular region surrounding the distal end of the suction catheter, the suction catheter, and the interior of the distal end of the suction catheter of length d may cause adverse, unsanctioned, or excessive aspiration or damaging of vessel wall, and parts of the apparatus. The controller may determine that requisite system conditions have been met using methods and electronic periphery in continuous data communication with the controller.

Figure 17A:
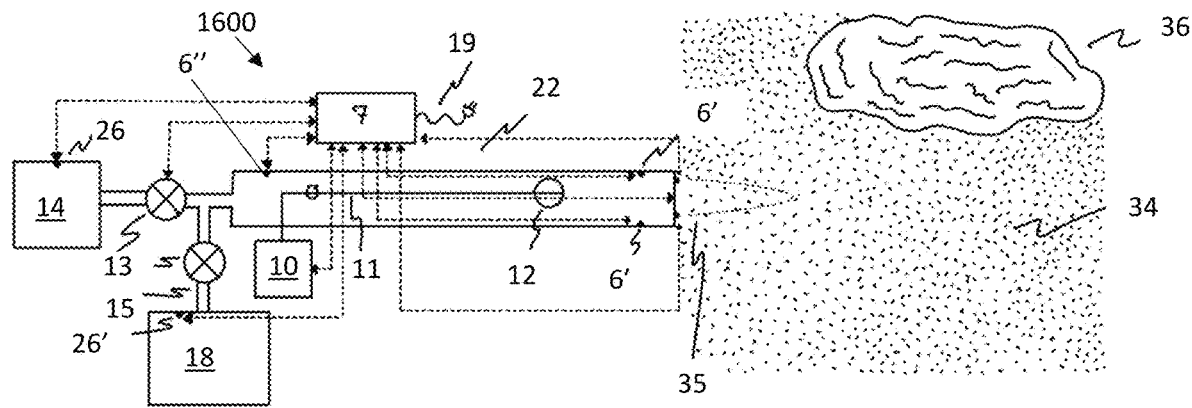
FIGS. 17A-17E illustrate operation of an apparatus similar to that shown in FIG. 16 removing clot material from a blood vessel with minimal blood loss.

FIGS. 17A-17E illustrate operation of an apparatus such as those shown schematically in FIGS. 1A, 1C and 14-16. For example, the apparatus shown in FIG. 17A is similar to that shown in FIG. 16 and includes a suction catheter 22 having a central lumen with an opening at the distal end of the suction catheter into the lumen. The suction catheter may include a distal cover, as described above. The apparatus also includes a suction (e.g., vacuum or negative pressure) reservoir 14 and a pressure modulator (e.g., suction modulator) 13 including one or more valves disposed between the suction reservoir and the central lumen of the suction catheter. The suction catheter central lumen is in fluid connection with the vacuum reservoir and (in this example) the pressure modulator through connecting tubes 15. One or more sensors 6 are disposed on the distal end 1, which may consist of but are not limited to monopolar impedance sensors, bipolar impedance sensors, pressure sensors, optical sensors, acoustic sensors, or applied-force sensors. The suction reservoir may include a gas or fluid chamber and a pump for regulating pressure within said chamber, and may be in communication (e.g., constant or periodic, bidirectional reciprocal data communication) with the controller. The controller may in turn be in communication (e.g., constant or periodic, bidirectional reciprocal data communication) with the suction modulator 13 and the sensors 6 located on the distal end. One or more sensors may be disposed internally within the lumen, e.g., at the distal end region within the suction catheter. In some examples the internal sensors are separated by a distance, d, from the suction catheter opening. External sensors 6 may be configured in multiple arrangements including but not limited to forward-facing and singular, forward-facing and proximally paired, forward-facing and plurally disposed radially about the catheter opening, and forward-facing and plurally disposed radially about the distal opening wherein each radial position consists of a proximal sensor pair as previously described. Internal sensors 6 may be configured in multiple arrangements including but not limited to inward-facing and singular, inward-facing and proximally paired, inward-facing and plurally disposed radially about the catheter wall, and inward-facing and plurally disposed radially about the catheter wall wherein each radial position consists of a proximal sensor pair as previously described. The controller may supply power to the various components of the system, including the sensors. An addressable motor macerator motor 10 is in fixed attachment through a flexible drive-shaft 11 with a macerator cutter 12 disposed at the distal end of the lumen. A user interface (e.g., external unit 13) may be coupled to (or part of) the controller and may include any selection of control interfaces and informational displays such as LED indicators, buttons, switches, and displays. The apparatus in FIGS. 17A-17E also includes a positive pressure reservoir 18 and pressure modifier 13 for the positive pressure valve, both in fluid communication with the lumen of the suction catheter through the connecting tubes 15.

In FIG. 17A the apparatus 1600 is show within a blood vessel, such the pulmonary artery. The distal end of the suction catheter lumen is immediately surrounded by blood 34. The vessel includes a large clot 13. One pair of forward-facing impedance sensors 6 disposed on the distal end of the suction catheter is monitored by the controller 7. In this example, the sensor is configured as a bioimpedance sensor that is bipolar and operates by sending electrical current 35 into the blood 14 of the vessel. In FIG. 17A, the large clot 36 is beyond the sensing range of the clot sensors 6, therefore the impedance value returned by the sensor is approximately that of blood, and the suction and macerator 17 remain off (e.g., no negative pressure through the suction catheter).

Figure 17B:
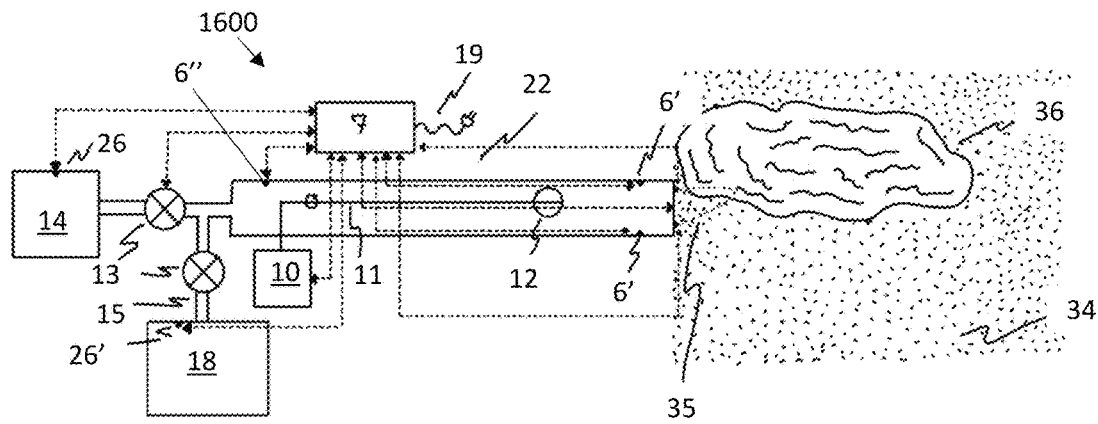

As the distal end of the catheter approaches closer to the clot 26, as shown in FIG. 17B, the bioimpedance sensor(s) 6 may detect the clot material as it approaches in closer proximity to the distal end of the suction catheter and enters a region of relatively high emitted current 35. The large clot 36 is close to the distal end; but in this example, the clot material is closer to one sensor 6 out of the pair, indicating that the clot 36 is relatively misaligned with the suction catheter opening. In some examples, the controller may turn on suction, or may wait until the clot material is more optimally positioned relative to the distal end of the suction catheter, as may be detected by the signal from the sensor. In some examples, the controller may turn on a brief pulse of higher suction to help better position the clot material.

Figure 17C:
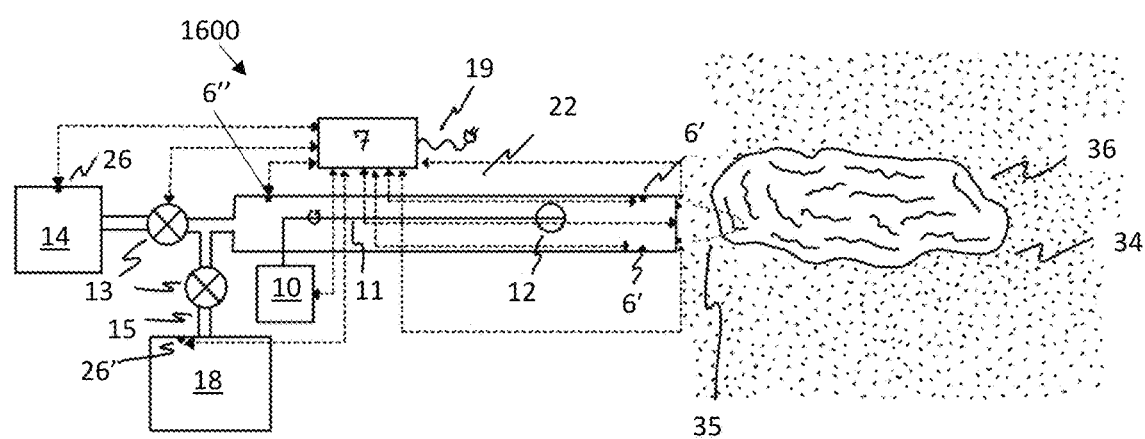

In FIG. 17C, the clot material 36 is proximal to the distal end 1 and approximately equidistant to both forward-facing sensors 6. The distal opening is approximately aligned with the clot 13. In this example, current 35 from the sensor(s) on the distal end of the suction catheter passes approximately symmetrically through the large clot in front of the distal opening. The controller may then apply suction through the lumen of the suction catheter. Centering the clot as described above may permit the clot material to be suctioned without requiring excessive blood take-up into the lumen of the suction catheter.

Figure 17D:
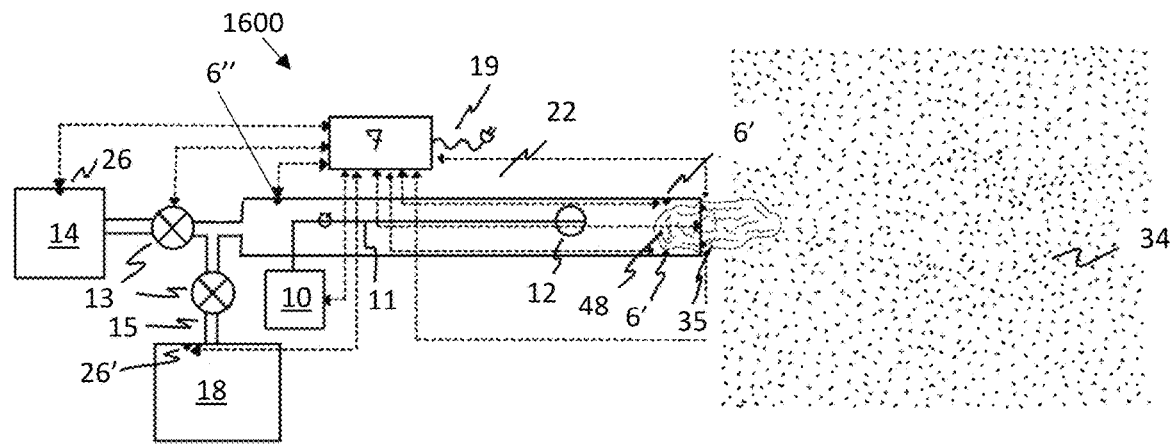

As shown in FIG. 17D, the clot is being aspirated into the lumen of the catheter. The clot material is in contact with sensors both internal to the lumen as well as with the forward-facing sensors 6. In this configuration the clot material may be detected by the bioimpedance signal from the internal sensors which emit a current 48 or field, in addition to the current emitted by the distal-facing sensors. The controller may activate the macerator so that the driver 10 engages the macerator drive shaft 11 to drive rotation of the macerator cutter 12. In some examples the macerator cutter may be positioned more distally within the lumen of the suction catheter so that it may enhance take-up of the clot material.

Figure 17E:
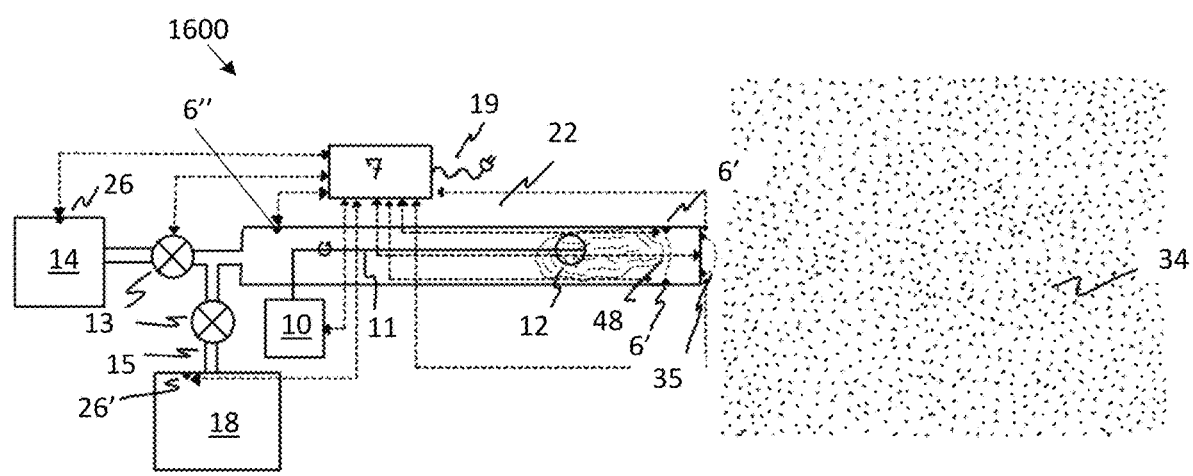

In FIG. 17E the clot material has been fully suctioned into the lumen of the suction catheter. The clot material may no longer be detected by the sensor(s) on the distal end of the suction catheter, and the signal from the first set of internal sensors 6 may decrease or stop as the clot is moved proximally through the lumen. In some examples additional sensors or sets of sensors may be included to track progression of the clot material down the lumen. The controller may continue to macerate and apply suction to pass the clot material for collection proximally.

Figure 18A:
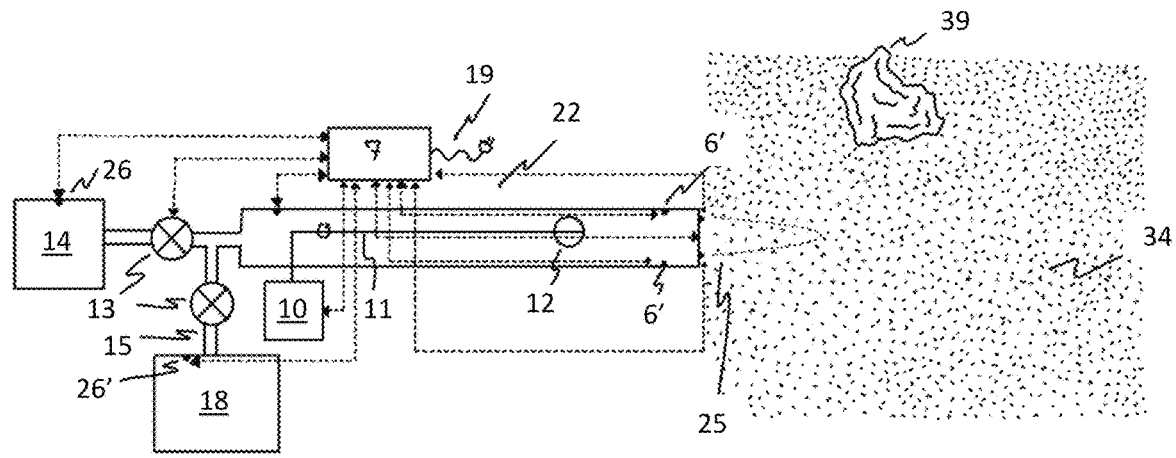
FIGS. 18A-18E illustrate operation of an apparatus similar to that shown in FIG. 16, including a suction catheter, removing clot material from a blood vessel.
Figure 18B:
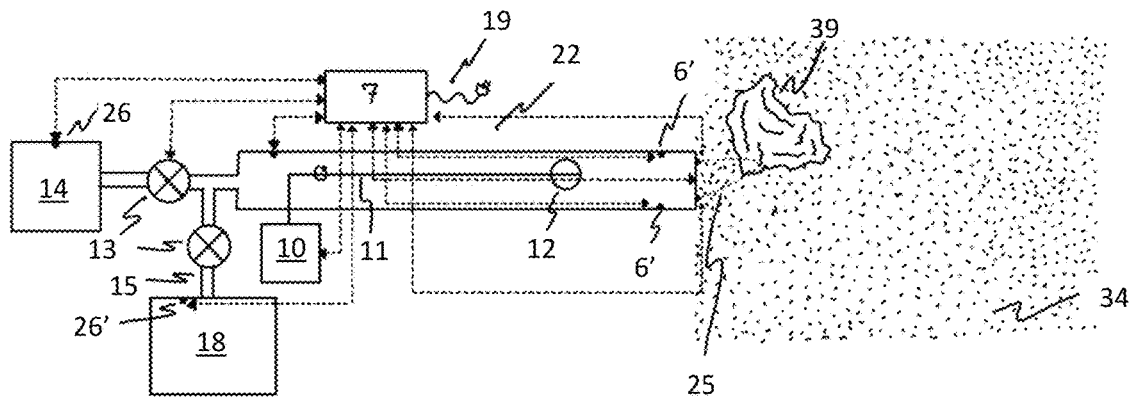

FIGS. 18A-18E illustrate another example of an apparatus similar to that shown in FIGS. 1A, 1C and 14-16, again within a pulmonary artery, in which a smaller amount of clot material may be sucked into the device. In FIG. 18A, the distal end of the device is within the pulmonary artery and the distal end is surrounded by blood 34. A small clot material 39 is outside of the range of the sensors (shown here as bioimpedance sensors, emitting a current 25 for detecting impedance). In FIG. 18B the clot material is in closer proximity to the distal end of the suction catheter. The clot material 39 is proximal to the distal end but is shown closer to one sensor 6 out of the pair of distal-facing sensors, and the resulting bioimpedance signal shows that the clot material is misaligned with the catheter opening. As before the controller may initiate suction or may wait until the clot is closer (and the sensors indicate better centering) in order to minimize blood loss.

Figure 18C:
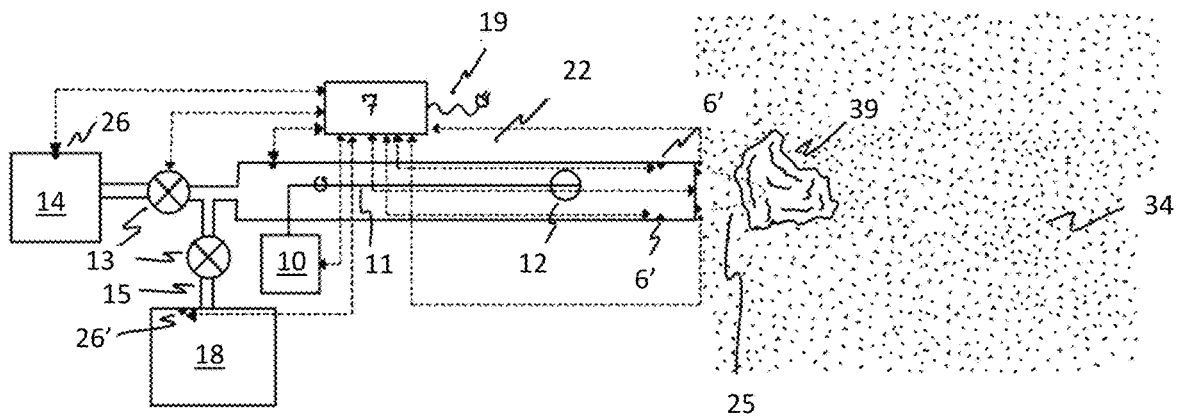
Figure 18D:
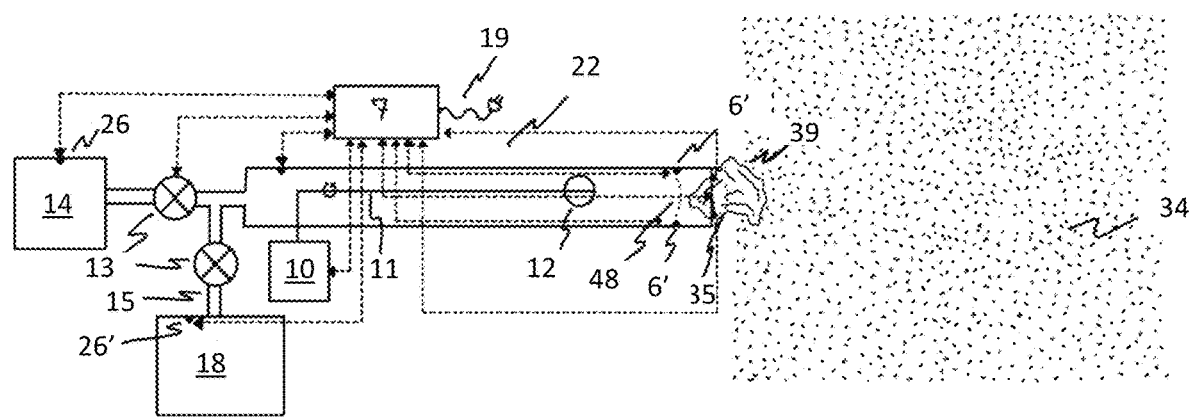

In FIG. 18C, the clot material is proximal to the distal end and approximately equidistant to both forward-facing sensors 6 so that the distal opening is approximately aligned with the clot material. Current 25 from the sensor(s) passes approximately symmetrically through the small clot 39 in front of the distal opening. The controller may engage aspiration of the clot material into the lumen, as shown in FIG. 18D. In FIG. 18D, the clot 21 is within the lumen entirely, and within the range d of the first set of internal sensors as described above. In this instance of FIG. 18D, the clot material is in contact with sensors internal to the lumen 6 (for detection by the emitted current 48) along with forward-facing sensors 6. The controller may therefore continue engaging aspiration as the clot material continues into the lumen.

Figure 18E:
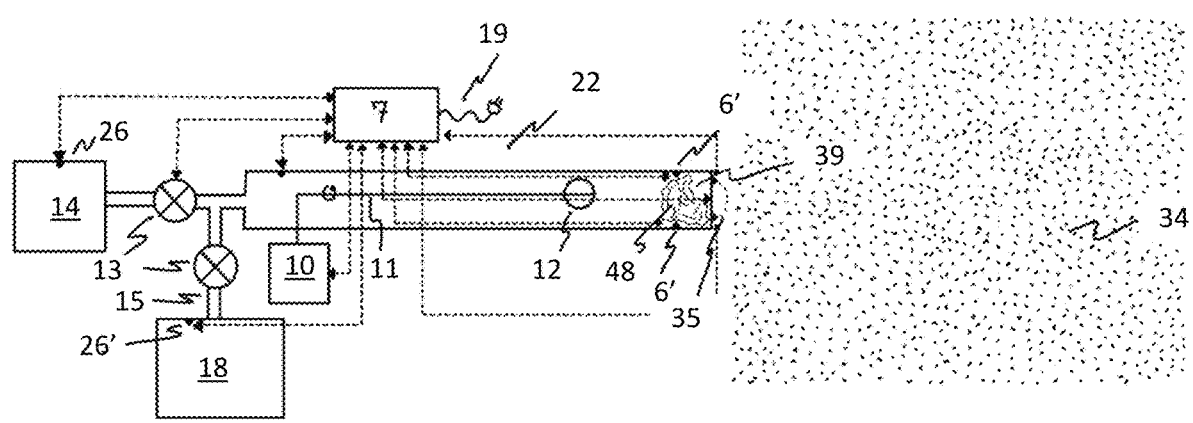

FIG. 18E shows the clot material is fully within the lumen, and while still in range of the internal sensors, has passed out of range of the external, distal-facing sensors.

Figure 19:
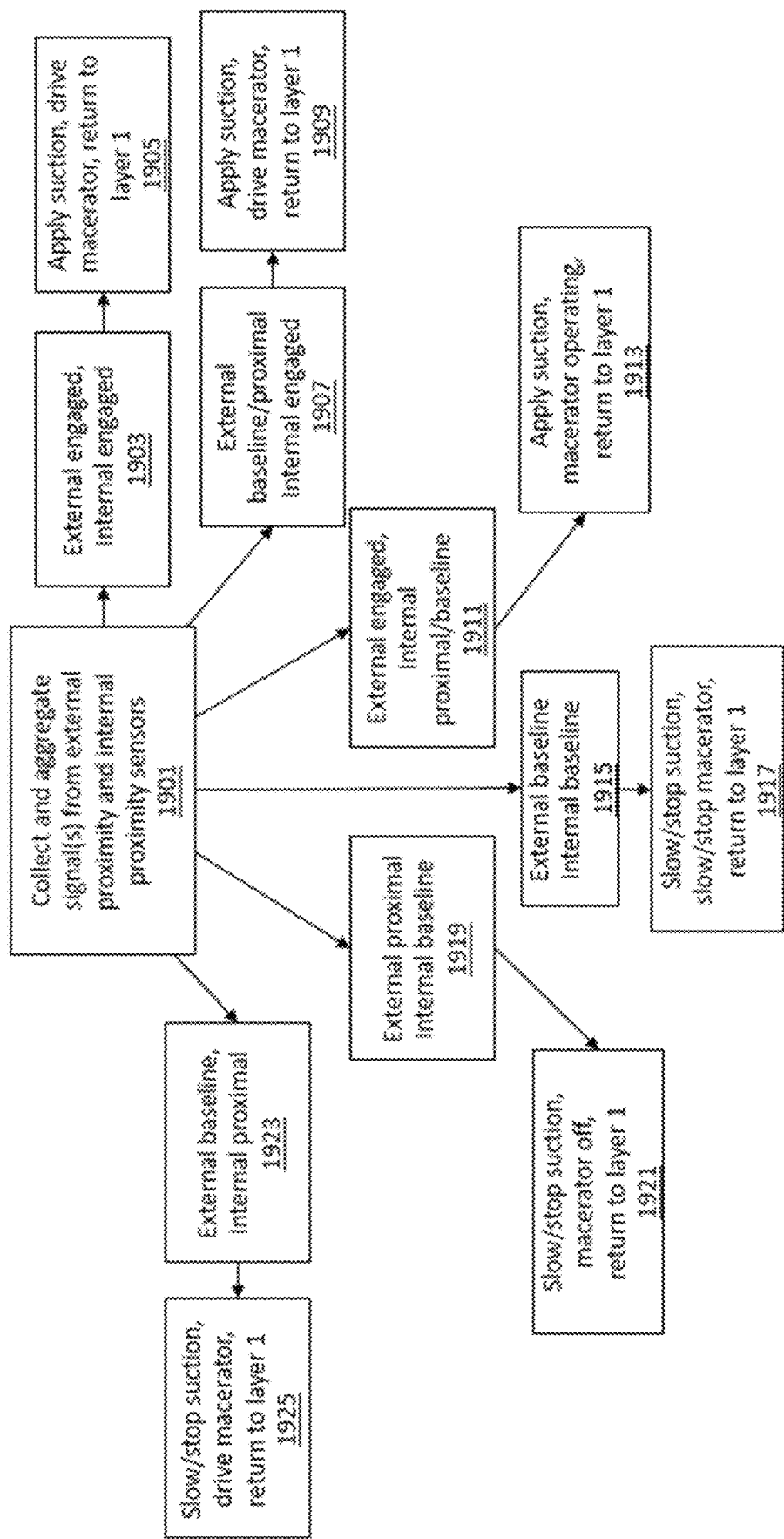
FIG. 19 is one example of a state diagram for an apparatus as described herein.

FIG. 19 shows one example of a control-loop model for an apparatus such as the one(s) shown in FIGS. 1C, 15, 16, 17A-17E and 18A-18E. In FIG. 19, the controller may follow the control loop based on input from the clot-sensing sensors within the lumen of the suction catheter and from the clot-sensing sensors that are external to the distal end of the suction catheter 1901. The sensor data may be analyzed to identify when the external sensors identify only blood or vessel wall ("external baseline"), when clot material is nearby ("proximal") or when clot material is present on the catheter ("engaged"). Similarly, the internal sensor(s) may be analyzed to determine when clot material is present ("engaged"), nearby ("proximal") or is absent, and only blood is present ("baseline"). In this simple example of a state diagram, the results of the combined external sensor(s) and internal sensor(s) data may set the state of the suction (on/off) or macerator (on/off). For example, if the external sensor(s) indicate that clot material is on the end of the catheter fully ("external engaged") and the internal is fully engaged with clot material ("internal engaged") 1903, then the suction may be "on," e.g., by opening a valve in the suction modulator and/or by directly activating the source of suction 1905. If the external sensor(s) indicate that the clot material is absent ("external baseline") or is nearby but not yet in contact ("external proximal"), while clot material is present on the internal sensor(s) ("internal engaged") 1907, then suction may be applied to continue to remove clot material from within the catheter while the macerator is driven (1909). If the external sensor(s) indicate that the clot material is present ("external engaged") while the internal sensor(s) indicate either that clot material is nearby or is absent ("internal proximal/baseline") 1911, then the controller may cause suction to be applied while the macerator is driven 1913. If the external sensor(s) indicate that clot is absent ("external baseline") while the internal sensor(s) indicate that clot is absent ("internal baseline") 1915, then the controller may keep the suction off (or in some examples, at a low level), while the macerator drive is also off 1917. If the external sensor(s) indicate that clot is nearby but not in contact ("external proximal") while the internal sensor indicate that clot is absent ("internal baseline") 1919, the controller may set or keep the suction off (or at a low level) while the macerator is kept off 1921. Finally, if the external sensor(s) indicate that clot is absent ("external baseline") while the internal sensors indicate that clot is nearby ("internal proximal") 1923, the controller may slow or stop the suction while continuing to drive the macerator 1925.

In some examples the states shown in FIG. 19 may be interconnected, as transitions between states (not shown in FIG. 19) may be predetermined, and the controller may base control states for the suction and/or macerator based on the prior state. Thus, the state diagram shown in FIG. 19 is exemplary only, and other state diagrams may be used and implemented by the controller. In some examples, the controller may also use data (e.g., feedback) from other components that may inform the state diagrams and control loop(s). For example, data from the sensors on the negative or positive pressure sources may be used, pressure sensors from within the catheter lumen may be used, user input, including user emergency override input may be used, etc. The primary control layer ("layer 1") may involve any preliminary data collection or analysis from peripheral components and exclusively involves functions of the controller. The secondary control layer ("layer 2") may involve the establishment of known system states including but not limited to clot out of range, clot proximal to distal end, clot engaged with distal end, clot within interval d, clot leaving interval d, clot aspirated/return to state clot out of range, etc. Control layer 3 ("layer 3") may exclusively involve control-loop actions such as layer changes or repeated steps, which in the case of the apparatus shown above may include returning to the primary control layer. The model control-loop described herein functions interchangeably with small and large clot examples.

Any appropriate macerator may be used. For example, FIGS. 20-24 illustrate examples of macerators that may be used. In general, the macerators shown (which may be referred to as shavers") include an outer housing 201, shown in FIGS. 20-24 as an insulated or insulating cannula. The outer housing may be flexible, so that the macerator may navigate within a curved suction catheter. The macerators shown in FIGS. 20-24 may also include an inner housing 202, e.g., in FIG. 20 the inner housing is an insulated rotating sleeve. The rotating sleeve includes an opening 203 and teeth forming the macerator cutter 204. In some examples the macerator may include a single housing in which a flexible macerator drive shaft (e.g., wire) may rotate to drive rotation of the macerator cutter. In some examples only a single (e.g., outer) housing is used, and may include a window (or multiple windows) exposing the rotating cutter. Alternatively in some examples the cutter extends from the distal end of the housing without sitting within a window.

Figure 20:
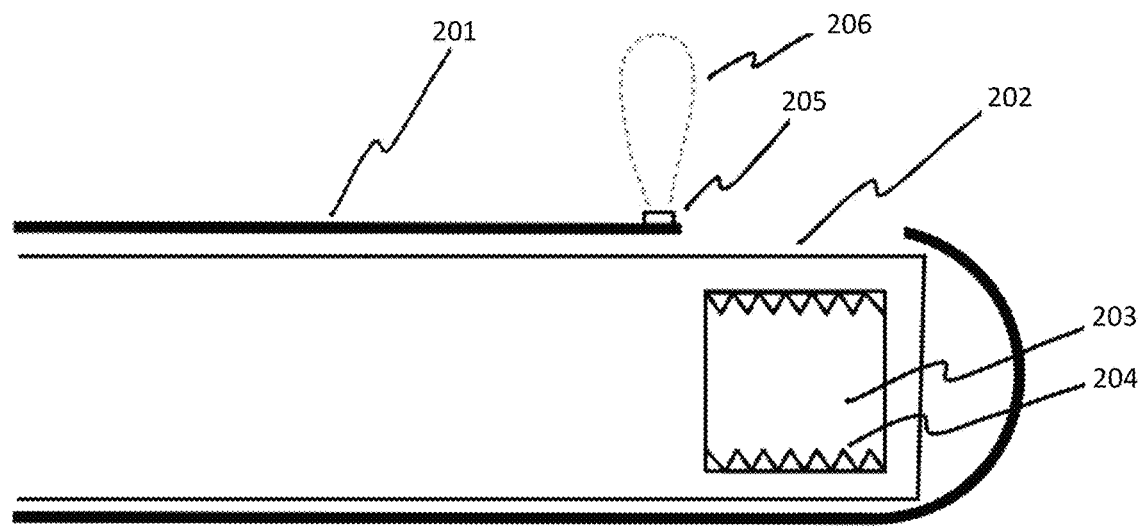
FIG. 20 illustrates one example of a macerator that may be used as part of any of the apparatuses described herein.

Any of the macerators described herein may include one or more sensors for detecting clot material. In any of these examples the sensor(s) may form the internal sensors or some (or part) of the internal sensors described above. These sensors may be clot-detecting sensors, and may include bioimpedance sensors, ultrasound sensors, optical sensors, etc. For example, in some examples the sensors may be configured as bipolar bioimpedance sensors. In FIG. 20, the macerator includes a monopolar impedance sensor 205 disposed radially external on the outer housing and proximal to the opening 203 (window exposing the cutter) of the inner rotating sleeve 202. In this configuration the impedance sensor may emit an electrical current 206, shown in FIG. 20 by the dashed lines representing the sensing field of the sensor. Current transferred from the monopolar impedance sensor 205 may returns to the sensor 205 after being affected by the surrounding region. Thus, this sensor configuration carries lower spatial specificity, enabling clot sensing across the volume within the distal end of the suction catheter (not shown in this example).

Figure 21:
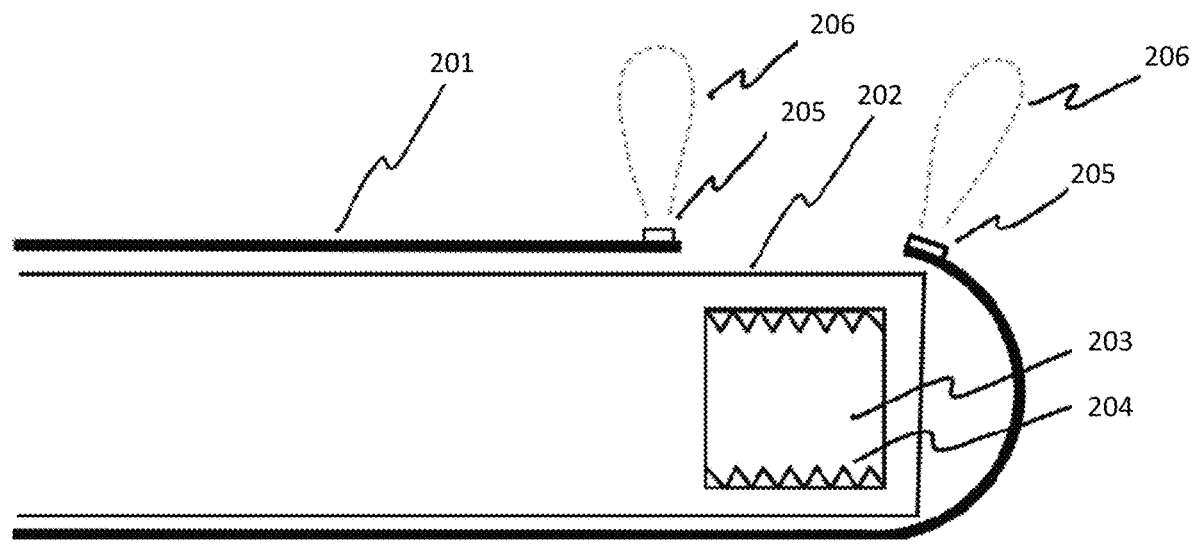
FIG. 21 is an example of a macerator that may be used as part of any of the apparatuses described herein.

FIG. 21 shows another example of a macerator. In FIG. 21, a second monopolar impedance sensor 205 is disposed on an opposing side of the opening 203 and radially external to the outer housing 201. In this example current 206 transferred from each monopolar impedance sensor 205 also returns to each respective sensor 205. The sensor configuration combines lower spatial specificity with multiple measurement locations radially disposed relative to the opening 203, enabling clot sensing across the volume within the suction catheter (e.g., the distal end of the suction catheter, as well as combined analyses including but not limited to clot proximity triangulation and signal denoising.

Figure 22:
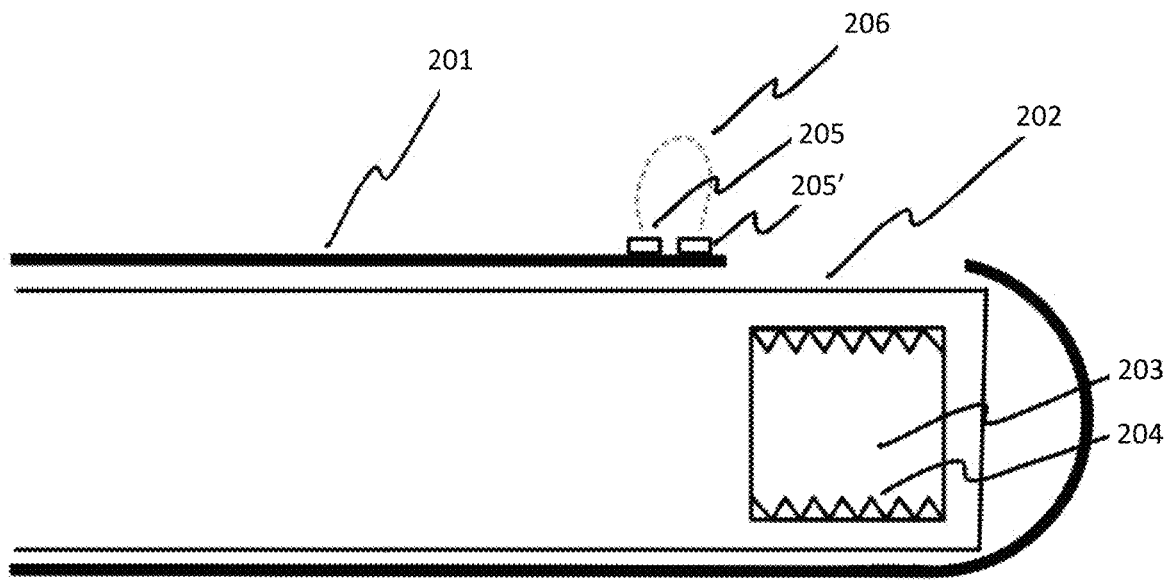
FIG. 22 is an example of a macerator that may be used as part of any of the apparatuses described herein.

FIG. 22 shows another example of a macerator similar to that shown in FIG. 20, except with a bipolar impedance sensor 205 replacing the monopolar sensor. In this example, the current 206 transferred from one electrode in the bipolar impedance sensor 205 returns through the opposing sensor in the pair 205'. This sensor configuration carries higher spatial specificity, enabling more precise analysis of clot near the window opening 203. Multiple sensors (including multiple bipolar sensors) may be used.

Figure 23:
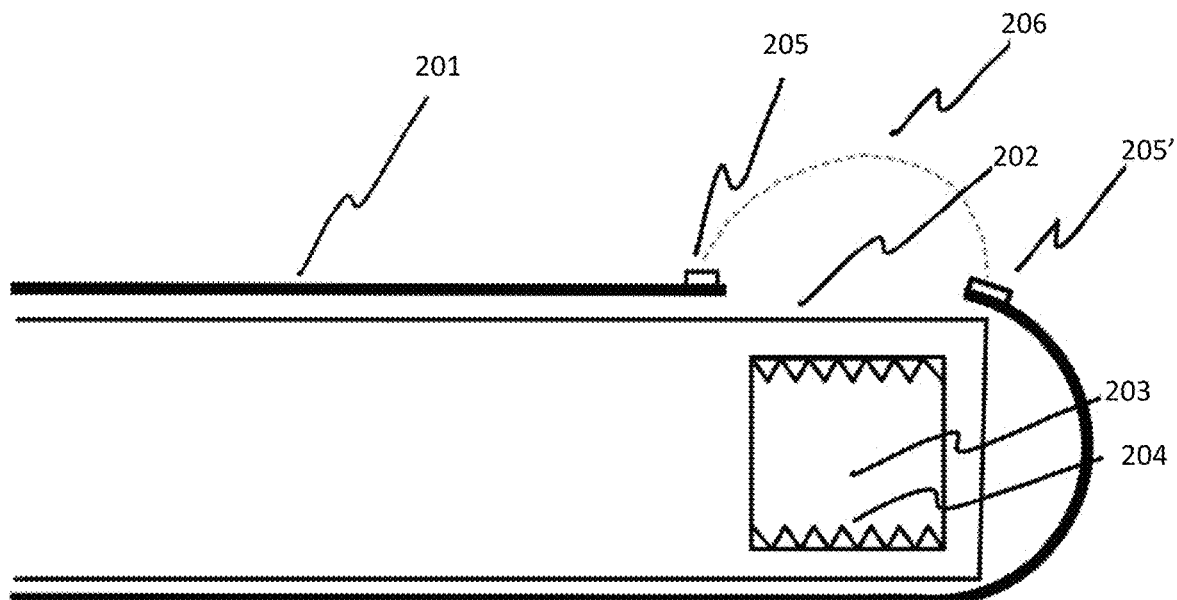
FIG. 23 is an example of a macerator that may be used as part of any of the apparatuses described herein.

FIG. 23 illustrates another example of a macerator in which the sensor includes a pair of electrodes 205, 205' forming a bipolar bioimpedance sensor that senses the region extending over the opening 202 exposing the window 203. In this example, current 206 transferred from one electrode in each bipolar impedance sensor returns through the opposing sensor in the respective pair. The sensor configuration combines higher spatial specificity with multiple measurement locations radially disposed relative to the opening 203, enabling clot sensing and positioning relative to the opening 203.

Figure 24:
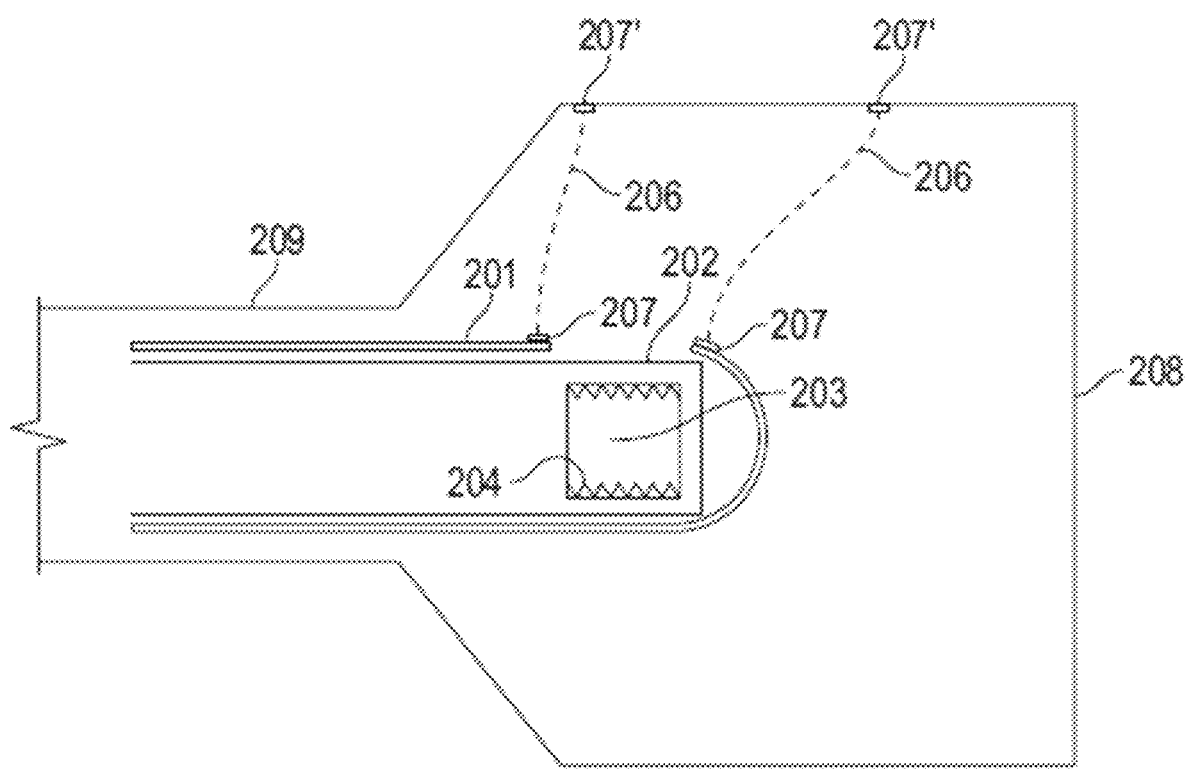
FIG. 24 is another example of a macerator that may be used as part of any of the apparatuses described herein.

FIG. 24 illustrates an example of a macerator inserted through the suction lumen to the distal end of the suction catheter. As illustrated in FIG. 24, the distal end of the suction catheter may include an expanding distal end region into which the macerator may be positioned. A cover 208, which may be elastically deformable and may include an opening or slit to allow passage of clot material, as described above, may be included. In FIG. 24 the macerator includes electrodes 207 that form sensing pairs of bipolar bioimpedance sensors with electrodes 207' located within the distal end region of the lumen. Thus, sensor pairs 207, 207' are made between electrodes disposed radially proximal to the opening 202 in the outer housing of the macerator and electrode residing on the wall of the suction catheter 209 (in this example, in the expandable, "funnel" region). The sensor in this example may allow bipolar impedance sensing with high spatial specificity and long-range current paths 206 in order to provide sensing for the entire volume of the lumen of the distal end region of the suction catheter.

Figure 25:
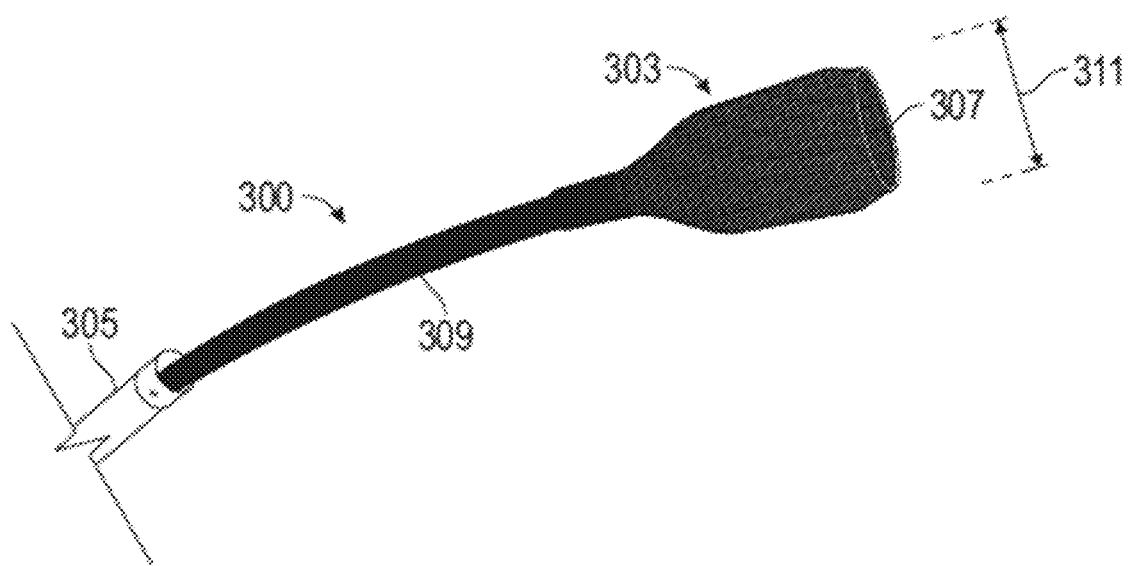
FIG. 25 illustrates one example of a suction catheter as described herein.

FIG. 25 illustrates an example of a distal end region of a funnel as described herein, similar to the example shown schematically in FIG. 24. In any of the apparatuses described herein the suction catheter may include an enlarged (larger diameter) distal end region. This distal end region may be expandable and collapsible from a compressed undeployed configuration (which may fit into a delivery catheter 305. The expandable distal end region 303 may be referred to as a funnel region and may be formed of a material that self-expands when released from the delivery catheter 305. For example, the distal end region may be formed of a knitted or woven material, such as a polymer or metal (e.g., nitinol) and may be laminated with a blood-impermeable material. In FIG. 25 the suction catheter 300 is shown in the expanded (deployed) configuration, with the distal funnel region shown expanded to a diameter 311 that is many times larger than the more proximal region 309.

The distal end face of the expandable region may include a cover as described above. The cover may be an elastically deformable material that may prevent blood from entering until suction is applied, which may deform to allow clot material to enter. The cover may include a slit or slits, and/or a hole that may be elastically enlarged as clot material is drawn into the funnel region. As described above, the outer distal face (the cover 307) may include one or more external sensors for sensing clot. A macerator may be inserted into the proximal end of the suction catheter and slid axially into the distal expanded (e.g., funnel) region, as shown in FIG. 24. One or more internal sensors may be present within the inside of the funnel region and or the elongate body 309 of the suction catheter for detecting clot material within the suction catheter.

Figure 26:
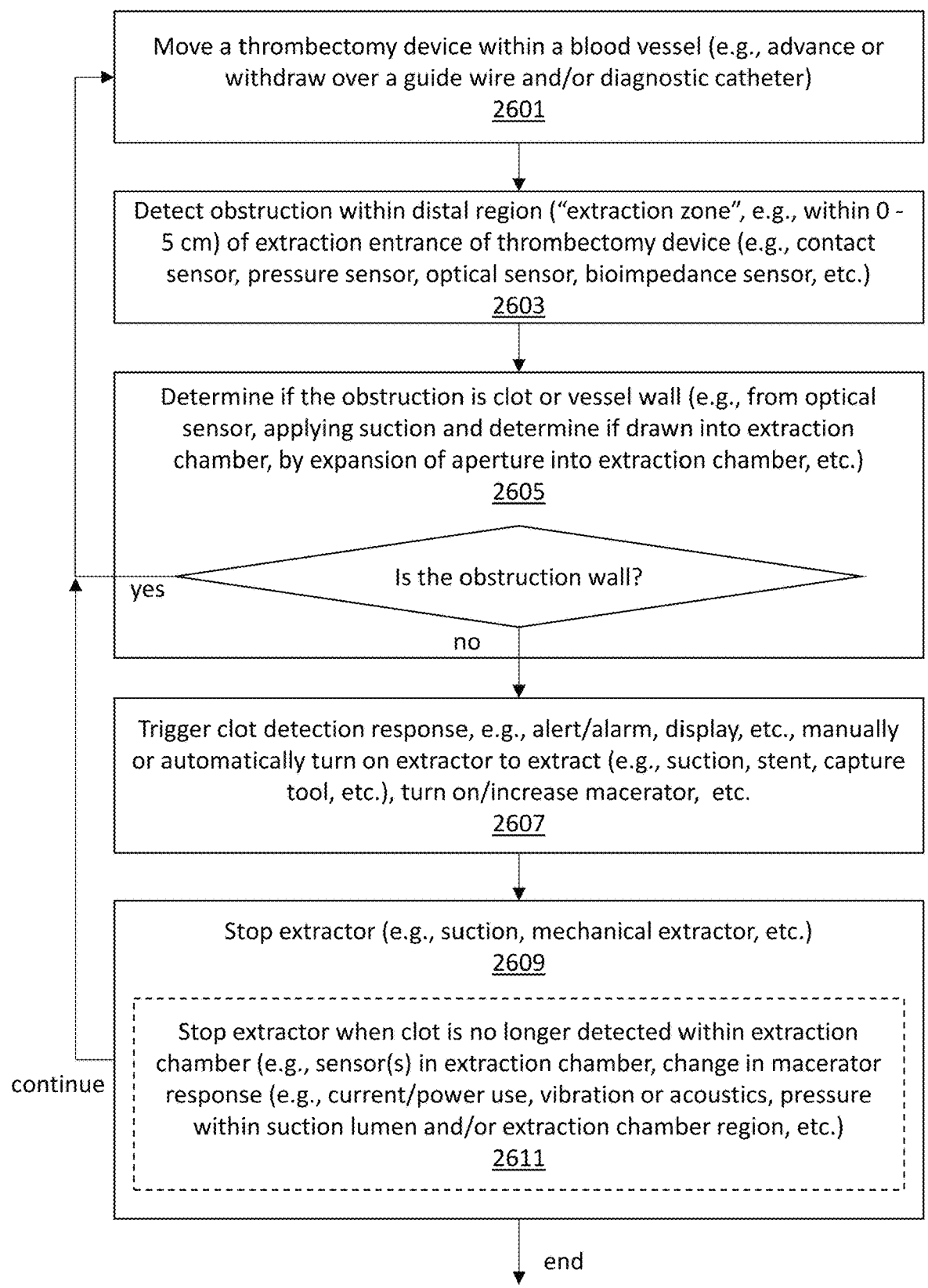
FIG. 26 illustrate one example of a method of detecting a clot material.

FIG. 26 illustrates methods of sensing clot and distinguishing clot material from non-clot (e.g., vessel wall). In general, the methods and apparatuses described herein may electrically, optically, pneumatically, and/or acoustically interrogate the vasculature of a human and the devices within the surgical field to inform clinicians during the removal of obstructive material from the vessels (i.e.: Pulmonary embolism). Current technologies for removing obstructive material such as pulmonary emboli from the vessels require the clinician to navigate up through heart and into the pulmonary arteries and blindly search for and attempt to remove the obstructive material from the vessels. In some instances when using the apparatuses described herein to remove the obstructive material from the vessels, the clinicians access the pulmonary vasculature with a tubular catheter and a guidewire and continuously aspirate blood from the body at the proximal side of the vessel in hopes to pull the obstructive to the catheter and eventually through the catheter and out of the body. This approach causes substantial blood loss, extended procedure time, and increased safety risks such as hemodynamic collapse and/or vessel dissection. In some instances, the clinician will pull vacuum on the proximal end of the catheter, and nothing aspirates back through the catheter. At this time, the clinician doesn't know if they are stuck causing trauma to a vessel wall or if they are attached to a large obstruction and they should wait and allow the suction to pull the obstruction through the catheter. Due to these limitations, there is a need for improved thrombectomy systems that inform the clinician where the obstruction is located within the vessel, what near and/or within distal end of the system, and when to attempt to extract the obstruction. In the present invention, there are embodiments described that address all of these limitations.

The methods and apparatuses described herein may use at least one sensing element near or attached (e.g., within a predetermined distance, e.g., 10 cm or less, 7.5 cm or less, 5 cm or less, 4 cm or less, 3 cm or less, etc.) from the distal end of the system identifying when device has encountered something firmer than blood. When a firmer object is sensed, the apparatus may determine if the obstruction is a clot material or a vessel wall, or some other obstruction. For example, the apparatus may automatically and momentarily apply a negative pressure on the aspiration lumen or informs the clinician to do the same. When the pressure is applied, the system may interrogate (e.g., using at one other sensor within the aspiration lumen or by otherwise detecting material within the extraction chamber of the apparatus) to determine if the system is against an obstructive material (e.g., clot material) or a vessel wall. If obstructive material is sensed, the system then applies continuous negative pressure and initiates the macerating element to chop up the obstructive material and extract the material from the body. If obstructive material is not sensed within the aspiration lumen, the apparatus will not apply additional negative pressure and may inform the clinician that the apparatus did not encounter obstructive material. In some embodiments, the apparatus may monitor the removal of the obstructive material being chopped up and removed and reduce or stop the negative pressure being applied to the aspiration lumen to minimize blood loss.

For example, FIG. 26 illustrates one example of a method of operation a thrombectomy apparatus to detect and remove clot material. For example, in FIG. 26, the general method may include moving a thrombectomy apparatus within a blood vessel (e.g., advance or withdraw over a guide wire and/or a diagnostic catheter) 2601 to position the apparatus within the body. The device may be steered with or without additional guidance (e.g., using fluoroscopy). The apparatus may detect an obstruction within a distal region (an "extraction zone", e.g., within 0-5 cm) of an extraction entrance of thrombectomy device, using, e.g., a contact sensor, a pressure sensor, an optical sensor, a bioimpedance sensor, etc. 2603. Once the apparatus determines that an obstruction present, it may determine if the obstruction is a clot material or a vessel wall (e.g., from optical sensor, applying suction and determine if drawn into extraction chamber, by expansion of aperture into extraction chamber, etc.) 2605.

If the apparatus (e.g., a controller of the apparatus) determines that the obstruction is a clot material, either by directly sensing a property (e.g., electrical, optical, tactile, etc.) of the obstruction, or be determining that the obstruction is capable of being drawn into the extraction chamber and/or cut by the macerator, which is typically only possible when the obstruction material is clot material based on the configuration of the apparatuses described herein, then the apparatus may trigger a clot detection response, e.g., an alert/alarm, a display, etc., either manually or automatically, and may turn on an extractor sub-system to extract; for example, the apparatus may turn on suction and/or a mechanical extraction element (e.g., stent, capture tool, etc.), and/or in some examples may turn on and/or increase macerator activity, etc. 2607. Alternatively if the apparatus determines that the obstruction is not a clot material, it may signal to the user to indicate this, and may continue moving the thrombectomy apparatus.

In any of these methods, the method may also optimally include stopping the extractor sub-system from extracting material when the apparatus determines that clot is no longer detected 2609. For example, the apparatus may stop the extractor sub-system (e.g., turn off suction and/or mechanical extraction elements) when clot is no longer detected within extraction chamber, e.g., when one or more sensor(s) configured to sense material within the extraction chamber no longer detect clot material and/or when the apparatus detects a change in macerator response (e.g., current/power use, vibration or acoustics, pressure within suction lumen and/or extraction chamber region, etc.) 2611.

Figure 27A:
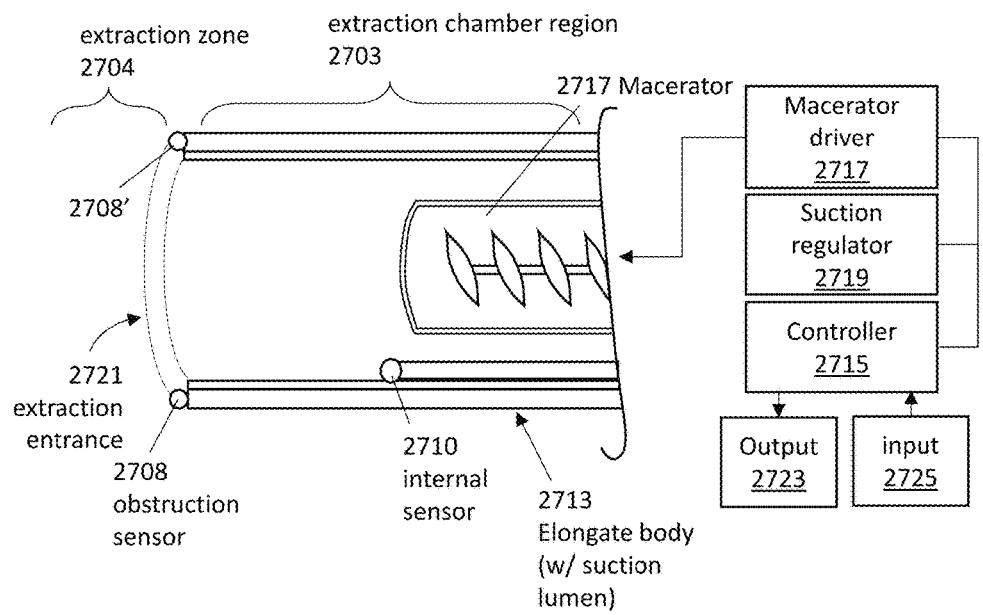
FIG. 27A illustrates one example of an apparatus for removing clot material, including a macerator.
Figure 27B:
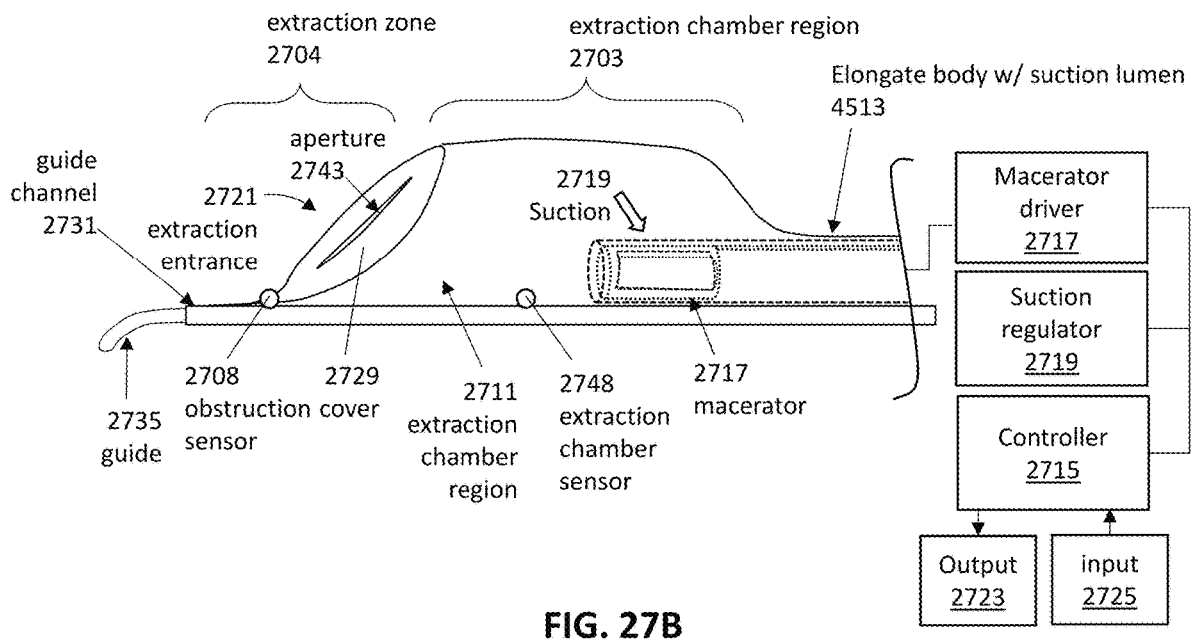
FIG. 27B illustrates an example of an apparatus for removing clot material, including a macerator.

FIGS. 27A-27B illustrate examples of thrombectomy apparatuses that may be configured to perform any of these methods. For example, FIG. 27A shows one example of an apparatus configured as a suction catheter including an elongate body 2713 with a suction lumen, and an extraction chamber region 2703 at a distal end of the catheter. The opening 2721 into the extraction chamber region may be referred to as the extraction entrance and may include one or more forward-directed obstruction sensors 2708, 2708' that are configured to detect or sense an obstruction within the distal-facing extraction zone 2704. The apparatus also includes a macerator 2717 within the extraction chamber region, as well as an internal sensor 2710 that is configured to detect material within the extraction chamber. The apparatus also includes a macerator driver 2717, and optionally a suction regulator 2719, and a controller 2715. The controller may receive inputs from the apparatus (e.g., from the obstruction sensor(s), internal sensors and/or the macerator driver, macerator sensor, and/or suction sensor). The controller may also include one or more inputs for the user to enter control commands and/or data.

The controller may also output one or more outputs 2723 that may include outputs (alerts) to the user based on the operation of the apparatus.

In FIG. 27A, the apparatus may apply suction through the macerator and/or around the macerator. In operation the apparatus may control the application of suction and/or the operation of the macerator based on input from the one or more sensors and/or evidence (e.g., by looking at the macerator drive) of resistance indicating material within the extraction chamber that may be affecting the operation of the macerator.

FIG. 27B shows another example of an apparatus in which the device includes an elongate body with a lumen (e.g., suction lumen) 4513 extending along the length. The distal end region may include a tapering extraction chamber region 2703 that may include an extraction entrance 2721 that is at least partially covered by a cover 2729 including an aperture 2743 (e.g., slit) formed through it. The cover may be permanently placed over the distal-facing extraction entrance, and the aperture may be formed to allow clot material to be drawn in. In the example shown in FIG. 27B, the apparatus includes a guide channel 2731 for passing a guidewire and/or a guide 2735. The extraction chamber region 2711 may be configured to expand and collapse and may include an extraction chamber sensor 2748 that may be within the extraction chamber or external to the reaction chamber but configured to sense within the chamber. The apparatus may also include a macerator 2717 within the suction chamber. In this example, suction passes through the macerator and into the suction chamber. The apparatus may also include a macerator driver 2717 for driving the macerator, and in some examples a suction regulator for regulating the suction applied through the apparatus. A controller 2715 (including on or more inputs 2725 and outputs 2723) may also be included and may include one or more processors, communication circuits, etc. The controller may also include wireless circuitry, and/or a memory for storing and/or transmitting data about the operation of the apparatus.

Figure 28:
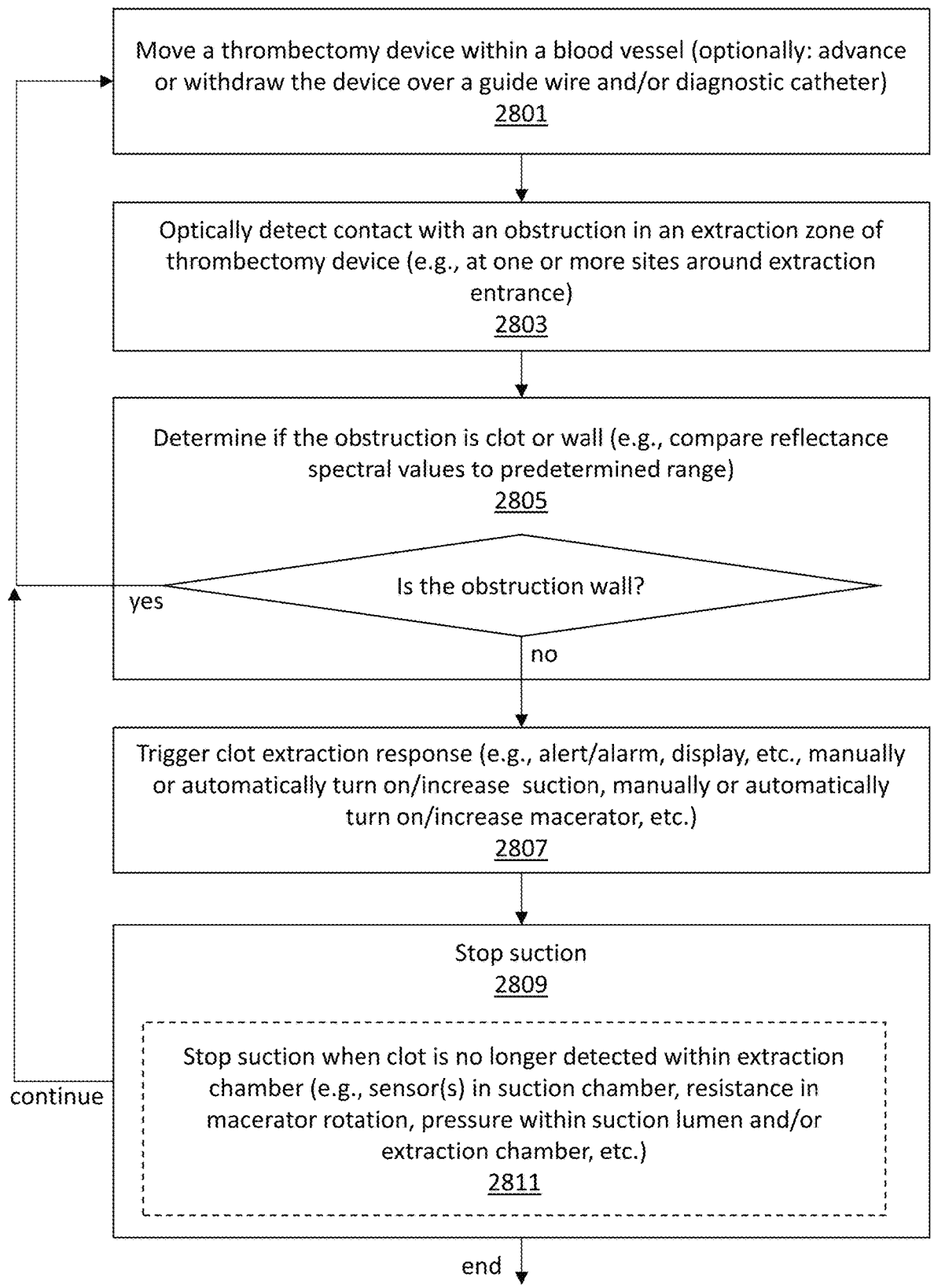
FIG. 28 illustrates an example of a method of detecting clot material using an optical sensor.

FIG. 28 illustrates another example of a method (which may be implemented by the apparatuses described herein. In this example, the method may include moving a thrombectomy device within a blood vessel, e.g., optionally, advance or withdraw the device over a guide wire and/or diagnostic catheter, while preparing to detect an obstruction and subsequently removing the clot material once detected and confirmed by the apparatus that the obstruction is clot material 2801.

In FIG. 28, which shows a particular instance of the methods of FIG. 26, the apparatus and method may be configured to optically detect contact with an obstruction in an extraction zone of thrombectomy device (e.g., at one or more sites around extraction entrance) 2803, and to determine if the obstruction is a clot material 2805. For example, the method or an apparatus configured to perform the method may include determining if the obstruction is clot or wall, e.g., by comparing reflectance spectral values taken from one or more optical sensors configure to detect properties of a material within the extraction chamber 2805. If the obstruction material is not clot material, the user may be alerted as such and the position of the apparatus may be adjusted (e.g., withdrawing away from the obstruction and continuing to advance the apparatus). However, if the obstruction material is determined to be clot material, e.g., based on the reflectance spectral values, a clot extraction response may be triggered 2807. For example, an alert/alarm, display, etc. may be triggered indicating clot material, and the apparatus may manually or automatically turn on/increase suction, manually or automatically turn on/increase macerator, etc. The method or apparatus configured to perform the method may also stop the suction 2809 when clot material is no longer detected, e.g., by stopping suction when clot material is no longer detected within extraction chamber (e.g., sensor(s) in suction chamber, resistance in macerator rotation, pressure within suction lumen and/or extraction chamber, etc.) 2811. Suction and/or the macerator may be stropped immediately (or may be reduced) and/or may optionally be stopped or reduced after a predetermined delay, e.g., to allow clot material within the apparatus to clear the elongate suction channel.

Figure 29A:
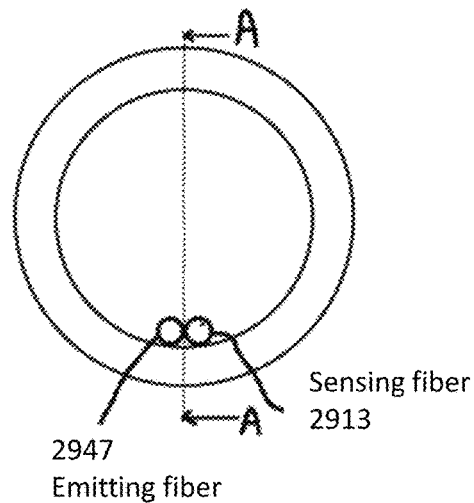
FIGS. 29A-29B illustrate an example of an apparatus for removing clot material using an optical sensor to detect clot material.
Figure 29B:
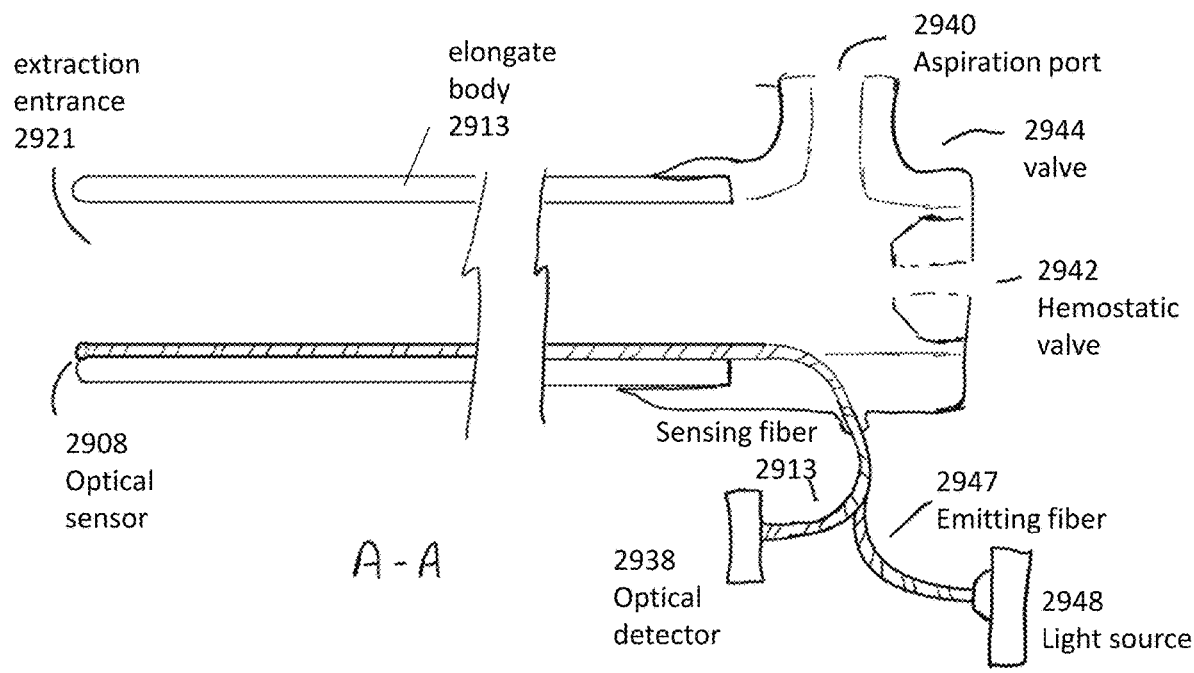

FIGS. 29A-29B illustrate one example of an apparatus that is configured to detect clot material within an extraction region ahead of (distal to) the apparatuses extraction entrance 2921. In this example the apparatus is shown as a catheter apparatus having an elongate body 2913 and a distal end region. An optical sensor 2908 may be positioned distally forward-looking at or near the distal end of the catheter. In some examples the optical sensor may be formed of two (or more) optical fibers; an emitting fiber 2947 and a receiving fiber 2913. As shown in FIG. 29B the apparatus may include a sensing fiber 2913 that is coupled to an optical detector 2938 and an emitting fiber 2947 that is coupled to a light source or sources 2948. The catheter may also include a port for coupling with a hemostasis port 2942, aspiration port 2940, and/or valve 2944. As mentioned above, the apparatus may also include a controller (not shown), a suction regulator (not shown), and optionally a macerator and/or macerator driver (not shown). FIG. 29A shows a transverse section though the distal end region (line A-A') of the apparatus of FIG. 29A, including the emitting fiber 2947 and sensing fiber 2913, shown positioned on an inner surface of the lumen, but may be within the wall of the catheter and/or on an outer surface.

Figure 30A:
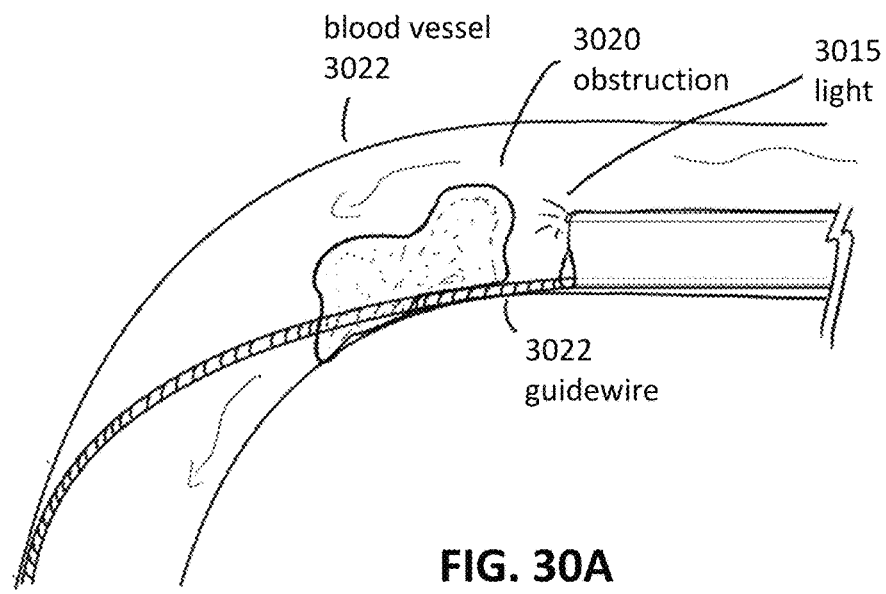
FIGS. 30A-30C illustrate a method of operating an apparatus for removing clot material using an optical sensor.
Figure 30B:
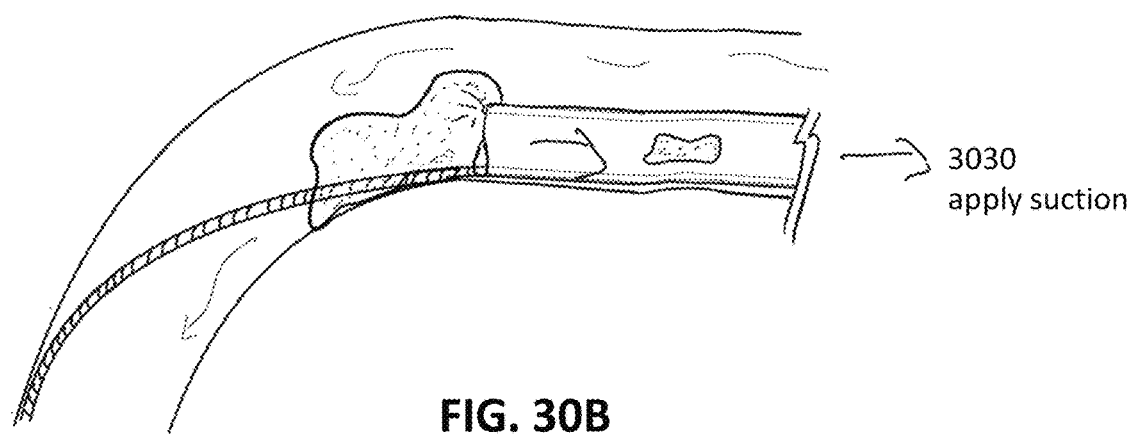
Figure 30C:
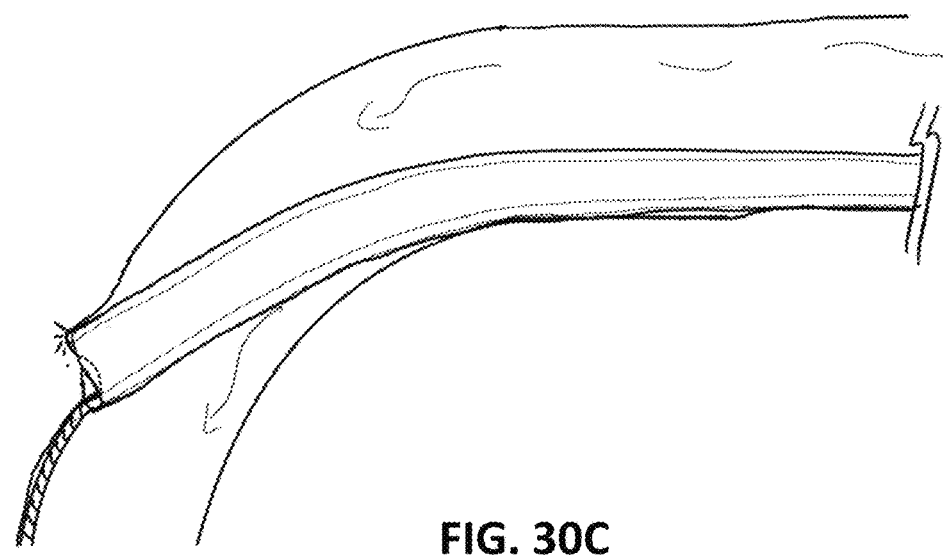

FIGS. 20A-30C illustrate the operation of one example of an apparatus as described above. In FIG. 20A the apparatus is guided through the vessel 3022 over a guidewire 3022 so that a distal end of the apparatus may include an optical emitter (or emitter/detector) that emits a light 3015 of one or more wavelengths, which may be used to distinguish between clot material and wall material as described above. In FIG. 30B the apparatus has driven just proximal to the obstruction 3020. In this example, the emitting/detecting light may detect the obstruction (or contact with the obstruction) and suction may be applied 3030, as shown. The suction may remove the clot material. Thereafter, as shown in FIG. 30C, the apparatus may be advanced distally over the guidewire, but may again hit an obstruction, as shown in FIG. 30C. In this case one or more indicators may indicate that the obstruction is not clot material, but may instead by vessel wall, as shown.

Figure 31A:
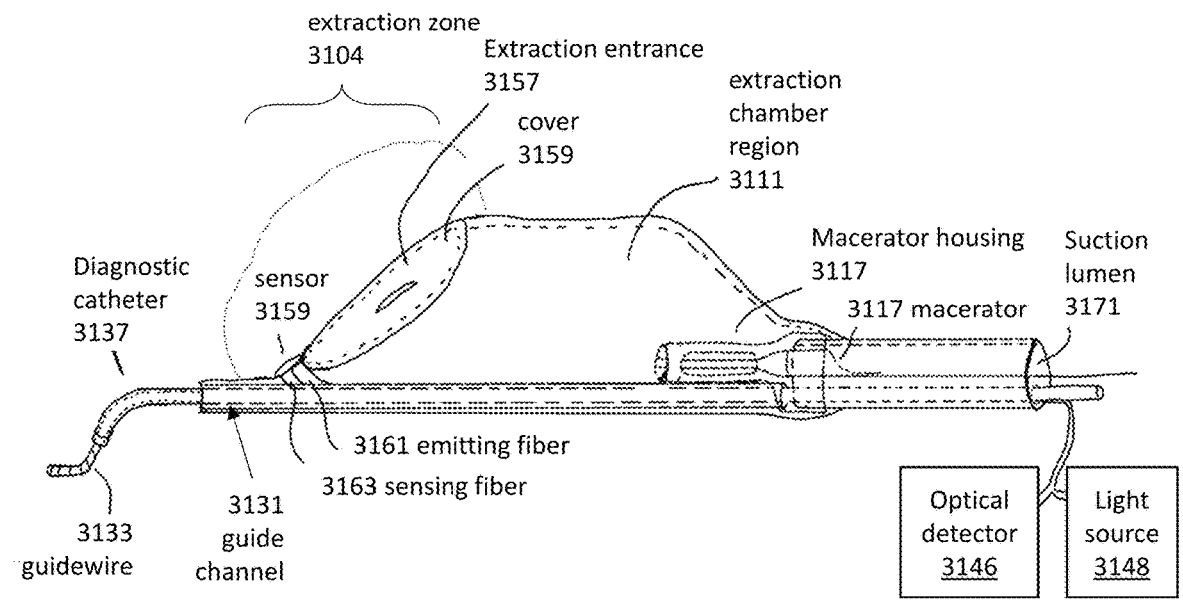
FIGS. 31A-31B illustrate examples of apparatuses for removing clot material.
Figure 31B:
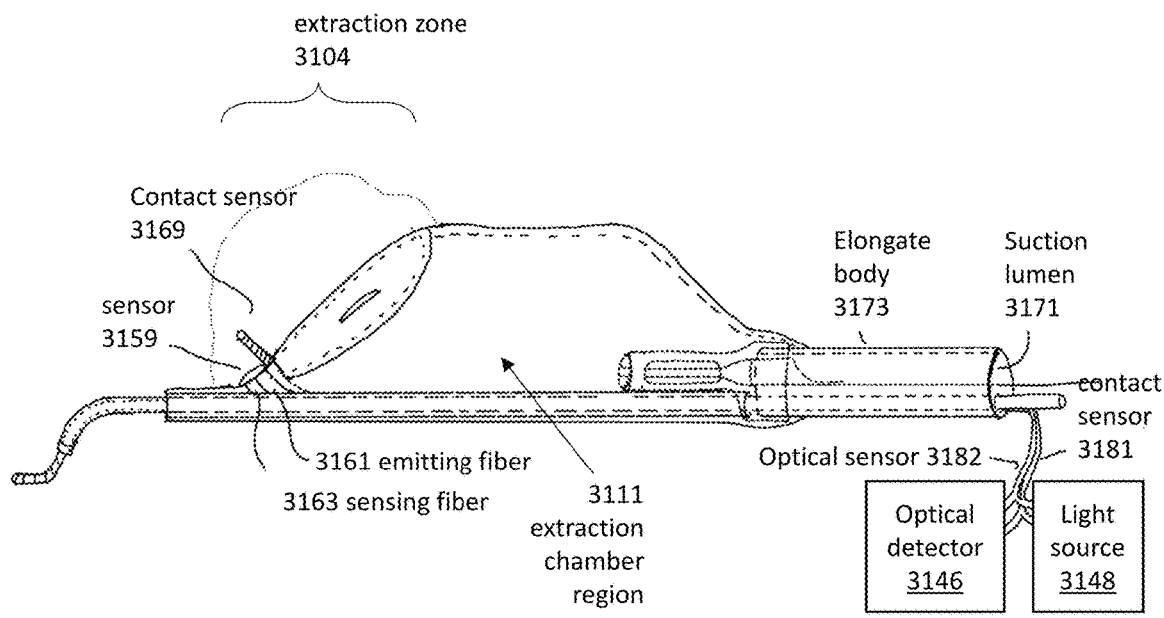

FIGS. 31A-31B illustrate examples of two thrombectomy apparatuses that include an elongate body having an extraction chamber region 3111. A macerator 3117 and/or macerator subsystem (e.g., macerator driver, suction regulator, etc.) may also be included. Suction may be applied through the macerator via a suction lumen 3171. The distal end face of the extraction entrance 3157 may be completely or partially covered by a cover (e.g., membrane 3159) that includes an aperture therethrough. The distal end face may be tapered slightly. In FIG. 31A the apparatus may include an optical sensor 3159 for sensing clot material and/or for distinguishing clot material as described above. The optical sensor may include an emitting fiber 3161 and a sensing fiber 3163 that are coupled to an optical detector 3146 and a light source 3148. A controller (not shown) may be used to coordinate sensing/detection and the response of the apparatus. FIG. 31A illustrates diffused reflectance spectroscopy optimally positioned to monitor the extraction zone of the system while minimizing the impact to the aspiration orifice cross sectional area of the system.

FIG. 31B shows a similar apparatus in which the optical sensor 3169 is configured as a contact sensor also including an emitting fiber 3161 and sensing fiber 3163. The contact sensor in this example may project into the extraction zone. 3104. FIG. 31B illustrates a distal region consisting of a flexible contact sensing element protruding within extraction zone distal to the aspiration orifice and an interrogating sensor positioned to optically analyze the object that enters the extraction zone. The flexible contact sensing element in this embodiment comprises of two flexible polymers fibers made of PMMA adjacently affixed together. The fiber assembly is then jacketed with a protective polymer jacket. In other embodiments, it can be conceived by one skilled in the art being reduced to a single fiber. The use of two fibers was utilized to make the proximal end processing simpler and cheaper. The distal ends of the fibers are cut and polished as above and a flexible optical finger is affixed over the distal ends. The flexible optical finger is designed to be 1-5 mm long, have a diameter range of 0.010-0.020", and a have soft atraumatic distal tip. In this embodiment, the flexible optical finger is made of a low durometer 20-40 shore A polymer such as silicone with a metallic wire helically wrapped around the polymer. The proximal end of the fibers is cut and polished and attached to a light source and a photon sensor. In use, the light source sends light through the emitting fiber into the flexible optical finger. The light shines into the flexible finger and reflects a portion of the light back through the sensing fiber where the photon sensor detects a signal. If the finger is touched, the amount of light reflecting back changes causing a signal change at the photon sensor. The elongated body of the fiber assembly is positioned within the aspiration lumen of the device. In some embodiments, the fiber assembly could have a dedicated lumen that runs throughout the device. The interrogating sensor of this embodiment is constructed similarly to the sensor element in FIG. 1 above. This interrogating element is affixed to the distal taper of the maceration chamber and positioned so the centerline of the optical lens is traversing the extraction zone. The example also contains an integrated reinforced shaped catheter with a guidewire lumen, an expanded collapsible Maceration Chamber having a conformable Aspiration Orifice, an elastic Distal Taper, and a proximal end that is affixed to a catheter body that fluidly connects the maceration chamber to the aspiration lumen of the catheter body. Inside the Maceration chamber, the macerator housing having a distal opening and at least one sidewall opening is position and affixed to the distal end of the Catheter Body shaft so there is still fluid communication between the maceration chamber and the aspiration lumen. Inside of the Macerator Housing, a Macerator Element having at least one sidewall opening axially positioned so that the Housing and Element openings overlap. The Macerator Element is free to rotate within the Macerator Housing and has a metallic wire affixed at the proximal end.

In use, the clinician sets up the system and inserts the distal end of the system into a lumen within the body per standard minimally invasive protocols and advances the system through the lumen towards the obstructive material under fluoroscopy guidance. When an object hits the Contact Sensing Element, the Element flexes changing the light intensity on the photon sensor. At this time, the system will inform the clinician something is in the extraction zone of the system using either a visual light, audible sound, or tactile feel on the handle or base station outside of the body. At the same, the system will interrogate the object using the interrogating sensing element as described above in a previous embodiment. If the object is obstructive material and within the extraction zone, the system will apply a negative pressure to the aspiration lumen pulling the obstructive material into the maceration chamber and activate the macerating element to chop up the material and allow it to pass through the catheter body and out of the body. The aspirating and macerating will continue until material is removed from the extraction zone. This process can be repeated as many times as needed.

Figure 31C:
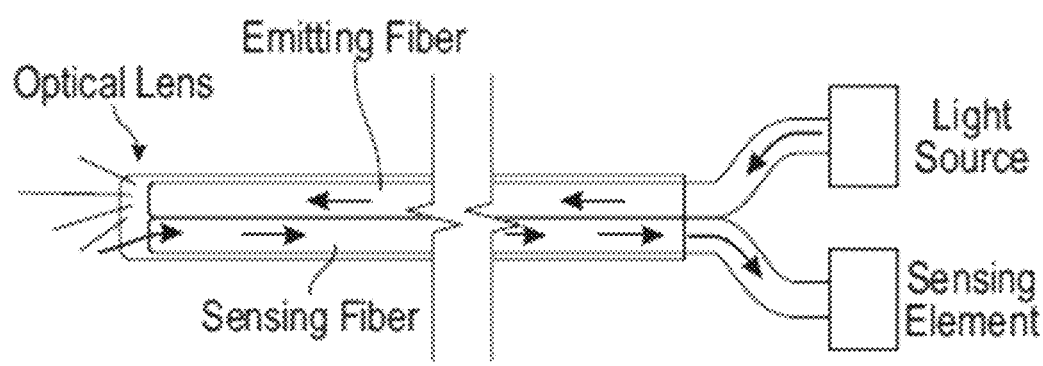
FIGS. 31C-31D show examples of optical sensors.
Figure 31D:
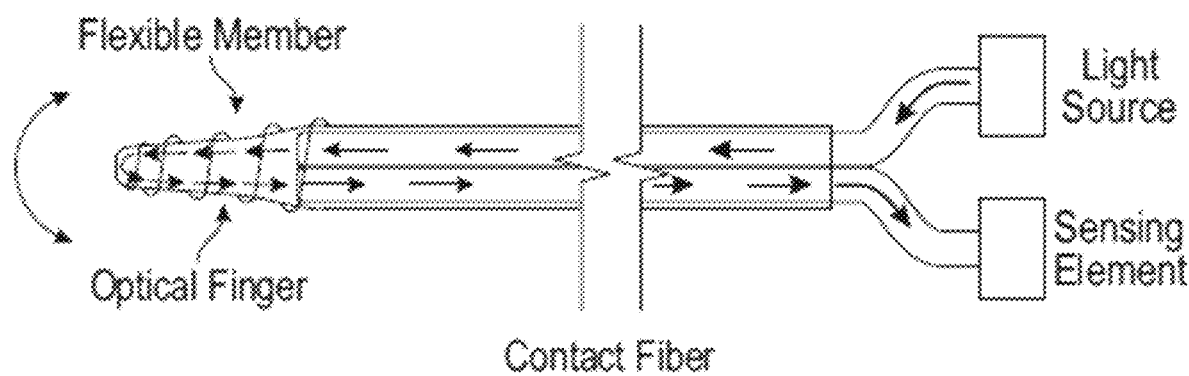

For example, FIG. 31C illustrates one example of an optical sensor or sensor subsystem that may be used. In this example the apparatus includes an emitting fiber, sensing fiber, and an optical lens at the distal end, as well as a light source coupled to the emitting fiber and a sensing element coupled to the sensing fiber. FIG. 31D shows another example of an optical sensor configured as a contact fiber similar to that shown in FIG. 31C, but with an optical finger projection at the distal end receiving input from the emitting fiber and output from a sensing fiber. The distal finger region may include a flexible member.

Figure 32:
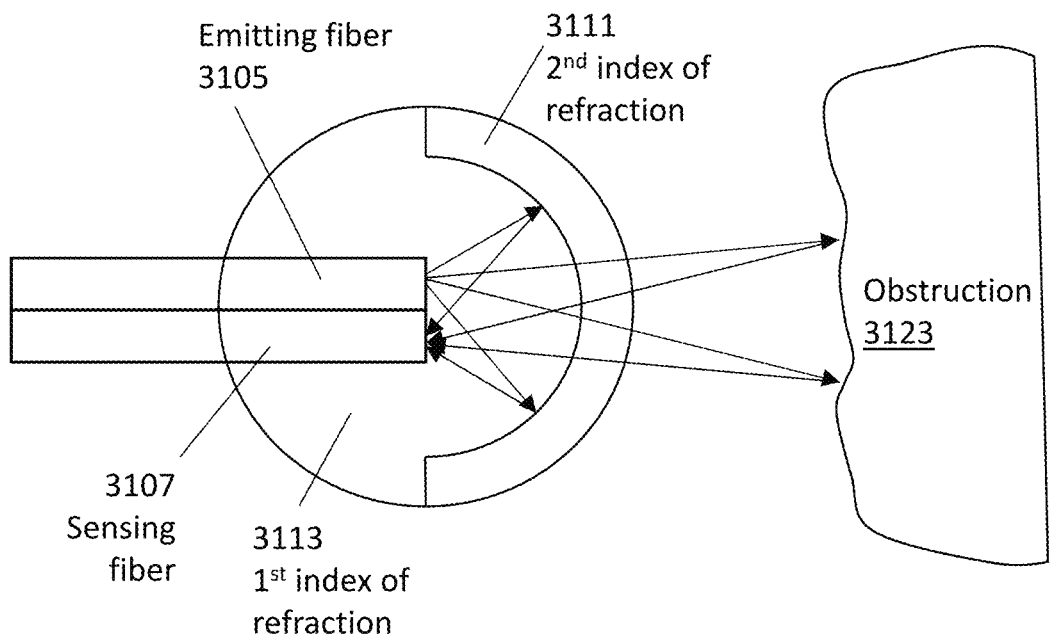
FIG. 32 schematically illustrates one example of an optical sensor.

FIG. 32 illustrates another example of an optical sensor configured to detect an obstruction as described herein. In this example the sensor includes an emitting fiber 3105 and a sensing fiber 3107 that terminate in the center of a spherical region having a first index of refraction 3113. A region having a second index of refraction 3111 may be present on the outer region of the sphere and the optical sensor may detect the difference between the first and second index of refraction may be detected; contact with the obstruction material 3123 may change the shape of the spherical region and therefore the difference between the indexes of refraction. This may allow the detection of contact with a material. In some examples the apparatus may also detect the change in refraction from contact with the obstruction.

Figure 33:
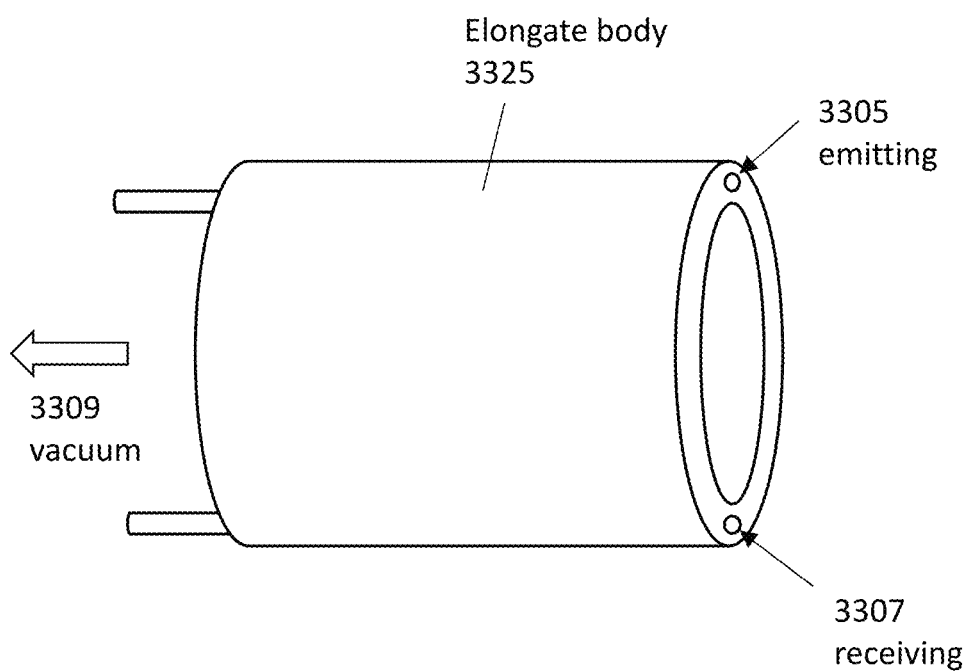
FIG. 33 schematically illustrates one example of an apparatus for removing clot material including an optical sensor.

FIG. 33 shows an example of an apparatus in which an emitting 3305 and sensing 3307 portion of the sensor are separated over the diameter of the elongate member 3325 at the distal opening into the extraction chamber. For example, the elongate member (elongate body) may be a suction catheter, into which suction 3309 may be controllably applied.

The methods and apparatuses described herein may electrically, optically, pneumatically, and/or acoustically sense the contents within a lumen of a human and the devices within the extraction region As illustrated above, examples of these apparatuses may have at least one sensing element to detect when an obstruction is located within extraction zone of the aspiration orifice and to interrogate the obstruction to determine if the obstruction shall be extracted or bypassed (i.e.: Clot vs vessel wall). Other examples have at least two sensing elements to detect when an obstruction is located within extraction zone of the aspiration orifice and to interrogate the obstruction to determine if the obstruction shall be removed or bypassed (i.e.: Clot vs vessel wall).

In some examples, optical sensing may detect and interrogate obstructions within the extraction zone. An elongated flexible catheter body with an inner lumen (aspiration lumen) may have a distal and proximal end, a handle with an aspiration port and hemostasis valve, and sensing fiber assembly containing an emitting fiber proximally connected to a light source, a sensing fiber connected to a photon sensor, and an optical lens attached the distal end of the fiber assembly as shown in FIGS. 29A-31B. The sensing fiber assembly may be affixed to the inner lumen of the catheter body such that the optical lens of the assembly is aligned (e.g., within 5 mm) of the distal end of the aspiration lumen and runs proximally throughout the catheter body out of the handle where the connectorized proximal end of the fibers are connected to a light source and photon sensor. The optical lens of the sensing fiber assembly may be positioned relative to the distal orifice of the aspiration lumen because obstructive material within this extraction zone can be brought into the aspiration lumen when negative pressure is applied to the lumen. The fiber assembly can be free to move independent of the catheter body and handle either in a dedicated lumen of the catheter body or within the aspiration lumen of the catheter body. The fibers of the fiber assembly may be made of flexible glass or plastic such as PMMA with a cladding having a diameter range of 50-500 microns, with a preferred diameter of 125 microns per fiber. The fibers are combined and covered with an outer protective jacket. The distal ends of two fibers are cut and polished ensuring the distal end is perpendicular to the centerline axis of the fiber. The distal ends are then potted together in a urethane or silicone substance creating the optical lens. The optical lens has an atraumatic distal geometry. The proximal end of the fibers may be cut and polished as the distal ends were and each fiber end may be potted into an independent connector (i.e.: SMA, ST, or MU connectors). In some examples, the proximal end of the emitting fiber could be permanently affixed to a single LED and placed inside the handle with a small electrical circuit and battery. The flexible catheter body of this example is a standard reinforced polymeric shaft constructed similarly to the flexible elongated shaft as disclosed in U.S. application Ser. No. 17/393,618 which is herein incorporated by reference in its entirety. The handle may be made of a rigid to semi-rigid plastic such as nylon, abs, or polycarbonate that can be injection molded or machined. The hemostasis valve may be made of an elastic material such as silicone.

As shown in FIGS. 31C-31D and 32, optical sensing may utilize diffuse reflectance spectroscopy using the fiber assembly to detect and interrogate an obstruction that is within the extraction zone. The light source used may emit a light range of 360-2500 nm and the sensing fiber will connect to at least one spectrometer to analyze the reflected light. In other examples, the emitting fiber(s) may be affixed to a specific wavelength LED such as 500 nm and the sensing fiber permanently affixed to a sensing element, such as silicon diode. 3 or 4-fiber assemblies may be used that utilizes two specific wavelengths such as 480-520 and 1530-1565 nm.

In use, a clinician may insert the system into a lumen within the body per standard minimally invasive protocols and advances the system through the lumen towards the obstructive material. As obstructive material enters the extraction zone or the aspiration orifice gets near the lumen wall, the intensity of the light returning changes and the system will either graphically display the changes for the clinician or compare the intensity readings from a lookup, determine what is in the extraction zone, indicate to the clinician what is in the extraction zone, and/or apply a negative pressure to the aspiration lumen.

The examples described above may use light to detect contact; the contact sensing element could use an electromechanical element that turns mechanical movement into an electrical signal such as a piezoelectric film or energizing a conductive element like a spring and monitoring the resistivity change due to wire displacement.

Figure 34:
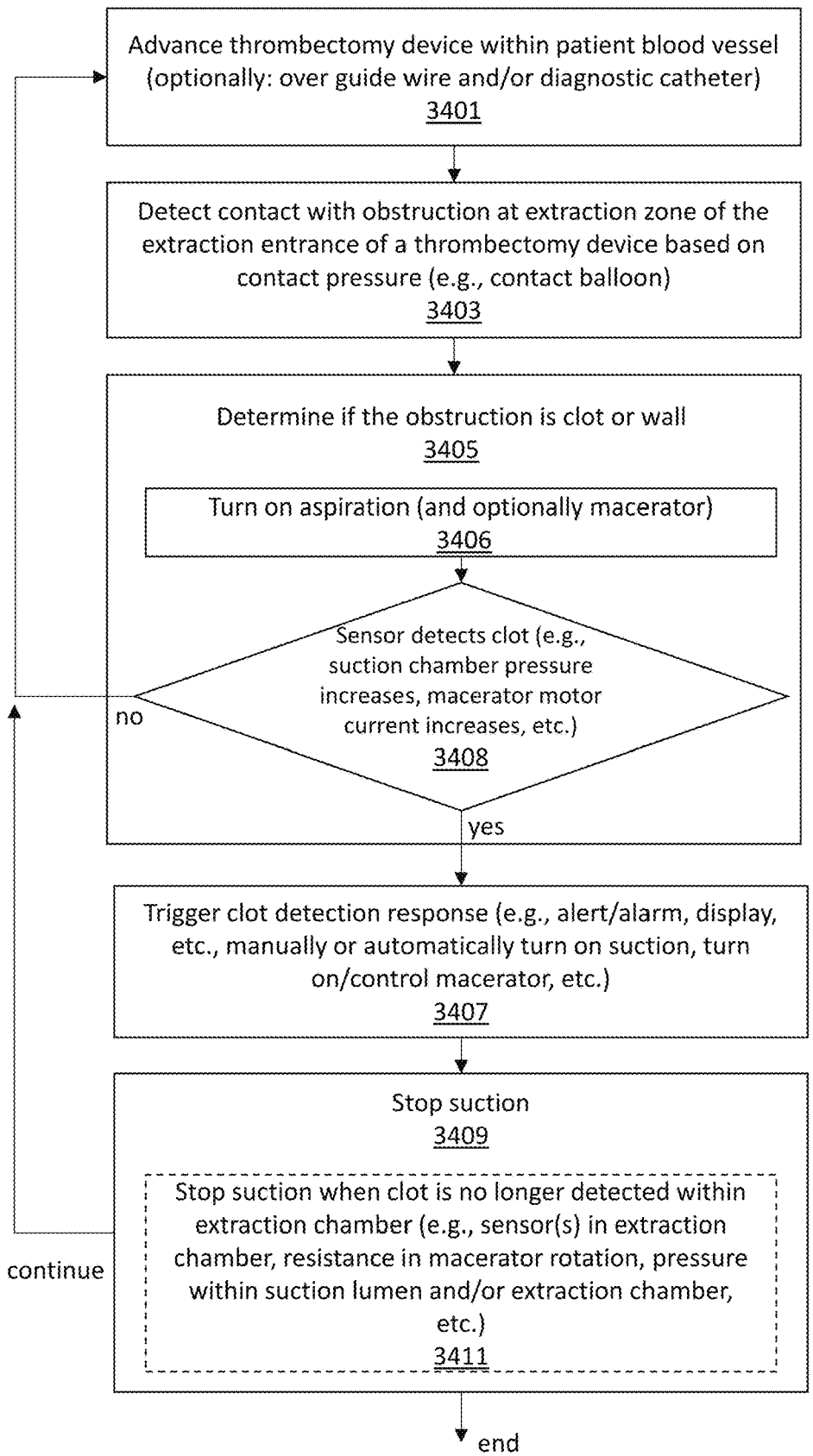
FIG. 34 illustrates an example of a method of detecting clot material including detecting a contact pressure.

Any of the methods and apparatuses described herein may be configured to detect clot material based on contact pressure. For example, FIG. 34 illustrates a method of identifying a clot material and distinguishing the clot material from vessel wall or other materials, using contact sensing. In FIG. 34, the method may include inserting and/or advancing a thrombectomy apparatus within a blood vessel of a patient (e.g., over a guidewire, over a diagnostic catheter, etc.) 3401, and detecting contact with an obstruction at an extraction zone of the extraction entrance of the thrombectomy apparatus, based on contact pressure. The contact pressure may be detecting by a contact sensor 3403 such as a pressure sensor, e.g., using a contact balloon or other inflated member that detects a change in pressure on the material within the contact balloon. Other contact sensors may include optically-based contact sensors, such as those described above (see, e.g., FIGS. 31C, 32D and 32).

Other contact sensors may be based on impedance sensing, which may detect contact by a change in electrical impedance.

Once contact is identified, the apparatus (e.g., using a controller portion of the apparatus) may trigger an alert indicating contact and may further identify that the contact is with a clot material or with some other material, including vessel wall 3405. The step of distinguishing between clot material and other (e.g., vessel wall) material may be performed in a number of ways. In some examples, as shown in FIG. 34, the apparatus may turn on or pulse suction, e.g., aspiration) through the apparatus if suction is not already being applied and may detect that clot material is within the extraction chamber, having entered from the extraction zone though the extraction entrance. In some examples, the closed or semi-closed extraction entrance, which may be at least partially covered by a cover (e.g., membrane) may allow clot material to pass through the aperture but would prevent lumen wall or other material from entering, or entering beyond a predetermined depth into the extraction chamber. Thus, the extraction chamber may be monitored to determine if a material, presumed to be clot material, has entered during the application (e.g., pulse) of suction/aspiration 3406. In some examples one or more sensors may be present within the extraction chamber or oriented to sense within the extraction chamber (even if outside of our downstream from the extraction chamber), which may sense when clot is present but not vessel wall 3408. In some example, clot material within the extraction chamber may be detected optically (by one or more optical sensors within the extraction chamber), and in general the internal sensor(s) may be oriented to sense at a desired internal proximal position, e.g., sufficiently far from the extraction entrance to distinguish clot material from vessel wall, such as 2 mm or more (e.g., 3 mm or more, 4 mm or more, 5 mm or more, 6 mm or more, 7 mm or more, 8 mm or more, 9 mm or more, 1 cm or more, etc.) within the extraction chamber. In some examples the method and apparatus may be configured to detect clot material within the extraction chamber by detecting a change in the activity of the macerator. For example, the macerator may be activated either continuously or when sensing clot (e.g., when applying suction, including the pulse(s) of suction); the interaction between clot material within the extraction chamber and the macerator may result in a change in the macerator behavior that is detectable when compared to a baseline (e.g., operated without suction or operated before contact is detected. In some examples the apparatus may detect contact between the macerator and a clot material within the extraction chamber by detecting a change in the driving energy (e.g., current applied), and/or a change in the rate of activation (e.g., rotation, reciprocation, etc.), and/or a change in the vibration, and/or a chance in the sound of the operation of the macerator. The activity of the macerator may be detected remotely, e.g., at the proximal end of the apparatus, as by monitoring the applied energy (e.g., current), the resistance to actuating, etc.

If clot material is detected within the extraction chamber the method or apparatus may trigger a clot detection response. If no clot material is detected the method or apparatus may indicate this as well. For example, if no clot material is detected, the apparatus may determine indicate an alert that the occlusion is likely a vessel wall, and/or may turn off (or reduce) suction and allow the device to be repositioned. Similarly, if clot material is determined to be present in the extraction chamber, the method and/or apparatus may trigger the clot detection response, which may include an alert/alarm (e.g., audible, visual, including but not limited to emitting or modifying a tone, indicator light (s), display, etc.) indicating that clot material is present, and allow for manual or semi-manual operation of the apparatus. Alternatively or additionally, the clot detection response may include manually or automatically turning on or increasing suction, and/or turning on or increasing the macerator, etc. 3407, in order to remove clot material. The clot detection response may be continued until clot material is no longer detected. For example, the clot detection response (e.g., suction and/or macerator activity) may be suspend or reduced if the clot is no longer detected distally outside of the extraction chamber and/or is no longer detected within the extraction chamber 3411. In any of these cases, the clot detection response may be immediately stopped or reduced or may be stopped or reduced after a delay. For example the clot detection response may be stopped or reduced after a delay of a few seconds, minutes, etc. to allow clot material to clear though the lumen (e.g., suction lumen) of the apparatus.

Figure 35A:
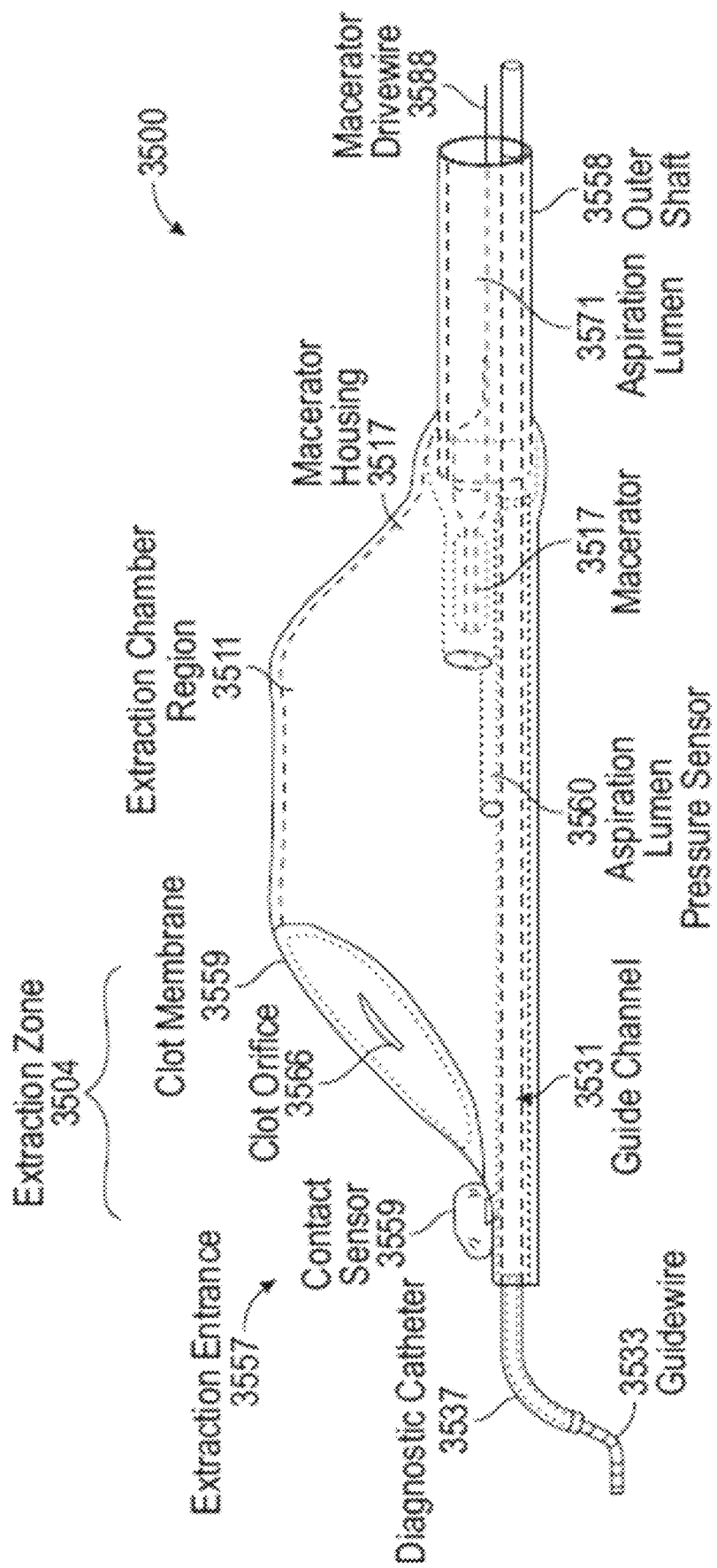
FIGS. 35A-35B illustrate an example of an apparatus for removing clot material.
Figure 35B:
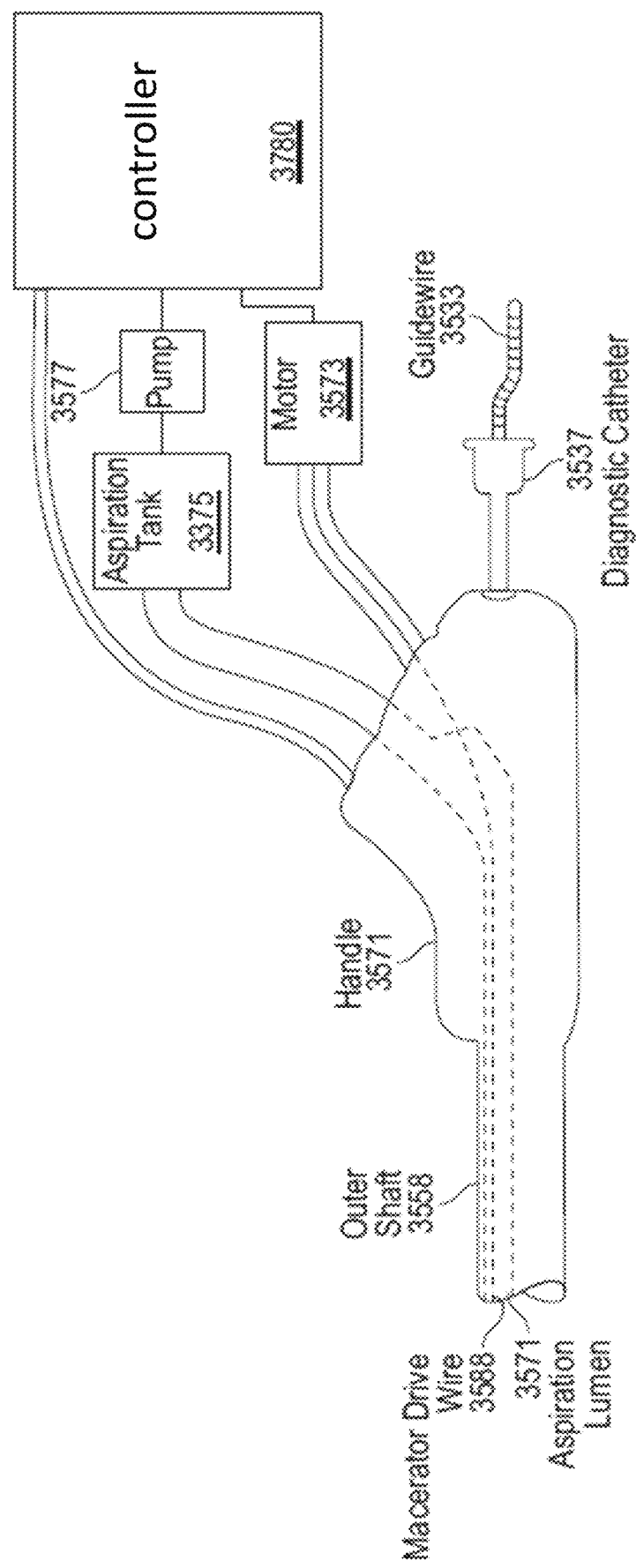

FIGS. 35A and 35B illustrate an example of a distal portion of an apparatus 3500 (FIG. 35A) and a proximal portion (FIG. 35B) that is configured for contact sensing as described above. In this example, the apparatus includes an expandable extraction chamber region 3511 at a distal end region of the apparatus. The extraction entrance 3557 is covered by a clover (membrane 3559) in which an aperture (orifice) 3566 is present to allow passage of clot material. In this example the cover 3559 is flexible and the aperture 3566 is configured as a cut or slit through the cover that may expand to pass (and hold) larger clots while closing to limit or prevent blood loss when clot is not present. The extraction chamber is formed on a distal end of an elongate catheter-like body including a suction lumen (aspiration lumen 3571). A macerator 3517 is positioned within the extraction lumen and the macerator may fit into and through the catheter body region so that the macerator extends distally into the extraction chamber region 3511. A drive shaft 3588 extends proximally; in this example the macerator may be rotated by rotating the flexible elongate drive shaft. The distal end of the extraction chamber, including the extraction entrance 3557 may be angled (e.g., wedge-shaped), concave or convex. In FIG. 35, the apparatus includes a guide channel 3531 for a guide element 3533 (e.g., guidewire and/or diagnostic catheter 3537, which may include a pre-bent, steering region).

The apparatus shown in FIG. 35A also includes at least one contact sensor 3559. In this example the contact sensor is a balloon element that may connect to a pressure sensor to detect contact with the balloon region; contact may increase the pressure of a fluid or other material within the balloon and/or an elongate member coupled to the balloon (not shown). The actual pressure sensor may be at a proximal end of the apparatus (e.g., near the proximal end, e.g., FIG. 35B).

Any of these apparatuses may include a proximal handle 3571 coupled to the outer shaft 3558 that encloses the suction lumen 3571 and macerator drive 3588. In some examples including a pressure sensor as part of the external contact sensor 3559, the contact sensor may be positioned within the extraction zone 3504 at the distal end of the device, but the pressure sensor coupled to the contact sensor may be part of or in communication with the controller 3780 at the proximal end of the apparatus.

In general, a controller may include circuitry for controlling operation of the macerator, suction and/or alerting the user. For example, the controller may couple to both the external sensor 3559 in examples including them, as well as any sensors for sensing clot material within the extraction chamber; in FIG. 35A the apparatus includes a pressure lumen 3560 that may be coupled to a pressure sensor in communication with the controller 3780. The controller may also control operation of a macerator driver (e.g., motor 3473, drive shaft 3588, etc.). The controller may also regulate the suction applied through the suction lumen 3571, e.g., by coupling to a pump 3577, suction/aspiration tank 3375 and/or one or more valves (e.g., bleed valves, etc.). As mentioned above, the controller may also monitor the operation of the macerator drive to detect a load on the macerator that may indicate a clot material within the extraction chamber region, e.g., by monitoring the current applied to drive the macerator.

Figure 35C:
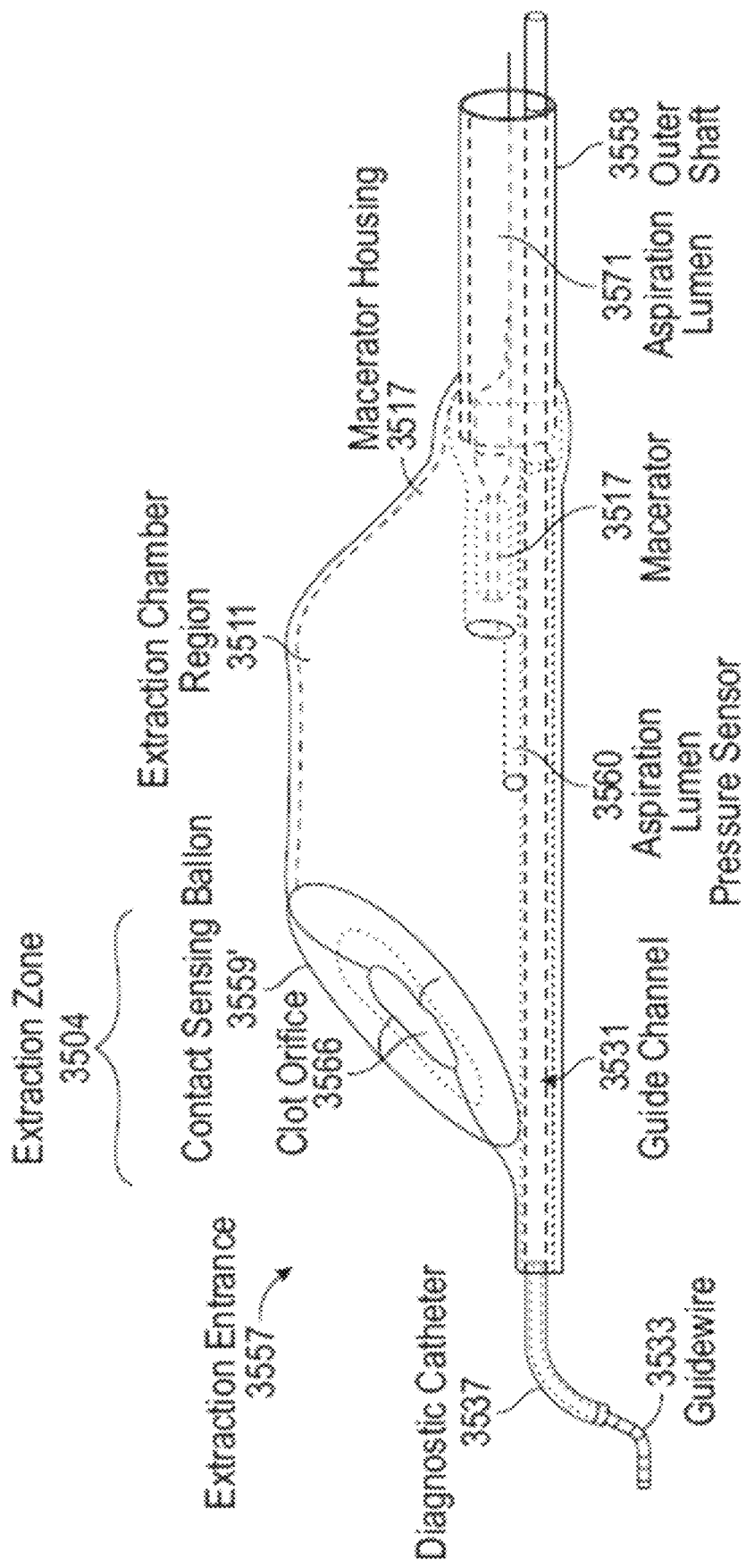
FIG. 35C shows another example of an apparatus for removing clot material including a contact sensor.

FIG. 35C illustrates an alternative version of an apparatus including a contact sensor similar to that shown in FIG. 35A. In this example the contact sensor 3559' is configured as an annular balloon that surrounds the extraction entrance and the aperture 3566 into the extraction chamber 3511. This may allow for detecting contact around any portion of the extraction entrance 3557 within the extraction zone 3504. A pressure lumen (not shown) may couple the internal region of the contact sensing balloon(s) 3559' with a pressure sensor, which may be monitored by the controller.

Figure 36:
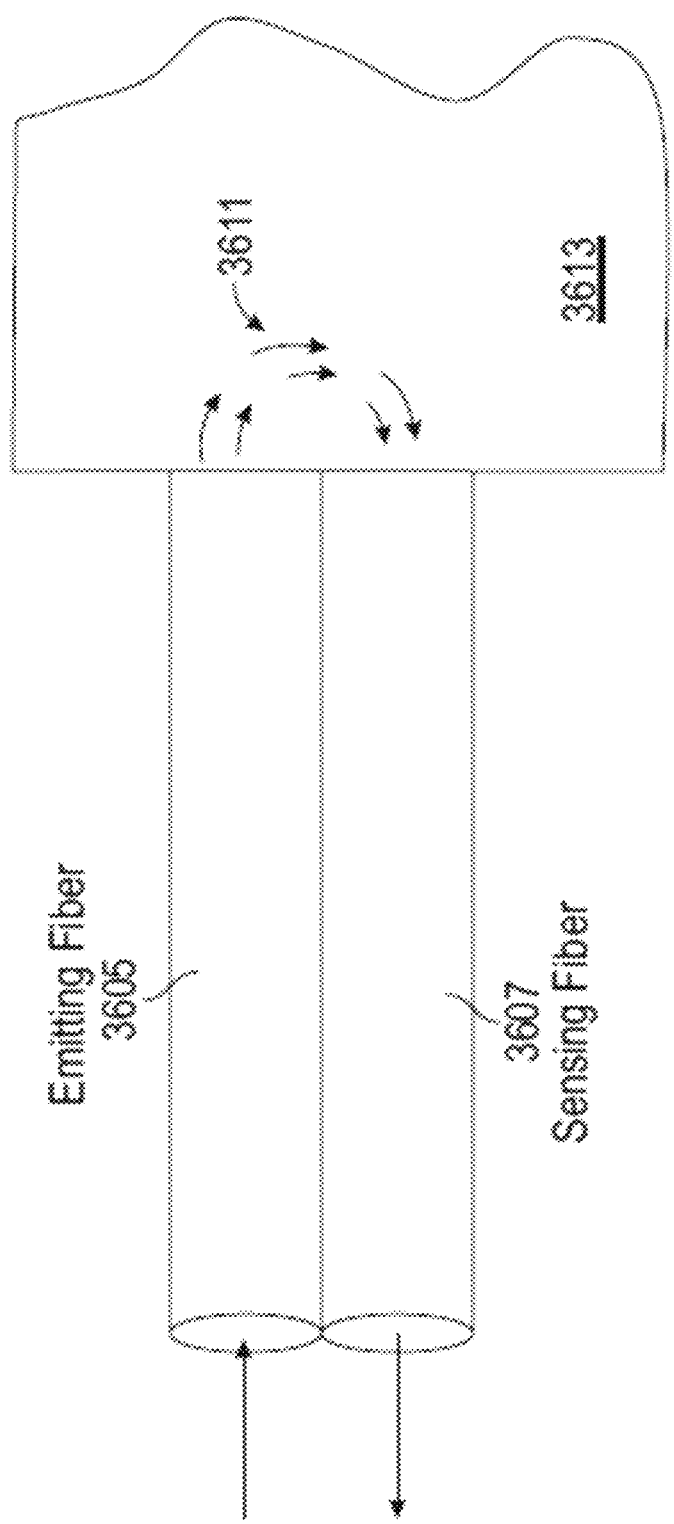
FIG. 36 schematically illustrates one example of an optical contact sensor including an emitting fiber and a sensing fiber.

FIG. 36 illustrates another example of a contact sensor. In this example, the contact sensor is an optical contact sensor that may be particularly well suited to detect contact with a vessel wall or other tissue. For example, in FIG. 35 the sensor includes an emitting fiber 3605 that is coupled adjacent to a sensing fiber 3607 so that light 3611 emitted from the sensing fiber may reflect off of the tissue and be detected by the sensing fiber. When the sensing and emitting fibers are in contact with a tissue 3613, depending on the wavelength of light emitted, characteristic changes in the absorption may be detected indicating tissue, including oxygenated tissue. For example, the sensor may be configured to detect pulse oxygenation. This sensor may be positioned external to the extraction chamber and may detect contact with an obstruction. As mentioned above, any appropriate contact sensor may be used.

Figure 37A:
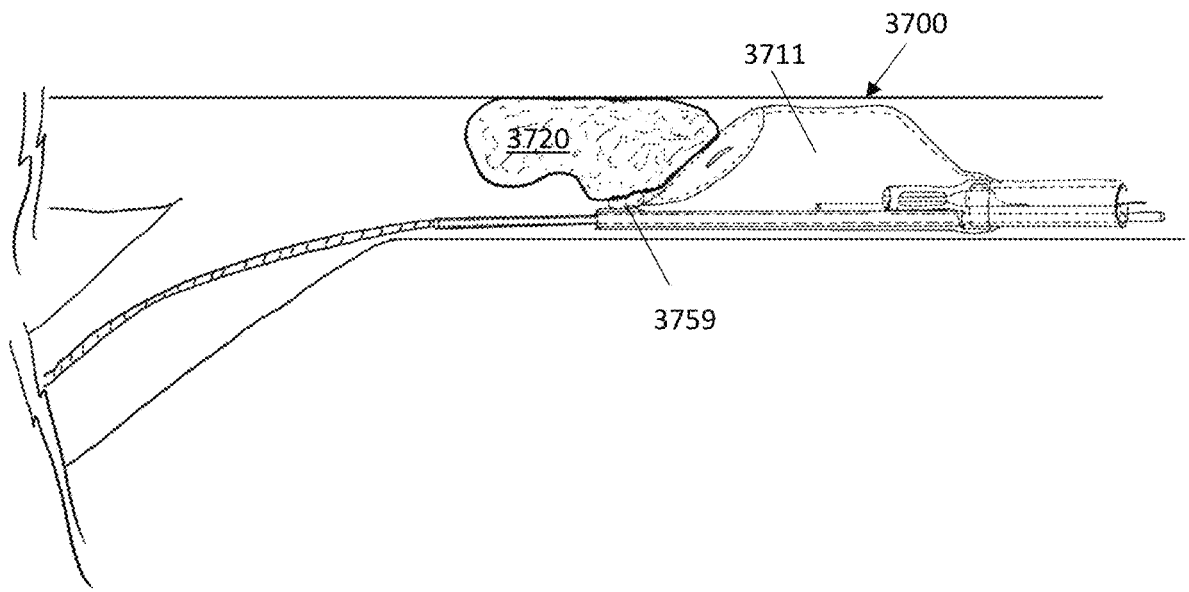
FIGS. 37A-37D illustrate operation of an apparatus for removing clot material including a contact sensor.
Figure 37B:
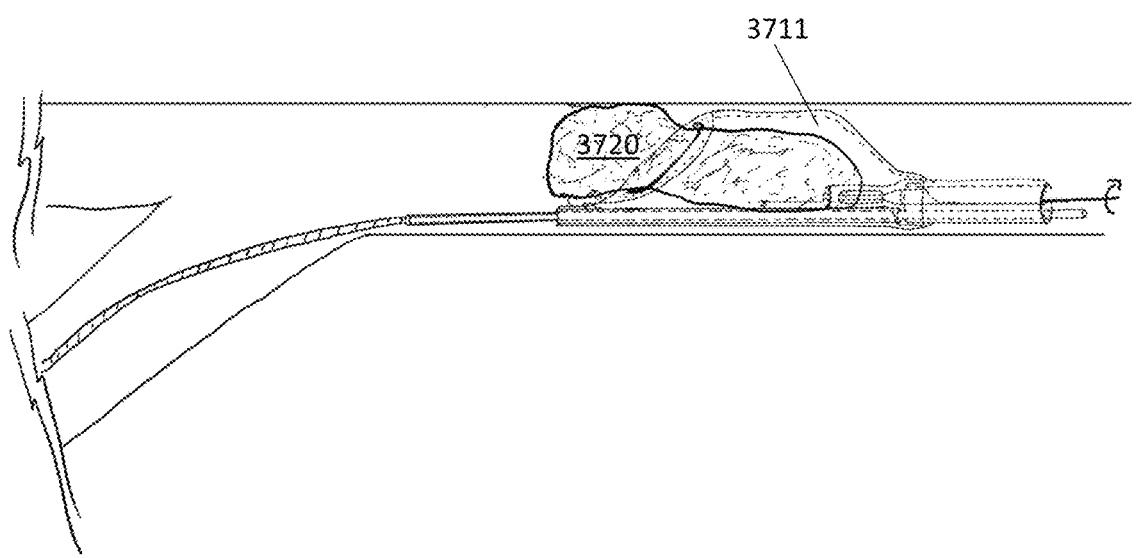

FIGS. 37A-37D illustrate operation of an apparatus using a contact sensor to detect an obstruction similar to that shown in FIGS. 35A-35C. In FIG. 37A the apparatus 3720 is advanced forward until a contact sensor 3759 in the extraction region distal to the extraction entrance into the extraction chamber indicates contact with an obstruction 3720. The controller may detect contact by comparing the contact sensor (e.g., a pressure sensor coupled to a balloon chamber at a distal end region of the device, optical sensor, impedance sensor, etc.) to a baseline. For example, if the contact sensor is a pressure sensor, the controller may determine that the pressure indicates contact with an obstruction (e.g., pressure increased above a threshold). The controller may then trigger an alert indicating an obstruction and may determine if the obstruction is clot material by, e.g., triggering or requesting that the user trigger a pulse of suction, as shown in FIG. 37B. If (as in this example) the obstruction is clot material, the material may be drawn into the extraction chamber 3711, as shown. The controller may detect material within the extraction chamber, e.g., by one or more sensors configured to detect material within the extraction chamber, and may trigger a clot extraction response (e.g., suction, macerator, etc.).

Figure 37C:
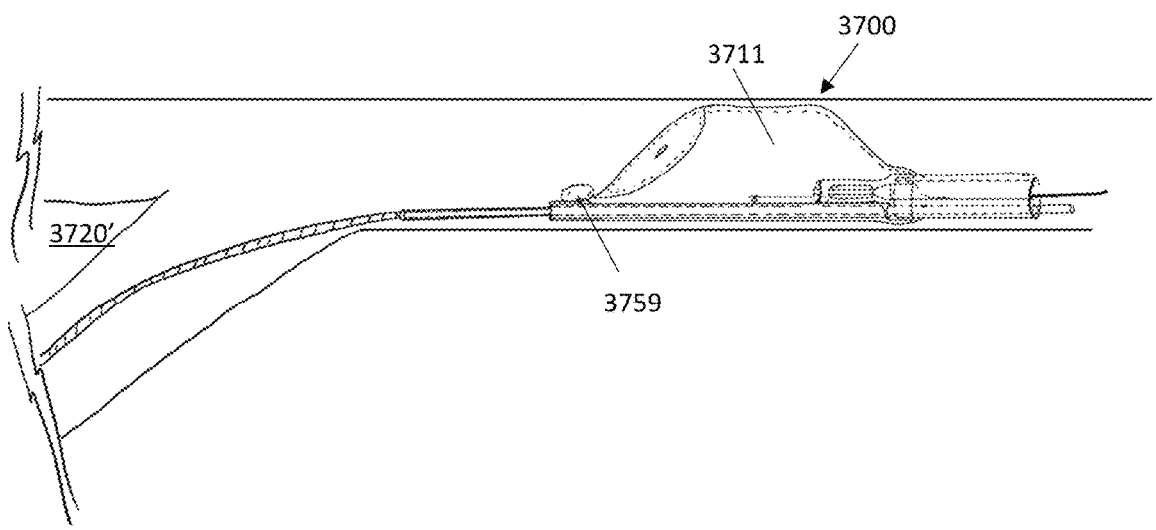
Figure 37D:
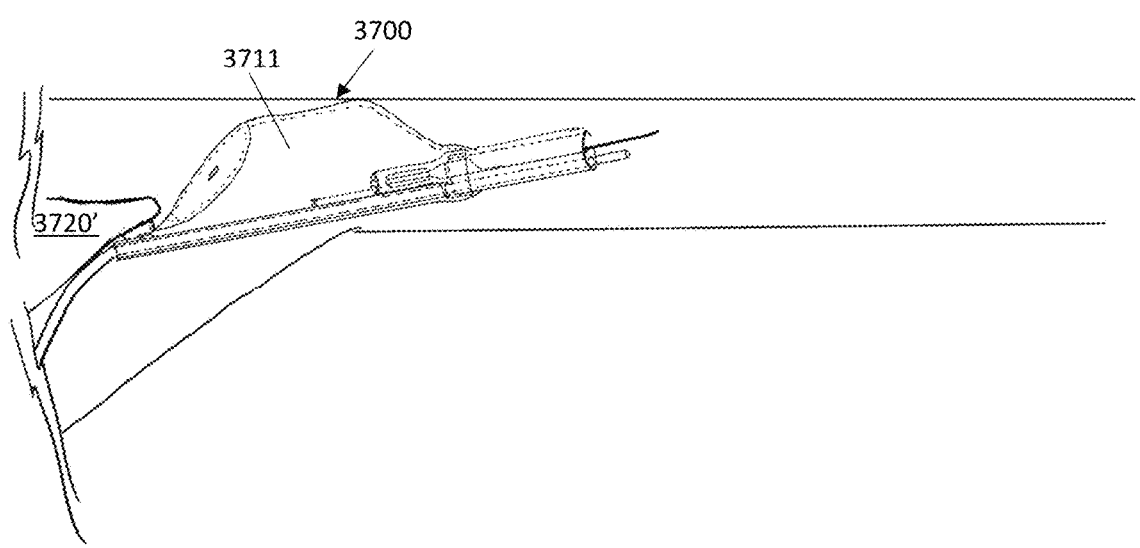

FIGS. 37C and 37D illustrate another possibility, in which the obstruction 3720' is a portion of the vessel wall (e.g., a bifurcation). For example, FIG. 37C may show the same apparatus after removal of the clot material following FIG. 37B. After removing the clot material the contact pressure may drop, and the sensor sensing the inside of the extraction chamber may no longer register a material (in some examples, chamber pressure may drop) and/or the macerator driving current may decrease, indicating the clot material has been removed. The suction may be reduced or discontinued, and the apparatus may continue to be advanced. In this example, the contact sensor 3759, in FIG. 37D may detect an obstruction 3720', and may apply suction (e.g., a pulse or low-level of suction) but will not detect the obstruction within (or very far within) the extraction chamber 3711, since the wall material will not be soft/pliant enough to be pulled very far into the extraction chamber, if at all. For example, the contact pressure on the contact sensor may increase, but the sensor within the chamber (e.g., chamber pressure) does not change above a threshold and/or the macerator driver does not indicate a significant change in the drive energy (e.g., current), so the controller concludes no obstruction is present, and may alert the user that a non-clot obstruction (e.g., wall) is present.

Figure 38A:
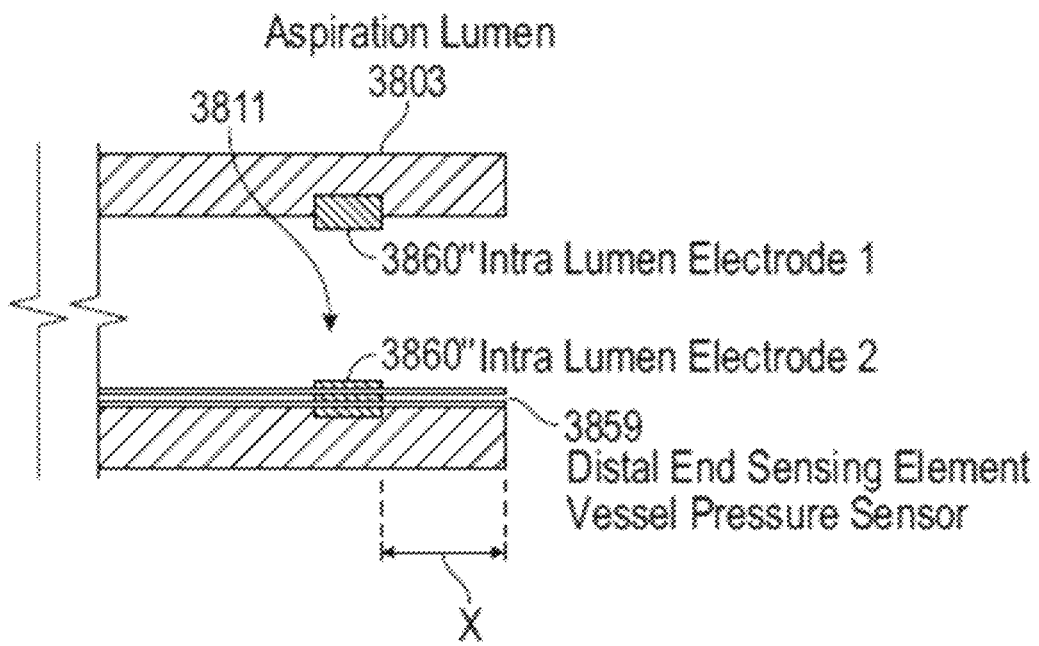
FIGS. 38A-38B illustrate examples of extraction entrances of apparatuses including sensors for detecting material entering the extraction chamber region of the apparatus.
Figure 38B:
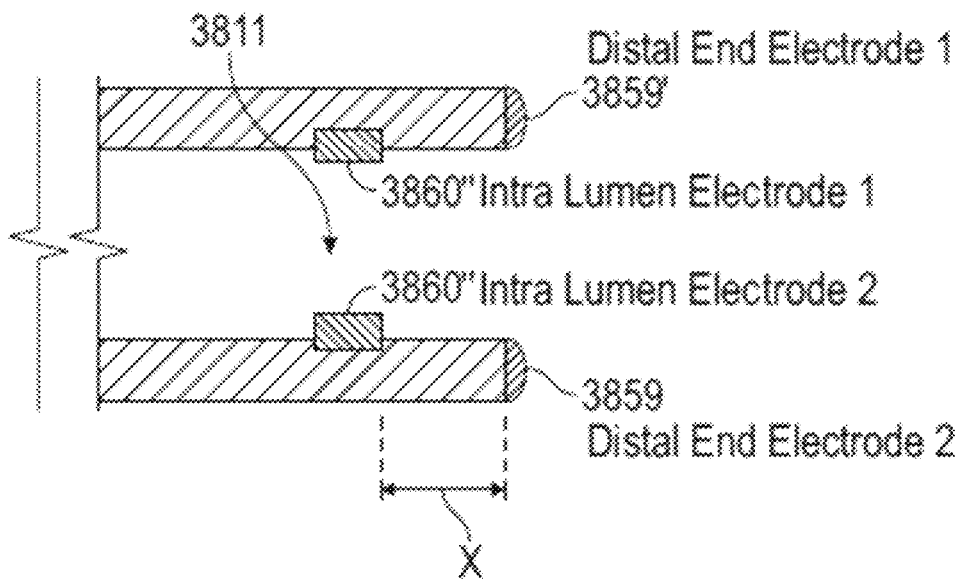

FIGS. 38A-38 illustrate another example of a distal end of an apparatus including an aspiration lumen 3803 that includes an extraction chamber 3811. The apparatus schematically illustrates an example in which the sensor 3859 is positioned to sense pressure from a distal face of the apparatus (e.g., the extraction region). In this example the sensor is a pressure channel coupled to a pressure sensing element that may detect contact by sensing pressure changes in this region. Alternatively, the sensor may detect a change in flow, if a small amount of positive or negative pressure is applied; either pressure or fluid flow may be monitored to detect an occlusion. The apparatus also includes a sensor (configured as a pair of electrical sensors 3860, 3860' between which an impedance may be measured to detect a material within the extraction chamber 3811. The electrodes are positioned at a recessed location (a distance, x, within the extraction chamber), so that suction applied through the extraction chamber may draw more pliant clot material into the chamber but will not be likely to draw wall material. FIG. 38B shows another, similar example, in which a pair of distal electrodes 3859, 3859' may detect contact with an occlusion.

Figure 39A:
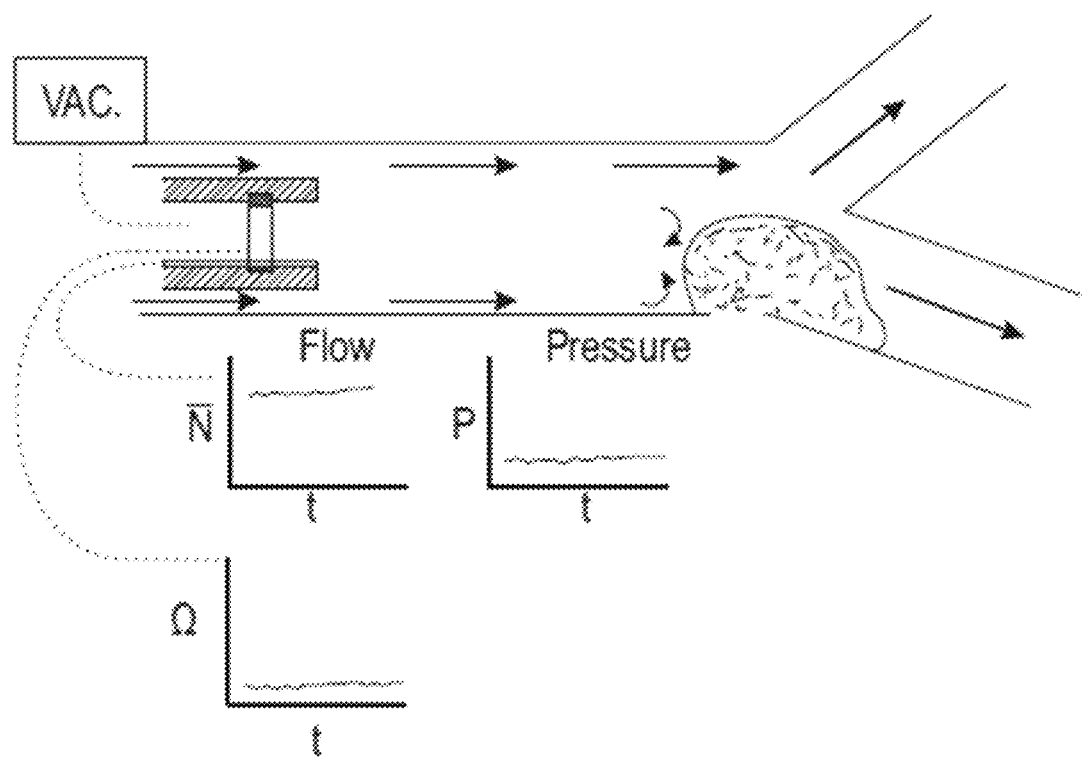
FIGS. 39A-39E illustrate a method of distinguishing clot material from vessel lumen using an apparatus as described herein.
Figure 39B:
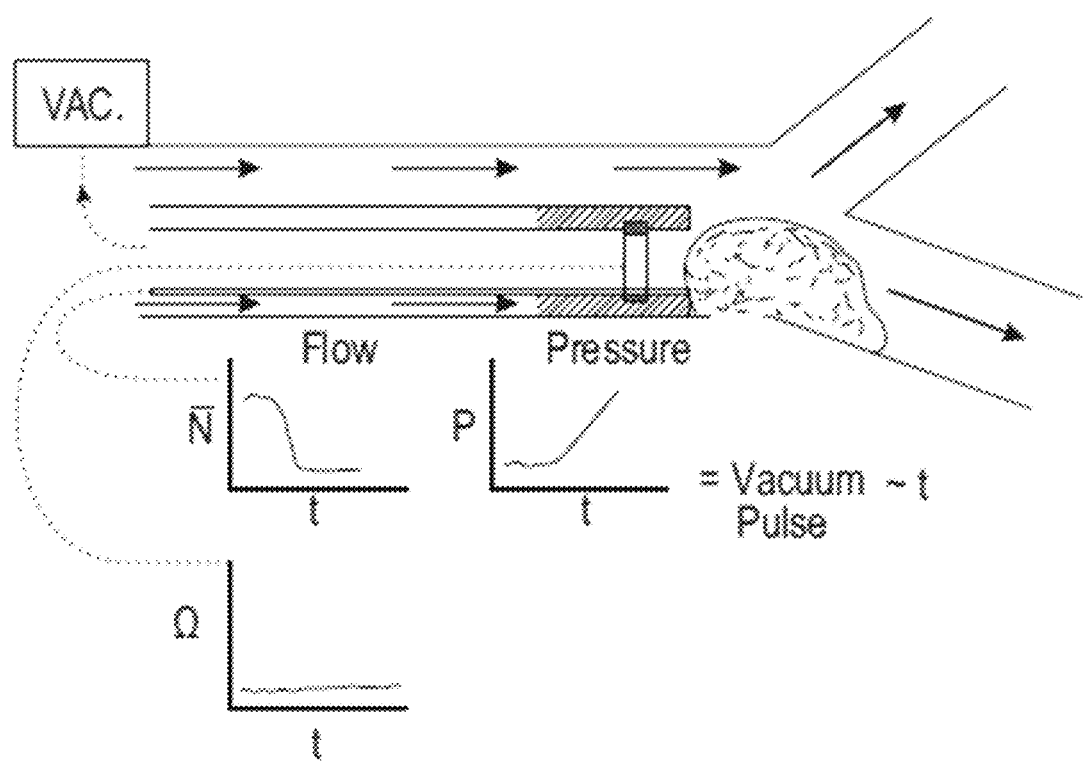
Figure 39C:
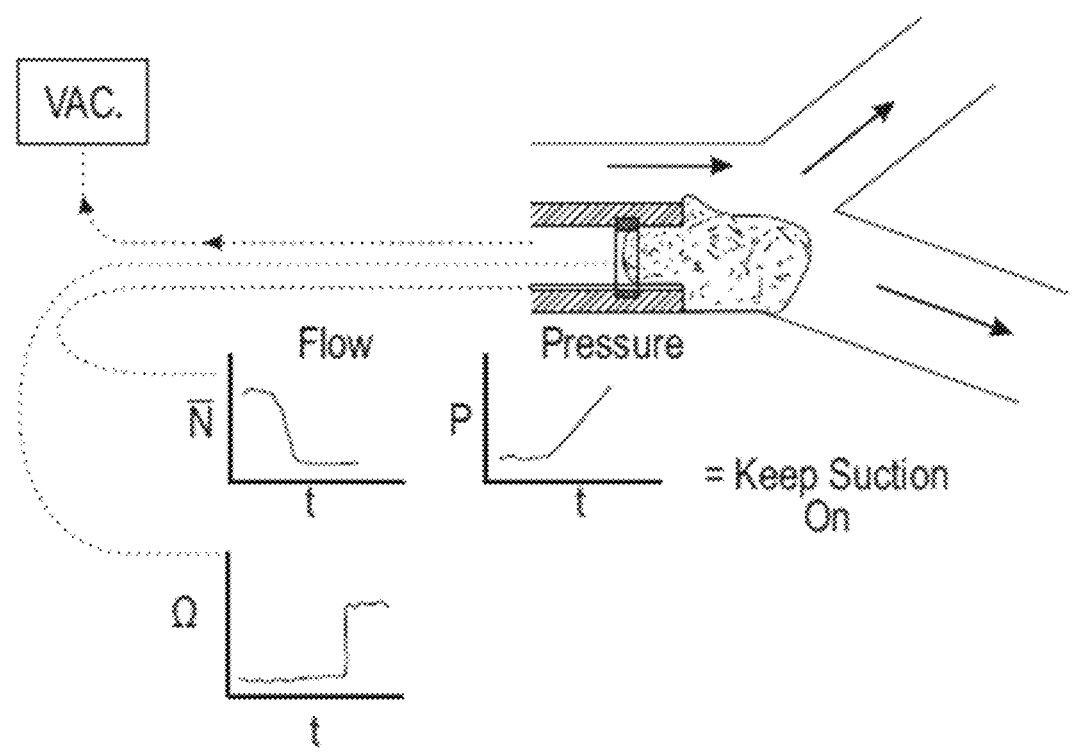
Figure 39D:
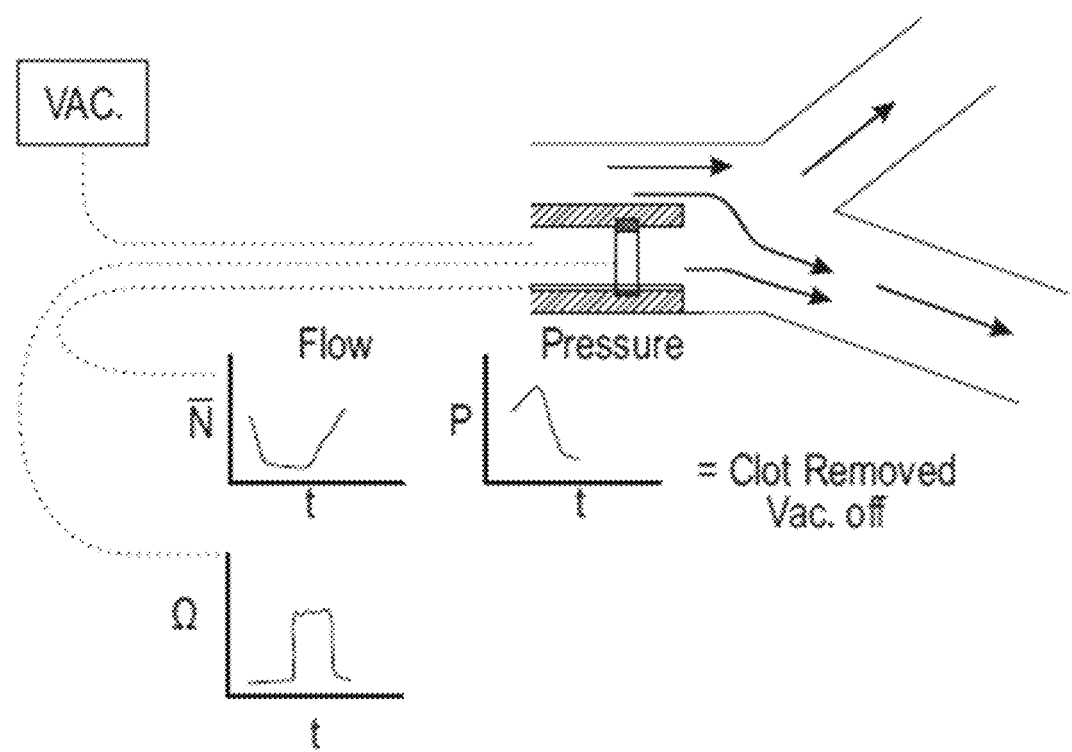
Figure 39E:
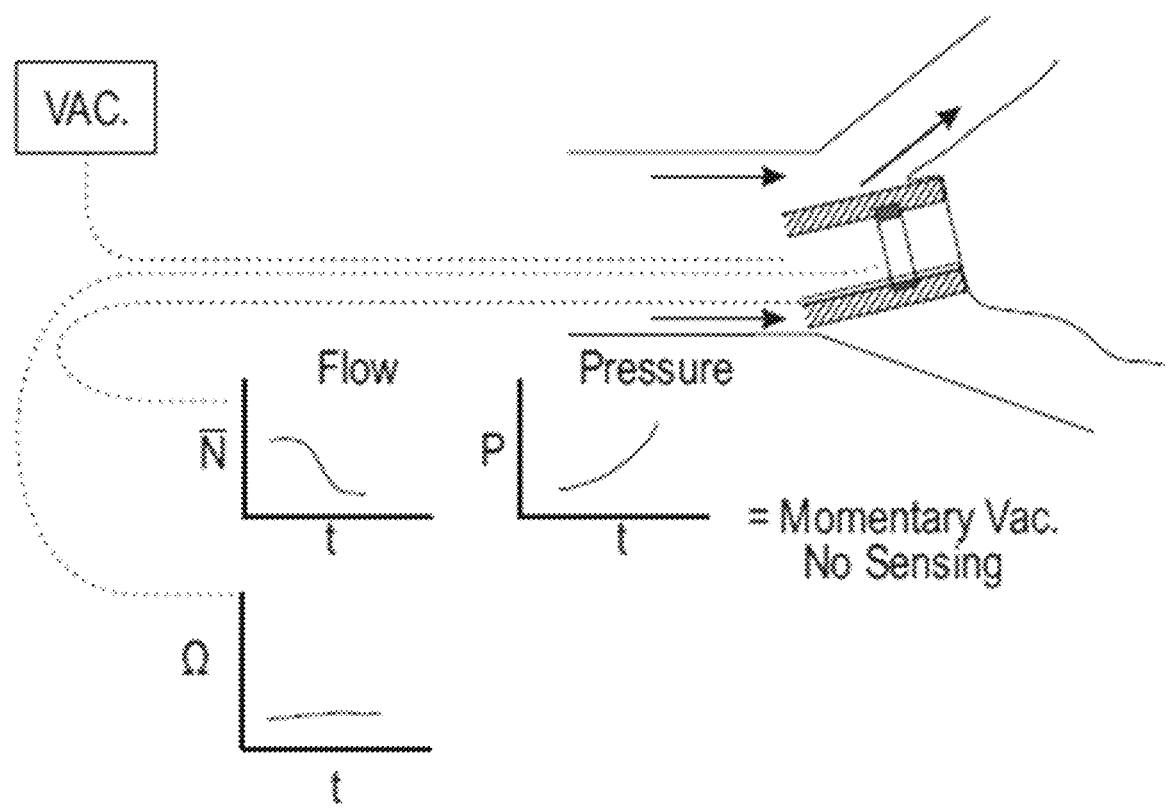

FIGS. 39A-39E illustrate operation of another example of an apparatus as described herein. In this example the controller may monitor pressure and/or flow around the through the apparatus and/or impedance/resistance within the extraction chamber. For example, in FIG. 39A the flow around the apparatus is relatively high, while pressure is relatively low, and the electrical impedance/resistance is consistent with a clear channel (e.g., no material occluding the chamber. As the apparatus approaches an occlusion, as shown in FIG. 39B, the flow and/or pressure may increase, while the electrical impedance within the extraction chamber remains the same. This may trigger the application of suction (or a pulse of suction), as shown in FIG. 39C, drawing the occlusion material into the extraction chamber, resulting in a change in the electrical impedance. Vacuum may be kept high until the occlusion is no longer detected either distally and/or within the extraction chamber, resulting in the flow increasing and pressure dropping, and the electrical impedance returning to an obstructed value. In contrast, when the obstruction is a vessel wall, as shown in FIG. 39E, the flow may decrease and the pressure may increase, but the sensed electrical impedance within the extraction chamber may remain essentially the same, indicating that the obstruction is not clot material, but is likely wall.

The methods and apparatuses described herein may also or alternatively include detection using just one or more internal sensors, e.g., sensing the region within the extraction chamber, without necessarily using a sensor sensing externally ahead of the extraction chamber (e.g., within the extraction zone). Instead, suction may be applied periodically or on demand when advancing or positioning the distal end of the apparatus and one or more sensors may detect a material (e.g., clot material) within the extraction chamber. In some examples the resistance to suction may be monitored to infer an occlusion (e.g., a high resistance to suction may indicate that the apparatus is in contact with an occlusion). Alternatively the apparatus may only monitor for material (clot material) within the extraction chamber.

Figure 40:
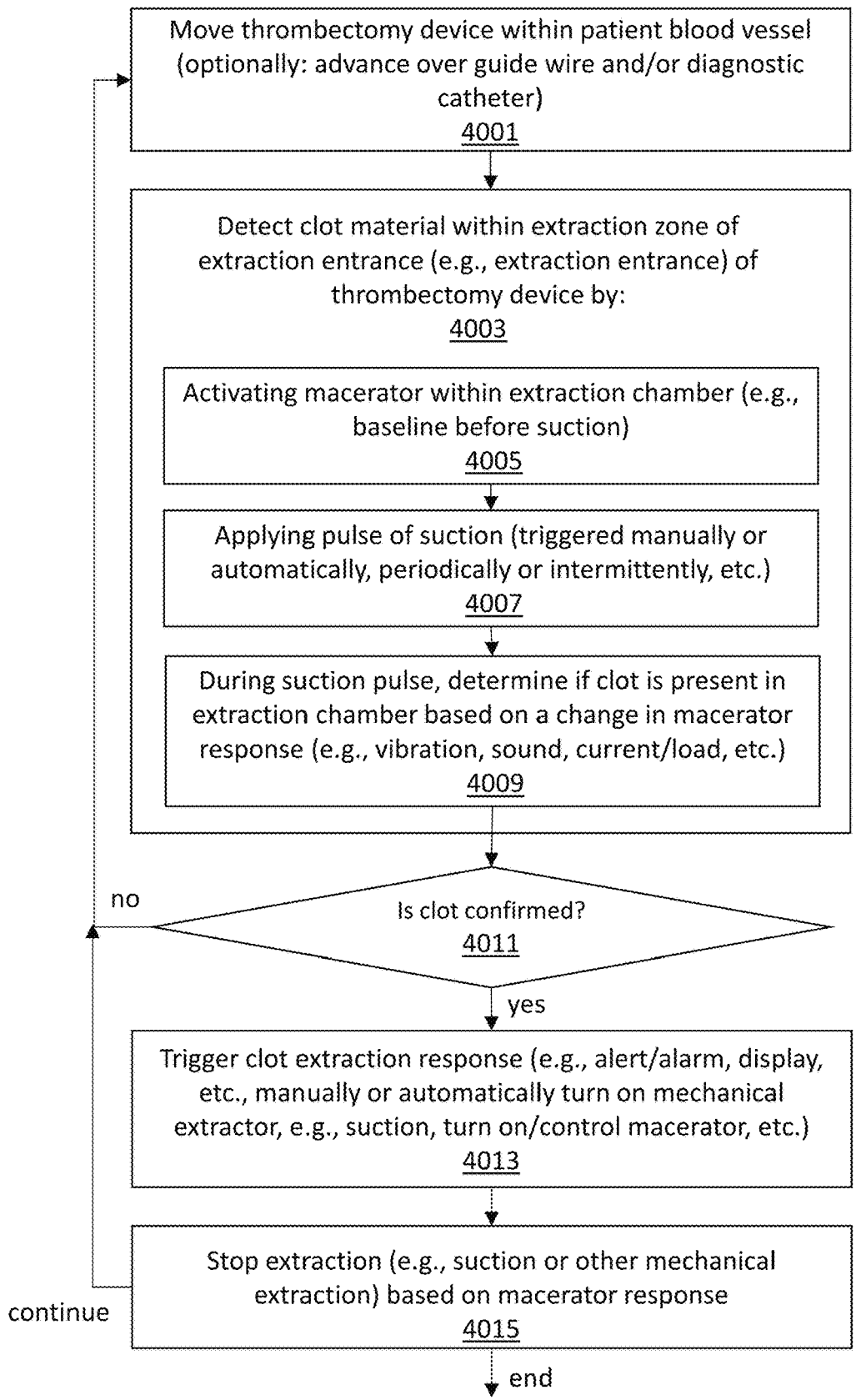
FIG. 40 illustrates an example of a method of detecting clot material using suction and confirming clot material is drawn into the extraction chamber of the apparatus.

For example, FIG. 40 illustrates one method of controlling clot removal using a suction pulse. The method may include moving a thrombectomy apparatus within a patient's blood vessel, which may include advancing the apparatus over a guide wire and/or over a diagnostic catheter 4001. Clot material may be detected within the extraction zone of the extraction entrance of the apparatus (e.g., in front of the extraction entrance) 4003 by activating a macerator within extraction chamber (the macerator may be activated before applying suction in order to get a baseline of macerator behavior for later comparison) 4005, and applying a pulse of suction (which may be triggered manually or automatically, periodically or intermittently, etc. 4007. The pulse may be, e.g., between 100 ms and 10 second long (e.g., between 200 ms and 9 second, between 200 ms and 8 seconds, etc.) or longer. During the suction pulse the controller may determine if a clot material is present in the extraction chamber based on a change in macerator response (e.g., vibration, sound, current/load, etc.) by comparison to the baseline 4009. If clot material is confirmed within the extraction chamber 4011, a clot extraction response may be triggered, as described above (e.g., alert/alarm, display, etc., manually or automatically turn on mechanical extractor, e.g., suction, turn on/control macerator, etc.) 4013.

The clot extraction response may be turned off, e.g., stopping extraction (e.g., stopping or reducing suction or other mechanical extraction) if the clot is no longer present in the extraction chamber, based on macerator response 4015, either immediately or after a delay.

Figure 41:
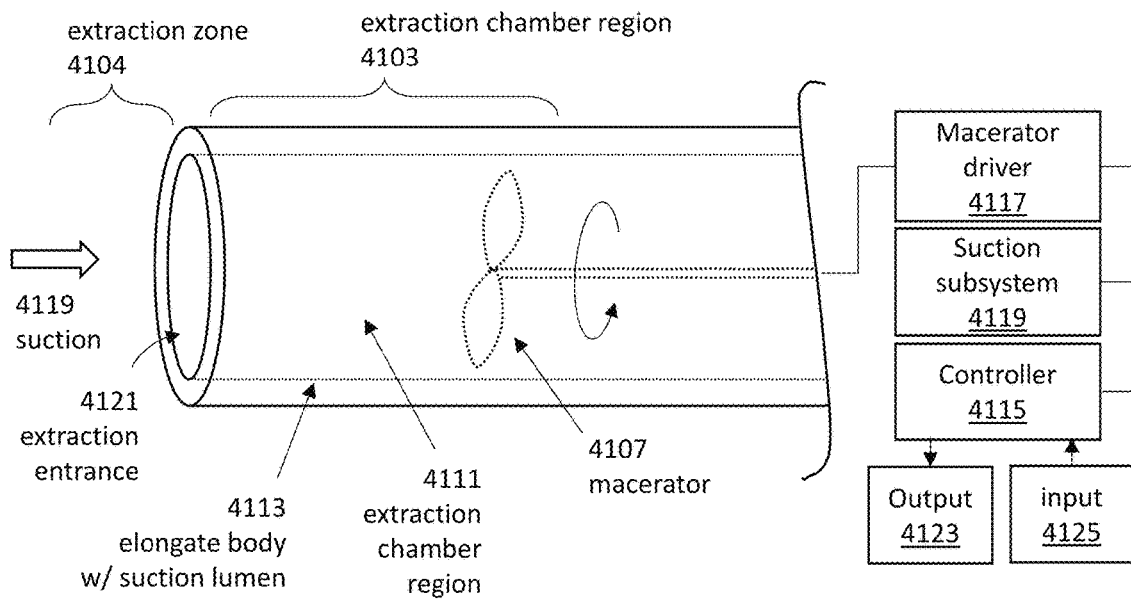
FIG. 41 illustrates one example of a thrombectomy apparatus that detects clot material within the extraction chamber region of the apparatus to control operation of the apparatus.

FIG. 41 illustrates one example of an atherectomy apparatus configured to perform a method as described above, including a method such as described in FIG. 40. In FIG. 41 the apparatus includes an elongate body having a distal end with an extraction chamber region 4103. The distal face of the elongate body may include an opening (extraction entrance 4121) into the extraction chamber region. Suction 4119 may be applied from the proximal end of the apparatus under the control of a controller 4115 that may control operation of a suction subsystem 4119 that may include a suction regulator, pump, suction tank and/or valves. The pump or source of suction may be separate and may be coupled to and regulated by the controller. The control may also control and receive input from (and provide output to) a macerator subsystem including a macerator driver 4117 that operates a macerator 4107 within the extraction chamber or positionable within the extraction chamber region 4111 of the apparatus. In this example apparatus the controller may also receive input 4125 from a user and may provide the output 4123, e.g., notifications, mentioned above.

In operation the apparatus of FIG. 41 may periodically (e.g., every few seconds or more frequently (provide a pulse of suction to see if clot material is drawn into the extraction chamber region from the extraction entrance 4121 and extraction zone 4104. Clot material may be confirmed within the extraction chamber when base, e.g., on the behavior of the macerator. For example, the macerator may indicate that clot material is present by driving the macerator when suction is being applied to determining if the response to the macerator is different than when suction is not being applied, as this difference may be characteristic of the breakup of clot material within the extraction chamber region by the action of the macerator. For example, the macerator may require a larger power, e.g., current, to operate and/or may otherwise behave as if under a load. In some examples the macerator may generate vibrations and/or sounds indicating a load is being applied when clot material is present.

Figure 42:
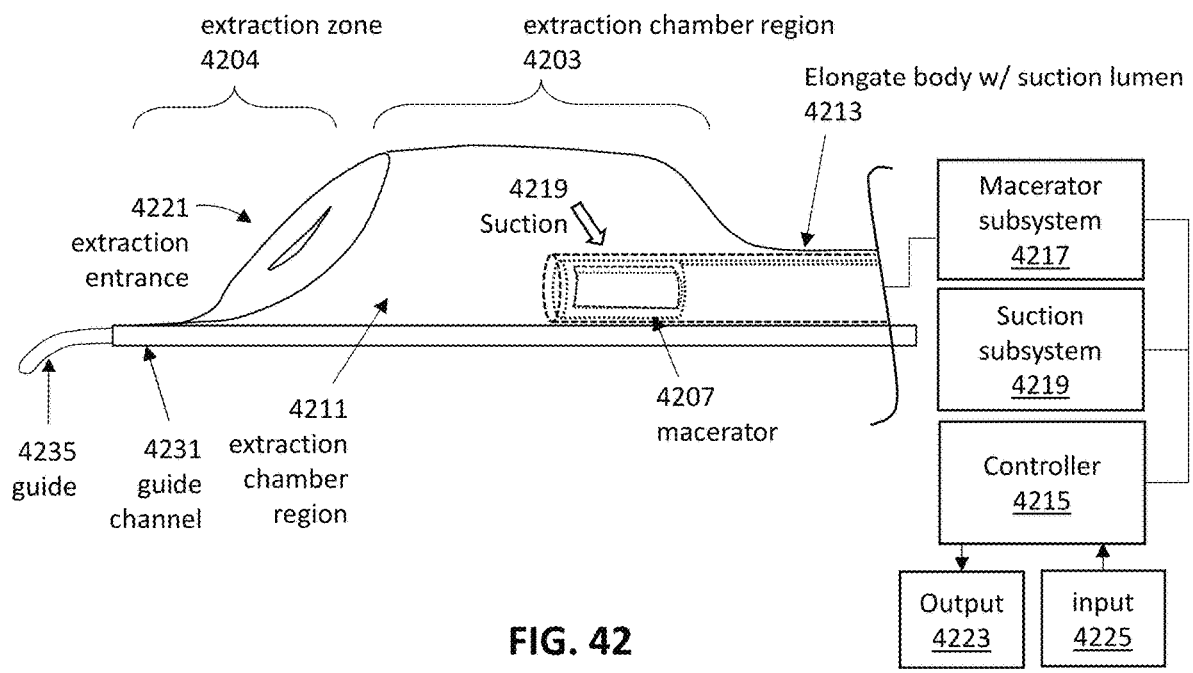
FIG. 42 illustrates another example of a thrombectomy apparatus configured to detect material within the extraction chamber (e.g., using suction) by monitoring the macerator and/or pressure within the extraction chamber.

FIG. 42 illustrates another example of a thrombectomy apparatus similar to that described above, that may also be configured to detect clot material within the extraction chamber 4211 of the extraction chamber region 4203. In this example the extraction chamber is covered by a cover including an aperture forming an entrance 4221 into the extraction chamber. The region distal to the entrance is the extraction zone 4202, and the apparatus may include a guide channel 4231 within which a guide 4235 (e.g., guidewire, diagnostic catheter, etc.) may be inserted and used to steer the apparatus. A macerator sub-system 4219 may be included to drive maceration via a macerator 4207 within the extraction chamber. The macerator may be configured so that suction 4219 is drawn through the macerator so that clot material within the extraction chamber is drawn into and through the macerator. The apparatus in FIG. 42 also includes a controller 4215 that may receive input 4225 from a user and/or from the macerator subsystem and/or from a suction subsystem 4219 including a suction regulator. The suction subsystem may be coupled to a source of suction (e.g., pump, wall line suction, suction tank, etc.) and may also include one or more valves. The controller may therefore coordinate the application of suction and activation of the macerator, either automatically or semi-automatically and/or manually. The controller may also include one or more outputs 4223 for outputting notifications to a user (e.g., alerts, messages, etc.).

Figure 43:
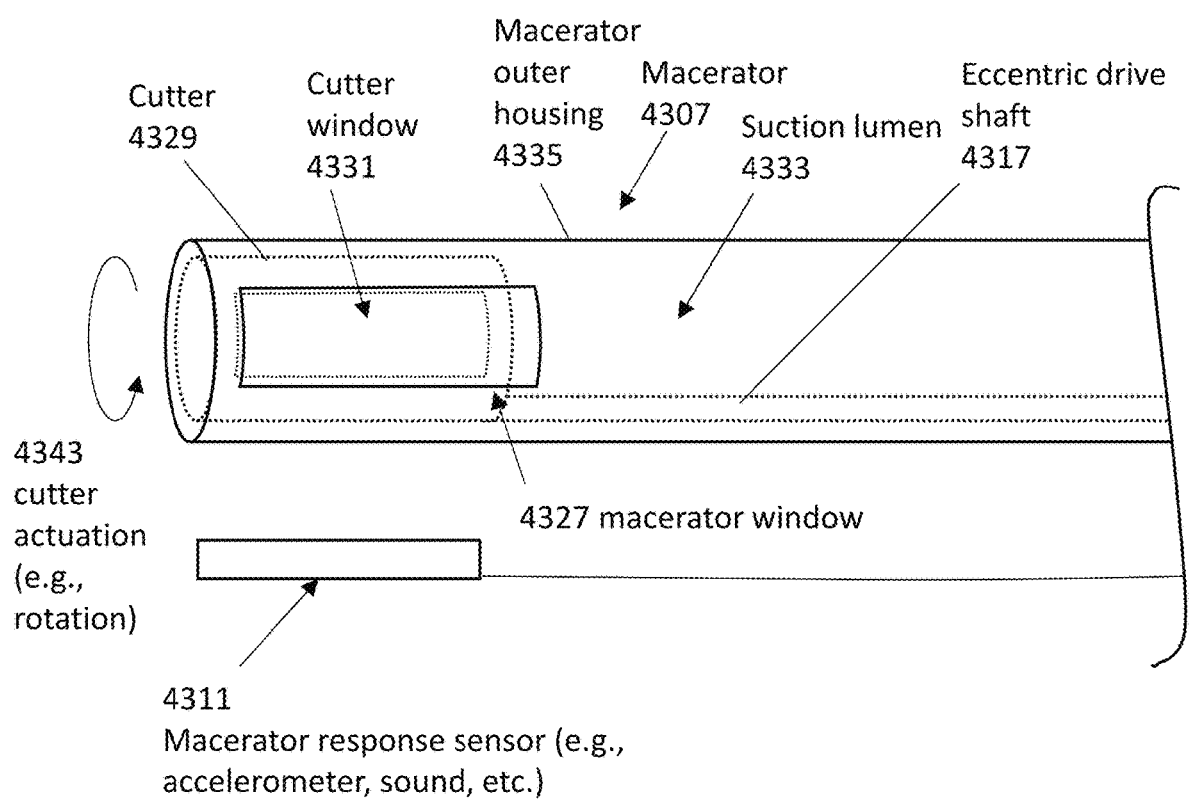
FIG. 43 schematically illustrates an example of a macerator as described herein.

Any appropriate macerator may be used, including reciprocating (e.g., biting) macerators, or rotating macerators. For example, FIG. 43 illustrates one example of a reciprocating macerator that may be used with any of the apparatuses described herein. In FIG. 43, the macerator includes a macerator outer housing 4335 that is enclosed around the circumference but may be open in one or more macerator windows 4327 and in some examples may be open at the distal end; in some examples the distal end may be closed. The macerator housing may be elongate and may be flexible. In some examples the macerator housing may be formed of a polymeric material, or a laser cut hypotube that is flexible along its length. The housing may be configured to apply suction therethrough (e.g., it may enclose a suction lumen 4333). The macerator housing may enclose a rotting cutter 4329. In FIG. 43 the cutter is a cylindrical cutter that includes one or more widows (cutter windows 4331) or openings therethrough. The cylindrical cutter may be configured to fit into the macerator housing and in some examples, to be retained within the distal end region. For example the distal end region may include a channel or waisted region that limits or prevents the cutter from moving proximally and/or distally away from the macerator window(s) 4327 that are formed in the elongate outer housing. The cutter may be coupled at a proximal end to a drive shaft 4317. In FIG. 43 the drive shaft is a wire that rotates eccentrically within the outer housing to rotate the cutter 4343 so that the cutter window rotates relative to the macerator window, shearing any clot material that is drawn, e.g., by suction, into the window region when opened.

In any of the cutters described herein the macerator activity may be monitored by monitoring the inputs to the macerator sub-system, including the power demand/load on the macerator driver, as mentioned above. In some examples a macerator sensor 4311 may be included to detect a response of the macerator based on vibration (e.g., accelerometer), sound (microphone), or the like. The sensor may be positioned near, including in some examples, adjacent, to the cutter.

Any of the methods described herein may include detecting the presence of clot and/or distinguishing clot material from other material such as vessel wall, based on the state or response of the aperture into the extraction chamber region in variations in which the extraction entrance is covered by a cover having an aperture. The relative opening state of the aperture may reflect the presence of absence of clot material. For example, FIG. 44 illustrates one example of a method of detecting clot material and/or distinguishing clot material from vessel wall material based on the opening state or response of an aperture through a cover of the extraction chamber.

Figure 44:
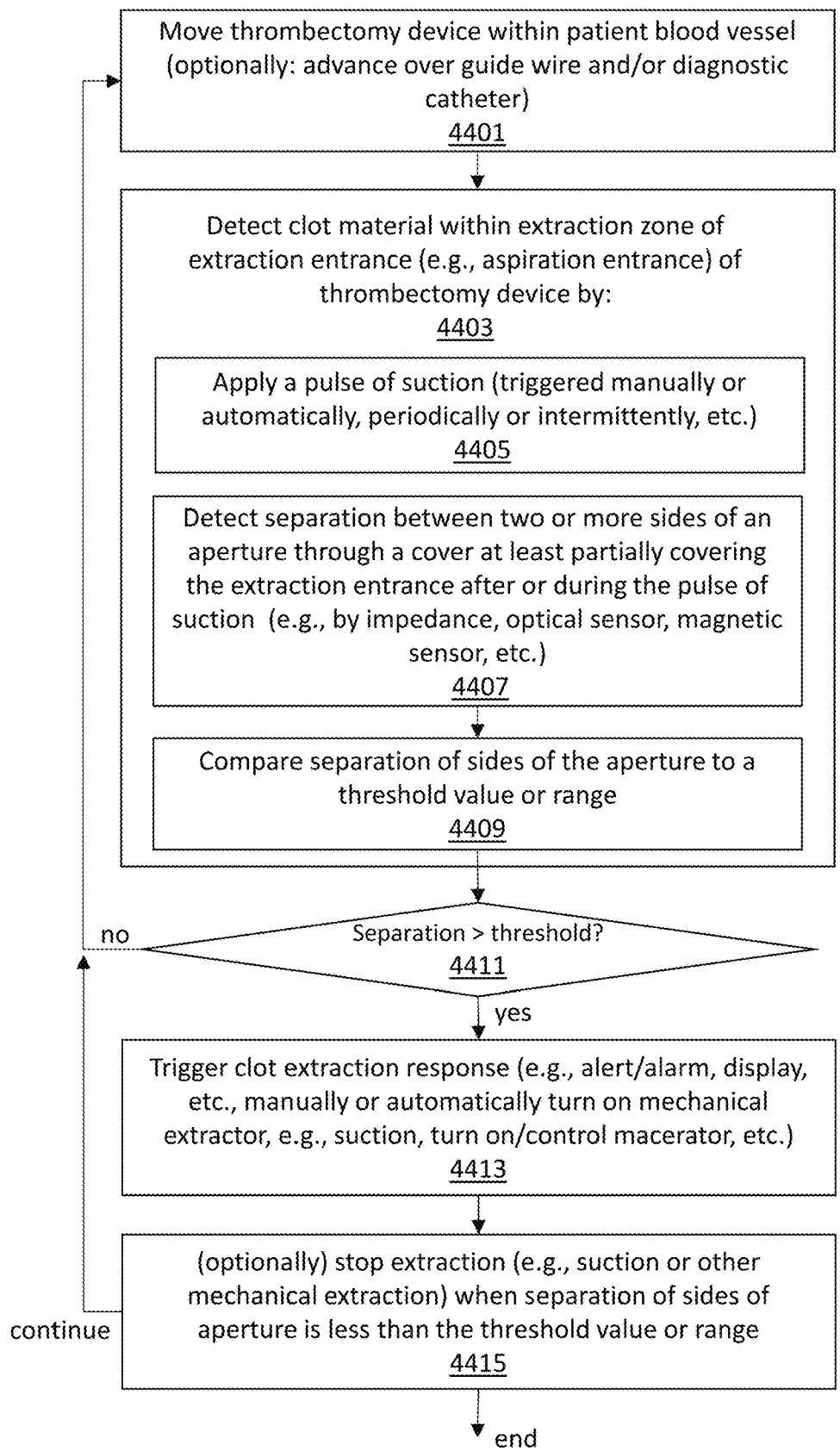
FIG. 44 illustrates an example of a method of controlling clot removing using an apparatus configured to detect opening of an aperture through a cover over the extraction chamber.

In FIG. 44, the method may include positioning (e.g., moving) the thrombectomy apparatus within a patient blood vessel, e.g., advancing the apparatus over guide wire and/or diagnostic catheter 4401. Clot material may be detected within an extraction zone of the extraction entrance (also referred to herein as the aspiration entrance) of the thrombectomy apparatus by detecting the opening of an aperture through a cover covering the extraction entrance 4403. For example, the apparatus may include applying a pulse of suction (e.g., triggered manually or automatically, periodically or intermittently, etc. as described above) 4405, and detecting the separation between two or more sides of the aperture through the cover that at least partially covers the extraction entrance before, and/or after, and/or during the pulse of suction. The separation between the two or more sides, which may be flaps, doors, etc. may be detected by detecting via any appropriate technique. For example, the opening may be detected by an impedance sensor(s), optical sensor(s), magnetic sensor(s), etc. 4407. The extent of the opening may be determined by comparing the separation of the sides of the aperture to a threshold value or range (e.g., based on the separation of the sides prior to approaching clot material) 4409. If the separation is greater than a threshold value 4411, then the controller (which may receive input from the one or more sensors detecting aperture opening/position) may determine that clot material is present based on the extent to which the aperture is opened; this may trigger a clot extraction response (e.g., alert/alarm, display, etc., manually or automatically turn on mechanical extractor, e.g., suction, turn on/control macerator, etc.) as mentioned above 4413. Optionally, the controller may also stop the clot extraction response (e.g., stopping or reducing suction and/or other mechanical extraction, and/or maceration) when the separation of sides of aperture is less than the threshold value or range 4415.

FIG. 45 illustrates an example of an apparatus similar to that described above but configured to detect the opening and/or separation of the aperture. In FIG. 45, the apparatus includes an elongate body enclosing a suction lumen 4513; the suction lumen may house the macerator 4507 that may also enclose the suction lumen for applying suction 4519 through the macerator in the extraction chamber 4511. The extraction chamber may extend from the distal end region of the apparatus and may expandable/collapsible. The extraction chamber region 4503 may include a distal face forming the extraction entrance 4521 which may be angled, curved (concave or convex) or en face (e.g., flat) relative to the distal end of the apparatus. The apparatus may also include a guide channel 4531 for coupling to a guide 4535 (e.g., guide wire, diagnostic catheter, etc.). The extraction entrance may be covered by a cover including an aperture 4566 that may open or close to allow passage of clot when suction is applied. In the example shown in FIG. 45 the aperture includes a pair of sensors 4505, 4505' on either side of this example of an aperture that may detect the opening of the aperture, including how open it is. In FIG. 45 the aperture is a slit, but other apertures may be used, including two or more (e.g., three, four, etc.) flaps, valves, etc. The apparatus also includes a controller 4545 that may control suction via a suction subsystem 4519 (e.g., suction regulator, pump, etc., as mentioned above). The controller may also control the macerator 4507 via a macerator subsystem 4517, such as a macerator driver, etc. The controller may receive input 4525 (e.g. user input) in addition to sensor input, such as the aperture opening sensor input. The controller may also provide output 4523 (e.g., notifications, alerts, etc.) to a user as described herein.

FIGS. 46A and 46B illustrate the operation of a pair of aperture sensors on a cover 4612 of an apparatus such as the one shown in FIG. 45. In FIG. 46A the aperture includes two sides, though apertures having more than two sides may be used, and a pair of sensors (e.g., a first aperture sensor 4605, and a second aperture sensor 4605') are positioned on either side of the aperture 4666. In FIG. 46A the aperture is mostly closed; this configuration may represent the baseline of the aperture when suction is being applied but no clot material (or other occlusion) is present. Some suction may be applied through the aperture resulting in minimal blood loss. However, when clot is present, the side of the aperture may be separated even more, as shown in FIG. 46B. The separation 4615 may represent the side when clot is passed and may retain the clot until all of it is suction in through the aperture, allowing it to close back to the baseline separation (FIG. 46A). As mentioned, the sensor may be optical sensors, electrical sensors (e.g., impedance sensor), contact sensor, magnetic sensors, etc.

Figure 47:
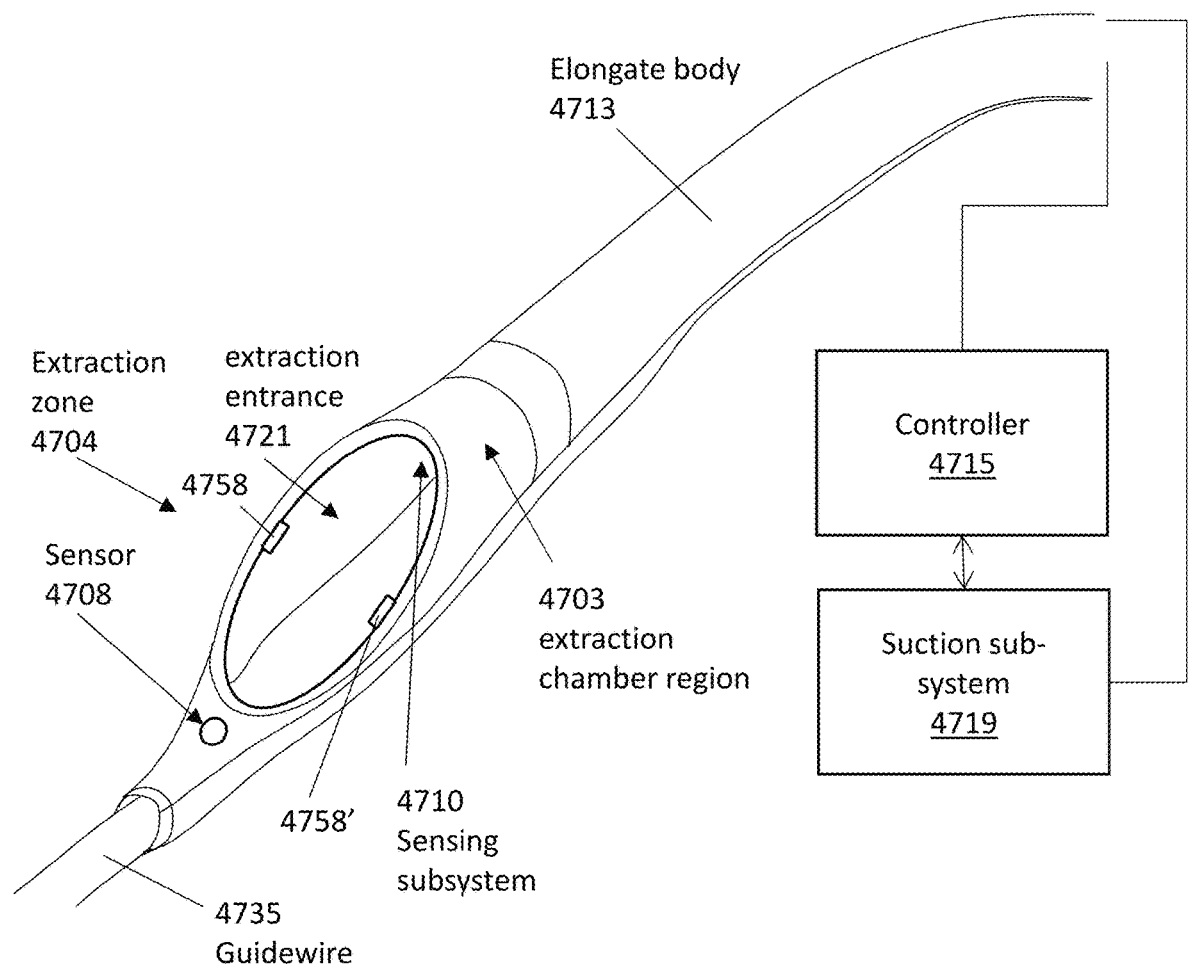
FIG. 47 illustrates one example of a thrombectomy apparatus as described herein.

FIG. 47 illustrates another example of an apparatus that is configured to detect and control the capture clot material. In FIG. 47 the apparatus includes an elongate body 4713 that encloses a suction lumen. The apparatus also includes a guide channel (shown with a guide lumen 4735). In this example, an external/outside sensor 4708 is also included for detecting an obstruction material within the extraction zone 4707 in front of the extraction entrance 4721 into the extraction chamber 4703. Alternatively or additionally, the apparatus may include an impedance sensor (e.g., a pair of electrodes 4758, 4758') configured as an aspiration opening sensor). The aspiration opening sensor may be on the rim of the aspiration opening 4721, or it may be recessed slightly into suction lumen. In some examples the aspiration opening sensor (electrodes) may be recessed within the rim of the aspiration opening 4721; alternatively in some examples, the aspiration opening sensor (e.g., electrodes) are flush with the rim or extend proud of the rim.

One or more internal sensors (forming a sensing subsystem 4710) for detecting clot material within the extraction chamber may be include. A controller 4715 may be used to coordinate the operation of the suction subsystem (e.g., suction regulator) 4719, as described above. The example shown in FIG. 47 may be modified to embody any of the features and/or examples described above. For example, the extraction entrance 4721 may be covered by a cover that may include an aperture. One or more sensors may detect the opening state of the apparatus. In some examples the external sensor 4735 may be absent. The example shown in FIG. 47 does not include a macerator; in some examples the apparatus may be configured to include a macerator. The controller may receive input from the sensor(s), including the aspiration opening sensor and/or one or more internal sensors (e.g., impedance sensing electrodes, mechanical sensors, etc.).

Deflection Sensors

As mentioned above, in any of the methods and apparatuses described herein, one or more deflection sensors may be used. The deflection sensor may include a deflectable member that is coupled to a wall of the lumen, e.g., suction lumen, of the apparatus at one end; the second end of the deflectable member is configured to move (deflect) away from an initial position in a first (undeflected) configuration into a second (deflected) configuration. The deflectable member may be configured to be elastically deformable, so that it may transition between the undeflected configuration in an unloaded state to a deflected configuration when force is applied by a clot material pushing on the deflectable member and may return to the undeflected configuration when the load is removed from the deflectable member. In general, the deflectable member is configured to project into the lumen of the suction lumen.

The deflection sensor (and the apparatus including the deflection sensor) may also include a sensing circuit to detect deflection of the deflectable member and encode deflection as a signal that may be used by the controller to detect a clot material and/or to distinguish between a clot material and a wall of the lumen. In particular the controller may be configured to use the signal from the deflection sensor and/or from one or more other sensors (e.g., pressure, flow, etc.) to determine that clot material is trapped in the suction lumen.

Figure 48A:
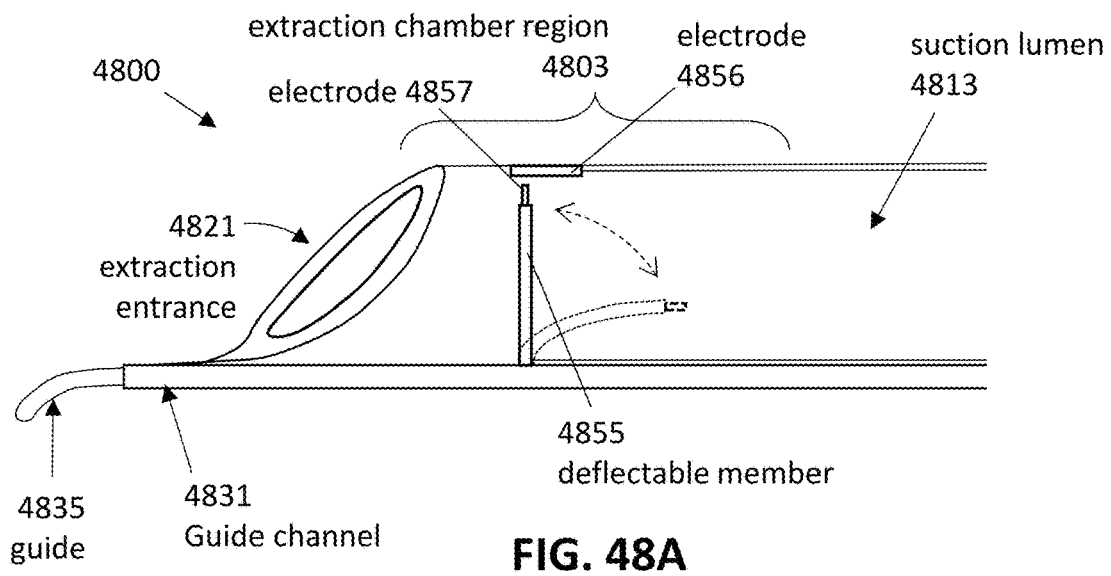
FIGS. 48A-48C show examples of a thrombectomy apparatus including an obstruction sensor configured as a deflectable member as described herein.
Figure 48B:
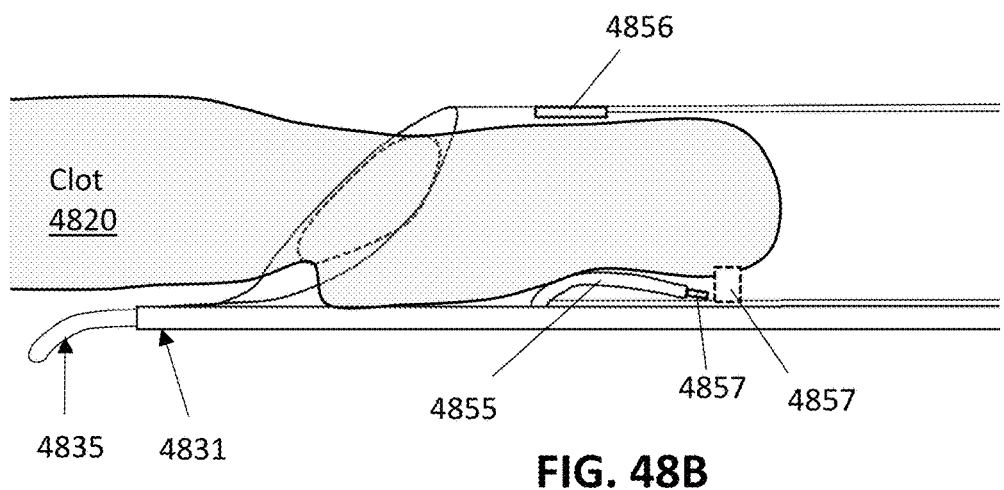
Figure 48C:
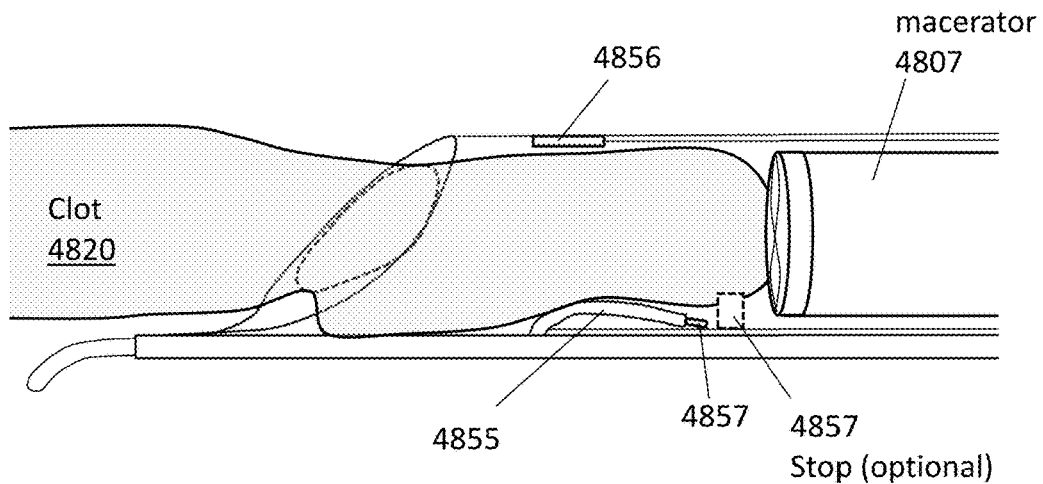

For example, FIGS. 48A-48C illustrate one example of an apparatus including a deflectable member 4855 configured to detect clot material within the distal end region (e.g., an extraction chamber region 4803) of the elongate body of the aspiration catheter 4800. The aspiration catheter includes an elongate body and a suction lumen 4813 extending from a distal end to a proximal end. In the example shown in FIG. 48 the aspiration catheter includes an extraction entrance 4821 at the distal end that is angled relative to the long axis of the catheter. The aspiration catheter also includes a guide channel 4831 within which a guide 4835 may be used to help navigate and position the apparatus. The guide 4835 may also be used to pass a guidewire. In this example the extraction entrance comprises a cover partially covering the distal end (forming a lip region).

In FIGS. 48A-48C the deflectable member 4855 is configured as a whisker that is configured to assume a first, undeflected, configuration (shown as a solid line) at rest, extending proud of the wall of the lumen, and traversing the suction lumen. In the example of the deflectable member shown in FIGS. 48A-48C, the deflection sensor including the deflectable member is configured to electrically detect displacement of the deflectable member. For example, a sensing circuit may include a first electrode 4856 that is positioned on the opposite side of the lumen from the base of the deflectable member. A second electrode 4857 is positioned on a distal end of the deflectable member 4855 and may be separated from the first electrode 4856 by a small distance in the undeflected configuration (or in some examples, may touch the first electrode). Optionally, a third electrode (not shown) may be included at an axially (e.g., longitudinally) offset position but on the same side of the lumen as the base of the deflectable member. As will be described in more detail below in FIGS. 51A and 51B, the deflectable member and electrodes may be used to detect deflection of the deflectable member in use.

For example, FIG. 48B shows the apparatus of FIG. 48A following the application of suction, including a pulse of suction. In this example a clot material 4820 is shown trapped (jammed) within the distal end region (e.g., the extraction chamber region 4803) of the apparatus. The deflectable member is shown fully deflected so that the second electrode on the distal end of the deflectable member 4855 is pushed away from the first electrode 4856. In this example the deflectable member 4855 (whisker) is thin and extends across virtually the entire diameter of the lumen. In some example, the deflectable member extends only partially across the diameter of the lumen. The deflection sensor may provide a signal indicating that the deflectable member is deflected for a prolonged period of time, indicating that the clot is trapped in the distal end region of the apparatus. In some examples the controller may determine that the clot is trapped and may alert the user to deploy manually (or may automatically deploy) a macerator 4807 to help remove the clot material. In some examples the macerator may be insertable/removable, as shown in FIGS. 48A-48C, or it may be held in position at the distal end region (e.g., within the extraction chamber region, which may also be referred to herein as a macerator chamber). For example, in FIG. 48C the macerator 4807 may be driven distally through the aspiration catheter suction lumen until it reaches a stop 4857 that prevents it from cutting the deflectable member 4855. Maceration of the clot may be performed with continuous and/or pulsatile suction.

In general, the deflectable member 4855 may be positioned within the suction lumen near the distal end at a position that prevents it from being substantially deflected by vessel wall that may be drawn partially into the lumen of the aspiration catheter but may allow it to be robustly deflected by even more rigid clot materials. For example, in some examples the deflectable member 4855 is positioned within the distal x mm of the distal end opening (e.g., distal 20 mm, 18 mm, 15 mm, 14 mm, 12 mm, 10 mm, 9 mm, 8 mm, 7 mm, 6 mm, 5 mm, 4 mm, 3 mm, 2 mm, 1 mm, etc., e.g., between 1 mm and 25 mm, between 2 mm and 25 mm, between 3 mm and 25 mm, between 4 mm and 25 mm, between 5 mm and 25 mm, between 2 mm and 20 mm, between 3 mm and 20 mm, between 4 mm and 25 mm, between 4 mm and 20 mm, between 3 mm and 15 mm, etc.). In examples (such as shown in FIGS. 48A-48C) in which the distal end opening is angled relative to the long axis of the catheter, the deflectable member 4855 may be positioned within 5 mm from the most proximally-positioned end of the opening. For example, the deflectable member 4855 may be between 2 mm and 20 mm of the distal end opening.

The example shown in FIGS. 48A-48C illustrate the use of electrical sensing to monitor the deflection of a deflectable member within the aspiration orifice (e.g., aspiration lumen) of an aspiration catheter to remove clot more efficiently from a blood vessel. The apparatus in this example includes an elongated shaft having a distal end and a proximal end defining a lumen, at least two electrodes 4857, 4856, and a proximal handle (not shown). The first pair of electrodes may be positioned axially within about 5 mm of the distal end and radially within the same plane (e.g. transverse to the long axis of the catheter). The second electrode is exposed at the distal end of the deflectable member 4855 includes a distal and proximal conductive section and an insulated body that runs the length of the elongated shaft of the deflectable member, within the wall. The distal section of the electrode then extends from the surface of the elongated shaft through the longitudinal axis of the inner lumen and is positioned within about 0.01-2 mm from the first electrode which is on the inner surface of the inner suction lumen 4813. A small area of the distal section of the second electrode near the first electrode may be conductive with the remaining portion of the electrode passing through the lumen and is insulated.

As mentioned, the deflectable member that extends across the aspiration lumen may be configured to be flexible and in some examples may have a minimal surface area to minimize the area being obstructed within the lumen it is crossing. The flexibility of the deflectable member allows the second electrode to easily flex outwardly towards the inner surface of the lumen away from the first electrode on the opposite wall when a sufficient force is applied; the deflectable member may return to starting position when the force is removed or lessened. The first electrode may be built into the inner surface of the suction lumen and a conductive area of the first electrode may be positioned to encounter the fluid or objects that pass through the aspiration lumen. Thus, the first electrode 4856 may be flush with the wall of the suction lumen, recessed into the wall of the suction lumen or may extend slightly proud of the wall of the suction lumen. When the electrodes are energized and placed in a conductive solution such as blood, as the electrodes separate, the resistance between the electrodes increases. The change in resistance and the duration of this change can indicate if there is something within the lumen, just attached to the distal end of the lumen, and/or passing through the lumen.

In some examples the elongated shaft of the deflectable member is constructed of a polymeric inner liner (e.g. Pebax, PTFE), a reinforced layer (e.g. SS braided wire), and a polymeric outer jacket (e.g. Pebax). The electrode at the end of the deflectable member may comprise of a 0.0005 to 0.003" round polyurethane coated copper wire (Magnet wire) and a 0.003-0.015" nitinol wire. The wires may be laid side by side together and joined together so that at least the distal ends aligned. In one example the wires are head together by dipping at least 5 mm of the distal section into silicone and allowing the silicone to dry. In doing this, the two wires may have a thin coating, e.g., less than 0.003" thick, surrounding the wires. The distal end of the magnet wire may then be exposed by removing the polyurethane and silicone coatings creating a small conductive section. In some embodiments, the exposed conductive section could be just proximal, ~0.5 mm, from the distal end of the deflectable member. The first (e.g., luminal wall) electrode may comprise a thin polyurethane coated copper wire (magnet wire) that is conductively affixed to a thin sheet (0.001-0.010" thick) of conductive material (e.g. copper). The body of the electrodes may be integrated into the elongated shaft by laying the insulated electrodes along the outer surface of the inner liner or reinforced layer. The outer jacket may then slid over the electrodes and elongated reinforced layer and shrunk down using heat and heat shrink to trap the electrodes in place along the body of the shaft. The thin conductive film of the second electrode is folded around the distal end of the inner liner and compressed into the inner liner affixing it in place. The distal section of the first electrode may then pierced through the inner liner near the second electrode and positioned through the longitudinal axis of the aspiration lumen so that the conductive section of the first electrode is within about 2 mm from the conductive section of the second electrode. The proximal ends of the electrodes may then extend to a distal end of the catheter (e.g., to the handle) to allow the circuit to be completed and energized/monitored, e.g., by a controller.

Figure 49:
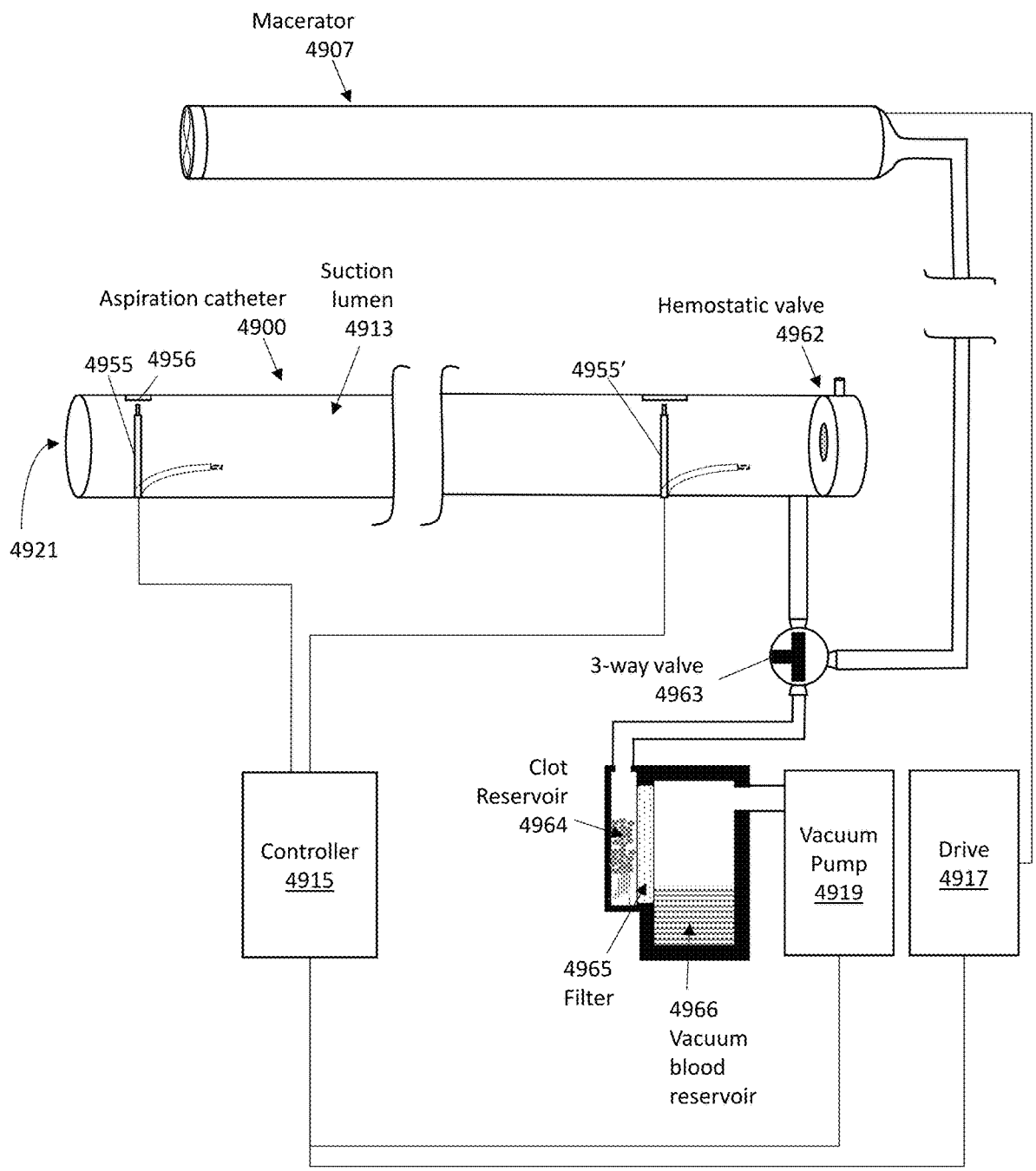
FIG. 49 illustrates one example of an apparatus (e.g., a thrombectomy apparatus) including an aspiration catheter configured to include a plurality of deflectable members and a macerator.

FIG. 49 shows a first example of an apparatus including an aspiration catheter 4900, a macerator 4907 that may be inserted/removed from the aspiration catheter and a controller 4915 controlling the application of suction through the macerator and/or aspiration catheter. The apparatus also includes a deflection sensor including a deflectable member 4955 for detecting when clot material is in the distal end of the aspiration catheter. In this example the aspiration catheter also includes one or more additional deflection sensors (including a second or more deflectable member 4955') located along the length of the suction lumen 4913 of the aspiration catheter. The deflectable members 4855, 4855' are shown in the un-deflected configuration by solid lines and in a deflected configuration by the dashed lines.

In FIG. 49, the aspiration catheter 4900 includes a distal end opening 4921 into the suction lumen (the distal end region extending proximally from the distal end opening may be referred to herein as an extraction region of the suction lumen). As mentioned, the deflectable member 4955 may be positioned slightly proximally relative to the distal end opening 4921 so that it will detect clot drawn into the distal end opening during suction pulse but will not be significantly deflected by a vessel wall. For example it may be recessed between 2 mm and 25 mm into the suction lumen 4913. The spacing may be dependent upon the diameter and orientation of the distal end opening 4921. In examples in which the deflection of the deflectable member 4855 is detected electrically as part of a detection circuit, the deflectable member may include an electrode at the deflecting distal end region and an electrode may be positioned opposite from an electrode 4956 on the lumen wall. In some examples one or more additional lumen electrode may be include (e.g., axially offset and on the same side of the lumen as the base of the deflectable member. The proximal end of the aspiration catheter may include a handle (not shown) and/or may include a hemostatic valve 4962 into which the macerator 4907 may be inserted, either manually or automatically (e.g., robotically) the macerator 4907 may include an elongate body and a distal cutter, such as a rotatable cutter. The macerator may also include a suction lumen (macerator suction lumen) and may include a drive member such as a drive wire (not shown) for driving rotation of the distal cutter.

In general, the controller may control the application of suction through the catheter 4900 and/or macerator, e.g., via a valve, such as a 3-way valve 4963. Alternatively or additionally, this valve may be manually controlled. The valve may allow suction to be applied from the vacuum pump 4919, which may pass through a clot reservoir 4964 to allow viewing of the clot material (e.g., through a transparent window), and filtering of blood through one or more filters 4965 into a blood collection reservoir 4966. The controller may also control the drive 4917 driving rotation of the macerator cutter (e.g., via a drive shaft, not shown). The drive may also or alternatively be manually controlled.

The controller may include one or more inputs (e.g., keyboard, touchscreen, buttons, touchscreens, dials, sliders, knobs, etc.) and one or more outputs (screens, lights/LEDs, speakers, etc.). In any of these apparatuses the controller may also receive input from the one or more deflection sensors. The controller may determine, based on the deflection of the deflectable member(s) 4955, 4955', if clot material is within the lumen of the catheter 4900 and may trigger one or more outputs (e.g., a clot extraction response). For example, in some cases the controller may apply or coordinate the application of a pulse or pulses of suction from the aspiration catheter 4900 and may determine if clot material is drawn into the suction lumen through the distal end 4921. Deflection of the deflectable member at the distal end 4955 in a sustained manner may include that a large clot is present at the distal end region the controller may be configured to trigger an alert so that the user may apply more sustained suction and/or may insert and use the macerator 4907 to remove the clot material if it is trapped at the distal end of the aspiration catheter.

Figure 50:
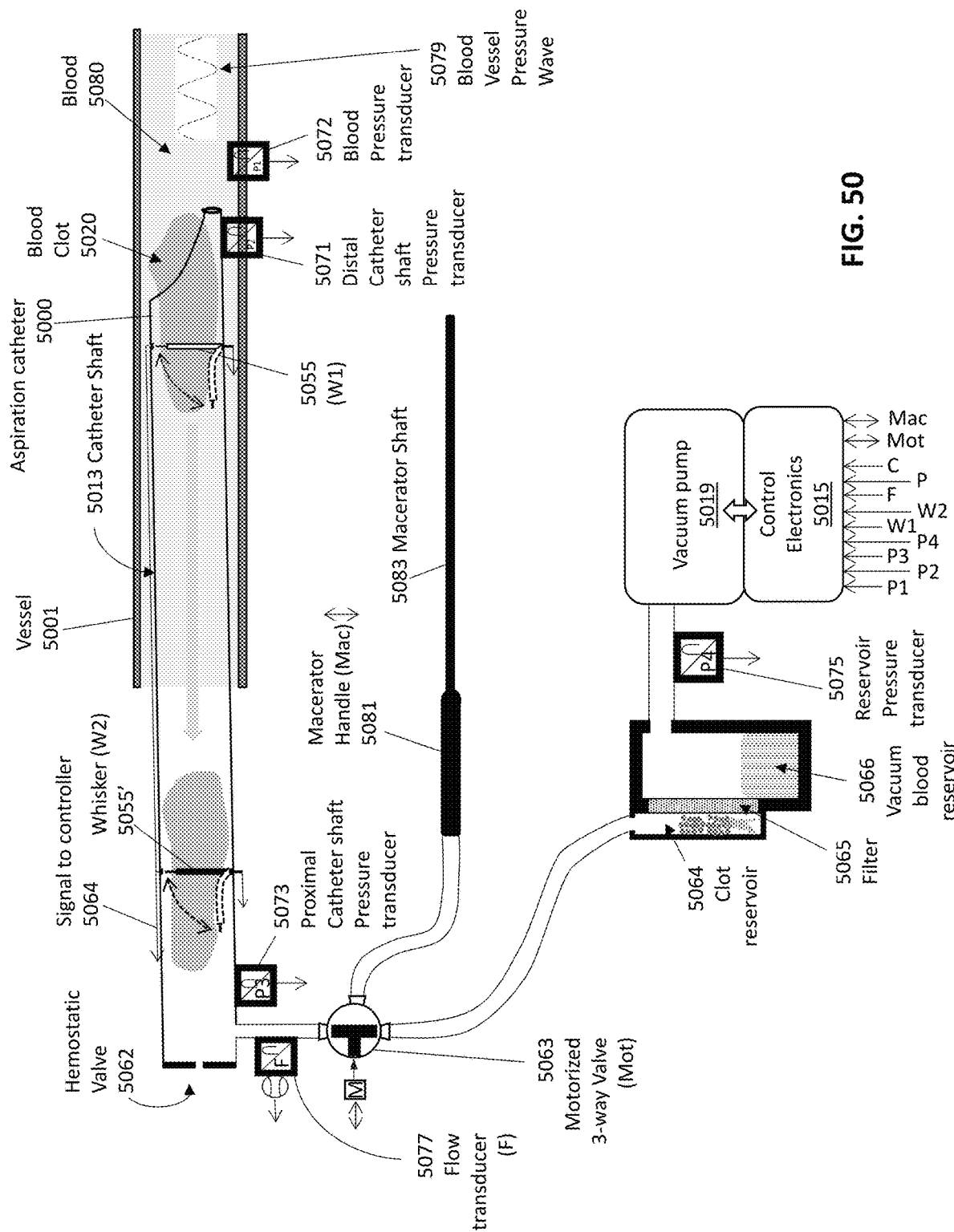
FIG. 50 illustrates an example of an apparatus (e.g., a thrombectomy apparatus) including an aspiration catheter including a plurality of deflectable member and a macerator.

FIG. 50 illustrates another example of an apparatus including an aspiration catheter 5000 (shown within a vessel 5001. The catheter 5000 includes a catheter shaft 5013. A deflection sensor including a deflectable member 5055 (configured as a whisker W1 in this example) is positioned at a distal end region within the suction lumen of the aspiration catheter. The aspiration catheter also includes a second deflection sensor including a deflectable member (W2) 5055' at the proximal end of the suction lumen. The catheter also includes a hemostatic valve 5062 through which a macerator shaft 5083 may be inserted manually or automatically. In FIG. 50 a valve (e.g., 3-way valve) 5063 is included to switch between applying suction to the aspiration catheter or the macerator (or neither). The valve may be a motorized 3-way valve (MOT) and may couple the catheter and/or macerator to the vacuum blood reservoir 5066 through a filter 5065 and clot reservoir 5064. The vacuum pump 5019 may be coupled to the catheter and/or macerator through the reservoir 5066. A controller 5015 may be used to coordinate the suction, macerator and/or sensor(s).

In any of the apparatuses described herein the controller may also coordinate the application of suction through the aspiration catheter 5000 and/or the macerator 5083 based on patient respiration and/or pressure within the blood vessel local to the distal end of the aspiration catheter. For example, suction may be applied in a pulsatile manner when (or only when) local pressure is low during the cycle of the blood pressure pumping the vessel.

Thus, and of these apparatuses may include a blood pressure transducer 5072 (P1). The pressure transducer may be on the catheter at or near the distal end or it may be separate, including external. Alternatively or additionally a distal catheter shaft pressure transducer 5071 (P2) may also be included on the aspiration catheter. The catheter may also include a proximal pressure transducer 5073 (P3). Any of these apparatuses may also include one or more flow sensors/flow transducers 5077 (F). In FIG. 50 the flow transducer is near the proximal end suction port. The controller may receive input from any or all of these sensors/transducers in addition to the deflection sensor(s).

The macerator may also include a drive in the macerator handle 5081 or may be in communication with the handle (Mac) and the controller may also receive input/direct output to the handle, allowing the drive to be turned on/off and/or increased/decreased.

In FIG. 50 the controller may coordinate one or more pulses of suction from the aspiration catheter based on the sensed pressure way of the blood vessel 5079 and may detect clot material entering and/or exiting the suction lumen via the two deflection sensors.

Figure 51A:
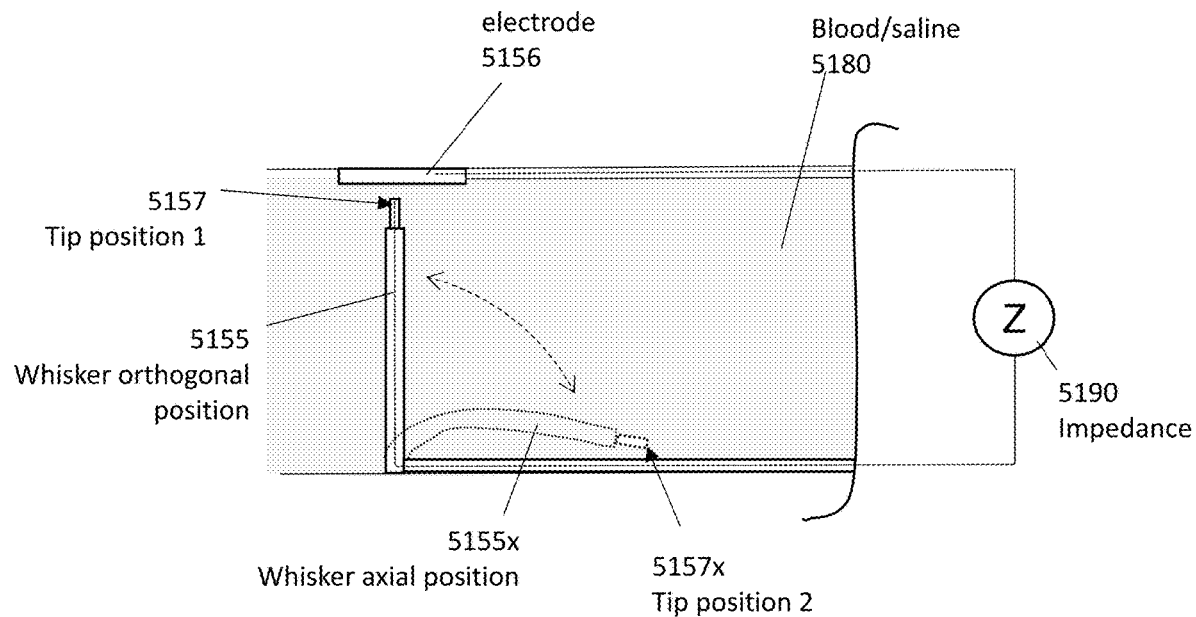
FIG. 51A schematically illustrates an example of a deflection sensing circuit for a deflectable member.

FIG. 51A illustrates the operation of a system such as those shown in FIGS. 48 and 49. In FIG. 51A the deflection sensor detects impedance changes as a function of the distance between the tip 5157, 5157x of the deflectable member 5155 and an electrode 5156. When the delectable member (e.g., "whisker") deflects towards an axial position as the clot passes over it, the distance between the electrode on the opposite wall and the tip of the deflectable member 5157 increases and thereby increases the impedance between those two points which is reflected in the impedance measurement Z 5190. The impedance measurement may be performed at a single or at multiple frequencies. The frequency range could be, e.g., between 0 Hz (DC measurement) to 100 kHz, and more specifically from few Hz to few kHz, for example around few hundred Hz (e.g., 100 Hz-900 Hz, 100 Hz-700 Hz, 100 Hz-500 Hz, 100 Hz-400 Hz, etc.). In any of these examples, the frequency may be further tuned to be a multiple of 50 Hz and 60 Hz to reduce the amount of power line interference specially when a long cable is used to reach the distal end of the catheter. Some examples of such frequencies may include 300 Hz, 600 Hz, 900 Hz etc. The higher frequencies may be susceptible to the long cable length stray capacitance/inductance and may experience cross-talk, however long cable length may be advantageous for reducing the effect of electrode/electrolyte interface impedance. Therefore, a mid-range frequency, e.g., of a few hundred Hz may be optimal for this type of measurement.

Compared to the DC measurement, the advantages of the AC measure include: the signal may be less sensitive to induced noise because the measurement could be performed at the same frequency using a locking amplifier or using synchronous demodulation (which has the advantage of lower cost implementation), the AC may be less susceptible to the electrode/electrolyte interface specially the double layer capacitance developed at such an interface. The impedance measurement may be implemented the by two wire or 4 wire techniques described herein.

Figure 51B:
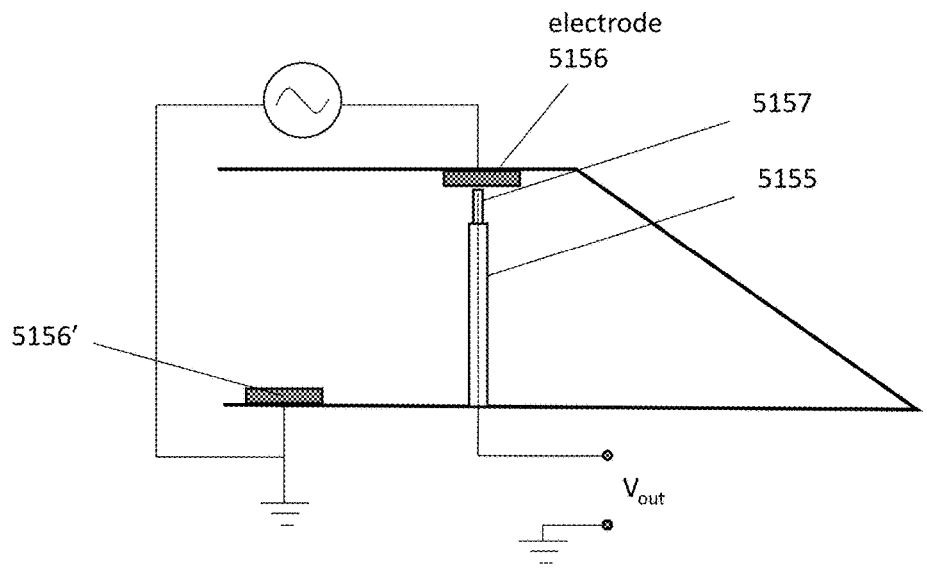
FIG. 51B schematically illustrates an example of a deflection sensing circuit for a deflectable member.

Alternatively, in some examples, the sensing circuit may instead include a second wall electrode, as shown in FIG. 51B. In this circuit the electrode 5157 at the distal tip of the deflectable member 5155 moves between the first electrode 5156 and the second electrode 5156'. The sensing circuit therefore allows sensing ($V_{out}$) of deflection by looking at the output voltage which varies depending on the tip position. In this example the deflectable member (e.g., whisker) position acts like an impedance divider, to divide the source AC signal into a value proportional to the relative position of the whisker to the source electrodes. This approach may be less sensitive to the absolute impedance value of the media (e.g., blood or blood clot) but may be more sensitive to the relative position of the deflectable member. Also this technique may be less sensitive to the accuracy of the impedance source voltage magnitude and frequency. This technique may convert the absolute impedance measurement to ratio-metric measurement which may be less sensitive to the measurement variations. Also, the AC signal may be sinusoidal, square wave, sawtooth or any other (including arbitrary) shape. The output may be calculated based on the RMS value of the signal.

Figure 52:
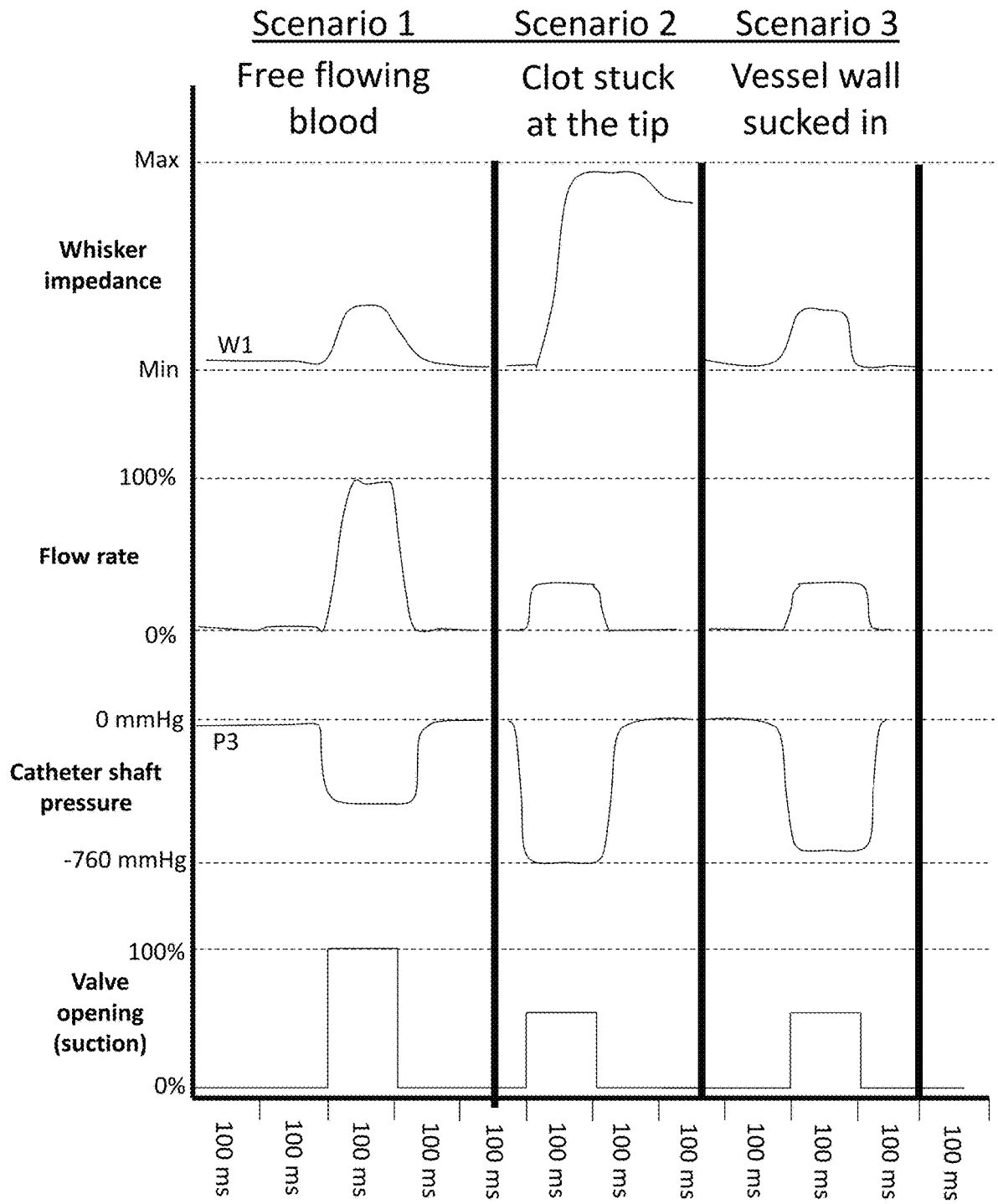
FIG. 52 is a graph illustrating different scenarios for operation of an apparatus using a deflectable member as an obstruction sensor as described herein.

FIG. 52 is a graph that illustrates the use of a deflectable member to determine characteristics of clot sensing in the distal end of the apparatus. For example, in FIG. 52 there are three possible scenarios of aspiration and shows graphs illustrating schematically how each of these cases would be reflected in the deflection of a deflectable member at the distal end region of the aspiration catheter, as well as the flow rate and pressure within the aspiration suction lumen. For example, in FIG. 52 at the far left side, the case in which no clot enters the catheter during a pules (100 ms pulse) of suction is applied through the aspiration catheter including a deflectable member. Deflection in this example may be determined by the impedance change of a sensing circuit (such as that shown in FIG. 51A). A small increase in impedance during the pressure pulse is seen but falls off as the suction is turned off. The flow rate increases maximally during the application of suction, whereas the catheter shaft pressure is modestly decreased during suction. During the period when the valve is fully open for 100 ms, a maximum flow occurs through the catheter, as shown. In contrast when the pulse of suction causes material to clog as shown by the middle column in FIG. 52, a large piece or pieces of clot material may be stuck in the distal end of the catheter. In this case, the deflectable member (e.g., whisker) deflection signal stays on even after the valve is shut off. In addition a much lower flow is seen, with a rather large pressure difference. In contrast if the vessel wall is engaged by the distal opening of the catheter, the deflectable sensor will not detect the deflection of the deflectable member, as shown, similar to the case in which no clot material is detected. In contrast, however, the deflectable member deflection may have similar flow, and pressure profiles as when the catheter is not occluded (far left scenario). For example, the pressure may increase during suction, but the flow rate may remain relatively low.

In general, the controller may use data such as that shown above, which may be collected using all or a subset of these components (e.g., sensors).

In some examples the system may initially close suction (e.g., the three way valve) to prevent any suction through the macerator or aspiration catheter and may start and run the vacuum pump until the reservoir vacuum pressure reaches a target range (e.g., −700 to −760 mmhg). At this point the user can activate the valve by pressing one of the controls (e.g., buttons) on the catheter shaft and may aspirate saline through the catheter to prime the system before insertion into the patient's blood vessel. Once the system is done with the initial set up (and any self-check steps), it is ready for operation.

The user may then insert the aspiration catheter into the patient's blood vessel and advance it until it reaches the target area, in order to perform a thrombectomy procedure using these apparatuses. At this point, the catheter tip may or may not be close enough to the clot to capture it by aspiration. In order to limit the blood loss, the system may activate the vacuum for a very short interval, for example 20-100 ms and then assess the sensors to see what the combination of information from the pressure sensors and/or the deflectable members indicate. As shown in FIG. 52, the first scenario is that of the tip of the catheter may be too far away from the clot and therefore unable to capture it when vacuum is activated. In this scenario, the valve is opened to its 100% of opening window and for a period of 100 ms. The catheter pressure measure by P2 goes negative but not to the maximum vacuum pressure given there is free flowing blood through the system. The deflectable member (e.g., whisker W1) moves a small amount due to the flowing blood exerting force on it but not to its maximum.

In the second scenario a large clot gets stuck at the tip of the catheter upon opening of the valve. The clot does not allow any flow other than some leakage around it, thus the pressure goes to near maximum, flow is minimal but the deflectable member (e.g., whisker W1) signal goes to its maximum level given the clot is pressing it to the side of the catheter lumen. Once the valve is closed, the whisker signal stays high as the clot is still present and needs to be macerated or otherwise forced to move.

In the third scenario, the tip of the catheter is placed against the wall of the vessel and upon opening of the valve, the wall is sucked into the opening of the catheter and blocks any fluid flow barring some possible leakage. In this case, pressure goes to near maximum vacuum while there is minimal flow signal and no whisker signal barring a minimal amount due to the leakage of blood into the catheter.

Figure 54A:
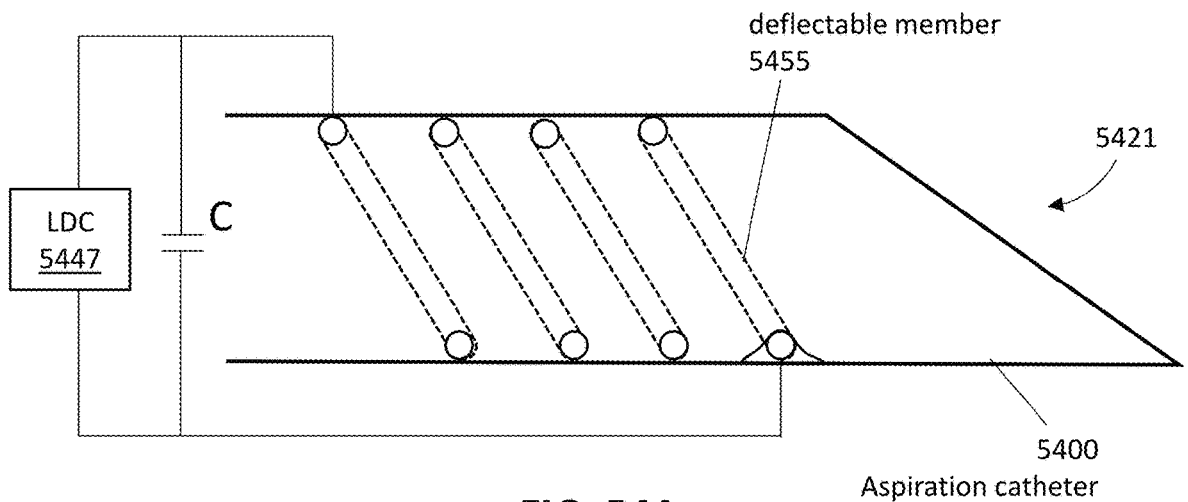
FIGS. 54A-54C illustrates an example of a deflectable member configured as a spring element that extends longitudinally (axially) within the suction lumen to detect clot material.
Figure 54B:
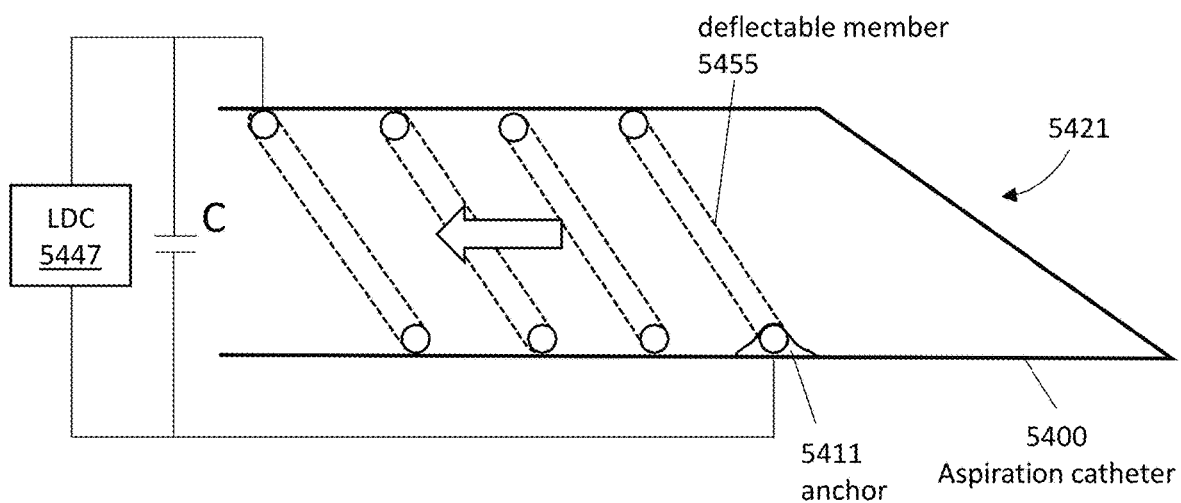
Figure 54C:
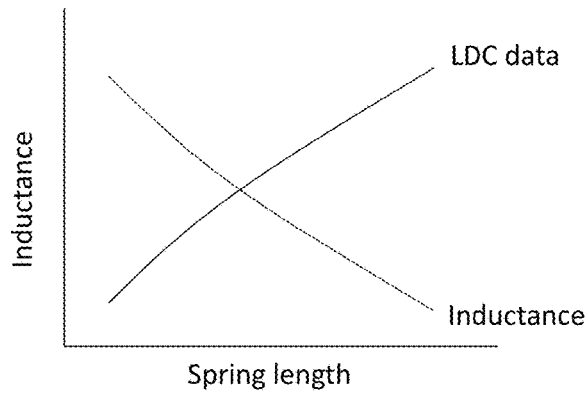

FIGS. 54A-54C, 55 and 56 show other examples of deflection sensors that include deflectable members. In any of these deflection sensors the deflectable member is configured so that a first part of the deflectable member is fixed to the suction lumen and a deflected end extends at least partially into the lumen so that force due to a blood clot contacting it deflects it. In FIGS. 54A-54C the deflection sensor includes a deflectable member 5455 that is configured as a deflectable spring within the suction lumen. The spring may be relatively easily moved within the lumen of the suction lumen with the distal end fixed and the proximal end free to move. The sensing circuit may include an inductance sensor (e.g., an inductance-to-digital, LDC sensor) 5447 that can be used to detect a change in impedance/inductance, as shown in FIG. 54B. As force (e.g., dure to a clot entering the distal end opening 5421 and pulling on the spring proximally under the force of suction, or when jammed into the distal end region) pulls the spring proximally, the change inductance may be detected, as shown in FIG. 54C.

Figure 55:
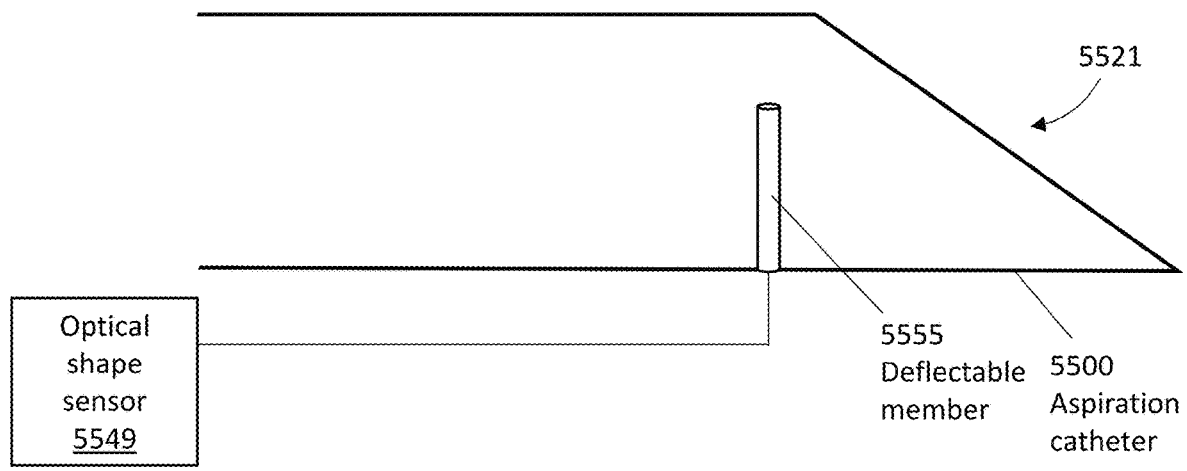
FIG. 55 schematically illustrates an example of a deflectable member configured as an optical, shape-sensing bend sensor.

FIG. 55 shows another example of a deflection sensor including a deflectable member 5555 in an aspiration catheter 5500 that includes a shape sensing optical fiber (e.g., an optical fiber bend sensor) near a distal end opening 5521 into the suction lumen. Bending of the deflectable member results in a signal of the optical shape sensor 5549 that reflects bending of the deflectable member 5555. In this example. As in any of these examples the deflectable member may be restored to the undeflected configuration when the force (e.g., the clot) is released or removed, e.g., by aspiration and maceration.

Figure 56:
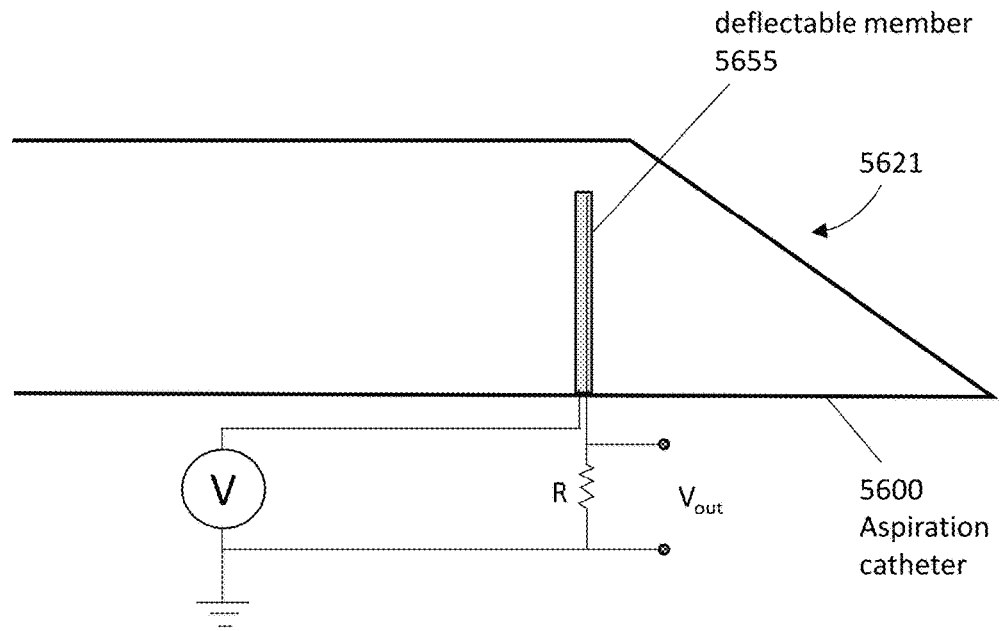
FIG. 56 schematically illustrates an example of a deflectable member configured as a resistive sensor in which the resistance changes as the deflectable member bends.

FIG. 56 shows another example of an apparatus 5600 including a deflection sensor with a deflectable member 5655 and a sensing circuit providing a deflection signal to the controller. For example, the deflecting member may include a material for which resistivity changes as it is bent. Thus, bending of the elongated deflectable member 5655 causes an increase in resistance across the conductive elements. The elongated deflectable member may be similar to sensors of the type available from Flexpoint Sensor Systems, Inc. of Draper, Utah. The deformable member 5655 may be secured to the side of the lumen as described above, e.g., by adhesives, fasteners, or other suitable techniques, within a predetermined distance from the distal end opening 5621. Alternatively a current source can be used to drive the resistive element to create a higher range signal.

Figure 57:
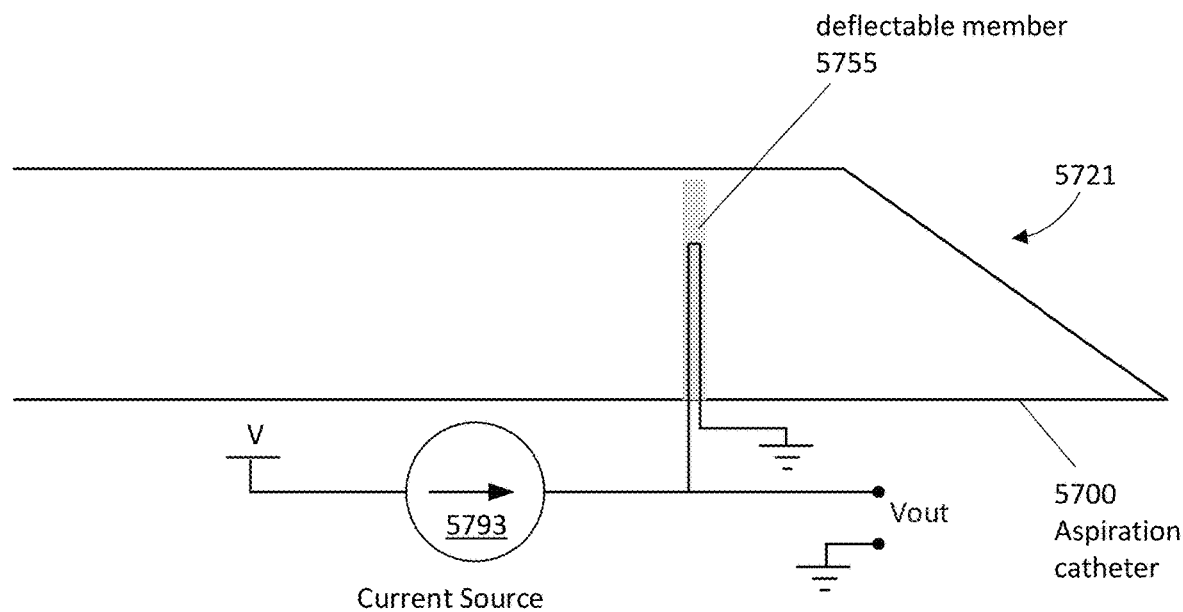
FIG. 57 schematically illustrates an example of an aspiration catheter including a deflectable member and a detection sensor (circuit) as described herein.

FIG. 57 illustrates another example of an aspiration catheter apparatus 5700, similar to that shown in FIG. 56, including a deflection sensor with a deflectable member 5755 and a sensing circuit providing a deflection signal to the controller. For example, the deflecting member may include a material for which resistivity changes as it is bent. Thus, bending of the elongated deflectable member 5755 causes an increase in resistance across the conductive elements. The deformable member 5755 may be secured to the side of the lumen as described above, e.g., by adhesives, fasteners, or other suitable techniques, within a predetermined distance from the distal end opening 5721. In this example, a current source 5793 can be used to drive the resistive element to create a higher range signal. A controller may process the output voltage to detect deflection.

Figure 53:
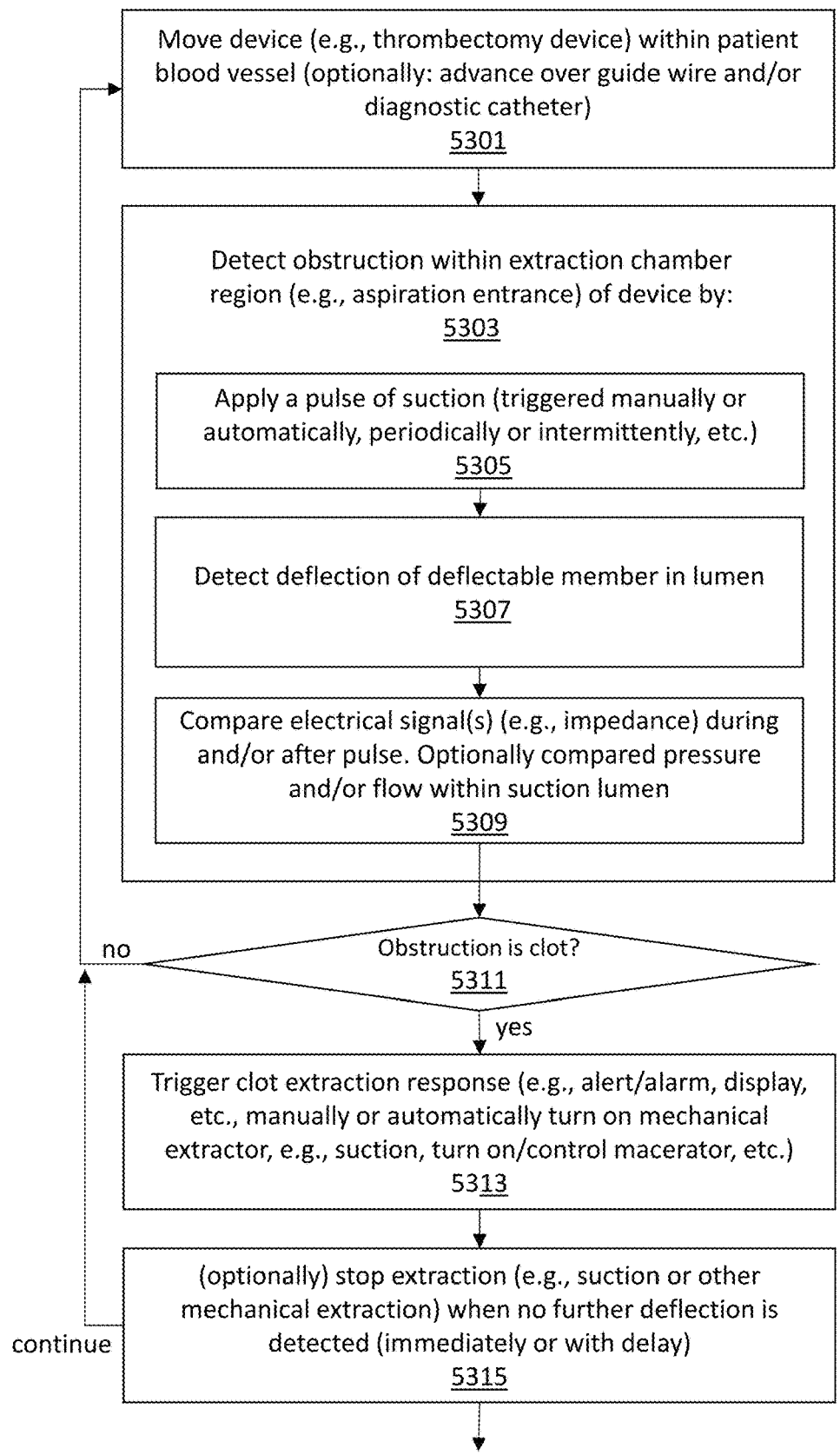
FIG. 53 illustrates an example of a method of controlling clot removing using an apparatus including one or more deflectable members as described herein.

FIG. 53 illustrates one method of operating an apparatus including a deflectable sensor as described. Optionally the apparatus may be positioned within a vessel of a patient 5301 near a clot material. The apparatus may then detect clot material 5303 near the distal end opening into the device by applying a pulse of suction 5305 and detecting deflection of a deflectable member 5507 (e.g., by detecting deflection of deflectable whisker based on electrical signal between tip of whisker and reference (fixed) electrode in lumen). The resulting signal(s) may be analyzed to determine if a clot material is present in the distal end of the device, and/or if the aspiration catheter is against the vessel wall. For example, the deflection signals may be compared from the period of time before/during and after the pulse. Optionally the pressure and/or flow may be analyzed. As described in FIG. 52, the clot may be distinguished from vessel wall or non-clot scenarios. If the obstruction is detected and is a clot 5311, the apparatus may trigger a clot extraction response 5313, such as alerting the user that the clot is present (in some cases the system may instead indicate the wall of the vessel has been contacted), and/or turning on suction and/or turning on maceration. Optionally the method may include stopping extraction (e.g., suction) where the deflection sensor no longer detects deflection of the deflectable member indicating that clot is present 5315.

Figure 58A:
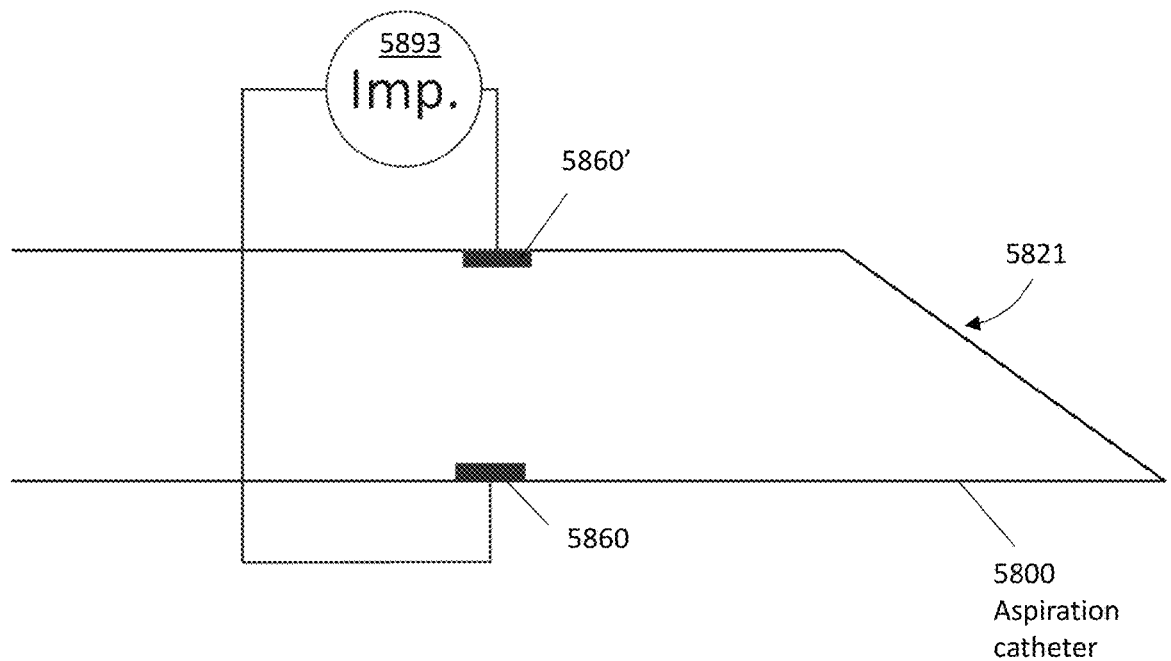
FIG. 58A schematically illustrates an example of an aspiration catheter including a general impedance sensor similar to that described above.
Figure 58B:
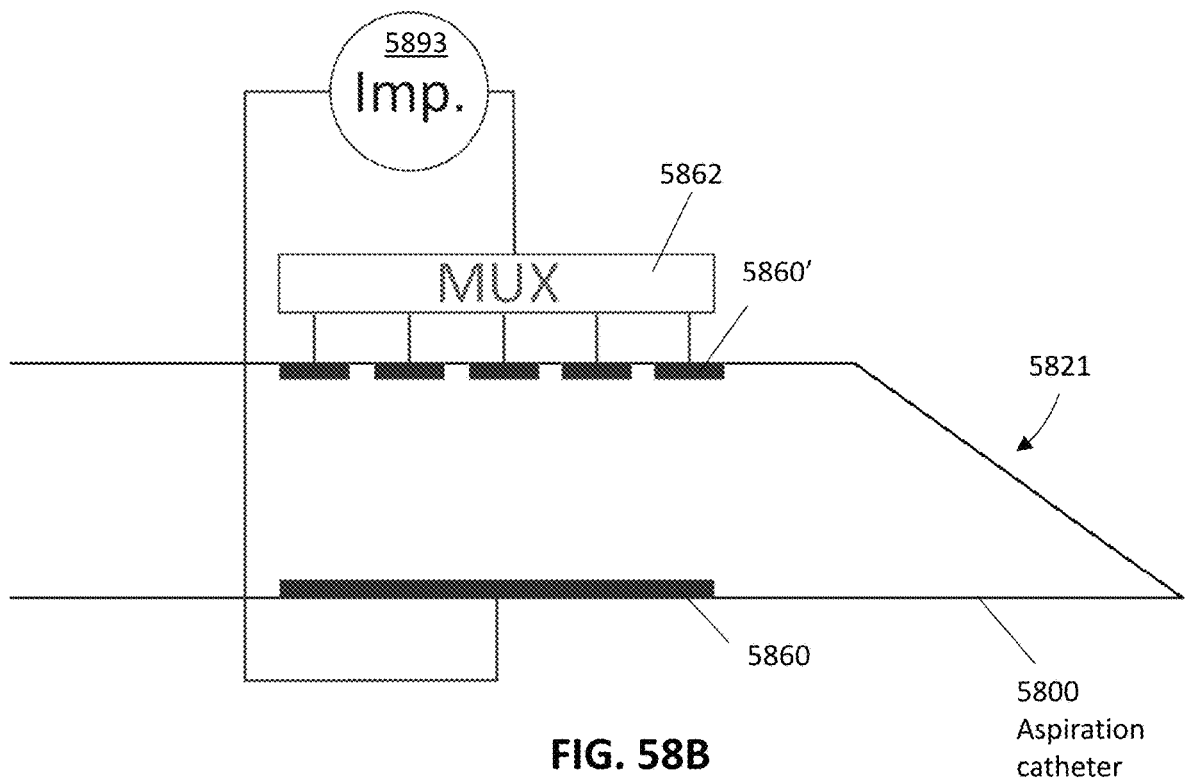
FIG. 58B schematically illustrates an example of an aspiration catheter including one variation of an impedance sensor.
Figure 58C:
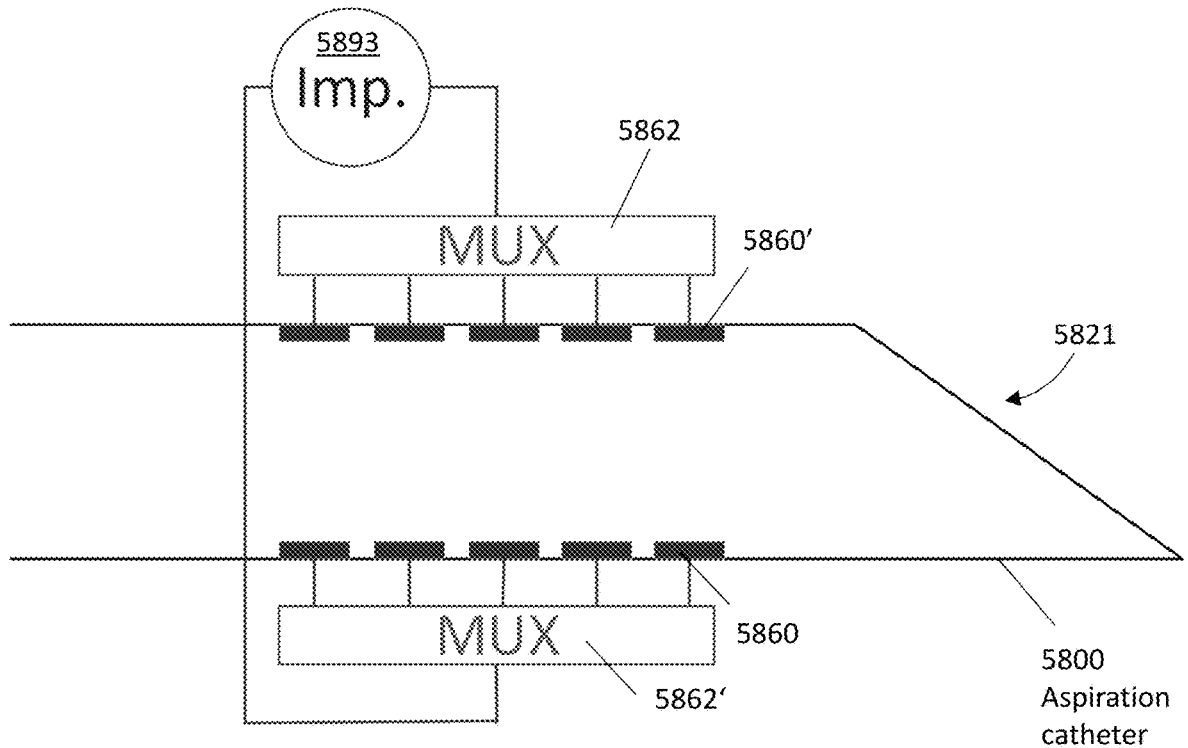
FIG. 58C schematically illustrates an example of an aspiration catheter including a second variation of an impedance sensor.

FIGS. 58A-58C illustrate examples of impedance-based sensing systems for detecting clot material within the lumen. In any of the apparatuses described herein, the sensor(s) within the lumen, which may generally be referred to herein as intraluminal sensors, shown as impedance sensors in FIG. 58A, include a pair of sensing electrodes 5860, 5860'. These intraluminal sensors may be positioned within the lumen of the distal end region of the aspiration catheter 5800 at a specified distance from the distal end opening 5821 so that a clot material may jam within the distal end region in contact with both the first 5860 and second 5860' electrodes, changing the impedance between the two, including changing the impedance when measured at different frequencies, as described above. The spacing distance from the distal end opening may be selected so that clot material may enter and jam within the lumen, but vessel wall may not extend sufficient close within the lumen of the aspiration catheter, and therefore changing impedance in a predictable and useful manner.

FIGS. 58B and 58C illustrate examples in which multiple impedance electrodes 5860 on one side distributed at different longitudinal positions along the inner wall of one side of the aspiration catheter 5800 lumen. In FIG. 58B, this may allow individual position signals to be taken using the individual electrodes 5860 of the array of electrodes and a single reference electrode 5860. Alternatively, FIG. 58C shows an example in which both side of the lumen of the aspiration catheter 5800 include multiple electrodes 5860, 5860', allowing further refinement of the longitudinal position of the occlusion (e.g., clot) within the lumen, and/or helping to distinguish clot material from vessel wall based on the signal and/or the location of the signal(s) when used.

Also described herein are methods of using an apparatus as described herein to perform a pulmonary embolectomy. In this example, the aspiration catheter is advanced through the pulmonic valve, bend or turn into the pulmonary artery to where a clot may be positioned. In some examples the aspiration catheter may be passed through an access vein (such as the right subclavian vein or jugular vein) into the superior vena cava through the right atrium through the tricuspid valve, through the right ventricle, and through the pulmonic valve, to a putative clot (thrombus or occlusive embolus) situated in the pulmonary artery or branches of the pulmonary artery, such as the left pulmonary artery or the right pulmonary artery. In practice, it has proven particularly difficult to capture clot from the left pulmonary artery by aspiration as the navigation required may tend to drive the tip of the aspiration catheter into the wall of the vessel, which is difficult or impossible for most devices to distinguish from clot.

The method may further include applying aspiration (e.g., suction/negative pressure). If the aspiration catheter is occluded, e.g., so that flow through the suction catheter is occluded, the apparatuses described herein may distinguish between occlusion by clot material and occlusion by the vessel anatomy (e.g., vessel wall, valve, etc.). The apparatus may output this information (e.g., occlusion identity information), which may be used by the apparatus to determine how to proceed with the method, including automatically proceeding or manually proceeding. In some cases the information may be used to trigger a clot extraction response if the obstruction is clot material. In some examples this information may be used to control the aspiration (suction) by increasing or modifying the suction if the occlusion is a clot material or turning off aspiration if the clot material is vessel anatomy. In some examples the apparatus may emit an output (e.g., alert) that the occlusion is clot material, or that the occlusion is vessel anatomy.

The apparatus may distinguish between clot material and vessel anatomy (e.g., vessel wall) by any of the techniques described herein. In some examples the apparatus may distinguish between clot material and vessel anatomy based on an intraluminal sensor at a predefined location within the lumen of the aspiration catheter. For example, the apparatus may determine that the occlusion material is clot material or vessel wall by detecting deflection of a deflectable member at a predetermined location within lumen of the vessel.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

EXAMPLES

As described above, any of the methods and apparatuses described herein may be used to detect and monitor (e.g., track) material, including clot material, within the lumen of the suction catheter. For example, a plurality of sensors (e.g., internal sensors) may be arranged along the length of the lumen extending proximally, allowing tracking of clot material as it passes through the lumen. The controller of the apparatus may transmit, store, analyze and/or output (e.g., display) the tracking and/or detection of material within the lumen of the suction catheter. These methods and apparatuses may improve remove of obstructive material from the vasculature by aspiration.

As described above, the use of large bore aspiration catheters to remove obstructive material from a blood vessel has been found effective especially within the venous vasculature. Current technologies have limitations that increase the time of the procedure and present a safety risk of damaging the vessel walls of the vasculature. Obstructive material (e.g., clot) within the venous vasculature that needs to be removed may be larger in cross sectional area than the cross-sectional area of the catheter used to access the obstructive material. For example, thrombus from a peripheral vein in the leg that dislodges and passes into the pulmonary arteries may obstructs blood flow though the pulmonary arteries. Such thrombus material can be approximately 10-20 mm in diameter and can be approximately 100 mm long, or longer. When the thrombus is dislodged, the thrombus is carried by the blood going to the lungs and the thrombus may become wedged within the pulmonary arteries as the arteries begin to narrow and branch into the segments of the lungs. Once wedged, the dislodged thrombus may straddle multiple vessels of the pulmonary arteries or may be balled up and occlude a main pulmonary artery. Venous thrombus is comprised of mainly red blood cells and fibrin formed under low wall shear rates, giving the thrombi unique material properties allowing the thrombus to be compressed and elongated without easily tearing apart. The material properties of the thrombus enable the large pieces of thrombus to be removed from the vasculature through a smaller catheter. Current aspiration catheter technologies typically rely on the compressibility of the thrombus and high aspiration flowrates created, e.g., by ultra-high vacuum pressures (e.g., <−700 mmHg) to pull the large mass of thrombus through the smaller aspiration lumen which frequently causes the thrombus to get stuck within the aspiration lumen of the catheter or, even riskier, may cause the vessel to collapse and the aspiration forces of the catheter to be applied to the thin wall of the vessel; the user typically has no way to assess if either event, or which of these events, is happening. Instead, all the user may see is that aspiration has been applied and there is minimal to no blood movement coming back through the catheter. Users will typically wait to see if the thrombus continues to compress so that it can eventually be pulled through the catheter. While they wait, the user may attempt to increase the vacuum within the aspiration lumen multiple times. This process can take several minutes and often results in no change, forcing the user to retract the catheter proximal and attempt to pull the potentially stuck thrombus with the catheter until the thrombus tears and blood flow starts to rush into the aspiration source. In some instances, the catheter must be completely retracted across the heart and pulled out of the body of the patient requiring the user to start the procedure over, meaning that the user must re-cross the heart and regain access to the pulmonary artery that was being treated. The additional time and steps required increase the risks of the procedure. Thus, it may be particularly beneficial to provide systems and methods for removing of obstructive material that enable the user to know what is happening in front of and/or within an internal lumen (i.e.: aspiration lumen) of a catheter.

The methods and apparatuses described herein may permit the user to monitor and/or track clot material within the lumen of the suction catheter, including identifying that clot material (or in some cases vessel wall) is clogged, and/or where it is clogged. The apparatus and methods may also allow the apparatus to distinguish between clogging of the vessel, which may be cleared mechanically, and/or by modulating, including increasing, the applied suction and collapse of the vessel, which may instead require decreasing the applied suction. In general, these methods and apparatuses may decrease the time and risk associated with removing thrombus from a blood vessel.

For example, these methods and apparatuses, including suction catheters, may detect the presence of thrombus within a lumen of the catheter, measure at least one fluidic parameter of the lumen of the catheter (e.g., flow rate, etc.), may estimate the volume of thrombus within and/or passing of clot material and/or blood through the lumen of the suction catheter, and may indicate this data to the user, store and/or transmit the data. In some examples the apparatuses and methods described herein may detect when an opening into the suction catheter (e.g., the aspiration orifice) is sucking onto a vessel wall and/or when the apparatus is clogged with clot material.

Figures 59A, 59B:
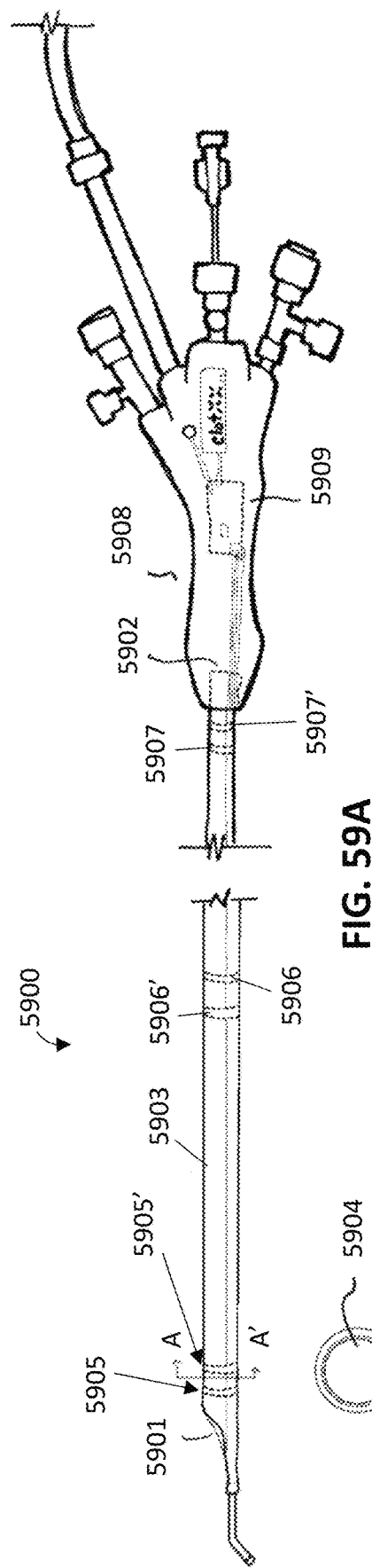
FIGS. 59A-59B show one example of a suction catheter apparatus as described herein, including sensors (e.g., impedance sensors) within the lumen to detect and/or track clot material within the lumen.

FIGS. 59A-59B illustrates one example of an apparatus as described herein. In this example, the apparatus includes a catheter 5900 having a distal 5901 and a proximal end 5902 with a flexible body 5903 extending between the ends. An internal (e.g., suction) lumen 5904 extending along the length of the catheter. At least one electrical property sensor (e.g., impedance sensor) having a least one conductive surface, and in some examples, preferably two conductive surfaces, is positioned within the lumen and configured to contact a material (e.g., blood, clot, etc.) within the lumen. As described above, e.g., FIGS. 1A, 11, 12, and 15-18E, multiple sensors (including surface electrodes) may be used. In FIG. 59, the sensor(s) include two conductive surfaces that are spatially positioned relative to each other such that the impedance of the substance contacting both surfaces can be measured and processed to determine contact with a clot material or other material within eh lumen. The conductive surfaces of the sensing element can be spatially aligned radially around the circumference of the internal lumen 5904 and/or axially aligned along the longitudinal axis of the internal lumen 5904) as shown herein. In this example, three sets of electrical (e.g., impedance) sensors are positioned longitudinally along the length of the lumen. The distal sensor (including a first sensing electrode 5905 and a second sensing electrode 5905') includes two conductive surfaces each made of a conductive material such as stainless steel, extending radially at least partially around the lumen of the suction catheter, e.g., extending between about 10-360 degrees (e.g., between about 20-360, between about 30-360 degrees, between about 40-360 degrees, between about 45-360 degrees, between about 60-360 degrees, more than 10 degrees, more than 20 degrees, more than 30 degrees, more than 45 degrees, more than 50 degrees, more than 60 degrees, more than 70 degrees, more than 80 degrees, more than 90 degrees, etc.) of the inner diameter of the lumen. The electrode sensor may be affixed to the body of the catheter so that the inward facing surface is exposed to the objects that pass through the internal lumen 5904 of the catheter. The conductive surfaces may form a continuous surface or may be discrete surfaces that are electrically connected as a single sensing electrode. In FIGS. 59A and 59B the sensing electrodes forming the sensors may be formed, e.g., of a continuous strip of conductive material that is approximately 1 mm wide by about 0.13 mm thick curved strips or bands, forming complete or partial rings extending around the lumen of the apparatus, including at the distal end (e.g., the distal end region, in some examples, the extraction zone). FIG. 59B shows a cross-section through the suction catheter of FIG. 59A. In this example, the section shows a suction lumen 5904 as well as a guide wire lumen 5933 and a navigation lumen 5934.

As used herein, a ring sensor electrode ("ring electrode" or "ring sensor") may extent fully, or partially, around the inner wall of the suction catheter lumen. Thus, in some examples the ring may be an annular ring or rings that are longitudinally arranged and may be either continuous (as shown in FIG. 59A), or may be discrete (see, e.g., FIGS. 11 and 12).

For example, in some variations the ring electrodes may be split and pressed outwardly into the inner lumen of the catheter. The surfaces of the ring electrode can be thermally embedded or chemically bonded to the inner surface of the lumen. In some examples, small insulated conductive wires may be mechanically affixed to each one of the conductive surfaces using a joining method such as soldering. The insulated conductive wires may run throughout the length of the lumen and into the handle 5908 of the catheter. In FIG. 59A, the apparatus includes three sets (e.g., pairs) of sensing electrodes, one each at the distal 5905, 5905', proximal 5908, 5907' and at least one intermediate region 5906, 5906'. In some embodiments, conductive wires can continue out of the handle 5908 and attach to an external signal processing source. In this example the signal processing source 5909 may include a small battery powered PCB encapsulated in the handle 5908 that is connected to an LED 5910 and a digital display 5911. The distal sensing electrodes 5905, 5905' may be distally positioned just proximal to the distal end 5901, e.g., up to 5 mm proximal to the distal opening, which may be a tapered or lateral (side-facing) suction opening in any of these suction catheters. In suction catheters including a tapered or slanted distal end, the distal positioning may be relative to the proximal edge of the distal end 5901 of the apparatus, as shown in FIG. 59A. The conductive surfaces of the sensing electrodes (ring electrodes) in this example may be spaced a distance of about 1-20 mm apart, preferably about 2-5 mm apart (edge-to-edge). The spacing of these surfaces may be selected to ensure thrombus passing through will bridge across the conductive surfaces, and to allow for multiple sampling points during contact as the thrombus passes through the lumen. The distal sensor (including sensing electrodes 5905, 5905') may be distally positioned relative to the distal end 5901 so that it may rapidly detect substances entering the internal lumen 5904, and not substance (e.g., clot) touching just, or stuck to, the distal end 5901 of the catheter. The second electrical sensor (including electrodes 5906, 5906') can be axially positioned along the internal lumen 5904 between the distal 5901 and proximal 5902 ends of the catheter. In this example, the second sensor may be positioned, e.g., between about 2-80 cm, preferably about 30 cm, proximal from the distal end 5901 of the catheter. This distance may be preferred as the thrombus passing through the lumen may be moving at a constant velocity when being extracted completely out of the catheter. This distance may also be preferred in some embodiments because it may position the electrical sensors in a portion of the catheter that is proximal to the tortuous anatomy such as when accessing and treating the pulmonary vasculature. In some use scenarios of this invention, the user could use this sensing element as an indicator to stop aspiration power either allowing momentum to continue passing the thrombus through the lumen or to allow the thrombus to reside in the lumen while going after more obstructive material. As described above, this may be useful to minimize the blood loss during a procedure. The conductive surfaces of the second electrical sensor (e.g., electrodes 5906, 5906') in this example may be constructed similarly to the distal sensor (e.g., electrodes 5905, 5905') also shown as spaced about 2-5 mm apart. Insulated conductive wires may run proximally from the sensors and may be attached to the same signal processing source 5909, e.g., in the handle 5908. The proximal electrical sensor 5907 is positioned between the second electrical sensor 5906 and the aspiration source (not shown) of the device. In this example the proximal sensor (electrodes 5907, 5907') is positioned just distal to the proximal end 5902 of the catheter within the internal lumen 5904. The proximal sensor positioned in this location may detect when the obstructive material (e.g., clot) has cleared the internal lumen 5904 of the catheter and may allow for analysis of material with the distal and second sensing elements to determine mechanical properties of the obstructive material such as mass and volume as well as the mechanical performance of the catheter such as flow rate of material (e.g., clot) through the apparatus. The conductive surfaces of the proximal sensor (e.g., of electrodes 5907, 5907') may be constructed identically to the second sensor (electrodes 5906, 5906') and may be connected to the signal processing source 5909.

Figure 60:
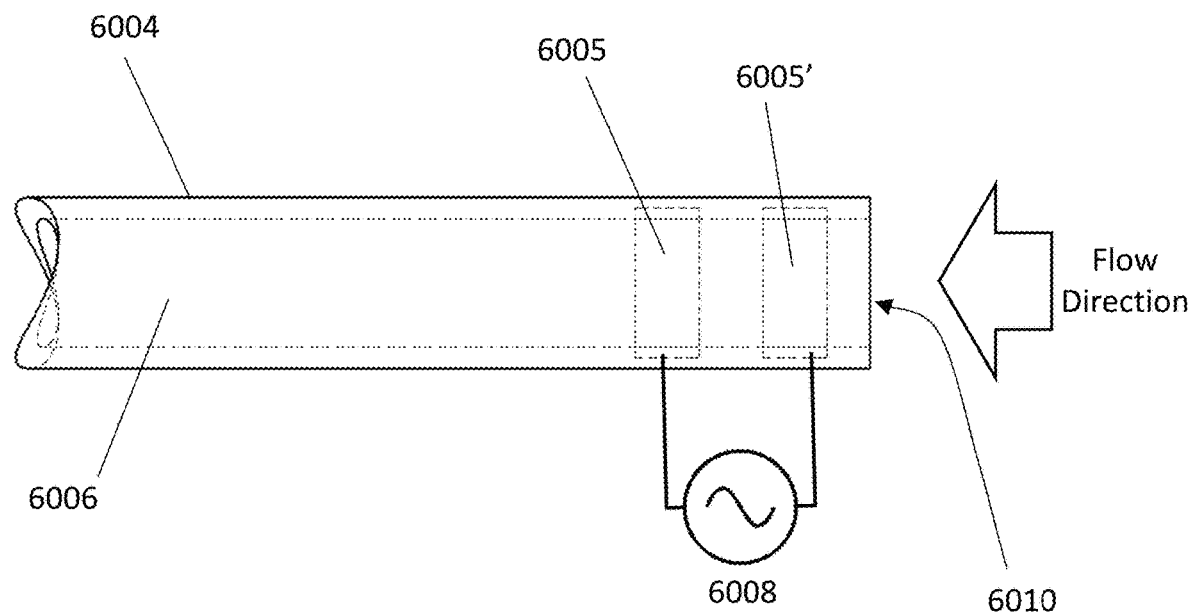
FIG. 60 schematically illustrates an example of a suction catheter including an internal distal electrical (e.g., impedance) sensor.

FIGS. 60-63C illustrate examples of electrical sensors as described herein, including in particular sensors comprising annular ring electrodes. For example, FIG. 60 shows an example of an apparatus (e.g., system) including an embolectomy catheter having an elongate tubular catheter body 6004; an internal lumen 6006 through which bio-fluids or other materials may pass, such as blood, and/or solid or semi-solid material, such as a blood clot; a pair of electrically conductive electrodes 6005, 6005' configured to be substantially in contact with said bio-fluid within the lumen; and an alternating electrical power source (AC Voltage) 6008 configured to establish and control a variable voltage between these sensing electrodes, and further configured to sense and measure and record the electrical impedance between said electrodes over time. In this example the electrodes 6005, 6005' may operate as an electrode pair, forming an electrical sensor, and may be configured with a known and fixed distance between the electrodes, as measured in the axial direction of the catheter, of between about 0.5 mm and 20 mm, and more preferably between about 1 mm and 10 mm, e.g., between about 2 mm and 5 mm. The electrode pair may be further configured to be located proximal to the open entrance of the catheter, preferably between 0 mm and 20 mm from said open entrance measured in the axial direction of the catheter, or more preferably between 1 mm and 10 mm from said catheter open entrance.

The system of FIG. 60 is configured to allow for the electrical impedance to be measured in the internal lumen of the catheter proximal to the electrode pair to detect changes in contents flowing through the catheter over time. Specifically, the system may allow for the detection of changes in material density, composition, and other properties that result in measurable changes in electrical impedance, such as the passage of a blood clot. The apparatus may be configured to detect impedance from the sensor electrodes, including magnitude and/or phase, at different frequencies.

Figure 61:
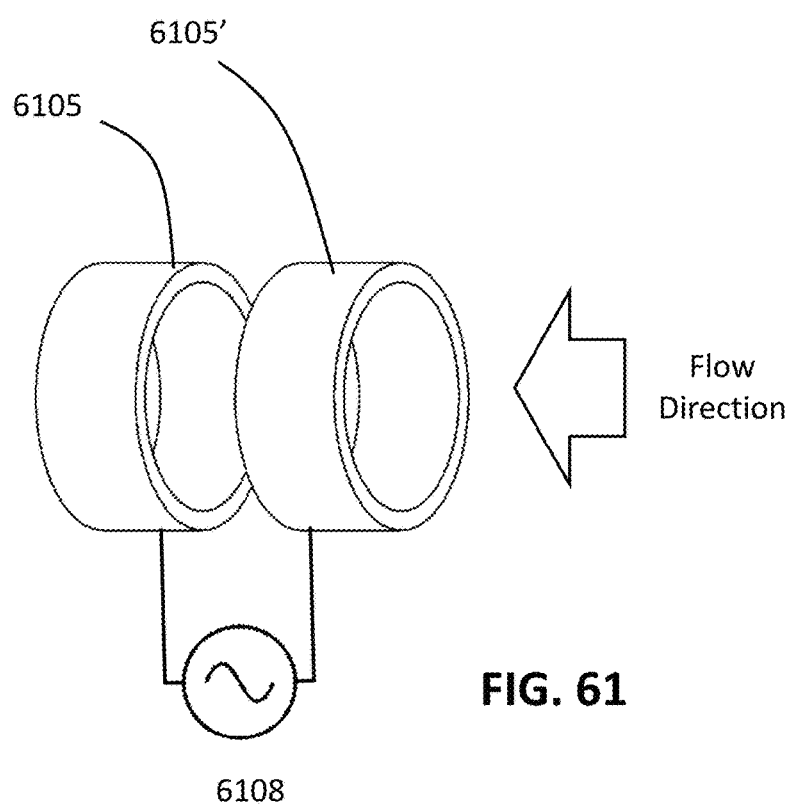
FIG. 61 schematically illustrates an example of a pair of ring electrodes that may be used as internal electrodes for any of the electrical sensors described herein.

FIG. 61 shows an example of a pair of electrically conductive electrodes 6105, 6105' shown configured as two electrically conductive annular rings through which a material may pass. The electrodes may be connected to a variable power source 6108, such as to an AC voltage, AC current, or other electrical configuration that changes the voltage and/or current between said electrodes over time. The variable power source is further configured to measure and record the electrical impedance between the two electrodes 6105, 6105'. In this example the electrodes may primarily measure fluid impedances in the axial space between the two annular electrodes.

Figure 62:
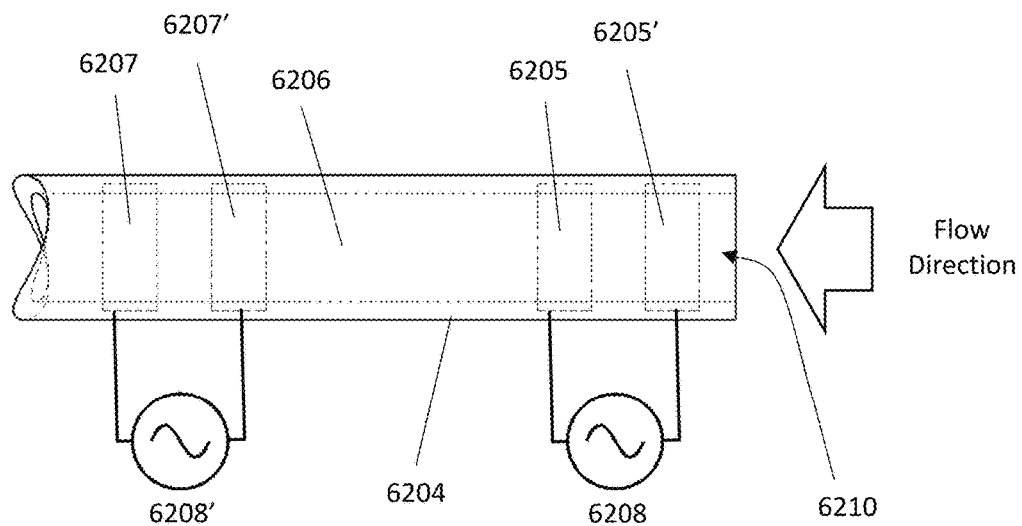
FIG. 62 schematically illustrates an example of a suction catheter including an internal distal electrical (e.g., impedance) sensor and an internal proximal electrical (e.g., impedance) sensor, not drawn to scale.

In one example, as shown in FIG. 62, the embolectomy catheter apparatus (e.g., suction catheter) may include a tubular catheter body 6204; an internal lumen 6206 through which bio-fluids or other materials may pass, such as blood, and/or solid or semi-solid material, such as a blood clot; a distal pair of electrically conductive electrodes 6205, 6205' configured to be substantially in contact with said bio-fluid and located proximal to the open entrance of said catheter; a proximal pair of electrically conductive electrodes 6207, 6207' configured to be a fixed distance from said distal electrode pair, as measured in the axial direction of the catheter, and in contact with the bio-fluid. The apparatus may also include a first alternating electrical power source (e.g., AC Voltage) 6208 configured to establish and control a variable voltage between said sensor (e.g., distal electrodes 6205, 6205'), and further configured to sense, measure and record the electrical impedance between said electrodes of the distal electrode pair over time. The apparatus may also include a second alternating electrical power source 6208' (e.g., AC Voltage) configured to establish and control a variable voltage between said proximal electrodes of the proximal electrode pair. The apparatus may also be configured to sense and measure and record the electrical impedance between said proximal electrodes over time.

In the example shown in FIG. 62, the suction catheter may be configured to make impedance measurements at the distal 6205, 6205' and proximal 6207, 6207' electrode pairs, allowing the system to cross-correlate the signals to determine flow characteristics such as: flow velocity: the size and/or volume of a blood clot flowing through the catheter, etc.

During normal catheter use the catheter tip at the location of the suction opening of the catheter may become occluded by venous tissue form the surround blood vessel wall, blocking flow and resulting in some amount of tissue entering the open entrance region of the catheter. In this condition the distal electrode pair may detect a characteristic change in impedance indicative of this venous wall material entering the catheter, and the system may supply the physician with this information in real time.

Figure 63A:
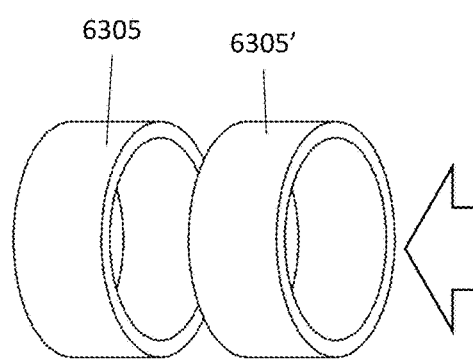
FIG. 63A schematically illustrates an example of a pair of annular ring electrodes similar to those of FIG. 61.
Figure 63B:
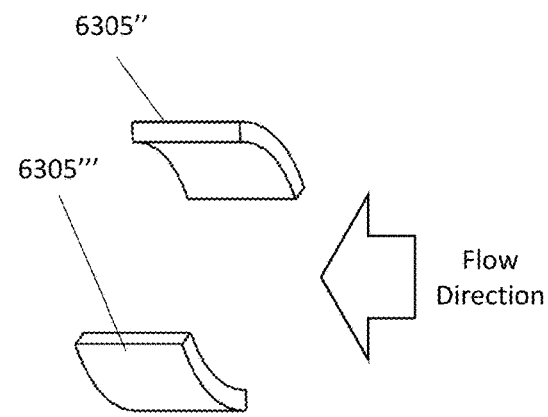
FIG. 63B schematically illustrates an example of a pair of ring electrodes that extend only partially around the annuls of the inner lumen of a suction electrode.
Figure 63C:
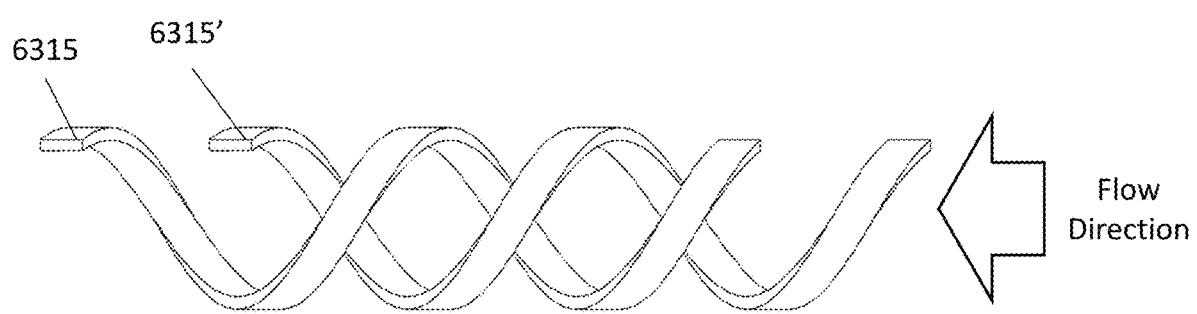
FIG. 63C schematically illustrates an example of a pair of helical electrodes that may be functionally equivalent to the ring electrodes shown in FIGS. 63A-63B.

FIGS. 63A-63C show another example of a set of electrodes forming an electrical sensor of a suction catheter, in which the electrodes 6305, 6305' are configured as partial annular segments which are substantially ring-like. As mentioned, in any of these examples the ring electrodes may extend just partially around the annulus of the suction lumen. For example, FIG. 63B shows an example in which the pair of electrodes 6305", 6305''' forming an electrical (e.g., impedance) sensor are configured as plate-like structures that extend just partially (e.g., between about 30-50 degrees) around the lumen and may be mounted diametrically opposing one another on internal surface of the catheter wall. In this example, the electrode pair may measure the electrical impedance across the catheter lumen when connected to a variable electrical power source. The electrodes 6305", 6305''' may be configured as a set of two electrodes, as a set of three electrodes, or as a set of any number of electrodes. Furthermore, multiple sets of annular segment electrodes may be employed at locations along the length of the catheter to measure and record additional flow characteristics such as flow velocity, size and mass of blood clots etc.

FIG. 63C shows an alternate example of an electrical (e.g., impedance) sensor for a lumen of a suction catheter. In this example, the electrode pair includes electrodes 6315, 6315' that are configured as helical conductive elements, with overlapping helical pitches such that that the resulting electrode pair behaves substantially as an annular ring pair (with the two electrode elements axially adjacent to one another) and as an annular segment pair (with the two electrodes diametrically adjacent to one another). These electrodes may be mounted on the internal surface of the catheter wall, in contact with the internal bio fluid within the catheter. Helical electrodes may be connected to a variable electrical power source (as described above) and may be configured to measure and record electrical impedance of the internal flow within the catheter over time. These helical electrode pairs may be located at any axial location in the catheter and the catheter system may be configured with one, two or a plurality of electrode pairs at different locations along the axial length of the catheter to measure and record additional flow characteristics such as flow velocity, size and mass of blood clots etc. Both the ring electrodes shown in FIGS. 63A-63B, and the helical electrodes shown in FIG. 63C are examples of annular electrodes extending radially around the suction lumen.

Figure 64:
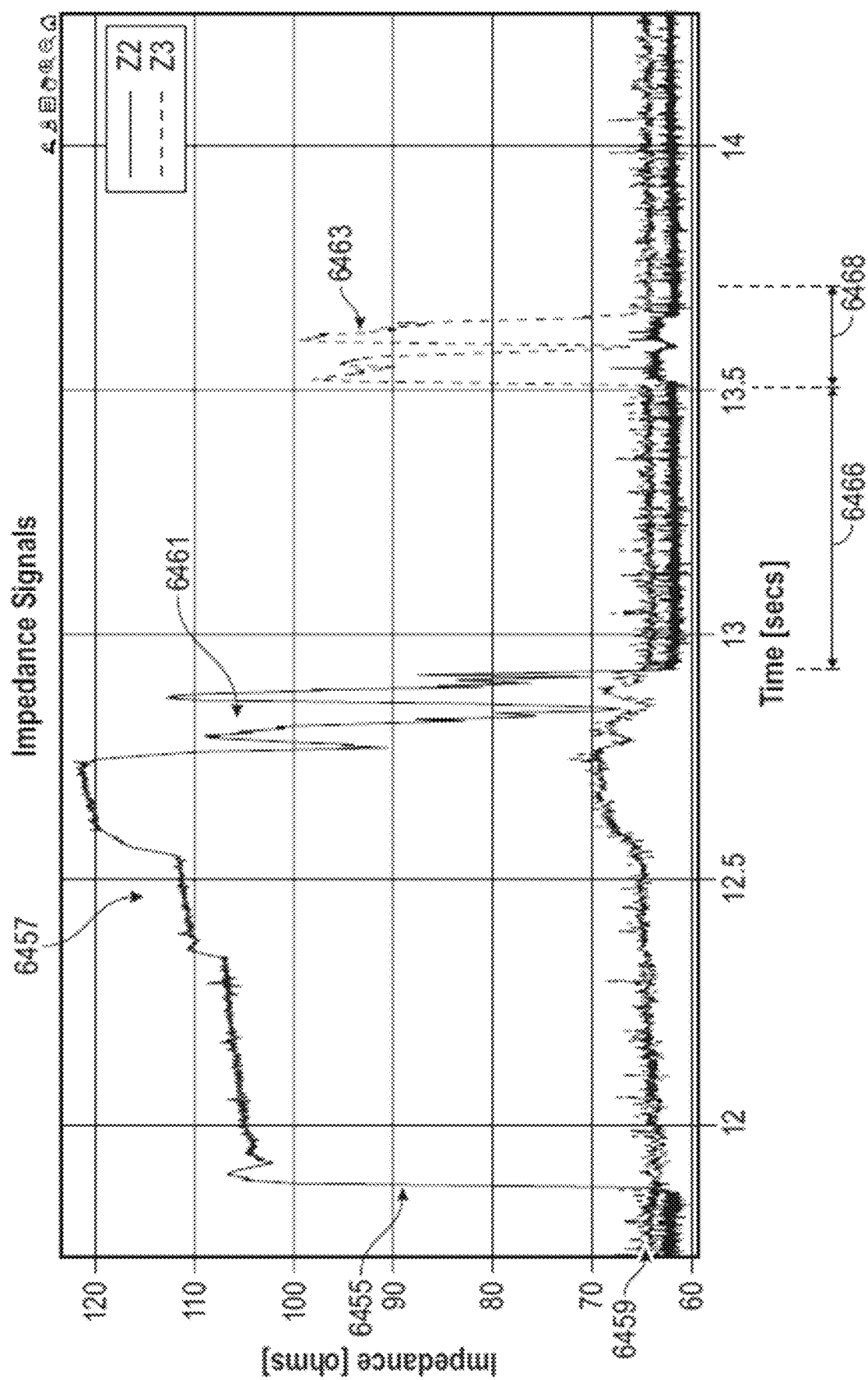
FIG. 64 is a graph illustrating impedance data over time from the operation of a suction catheter including an electrical sensor at a distal end and an electrical sensor at a distal end of the catheter, as the suction catheter removes clot material.

FIG. 64 illustrates an example of an output of an apparatus such as the apparatus shown in FIG. 62, illustrating the impedance output over time of a distal sensor, comprising a first pair of distal internal ring electrodes (that extend about almost completely around the lumen and are separated from each other by between about 5 mm), and a second pair of proximal ring electrodes (that extend almost completely around the lumen and are separated from each other by between about 5 mm). As shown in the graphs, the trace from the distal sensor (sensing electrode pairs) 6455 show an initially low impedance (in Ohms) that rises dramatically as thrombus enters the internal lumen at about 11.75 seconds and is initially held-up in the distal end region so that the impedance signal remains high as thrombus is pulled into the lumen 6457. The proximal sensor (sensing electrode pairs) 6459. At about 12.75 seconds, the first sensor at the distal end region shows a rapid rising and falling of the impedance, indicating that the clot material is breaking up within the internal lumen of the catheter 6461. After a brief time period (e.g., approximately 0.6 seconds) the proximal sensor (sensing electrode pairs) signal shows a similar impedance fingerprint 6463 for the thrombus material as it passes out of the lumen of the catheter. As shown from the sample data of FIG. 64, these apparatuses may detect the presence of clot material within the lumen of the catheter and based on the differential timing 6466 of the signal between the distal sensor and proximal sensor signals (e.g., 0.6 s) the rate of travel of the clot material down the known length of the catheter may be estimated and presented. In addition, this data may also be used to determine the approximate size of the clot material. For example, the length of the thrombus may be estimated based on the size (in time) 6468 of the proximal signal and the rate of travel of the clot through the catheter (based on the time between similar signals from the distal sensor to the proximal sensor 6466 and the length of the catheter lumen).

Figure 65:
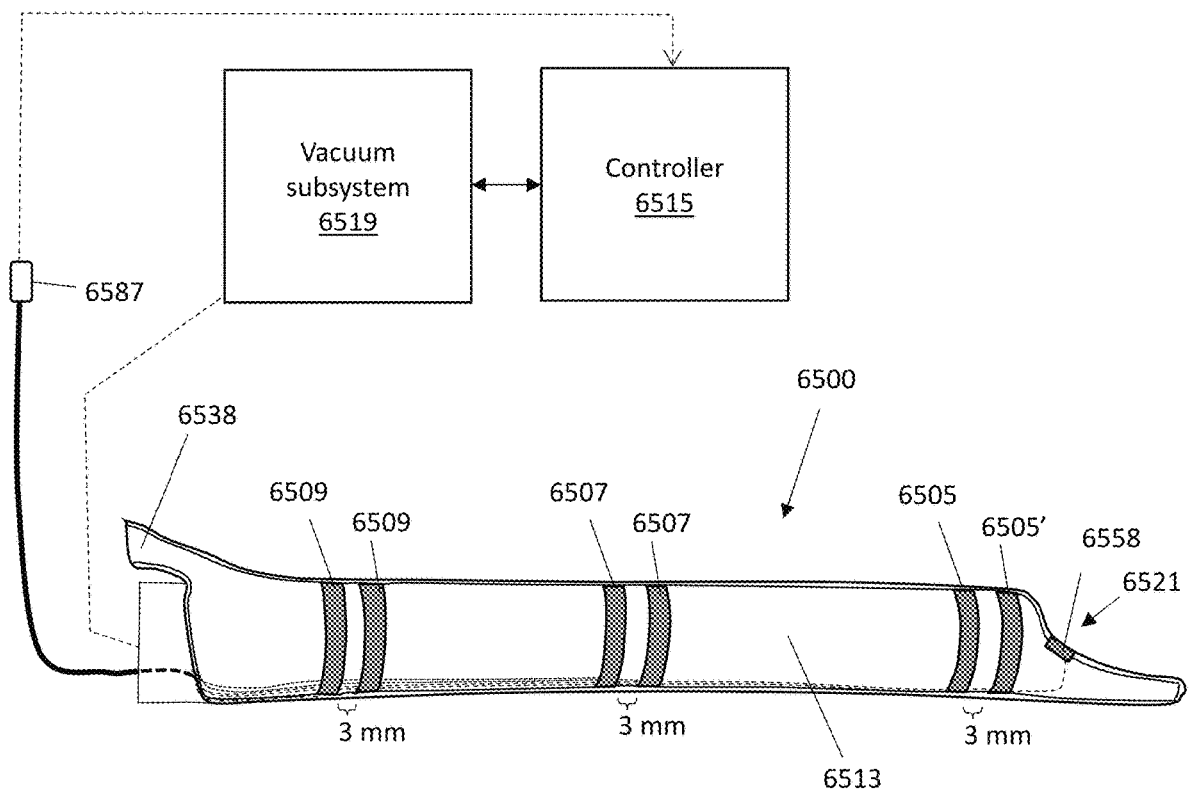
FIG. 65 schematically illustrates an example of an apparatus for sensing clot material including a catheter (not shown to scale) with a suction lumen and internal electrical impedance sensors as well as a pair of impedance sensors at the distal aspiration opening.

FIG. 65 shows another example of an apparatus as described herein, including a catheter (e.g., aspiration catheter) 6500 for removing material from within a blood vessel, a vacuum/suction subsystem 6519 (e.g., including a vacuum/suction pump, filter(s), etc.), and a controller 6515 for receiving sensor data from the aspiration opening sensor(s) 6558 and/or the internal sensors 6505, 6505', 6507,

6507', 6509, 6509'. In FIG. 65 the aspiration opening sensor 6558 may include two or more (e.g., a pair) of electrodes on or adjacent to the rim of the aspiration opening 6521. For example the electrodes forming the aspiration opening sensor may be recessed slightly into the aspiration opening, or they may be on the rim of the aspiration opening (flush, recessed into the rim, or extending proud of the rim). In FIG. 65 only a single electrode is shown. The aspiration opening is on a lateral side of the catheter. Three internal electrical impedance sensors are shown. For example, a first internal electoral impedance sensor includes a first set 6505, 6505' of electrodes is shown at a distal end region (e.g., near or adjacent to the aspiration opening sensor) comprising a pair of annual electrodes, expending partially or fully around the inner diameter of the suction lumen, as described above. A second internal electrical impedance sensor is shown comprising a second pair 6507, 6507' of annular electrodes expending partially or fully around the inner diameter of the suction lumen, about midway along the catheter (note that FIG. 65 is not shown to scale). A third internal electrical impedance sensor having a second set of annular electrodes 6509, 6509' is shown in FIG. 65. More or fewer internal electrodes may be included. The flexible elongate catheter 6500 has a suction lumen 6513 extending therethrough and the internal electrical impedance sensors are all within the suction lumen.

In FIG. 65, the controller 6515 may be coupled to the internal electrical impedance sensors and to the aspiration opening sensor. The controller may also include or be coupled to a power source for applying energy to the internal electrical impedance sensors and to the aspiration opening sensor. For example the controller may control the application of an alternating current between the two or more electrodes of each sensor. Each sensor may be separately energized, or energy (e.g., alternating current) may be applied to all or a subset of the sensors together. The controller may be configured to apply a single frequency or a plurality of frequencies, (e.g., between 1 Hz and 5 MHz, e.g., between 100 Hz and 3 MHz, etc.). The internal electrical impedance sensors and to the aspiration opening sensor may be used to determine an impedance spectrum using multiple different frequencies. The frequency of alternating current applied to the internal electrical impedance sensors may be the same or different from the frequency applied between the electrodes of the aspiration opening sensor. In general, the controller may receive signals (e.g., impedance signals) from the internal electrical impedance sensors and to the aspiration opening sensor and may store, analyze and/or transmit the electrical signals (impedance signals). For example, the controller may detect an obstructive material (e.g., clot) within the suction lumen based on electrical impedance signals from the internal electrical impedance sensor.

In any of the apparatuses described herein the internal electrical impedance sensors and the aspiration opening sensor may be connected via one or more wired or wireless connections to the controller 65015. For example, in FIG. 65 the apparatus including a conductive trace (e.g., wire, etc.) extending from each electrode of the internal electrical impedance sensors and the aspiration opening sensor to a connector 6587. The connector may couple directly or indirectly to the controller 6515. In some examples the catheter apparatus may include circuitry to precondition the signals from the internal electrical impedance sensors and/or the aspiration opening sensor. For example, the catheter apparatus may include circuitry to amplify, filter and/or combine signals from the internal electrical impedance sensors and/or the aspiration opening sensor. In some examples the circuitry may be part of the connector 6587.

In the example apparatus shown in FIG. 65, the suction lumen 6513 of the apparatus 6500 may couple to the vacuum subsystem 6519 and/or may couple 6538 to a guide channel or navigation channel (not shown), as described above.

Although FIG. 65 is described with three separate internal electrical impedance sensors and an aspiration opening sensor, in some examples the electrodes forming these sensors may be shared between the different sensors (e.g., current may be applied to a first electrode of the distal internal electrical impedance sensor and impedance may be measured from one or more electrodes of the second internal electrical impedance sensor and/or the third internal electrical impedance sensor. Alternatively or additionally, the signals may be applied and sensed between just the subset of electrodes forming the internal electrical impedance sensors and/or the aspiration opening sensor.

The internal electrical impedance sensors described herein, such as those shown in FIG. 65, may be used to reliably and robustly detect obstructive material, such as clot material or vegetation, from within the suction lumen of the aspiration catheter. The impedance measurements may also be used to track movement of the material within/through the lumen (including but not limited to rate of movement), detect or determine blockage of the suction lumen, and/or to determine an estimate of the amount of material passing through the suction lumen (e.g., removed from the vessel), and may determine how disrupted the material is.

Figure 66:
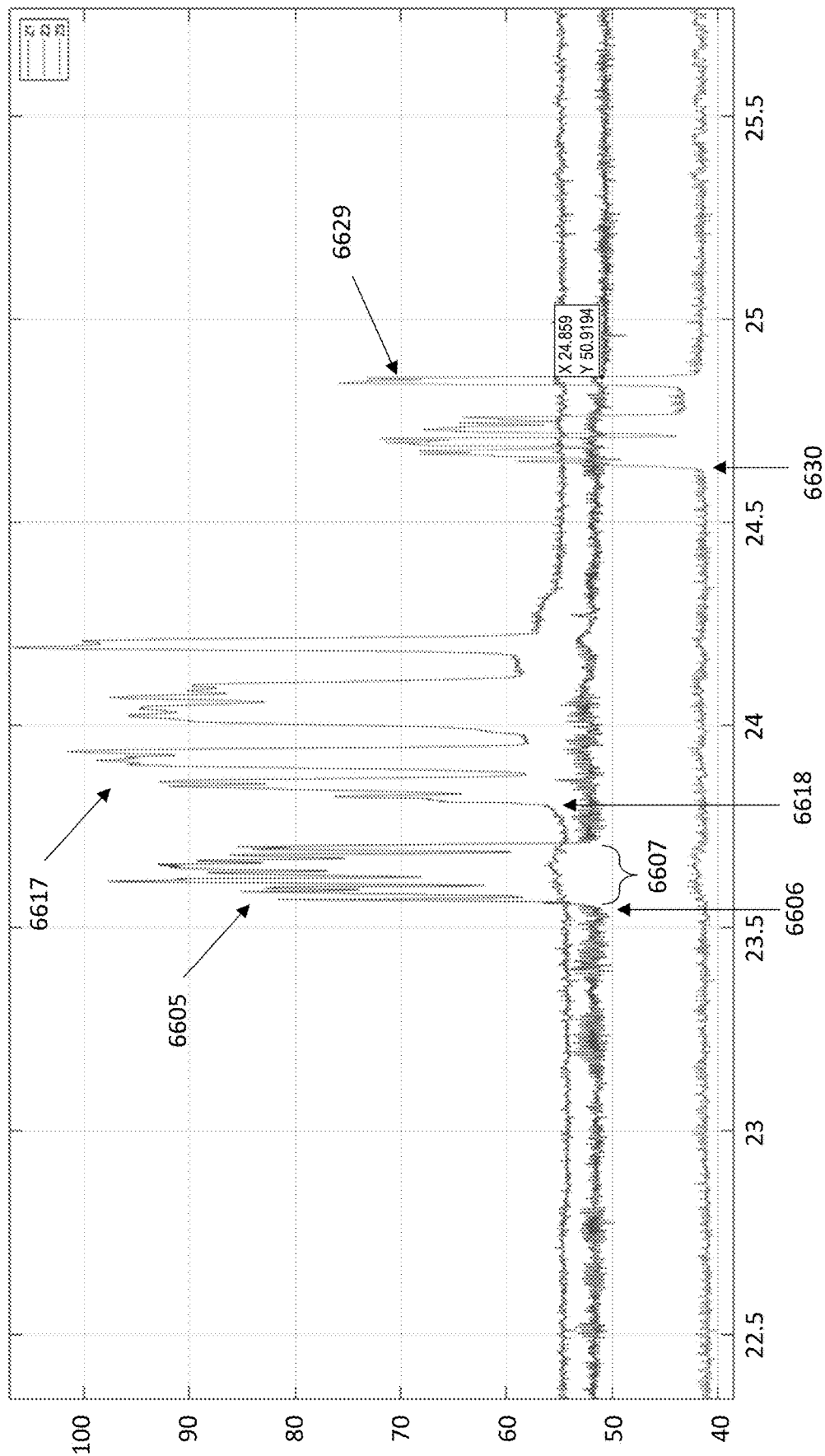
FIG. 66 is a graph showing impedance signals over time from each of the three sets of internal impedance sensors (e.g., pairs of electrodes) within the lumen of an apparatus such as the apparatus shown in FIG. 65.

FIG. 66 illustrates one example showing the detection and/or tracking of clot material through the lumen of an aspiration catheter similar to that shown in FIG. 65, including three sets of internal electrical impedance sensors (distal tip, mid and proximal). The internal electrode sensors each included a pair of annular electrodes that extend partially around the lumen of the suction catheter. The controller was configured to sense Vrms using an AC frequency initially set to 1 MHz. A sample blood clot in saline was aspirated through the aspiration opening a distal end of the catheter and impedance of each internal electrical impedance sensor (e.g., across each pair of electrodes forming the sensor) was detected. In this example, the distal internal electrical impedance sensor included a pair of annular electrodes that were spaced approximately 2.5 mm from the proximal end of the aspiration opening, and were separated from each other by approximately 3 mm. The catheter had an inner diameter of approximately 0.275". Repeated testing showed a 100% success rate in detecting an tracking clot material through the aspiration catheter. In FIG. 66, an exemplary trace shows the impedance signal detected at the first internal electrical impedance sensor 6605, which first detected clot material near the first internal electrical impedance sensor beginning at a start time 6606, and lasting for a first duration 6607. The impedance signal for the second internal electrical impedance sensor 6617 at the middle region of the catheter also showed detecting of the impedance signal indicating the clot material at a start time 6618 (showing some fragmentation of the clot, as a rise and fall of the impedance over time). Finally, the third internal electrical impedance sensor showed impedance signal 6629 indicating the presence of clot material at the proximal end of the catheter, beginning at a start time 6630. The controller may use these impedance signals to track the movement of obstructive material through the lumen of the catheter, including determining an estimate of the rate of movement through the lumen. In this example, the positions of the internal electrical impedance sensors is known, and the impedance measurement of each internal electrical impedance sensor may be used to determine the start of the passage of the material near each internal electrical impedance sensor. As is apparent in FIG. 67, the characteristic shape of each impedance measure (at 1 MHz in this example) may be correlated to confirm that a particular material is passing by each internal electrical impedance sensor. The number of peaks from the impedance signal, as well as the change in spacing between the peaks, may also be used to determine disruption (e.g., fragmentation) of the material. The controller may also detect, based on a threshold for the impedance signal, the start (e.g., when clot material begins passing through the lumen), the rate of material through the lumen and/or the finish, when clot material has completely passed through the lumen. The controller may also sense blockage of the lumen based on the impedance signal. The controller may control the operation of the suction to increase/decrease and/or turn on/off suction based on the impedance signals from the internal electrical impedance sensors. For example if clot material is moving slowly through the lumen the suction may be increased (or conversely decrease if clot material is moving too quickly, which may increase undesirable blood loss). The controller may also turn off or reduce suction when no more clot material is detected, e.g., at the proximal internal electrical impedance sensor.

The apparatus shown in FIG. 65 (similar to those also described in FIGS. 1A-1D, 2-13, 20-23, 27A, 39B, 45-46B, 47) may also include an aspiration opening sensor to detect when an obstructive material is at or near the aspiration opening. The impedance-based aspiration opening sensors described herein may be used with the application of force (e.g., by driving the aspiration opening against the material and/or wall) to more clearly detect and distinguish between target material (e.g., clot material) and non-target material (e.g., vessel wall). Thus, any of these apparatuses may be configured (e.g., the controller may be configured) to detect clot material when force is being applied at the aspiration opening. In any of these examples the force applied may be suction (e.g., aspiration) applied through the aspiration opening. Thus, in any of these apparatuses the controller may determine when a force (e.g., a threshold valve for the force) is being applied and may analyze the resulting signal from the aspiration opening sensor only while this force is being applied. For example, in any of these examples controller may analyze the signal (e.g., impedance signal or other signal) from the aspiration opening sensor when the pressure within the lumen (and therefore at the aspiration opening) is above a minimum threshold indicating that the aspiration opening is being held/driven against an occlusion (clot, wall, etc.) within the vessel. Surprisingly, the resulting aspiration opening sensor signal may be more reliable during this period, perhaps because the force applied may prevent more than one material (e.g., wall and clot, or clot and blood, or wall and blood or wall, clot and blood) from being present in close proximity to the aspiration opening sensor. Thus, the resulting signals from the aspiration opening sensor may be more characteristic of either clot, wall or blood, rather than being a combination of these signals.

The methods described above may be used with virtually any type of sensor, including the electrical (e.g., impedance) sensors illustrated above. In general, the methods and apparatuses may include the use of techniques for identifying the type of tissue (e.g., clot, vessel wall, or blood) which may be sensed and classified when sampling from the tip of an aspiration lumen as part of a thrombectomy procedure, e.g., for a pulmonary embolism. As described above, these techniques may include electrical impedance, electrical capacitance (e.g., transient electrical response), ultrasound, optical transmission (e.g., spectroscopy), optical reflectivity, inductive coupling, mechanical deflection, thermal conductivity and elasticity.

For example, electrical impedance may be sensed between two or more electrodes located at the orifice of the aspiration lumen. This electrical impedance may be used to differentiate tissue type and may be measured at different frequencies (e.g., between about 100 Hz to about 10 MHz) using alternating current (e.g., sinusoidal, sawtooth, square wave, etc.). One single frequency or several frequencies may be used, including a spectrum of frequencies. In any of the impedance techniques described herein, the amplitude and phase of the response may be measured to fully characterize the impedance of the load seen between the electrodes. In some examples, just the magnitude may be used. The effective resistance, capacitance and/or inductance of the tissue may be calculated at each frequency and compared to known thresholds to categorize the tissue as either clot, vessel wall, or blood. These thresholds may be different depending on the size and spacing of the sensing electrodes.

In any of these apparatuses and methods, the sensing electrodes may either be located at the edges of the orifice (e.g., the rim) or just slightly inside the lumen facing internal to the shaft, e.g., recessed from the rim into the suction lumen. Separately the one or more electrodes may be recessed into the material forming the rim, and/or the wall of the lumen, or they may be flush with or may extend proud of the rim or wall. Preferably, the electrodes may be recessed somewhat and may be internally facing electrodes in order to help ensure the measured tissue is just the desired specimen and not other material nearby. For example, FIG. 67 illustrates one example of a distal end of a catheter having a distal-facing opening 6721 forming the aspiration opening with a pair of electrodes 6758, 6758' on the rim. The aspiration opening opens into the suction lumen 6713.

In any of the methods an apparatuses described herein a second sensor may be used in conjunction with the aspiration opening sensor to detect and/or identify clot material or to distinguish clot material from vessel wall and/or blood. For example in FIG. 68 the apparatus includes an aspiration opening 6821 with an aspiration opening sensor including a pair of electrodes 6809, 6809' at the distal end. The apparatus also includes an internal impedance sensor comprising a pair of sensing electrodes 6807, 6807' that are positioned just proximal of the aspiration opening in FIG. 68; alternatively, they may be within the lumen and opposite of the aspiration opening in variations in which the aspiration opening is on a slide of the catheter. Thus, in some examples the apparatus may use electrical impedance with a second set of electrodes, as shown in FIG. 68. For example, the controller may include information from the internal sensor as an independent measure to confirm whether the apparatus (e.g., when force is applied to the tip, e.g., such as by applying suction to the aspiration opening from the suction lumen) is in contact with a vessel wall or a clot material. This second pair of electrodes may be used to measure impedance a bit further into the aspiration lumen, and if the material in contact with the aspiration opening shows a large change at those sensors it may be more likely to be clot material, vs. vessel wall which cannot penetrate that deeply down the aspiration lumen even under negative pressure.

In any of these apparatuses and methods a transient electrical response may be used to help identify the type of material in contact with the aspiration opening. For example, the electrical properties of the tissue specimen between the sense electrodes described above may also be evaluated using a square-pulse and measuring the transient response of the electrode-tissue interface. This is illustrated in FIGS. 69A and 69B. The rise-time of voltage when exposed to a square pulse through a series resistor may be used to quantify the effective capacitance of the electrode-tissue interface, which is another possible differentiating property between tissue types. In FIG. 69A the example circuit schematic shows an applied square wave pulse that is applied across the sensing electrodes and a voltage measured (Vmeas). The time constant for the rise time and/or the time constant for the falling time (shown in FIG. 69B) when a square wave pulse is applied may be analyzed, as shown in FIG. 69B. The time constant(s) may be characteristic of the material being examined, e.g., clot material, blood and/or vessel wall.

Figure 70:
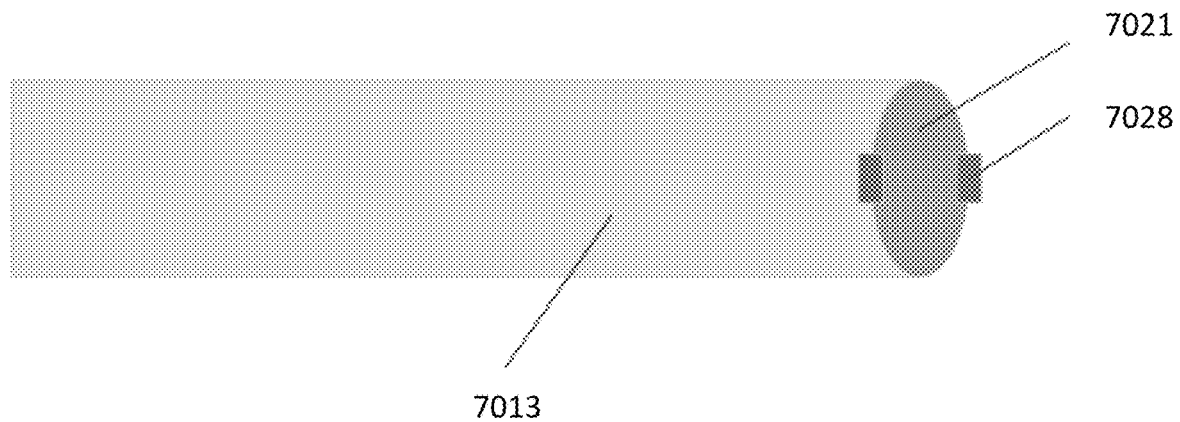
FIG. 70 schematically illustrates an example of an apparatus including an aspiration opening sensor comprising a piezoelectric transducer (e.g., shown as a pair of piezoelectric transducers).

Alternatively or additionally, in some examples an ultrasound transducer may be used to characterize material at the aspiration opening. For example, as shown in FIG. 70, a pair (or more) of piezoelectric transducers 7028 may be used to discriminate between tissue types at or near the aspiration opening 7021 (opening into the suction lumen 7013) by either looking at: acoustic impedance in continuous-wave mode, or performance a discrete ping on one transducer and measure the response on another, looking at amplitude. For example, the controller may check the response amplitudes vs. thresholds for each tissue type (e.g., blood, clot, vessel wall). As shown, the transducers may be placed at the tip of the catheter on either side of the aspiration opening.

Figure 71:
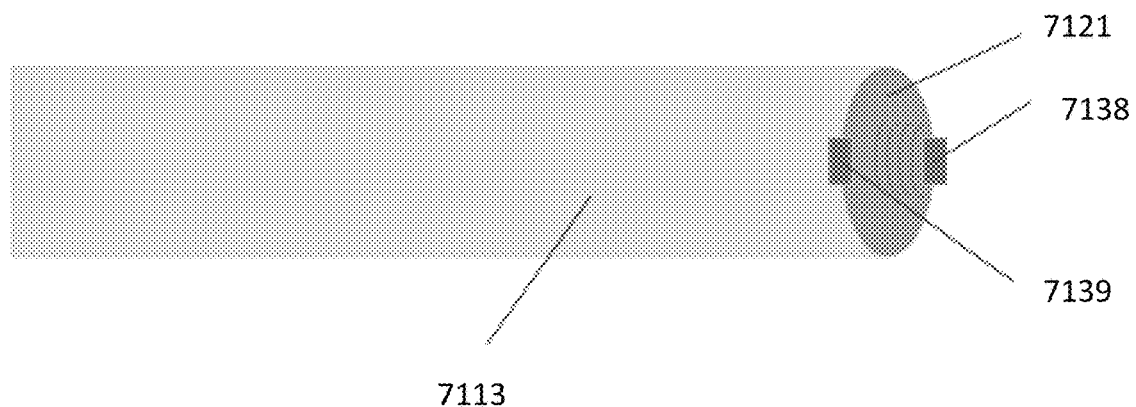
FIG. 71 schematically illustrates an example of an apparatus including an aspiration opening sensor comprising an optical sensor as described herein.

FIG. 71 schematically illustrates an example of a catheter including a suction lumen 7213 in which optical transmission/spectroscopy may be used to determine and/or confirm the presence of a particular type of material (blood, vessel wall, clot, etc.) at the aspiration opening 7121 of the catheter. For example, the optical transmission properties of the tissue types may be another way to discriminate them from each other. Specifically, if an LED or other light source 7138 is placed at the tip of the catheter, and an optical detector 7139 may be positioned at the tip of the catheter on the opposite side from the emitter 7138, the detector 7139 can receive the optical signal from the source, altered by the transmission properties of the material in between the two (e.g., against the aspiration opening). This can be done at one frequency or a spread of different electro-magnetic frequencies to obtain spectroscopy information about the optical transmission characteristics of the tissue sample. The tissue types may then be categorized by thresholds in the transmission properties at certain frequencies.

Figure 72:
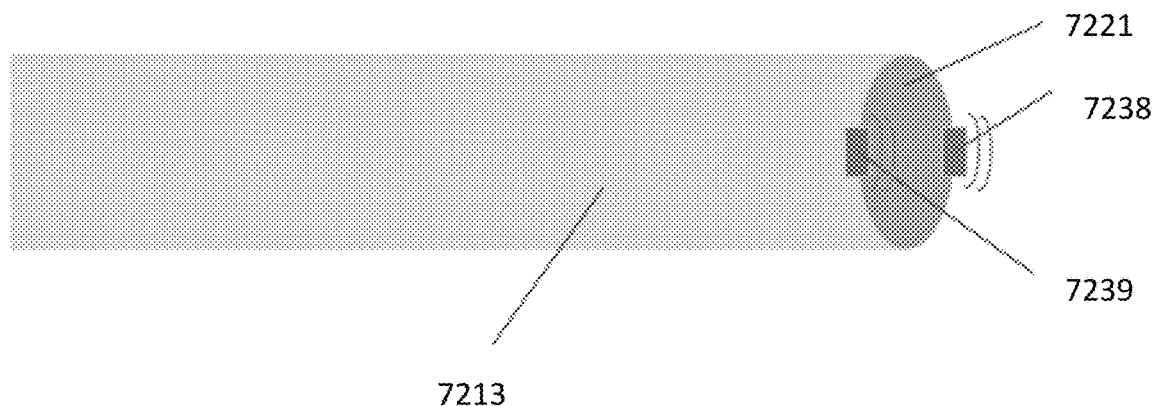
FIG. 72 schematically illustrates an example of an apparatus including an aspiration opening sensor comprising an electromagnetic sensor as described herein.

FIG. 72 illustrates a similar configuration using optical reflectivity/spectroscopy. In this example the catheter includes an aspiration opening 7221, opening into a suction lumen 7213, and the optical reflective properties of the tissue types may be used to discriminate them from each other. For example, an LED or other light source (emitter 7238) may be placed at the rim (or within the rim) of the aspiration opening, and may be integrated with an optical detector 7239 also placed at or on the rim of the aspiration opening near the that emitter (LED or light source), and the optical reflective properties of the material in front of this sensor may be used to characterize the material. One or more of these light sources/sensors at the tip of the catheter may be used to determine the average "color" of the material in front of the orifice. In some examples one frequency, a spread of several frequencies, or a broad spectrum of frequencies may be used look for the reflected amplitudes. The type of the material may then be determined based on categories by thresholds of the reflective properties at certain optical frequencies.

Figure 73:
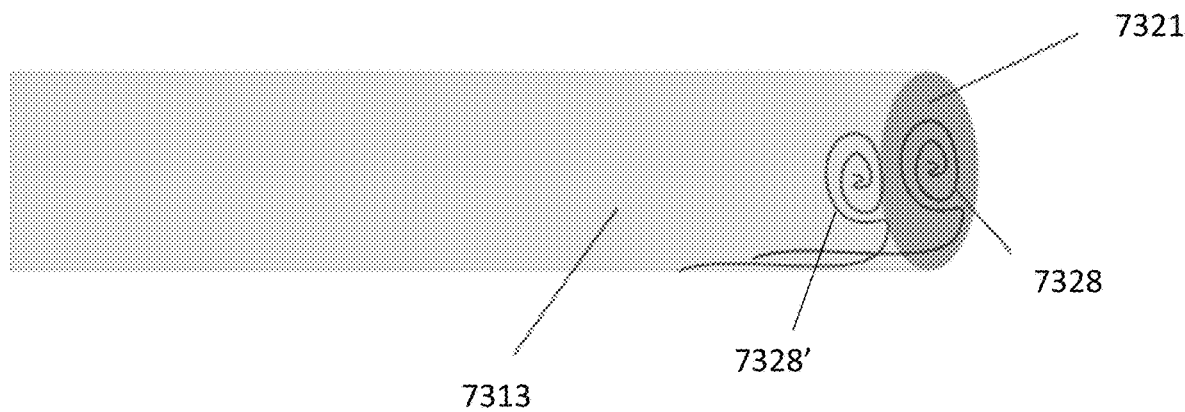
FIG. 73 schematically illustrates an example of an apparatus including an aspiration opening sensor comprising an inductive sensor.

FIG. 73 illustrates an example of a catheter including an aspiration opening sensor that is configured as an inductive coupling coefficient sensor. For example, the inductive coupling coefficient may be used to differentiate between tissue types based on the degree to which tissue alters the coupling coefficient between two inductive coils 7328, 7328' placed, e.g., near the tip of the catheter (e.g., on either side of the aspiration opening 7321 into the suction lumen 7313). The coupling coefficient between the coils (which may be based on the original designed geometry) may change when different materials are placed in between them. Thus, the coupling coefficient may be measured and thresholds in this value may be used to differentiate types of material. The construction of these coils may be embedded as traces in a flex board that wraps around the end of the catheter.

Figure 74:
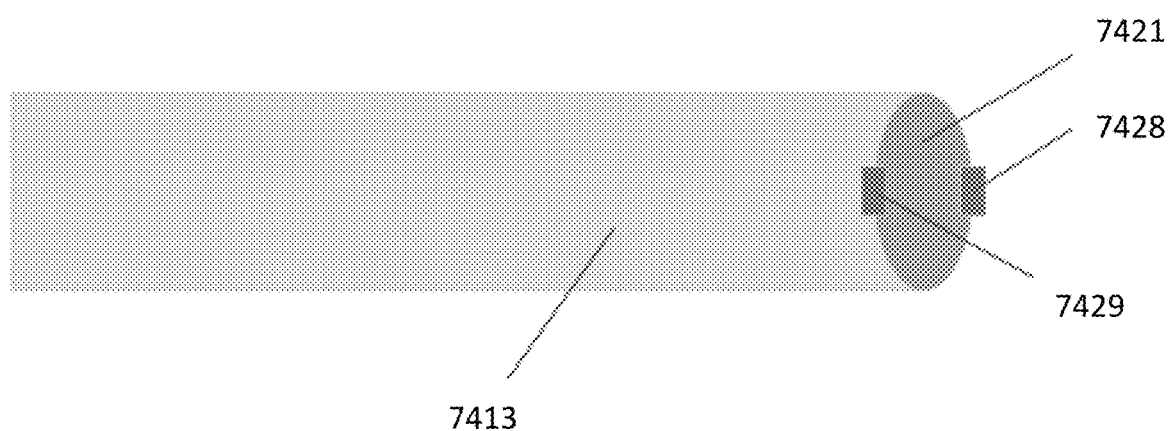
FIG. 74 schematically illustrates an example of an apparatus including an aspiration opening sensor comprising a thermal sensor.

Any of the apparatuses and method described herein may alternatively or additionally use thermal conductivity to help identify the material adjacent to (and/or in contact with) the aspiration lumen. Thermal conductivity can be used to differentiate material types at the end of the catheter by determining the degree to which that material conducts heat. For example, as shown in FIG. 74, a heat source 7428 such as a resistor may be used at the end of the catheter and one or more heat sensitive elements 7329 such as a thermistor or thermocouple may be used to measure the temperature of a nearby location, which requires the heat to traverse through the unknown material. For example, the heat source 7428 and heat sensor 7429 may be part of the aspiration opening (or just recessed relative to the aspiration opening 7421 into the suction lumen 7413. The thermal conductivity may be measured to see how quickly the temperature is able to increase when a heat source is started. This thermal conductivity may be used to characterize which type of material (e.g., blood, clot material, vessel wall) is in between the heat source and the temperature sensor.

Figure 75:
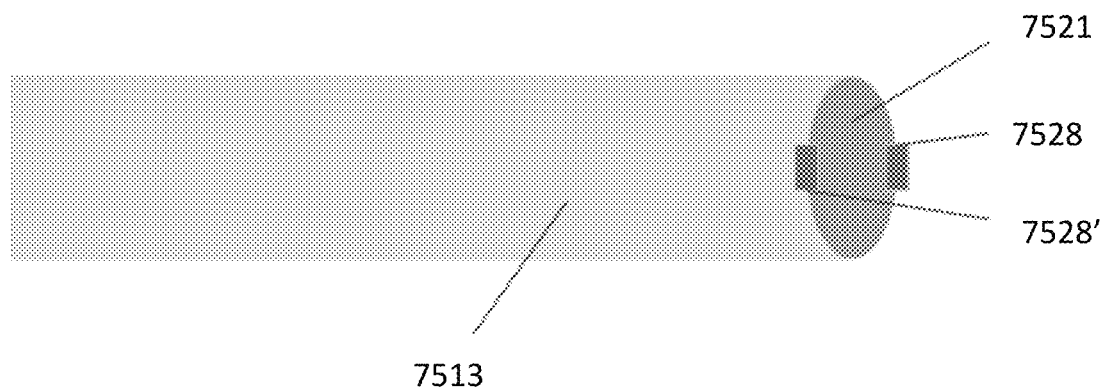
FIG. 75 schematically illustrates an example of an apparatus including an aspiration opening sensor comprising a mechanical sensor.

Alternatively or additionally, the elasticity of the material at the aspiration orifice may be used to identify the material. For example, the elasticity of the material may be used to discriminate among blood, clot, and vessel wall based on the amount of force that material pushes back when faced with an impinging force. Pressing into the material with a known force (either spring force or air or saline) and measuring the amount of force pushed back by the material may discriminate between the tissue types, in part because the different materials (blood, clot, wall) may be a liquid, a gel, and a fibrous solid, which have very different properties of elastic force push-back when faced with an impinging mechanical force. For example, FIG. 75 illustrates an apparatus with one or more mechanical members 7528, 7528' at the distal end aspiration opening 7521 into the suction lumen 7513 that may exert a force in a first direction and measure the response force in a reverse direction pushed back by the material.

As mentioned above, in general, any of these sensor types and methods may be combined with a force and/or pressure sensor to detect a force acting on the aspiration opening and/or a negative pressure in the aspiration lumen, which may indicate that something is blocking the aspiration opening; in general, the block may be due to either clot material or vessel wall.

Figure 76:
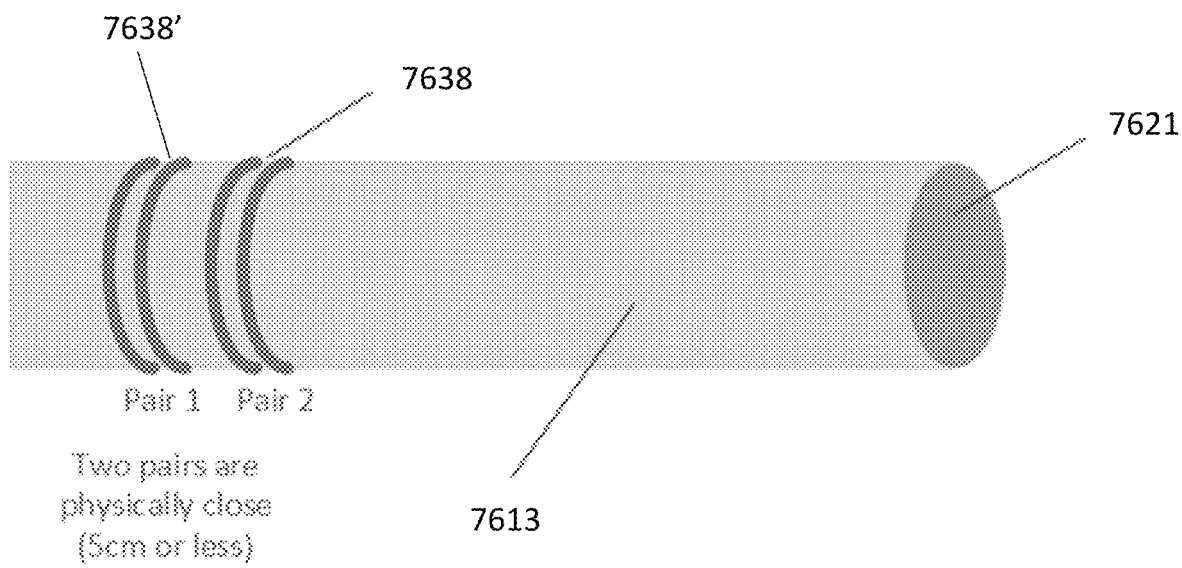
FIG. 76 illustrates an example of a quad detector comprising four electrodes (two electrode pairs) separated by a predetermined distance within a suction lumen of a catheter as described herein.

Alternatively or additionally, any of these methods may be used as part of an internal sensor within the suction lumen. For example, FIG. 76 illustrates a pair of internal sensors within the lumen 7613 of a catheter that are positioned proximal to the distal aspiration opening 7621. The first intra-lumen sensor 7638 in this example may be an electrical (e.g., impedance) sensor, including a first electrode and a second electrode. A second intra-lumen sensor 7638' is shown just proximal to the first intra-lumen sensor 7638, separated by, e.g., 5 cm or less. For example, two pairs of electrodes in close proximity within the lumen may be able to measure the velocity of the clot as it passes through the lumen, by looking at the difference in time onset of the signal. The duration of the signal may be used along with that velocity to determine the distance of clot within the lumen and therefore the volume estimate. This may allow for an estimate of clot volume even in the case that the velocity of the clot in the lumen is non-constant.

Figure 77A:
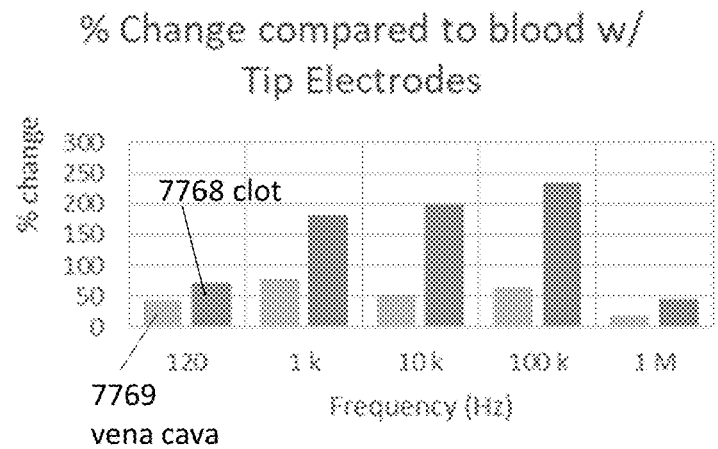
FIGS. 77A-77C illustrate examples of impedance signals measured using a first configuration of an aspiration opening sensor comprising a pair of electrodes measuring electrical impedance at different frequencies when force is applied (e.g., by applying suction) against different materials (e.g., vena cava/wall or clot material).
Figure 77B:
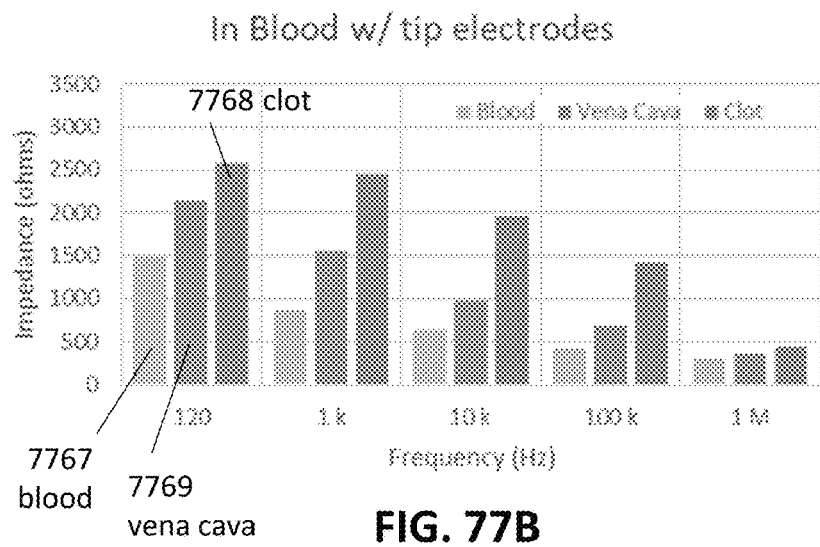
Figure 77C:
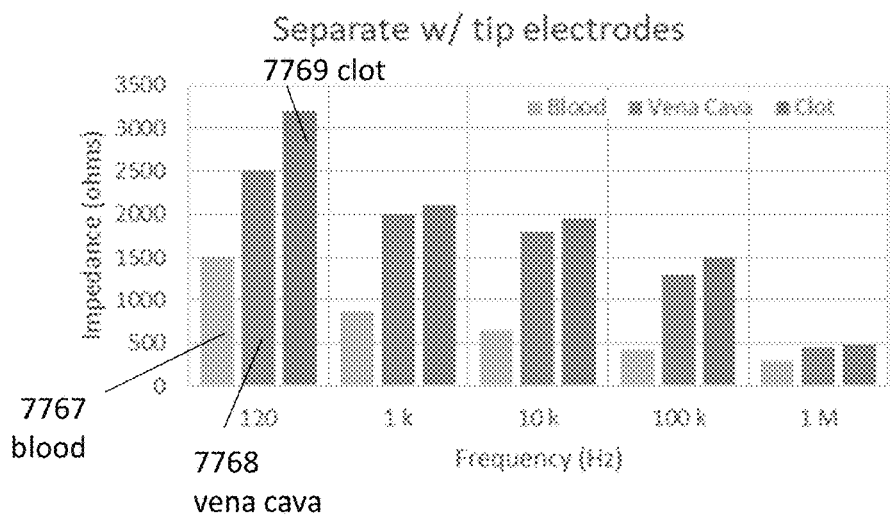

As discussed above, when impedance is used to determine material properties at the distal end (e.g., at the aspiration opening) and/or within the suction lumen, or multiple frequencies may be used to distinguish the type of material near or in contact with the electrodes. For example, FIGS. 77A-77C illustrate the effect of different frequencies of applied alternating current when measuring the magnitude of impedance for an aspiration opening sensor on either side of an aspiration lumen. For example, FIG. 77A shows the effect of the application of 120 Hz, 1 kHz, 10 kHz, 100 kHz, and 1 MHz when the aspiration opening (and sensing electrodes) are in contact with either vena cava (a model of the vessel wall) 7768 or clot material 7769. For each frequency, the percentage of change (% change) of the impedance for each material compared to blood is shown. In FIG. 77B, the impedance measured (in Ohms) of each of blood 7767, vena cava (wall) 7768, or clot 7769 are shown for each frequency (120 Hz, 1 kHz, 10 kHz, 100 kHz, 1 MHz). Similarly, in FIG. 77C, the impedance measured for each material at different frequencies is shown. In FIG. 7A-7C the electrodes are part of an aspiration opening sensor in which the electrodes are positioned on the rim of the aspiration opening and suction is applied to secure the material against the aspiration opening sensor.

Figure 78A:
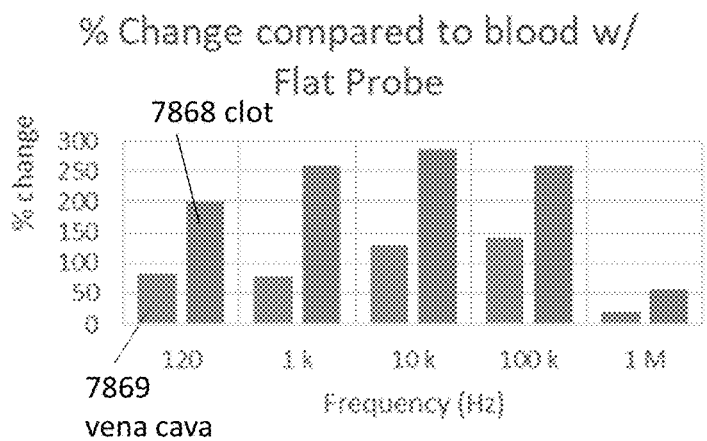
FIGS. 78A-78C illustrate examples of impedance signals measured using an aspiration opening sensor comprising a pair of electrodes measuring electrical impedance at different frequencies when force is applied (e.g., by applying suction) against different materials (e.g., vena cava/wall or clot material).
Figure 78B:
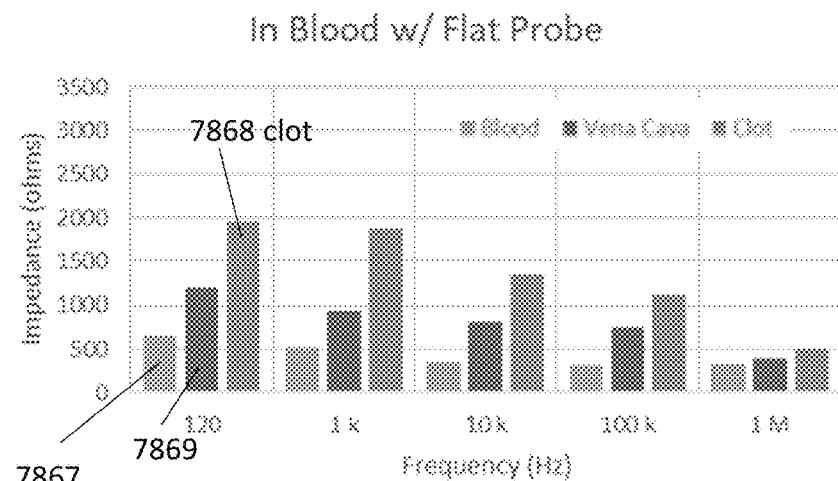
Figure 78C:
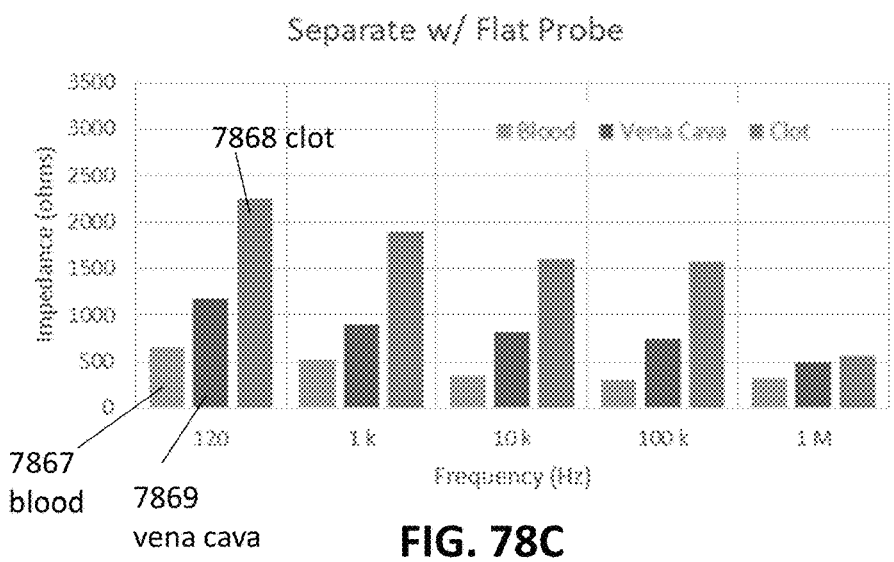

Similar results are seen when a different impedance sensor electrode is used, as shown in FIGS. 78A-78C. In this example, the electrode is a flat headed probe rather than the annular electrodes shown, e.g., in FIG. 55 or 76. In FIG. 78A the percentage of change in impedance compared to blood is shown for both vessel wall 7869 (e.g., vena cava test tissue) or clot material 7868, at 120 Hz, 1 kHz, 10 kHz, 100 kHz and 1 MHz. In FIG. 78B the impedance measured (in Ohms) of each of blood 7867, vena cava (wall) 7868, or clot 7869 are shown for each frequency (120 Hz, 1 kHz, 10 kHz, 100 kHz, 1 MHz). Similarly, in FIG. 78C, the impedance measured for each material at different frequencies is shown.

In general, in any of these apparatuses and methods, impedance levels may vary by the sensor geometry (e.g., flat probe vs tip electrode) but the general trends remain, and when sensing across the aspiration opening, the frequencies between about 100 Hz (e.g., 120 Hz) and 100 kHz (less than 1 MHz) appeared to work best regardless of the geometry of these distal electrodes, and the largest delta was seen at 100 kHz (most like actual model).

In general, when measuring impedance in any of the apparatuses and methods described herein the configuration of the sensor(s) may provide for more robust and effective sensing. FIGS. 79A-79B, 80 and 81A-81B illustrate examples of different configuration of internal impedance sensors that may be used to sense and/or track material within the lumen. For example, FIG. 79A shows a first configuration of an internal electrical impedance sensor comprising two or more electrodes within the suction lumen. In this example each sensor is coupled to a wire extending proximally to a coupler that can be coupled to a controller for processing, storing and/or transmitting the impedance value(s). In each of these examples the suction lumen has an inner diameter of about 0.25" (0.635 cm). In FIG. 79A a pair of at least partially annular electrodes surround the lumen; the first electrode is separated from the second electrode by approximately 1 mm. In FIG. 79B a similar arrangement is shown, but with a much larger separation (e.g., 3 mm) between the first and second electrodes, and the first and second electrodes in this example may be annular electrodes that extend completely (or nearly completely) around the inner lumen. FIG. 80 shows another example of an internal electrical impedance sensor in which a pair of annular electrodes extend as a full ring around the suction lumen wall and the electrodes are separated by about 5 mm.

Any of these internal electrical impedance sensors may be configured as quad detectors, as shown in FIGS. 81A-81B, having four electrodes divided in to two sets of two (e.g., two pairs) of electrodes that are separated by a small distance. In FIG. 81A, the first and second electrodes of the first pair of annular electrodes are separated by about 3 mm and the first and second electrodes of the second pair of annular electrodes are separated by about 3 mm. The first pair of annular electrodes are separated from the second pair of annular electrodes by about 10 mm. this configuration may allow for detection of the rate of movement of a material (e.g., clot material) within the suction lumen from the single quad detector (internal electrical impedance sensor). FIG. 81B is similar to FIG. 81A but with a separation of about 5 mm between the pairs of annular electrodes.

Figure 82:
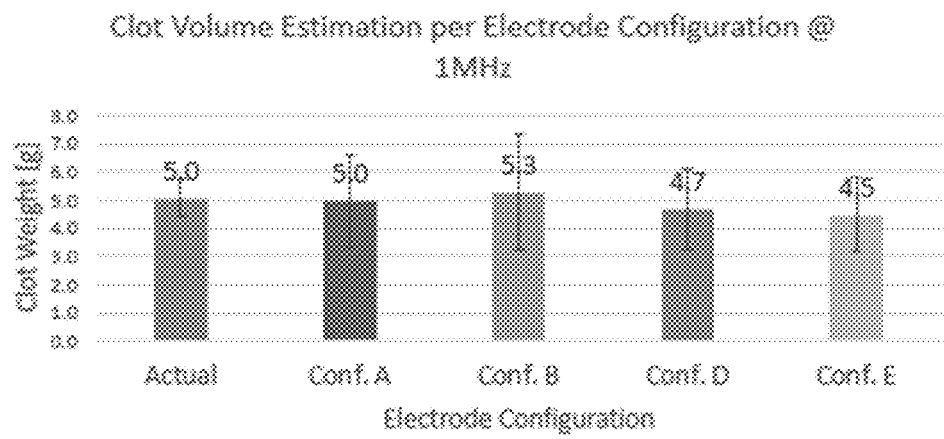
FIG. 82 illustrate one example of a estimates of clot volume using impedance measurements taken from various configurations of internal impedance sensors (similar to those shown in FIGS. 79A-79B, 80 and 81A-81B.

The various configuration of the internal electrical impedance sensors shown in FIGS. 79A-79B, 80, and 81A-81B were tested to estimate clot volume based on the impedance measurements taken with the internal electrical impedance sensors and the results are shown in the graph of FIG. 82. In this example, configuration A corresponds to the example shown in FIG. 79A, configuration B corresponds to the example shown in FIG. 79B, configuration D corresponds to the example shown in FIG. 81A and configuration E corresponds to the example shown in FIG. 81B. As can be seen in FIG. 82, all of these variations had similar results.

Figure 83:
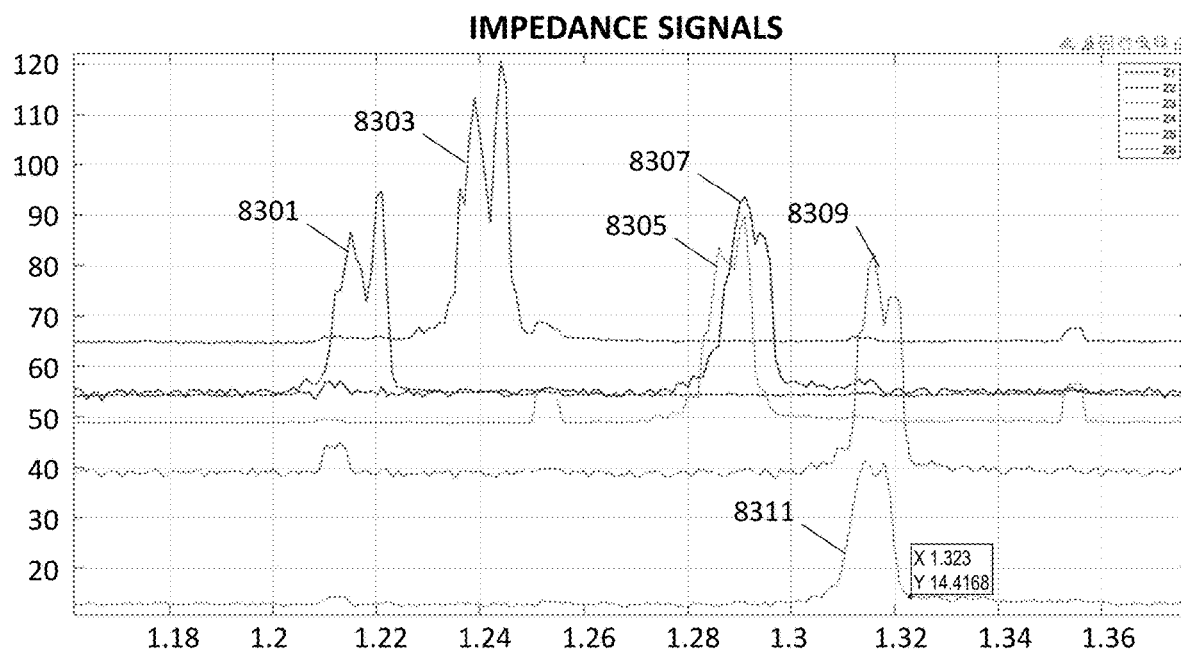
FIG. 83 is a graph showing an example of impedance measurements over time from various internal impedance sensors tracking clot material moving through the suction lumen of the apparatus, in which the clot material remains together.
Figure 84:
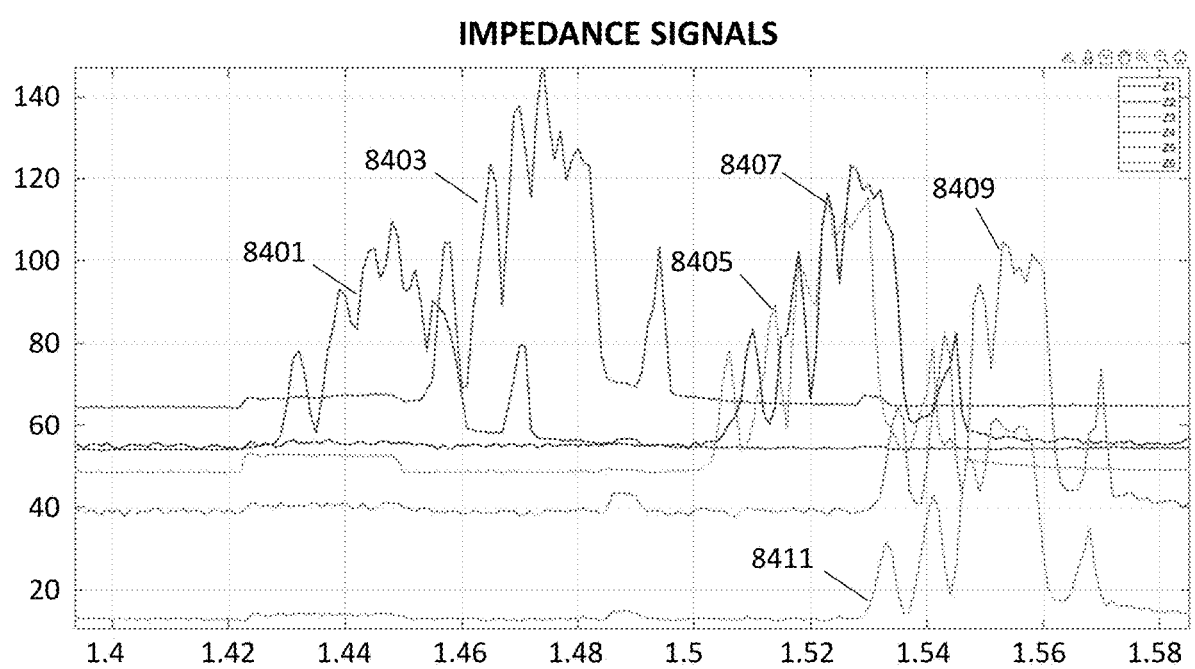
FIG. 84 is a graph showing an example of impedance measurements over time from various internal impedance sensors tracking clot material moving through the suction lumen of the apparatus, in which the clot material breaks up as it moves through the suction lumen.

FIGS. 83 and 84 illustrate tracking of clot material using different internal electrical impedance sensors similar to those shown in FIGS. 79A-79B, 80 and 81A-81B. In FIG. 83, the impedance over time was monitored when the apparatus removed clot material through the suction lumen using different configurations of internal impedance sensors. For example the signal 8301, 8401 from an internal impedance sensor such as the one shown in FIG. 79A is similar to that shown by the signal 8303, 8403 from internal impedance sensor such as the one shown in FIG. 79B. Each of the internal impedance sensors configured as quad detector/sensors returned two signals that are slightly delayed in time (reflecting the travel time). For example the internal impedance sensor of FIG. 81A returned signals 8305, 8405 and 8307, 8407 that are slightly offset. Similarly, an impedance sensor such as that shown in FIG. 81B returned signals 8309, 9409 and 8311, 8411. In this example the impedance showed removal of clot material that stayed fairly organized as it traveled down the length of the suction lumen. In contrast, in FIG. 84, the clot material can be observed to break apart during travel down the suction lumen. In this example, when clot breaks up, the clot volume estimation may be highly variable, as clot volume determination may depend in part on the rate of travel of the clot material as well as the spacing of the electrodes. Further, clot packing may affect the ability to estimate clot volume and transit velocity, and impedance amplitude may be higher when clot breaks up, as shown in FIG. 84.

In any of the apparatuses and methods described herein, the size of clot material (which may be further estimated from the known cross-sectional area of the suction lumen, as well as the length of the clot material), the rate of travel of the clot material within the lumen, the presence or absence of clot material clogged within the suction catheter, etc. may be determined and output to a user, stored, transmitted and/or further processed.

Figure 85:
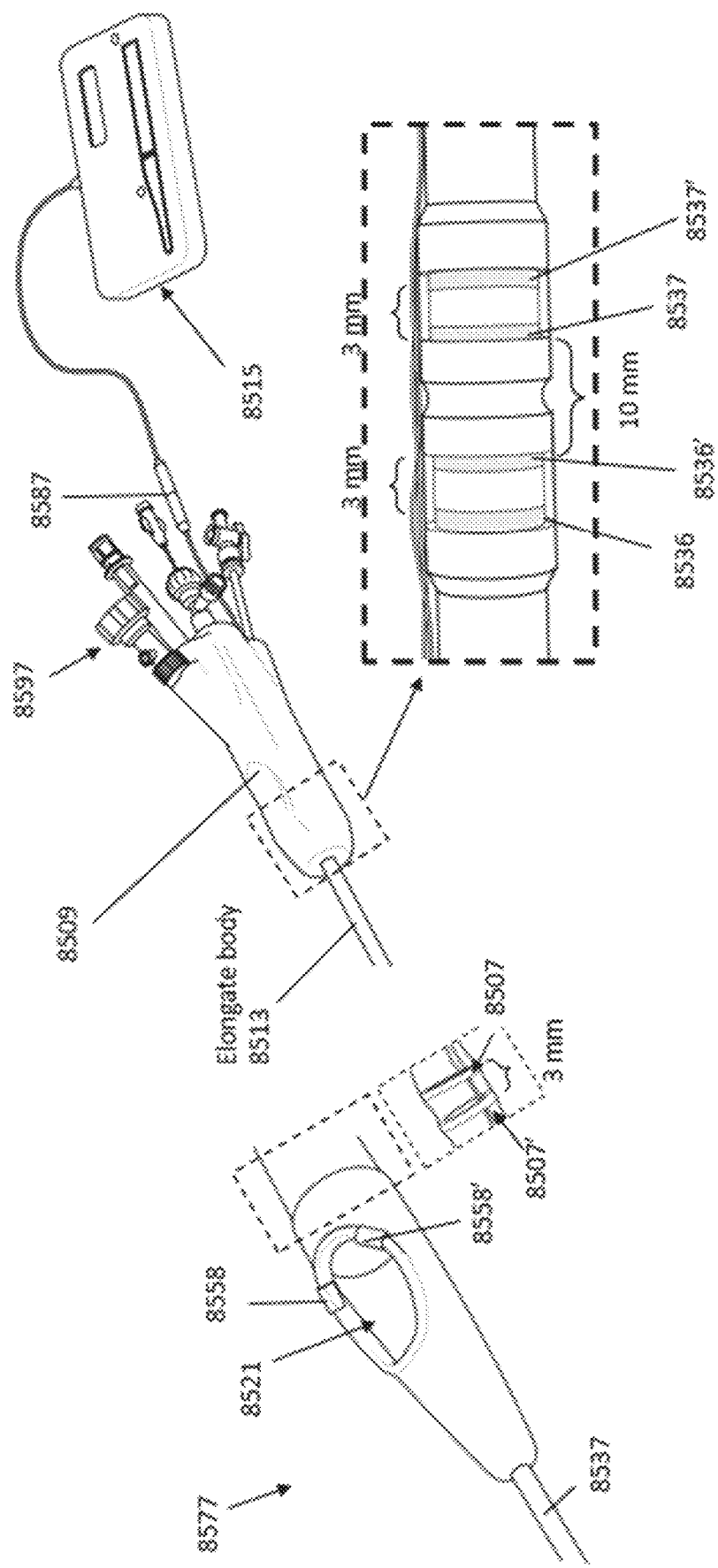
FIG. 85 illustrates one example of an apparatus for aspiration material, confirming/detecting material at the aspiration opening, and tracking material within the suction lumen of the apparatus.

FIG. 85 shows one example of an apparatus as described herein including many of the features described above. For example, FIG. 85 includes a flexible elongate body 8513 (shown in two parts) that includes a distal end region 8577 with a guide channel 8531 for a diagnostic catheter 8537 (and/or guidewire) extending from a distal end opening through the length of the elongate body. The distal end region may include an extraction chamber region having an aspiration opening 8521 into a suction lumen that extends along the length of the flexible elongate body. The aspiration opening at the distal end region of the flexible elongate body in this example is side-facing (e.g., on a tapered distal end region). The distal end region may also include one or more opening into the suction lumen on a side of the distal end region that is opposite from the aspiration opening (not visible in FIG. 85).

The distal end of the apparatus also includes an aspiration opening sensor comprising two electrodes 8558, 8558' positioned at a rim of the aspiration opening. In this example the electrodes are positioned at the 2 o'clock and 10 o'clock position, generally towards the proximal end of the aspiration opening. The electrodes of the aspiration opening sensor may be between about 0.1 and 3 cm (e.g., between about 0.5 and 2 cm, etc.) long (around the perimeter of the aspiration opening). In general, it may be helpful to sensing material in contact with the aspiration opening to position these electrodes in the proximal half (e.g., the proximal 40%, proximal 35%, proximal 30%, etc., such as between the 9 o'clock and 3 o'clock, or more preferably between 10 o'clock and 2 o'clock, or between 11 o'clock and 1 o'clock positions), as this is the region of highest flow density into the aspiration opening. A second set of internal impedance sensing electrodes 8507, 8507' are positioned just proximal to the aspiration opening and the aspiration opening sensor electrodes 8558, 8558'. The second set of internal impedance sensing electrodes may be configured to detect material (e.g., clot material) within the suction lumen and may be used in conjunction (or coordinated) with the aspiration opening sensor electrodes to confirm that the aspiration opening is in contact with clot material, or to distinguish from vessel wall when force (e.g., suction) is applied to drive the distal end region, including the aspiration opening, into a material. The internal impedance sensing electrodes may be spaced from the aspiration opening (proximal end) by between about 0.1 and 30 mm (e.g., between about 1 and 20 mm, between about 1 and 10 mm, etc.). The internal impedance sensing electrodes in this example includes two annular electrodes, extending partially around the wall of the suction lumen, but any shape electrode may be used. The internal impedance sensing electrodes may be separated from each other by any appropriate distance, e.g., between about 0.1 and 10 mm (e.g., between about 0.5 and 5 mm, 0.5 and 3 mm, etc.). The internal impedance sensing electrodes shown in FIG. 85 have a diameter (in the proximal-to-distal direction) of about 1 mm each.

The internal impedance sensing electrodes and the aspiration opening sensor electrodes may each be electrically coupled to an electrical line, wire, trace, etc., extending proximally down the length of the flexible elongate body and into the proximal handle 8509. In the example apparatus shown in FIG. 85, a second internal impedance sensor, configured as a quad detector/sensor including two sets of two internal impedance sensing electrodes 8536, 8536', 8537, 8537'. The second internal impedance sensor is still within the suction lumen, but is positioned within the portion of the suction lumen in the handle. The suction lumen may extend from the elongate body into the handle and may include a suction port 8597 at the proximal end.

In FIG. 85 the apparatus also includes a controller 8515 that couples or connects (via a connector 8587 to each of the electrodes of the internal impedance sensor (e.g., first and second internal impedance sensors) and the aspiration opening sensor. The controller in this example includes one or more outputs (e.g., display/LED, lights, tone/sound, etc.) and is configured to track material within the suction lumen. The controller may indicate (by a first LED) that material is within the distal end of the suction lumen and/or at the aspiration opening. For example, the controller may process impedance signals (received following the application of a current to the distal internal impedance sensor and/or aspiration opening sensor) to determine if or when the impedance is greater than a threshold indicating the likelihood of material (e.g., clot material) rather than blood and/or vessel wall in the internal impedance sensor and/or the aspiration opening sensor. The controller may also indicate (e.g., by a second LED) that material has passed (or is positioned proximal to) the proximal sensor, such as a quad detector/sensor shown in FIG. 85. In some example, the controller may indicate that the material has passed and/or is nearby when the change in impedance (relative to the impedance in blood) exceeds a threshold. In some examples, the controller may determine a flow rate of the clot material by tracking the impedance change between the two pairs of electrodes at a known (e.g., 10 mm) distance, and may estimate a total volume of material passing through the proximal end (and out of the apparatus) based on the flow rate, as well as the total size of the clot material (e.g., the product of the time clot material is detected and the flow rate, as well as the known cross-sectional area of the suction lumen at the region of the second internal impedance sensor). The controller may display an estimate of the volume and/or may store, transmit or otherwise process this information.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc.

Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of removing a blood clot material, the method comprising:
   advancing a flexible elongate catheter though a blood vessel, wherein the flexible elongate catheter comprises a distal end region having an aspiration opening therein;
   sensing an electrical signal between at least two sensors in the distal end region of the flexible elongate catheter to determine if the aspiration opening is within proximity to a blood clot based on the electrical signal; and applying suction when the electrical signal indicates that the aspiration opening is within proximity to the blood clot.

2. The method of claim 1, wherein advancing comprises advancing without applying negative pressure from the flexible elongate catheter.

3. The method of claim 1, further comprising emitting an alert indicating if the aspiration opening is within proximity to the blood clot.

4. The method of claim 1, wherein sensing the electrical signal comprises applying alternating signal having a frequency of between about 1 kHz and 1 MHz.

5. The method of claim 4, wherein the alternating signal has a frequency of between about 10 kHz and 100 kHz.

6. The method of claim 1, wherein the step of sensing is performed while advancing the flexible elongate catheter.

7. The method of claim 1, wherein determining if the aspiration opening is within proximity to the blood clot is based on both an impedance measurement based on the electrical signal from the at least two sensors and a second sensor positioned at the distal end region of the flexible elongate catheter.

8. The method of claim 1, further comprising adjusting suction through the flexible elongate catheter based on the electrical signal measured from the at least two sensors.

9. The method of claim 1, further comprising stopping suction when the electrical signal measured from the at least two sensors indicates that the aspiration opening is no longer within proximity to the blood clot.

10. The method of claim 1, wherein the aspiration opening at the distal end region is on a tapered side of the distal end region of the flexible elongate catheter.

11. A method of removing a blood clot material, the method comprising:
    positioning a flexible elongate catheter within a blood vessel, wherein the flexible elongate catheter comprises an aspiration opening on a tapered side of a distal end region and two or more electrodes on the distal end region;
    sensing an electrical signal between the two or more electrodes while positioning the flexible elongate catheter, to determine if the aspiration opening is within proximity to a blood clot based on the electrical signal from the two or more electrodes; and
    applying suction when the electrical signal indicates that the aspiration opening is within proximity to blood clot.

12. The method of claim 11, wherein advancing comprises positioning without applying negative pressure within the flexible elongate catheter.

13. The method of claim 11, further comprising emitting an alert indicating if the aspiration opening is within proximity to blood clot.

14. The method of claim 11, wherein sensing the electrical signal comprises applying alternating current having a frequency of between about 1 kHz and 1 MHz.

15. The method of claim 14, wherein the alternating current has a frequency of between about 10 kHz and 100 kHz.

16. The method of claim 11, wherein determining if the aspiration opening is within proximity to blood clot is based on both a measurement based on the electrical signal from the two or more electrodes and a second sensor positioned at the distal end region of the flexible elongate catheter.

17. The method of claim 11, further comprising adjusting suction through the flexible elongate catheter based on the electrical signal measured from the two or more electrodes.

18. The method of claim 11, further comprising stopping suction when the electrical signal measured from the two or more electrodes indicates that the aspiration opening is no longer within proximity to the blood clot.

19. A method of removing a blood clot material, the method comprising:
    positioning a flexible elongate catheter within a blood vessel, wherein the flexible elongate catheter comprises an aspiration opening on a distal end region and at least two or more electrodes on the distal end region;
    sensing an electrical signal between the two or more electrodes while positioning the flexible elongate catheter to determine if the aspiration opening is within proximity to a blood clot based on the electrical signal from the two or more electrodes; and
    adjusting suction through the flexible elongate catheter based on the electrical signal measured from the two or more electrodes, wherein suction is applied when the electrical signal indicates that the aspiration opening is within proximity to the blood clot.

20. The method of claim 1, wherein applying suction when the electrical signal indicates that the aspiration opening is within proximity to the blood clot comprises applying suction when the electrical signal indicates that the aspiration opening in contact with the blood clot.

* * * * *